(12) United States Patent
Francesch et al.

(10) Patent No.: US 7,420,051 B2
(45) Date of Patent: Sep. 2, 2008

(54) SYNTHETIC PROCESS FOR THE MANUFACTURE OF AN ECTEINASCHIDIN COMPOUND

(75) Inventors: Andrés Francesch, Madrid (ES); Carolina Fernández, Madrid (ES); José Luis Chicharro, Madrid (ES); Pilar Gallego, Madrid (ES); Maria Zarzuelo, Madrid (ES); Ignacio Manzanares, Madrid (ES); Marta Perez, Madrid (ES); Carmen Cuevas, Madrid (ES); María Jesús Martin, Madrid (ES); Simon Munt, Madrid (ES)

(73) Assignee: Pharma Mar, S.A., Madrid (ES)

( * ) Notice: Subject to any disclaimer, the term of this patent is extended or adjusted under 35 U.S.C. 154(b) by 241 days.

(21) Appl. No.: 11/249,172

(22) Filed: Oct. 11, 2005

(65) Prior Publication Data

US 2006/0111570 A1    May 25, 2006

Related U.S. Application Data

(63) Continuation of application No. 10/257,856, filed as application No. PCT/GB01/02120 on May 15, 2001, now abandoned.

(30) Foreign Application Priority Data

May 15, 2000    (WO) ..................... PCT/GB00/01852

(51) Int. Cl.
| | |
|---|---|
| C07D 267/22 | (2006.01) |
| C07D 281/18 | (2006.01) |
| C07D 291/00 | (2006.01) |
| C07D 337/16 | (2006.01) |
| C07D 487/00 | (2006.01) |

(52) U.S. Cl. ..................................... 540/454
(58) Field of Classification Search .................. 540/454
See application file for complete search history.

(56) References Cited

U.S. PATENT DOCUMENTS

| | | | |
|---|---|---|---|
| 5,089,273 | A | 2/1992 | Rinehart et al. |
| 5,149,804 | A | 9/1992 | Rinehart et al. |
| 5,256,663 | A | 10/1993 | Rinehart et al. |
| 5,478,932 | A | 12/1995 | Rinehart et al. |
| 5,654,426 | A | 8/1997 | Rinehart et al. |
| 5,721,362 | A | 2/1998 | Corey et al. |
| 5,985,876 | A | 11/1999 | Rinehart et al. |
| 6,124,292 | A | 9/2000 | Corey |
| 6,316,214 | B1 | 11/2001 | Rinehart et al. |
| 6,348,467 | B1 | 2/2002 | Corey |
| 6,686,470 | B2 | 2/2004 | Danishefsky et al. |
| 6,867,334 | B2 | 3/2005 | Rinehart et al. |
| 7,202,361 | B2 * | 4/2007 | Flores et al. ............... 544/338 |
| 2003/0216397 | A1 | 11/2003 | Flores et al. |
| 2004/0019056 | A1 | 1/2004 | Manzanares et al. |

FOREIGN PATENT DOCUMENTS

| | | |
|---|---|---|
| EP | 0 055 299 | 7/1982 |
| EP | 0 309 477 B1 | 11/1991 |
| JP | 59-225189 | 12/1984 |
| JP | 60-84288 | 5/1985 |
| WO | WO 87/07610 | 12/1987 |
| WO | WO 92/09607 | 6/1992 |
| WO | WO 98/12198 | 3/1998 |
| WO | WO 98/46080 | 10/1998 |
| WO | WO 99/58125 | 11/1999 |
| WO | WO 00/18233 | 4/2000 |
| WO | WO 00/69862 | 11/2000 |
| WO | WO 01/77115 | 10/2001 |
| WO | WO 01/87894 | 11/2001 |

OTHER PUBLICATIONS

Calabresi et al., "Chemotherapy of Neoplastic Diseases", Goodman & Gilman's The Pharmacological Basis of Therapeutics, 9th ed. New York: McGraw-Hill, 1996, pp. 1225-1229.

Cecil Textbook of Medicine (Bennet, J.C. and Plum, F., eds.) 20th Edition, vol. 1, pp. 1004-1010 (1996).

Kania, "The first Enantioselective Total Synthesis of Dolabellatrienone and Ecteinascidin 743", Harvard University, Sep. 1997, pp. 1-225.

Valoti et al. Clin. Cancer Res. 4(8): 1977-83 (1998).

Arai, T. et al., "The Structure of a Novel Antitumor Antibiotic, Saframycin A", *Experientia*, vol. 36, pp. 1025-1027 (1980).

Arai, Tadashi et al., "Directed Biosynthesis of New Saframycin Derivatives with Resting Cells of *Streptomyces lavendulae*", *Antimicrobial Agents and Chemotherapy*, vol. 28, No. 1, pp. 5-11 (1985).

(Continued)

*Primary Examiner*—Zachary C Tucker
(74) *Attorney, Agent, or Firm*—Fish & Richardson P.C.

(57) ABSTRACT

Processes are provided for preparing compounds with a fused ring structure of formula (XIV). Such products include ecteinascidins and have a spiroamine-1,4-bridge. The process involving forming a 1,4 bridge using a 1-labile, 10-hydroxy, 18-protected hydroxyl, di-6,8-en-5-one fused ring compound. After formation of the 1,4 brige, C-18 protection is removed before spiroamine introduction.

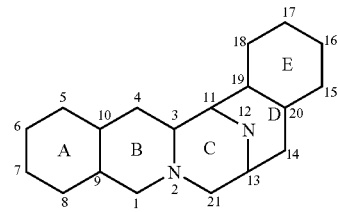

(XIV)

16 Claims, No Drawings

OTHER PUBLICATIONS

Arai, Tadashi et al., "Increased Production of Saframycin A and Isolation of Saframycin S", *The Journal of Antibiotics*, vol. XXXIII, No. 9, pp. 951-960 (1980).

Arai, Tadashi et al., "Isoquinolineinones from Actinomycetes and Sponges", *The Alkaloids Chemistry and Pharmacology*, vol. XXI, pp. 56-100 (1983).

Arai, Tadashi et al., "New Antibiotics, Safraycins A, B, C, D and E", *The Journal of Antibiotics*, vol. XXX, No. 11, pp. 1015-1018 (1977).

Asaoka, Takemitsu et al., "A New Saframycin, Saframycin R", *The Journal of Antibiotics*, vol. XXXV, No. 12, pp. 1708-1710 (1982).

Barton, Derek H.R. et al, "Synthesis and Properties of a Series of Sterically Hindered Guanidine Bases[1]", *Journal of the Chemical Society Perkin Transactions 1*, No. 9, pp. 2085-2090 (1982).

Brown, J.M., "NCI's Anticancer Drug Screening Program May Not Be Selecting for Clinically Active Compounds," Oncol. Res. 9(5):213-215 (1997).

Cable, Karl M. et al., "The Biosynthesis of Tuberin from Tyrosine and Glycine; Observations on the Stereochemistry Associated with the Conversion of Glycine through Methylenetetrahydrofolate into Methenyltetrahydrofolate", *Journal of the Chemical Society Perkins Transactions I*, No. 7, pp. 1593-1598 (1987).

Cooper, Raymond et al., "Structure of the Quinone Antibiotic EM5519 and the Behavior of Quinones in Fast Atom Bombardment Mass Spectrometry", *The Journal of Antibiotics*, vol. XXXVIII, No. 1, pp. 24-30 (1985).

Corey, E.J. et al., "Enantioselective Total Synthesis of Ecteinascidin 743", *Journal of the American Chemical Society*, vol. 118, No. 38, pp. 9202-9203 (1996).

Cuevas, Carmen et al., "Synthesis of Ecteinascidin ET-743 and Phthalascidin Pt-650 from Cyanosafracin B", *Organic Letters*, vol. 2, No. 16, pp. 2545-2548 (2000).

Draetta, G. and Pagano, M., "Annual Reports in Medicinal Chemistry, vol. 31," Academic Press, San Diego, pp. 241-246 (1996).

Eckhardt, S.G. et al., "Activity of ecteinascidin, a novel marine cytotoxic, against primary human tumor colony-forming units", *Proceedings of the American Association for Cancer Research*, vol. 37, #2791, pp. 409 (1996).

Faircloth, G. et al., "Ecteinascidin-743 (ET743): in vitro (IVT) and in vivo (INV) Results in Tumor Models", *The European Journal of Cancer*, vol. 32A, Suppl. 1, #24 O, pp. S5 (1996).

Flam, Faye, "Chemical Prospectors Scour the Seas for Promising Drugs", *Science*, vol. 266, pp. 1324-1325 (1994).

Frincke, James M. et al., "Antimicrobial Metabolites of the Sponge Reniera sp.", *Journal of the American Chemical Society*, vol. 104, pp. 265-269 (1982).

Fukuyama, Tohru et al., "Stereocontrolled Total Synthesis of (±)-Saframycin B", *Journal of American Chemical Society*, vol. 104, pp. 4957-4958 (1982).

Fukuyama, Tohru et al., "Total Synthesis of (±)-Saframycin A", *Journal of American Chemical Society*, vol. 112, pp. 3712-3713 (1990).

Garcia-Rocha, M. et al., "Characterisation of antimitotic products from marine organisms that disorganize the microtubule network: ecteinascidin 743, isohomohalichondrin-B and LL-15", *British Journal of Cancer*, vol. 73, pp. 875-883 (1996).

Goldwasser, F, et al. "Characterization of ecteinascidin 743-induced DNA damages in cells", *Proceedings of the American Association for Cancer Research*, vol. 39, #4066, pp. 598 (1998).

Guan, Yue et al., "Molecular and Crystal Structures of Ecteinascidins: Potent Antitumor Compounds from the Caribbean Tunicate *Ecteinascidia turbinata*", *Journal of Biomolecular Structure & Dynamics*, vol. 10, No. 5, pp. 793-818 (1993).

Gulavita, Nanda K., et al., "Antimicrobial Constituents of a Sponge-Nudibranch Pair from Sri Lanka", *Bioactive Compounds from Marine Organisms*, Oxford & IBH Publishing Co. Pvt. Ltd., pp. 229-233 (1991).

He, Hai-yin et al., "Renieramycins E and F from the Sponge Reniera sp.: Reassignment of the Stereochemistry of the Renieramycins", *The Journal of Organic Chemistry*, vol. 54, No. 24, pp. 5822-5824 (1989).

Hendriks, H.R. et al., "High antitumor activity of ET743 in human tumor xenograft models", *Proceedings of the American Association for Cancer Research*, vol. 37, #2653, pp. 389 (1996).

Ikeda, Yoshifumi et al., "Safracins, New Antitumor Antibiotics I. Producing Organism, Fermentation and Isolation", *The Journal of Antibiotics*, vol. XXXVI, No. 10, pp. 1279-1283 (1983).

Ikeda, Yoshifumi et al., "Safracins, New Antitumor Antibiotics I. Producing Organism, Fermentation and Isolation", *The Journal of Antibiotics*, vol. XXXVI, No. 10, pp. 1284-1289 (1983).

Ito, Yoichiro, "High-Speed Countercurrent Chromatography", *Critical Reviews in Analytical Chemistry*, vol. 17, No. 1, pp. 65-143 (1986).

Koenig, Karl E., "The Applicability of Asymmetric Homogeneous Catalytic Hodrogenation", *Asymmetric Synthesis*, Ed. Morrison, Academic Press, Inc., Orlando, FL, vol. 5, pp. 71 (1985).

Kofron, William G. et al., "A Convenient Method for Estimation of Alkyllithium Concentrations", *The Journal of Organic Chemistry*, vol. 41, No. 10, pp. 1879-1880 (1976).

Kubo, Akinori et al., "Structure of Saframycin D, A New Dimeric Isoquinolinequinone Antibiotic", *Chem. Pharm. Bull.*, vol. 35, No. 1, pp. 440-442 (1987).

Kuffel, M.J. et al., "Cytochrome P450 catalyzed metabolism of Ecteinascidin 743 by rat and human liver microsomes", *Proceedings of the American Association for Cancer Research*, vol. 38, #4003, pp. 596 (1997).

Lichter, W. et al., "Biological Activities Exerted by Extracts of *Ecteinascidia turbinata*", *Food and Drugs from the Sea Proceedings*, pp. 117-127 (1972).

Lown, J. William et al., "Molecular Mechanisms of Binding and Single-Strand Scission of Deoxyribonucleic Acid by the Antitumor Antibiotics Saframycins A and C", *Biochemistry*, vol. 21, No. 3, pp. 419-428 (1982).

Lown, J. William et al., "Structure and Confirmation of Saframycin R Determined by High Field $^1$H and $^{13}$C NMR and its Interactions with DNA in Solution", *The Journal of Antibiotics*, vol. XXXVI, No. 9, pp. 1184-1194 (1983).

Martinez et al., "A New, More Efficient, and Effective Process for the Synthesis of a Key Pentacyclic Intermediate for Production of Ecteinascidin and Phthalascidin Antitumor Agents", *Organic Letters*, 2(7):993-996 (2000).

Martinez et al., "Enantioselective Synthesis of Saframycin A and Evaluation of Antitumor Activity Relative to Ecteinascidin/Saframycin Hybirds", *Organic Letters*, 1(7):75-77 (1999).

Martinez, Eduardo J. et al., "Phthalascidin, a synthetic antitumor agent with potency and mode of action comparable to ecteinascidin 743", *Chemistry*, vol. 96, pp. 3496-3501 (1999).

Mikami, Yuzuru et al., "Structural Studies on Minor Components of Saframycin Group Antibiotics Saframycins F, G and H", *The Journal of Antibiotics*, vol. XLI, No. 6, pp. 734-740 (1988).

Mirsalis, J.C. et al., "Toxicity of Ecteinascidin 743 in female Fischer-344 rats administered i.v. in a multiple-dose regimen", *Proceedings of the American Association for Cancer Research*, vol. 38, #2073, pp. 309 (1997).

Moore, B.M. et al., "The NMR model of an ecteinascidin 743-DNA adduct", *Proceedings of the American Association for Cancer Research*, vol. 38, #2105, pp. 314 (1997).

Myers et al., "A Concise, Stereocontrolled Syntheis of (-)-Saframycin A by the Directed Condensation of α-Amino Aldehyde Precursors", *J. Am. Chem. Soc.*, 121:10828-10829 (1999).

Nakagawa, Masako et al., "Total Synthesis of (-)-Eudistomin L and (-)-Debromoeudistomin L", *Journal of the American Chemical Society*, vol. 111, No. 7, pp. 2721-2722 (1989).

Parulekar, A.H. et al., "Bioactivity and Chemical Ecology of Some Interdial Animals", *Bioactivity and Chemical Ecology*, pp. 29-35.

Pommier, Yves et al., "DNA Sequence- and Structure-Selective Alkylation of Guanine N2 in the DNA Minor Groove by Ecteinascidin 743, a Potent Antitumor Compound from the Caribbean Tunicate *Ecteinascidia turbinata*", *Biochemistry*, vol. 35, pp. 13303-13309 (1996).

Pretsch et al., *Tables of Spectral Data for Structure Determination of Organic Compounds*, pp. H125 (1983).

Reid, Joel M. et al., "Preclinical Pharmacology of ecteinascidin 729, a marine natural product with potent antitumor acitivity", *Cancer Chemotherapy and Pharmacology*, vol. 38, No. 4, pp. 329-334 (1996).

Remers, William A., "Saframycins, Renieramycins, and Safracins", *The Chemistry of Antitumor Antibiotics*, vol. 2, pp. 93-119 (1988).

Rinehart et al., "Novel Bioactive Natural Products from Marine Organisms", *Topics in Pharmaceutical Sciences 1989*, pp. 613-626, D.D. Breimer, D.J.A. Cromwelin, K.K. Midha, Eds., Amsterdam Medical Press B.V. Noordwijk, The Netherlands (1989).

Rinehart, Kenneth L. et al., "Applications of High-Resolution Tandem FAB Mass Spectrometry", *Biological Mass Spectrometry*, eds. Burlingame et al., Elsevier Amsterdam, pp. 233-258 (1990).

Rinehart, Kenneth L. et al., "Bioactive Compounds from Aquatic and Terrestrial Sources", *Journal of Natural Products*, vol. 53, no. 4, pp. 771-792 (1990).

Rinehart, Kenneth L. et al., "Biologically active natural products", *Pure and Applied Chemistry*, vol. 62, No. 7, pp. 1277-1280 (1990).

Rinehart, Kenneth L. et al., "Ecteinascidins 729, 743, 759A, 759B, and 770: Potent Antitumor Agents from the Caribbean Tunicate *Exteinascidia turbinata*", *The Journal of Organic Chemistry*, vol. 55, No. 15, pp. 4512-4515 (1990).

Rinehart, Kenneth L., "Antitumor Compounds from Tunicates", *Medicinal Research Reviews*, vol. 20, No. 1, pp. 1-27 (2000).

Saito, Naoki et al., "Synthesis of Saframycins. 3. Preparation of a Key Tricyclic Lactam Intermediate to Saframycin A", *The Journal of Organic Chemistry*, vol. 54, No. 22, pp. 5391-5395 (1989).

Sakai, Ryuichi et al., "Additional antitumor ecteinascidins from a Caribbean tunicate: Crystal structures and activities in vivo", *Proceedings of the National Academy of Sciences*, vol. 89, No. 23, pp. 11456-11460 (1992).

Sakai, Ryuichi et al., "Ecteinascidins: Putative Biosynthetic Precursors and Absolute Stereochemistry", *Journal of the American Chemical Society*, vol. 118, No. 38, pp. 9017-9023 (1996).

Shamma, Maurice et al., *Carbon-13 NMR Shift Assignments of Amines and Alkaloids*, pp. 206 (1979).

Still, W. Clark et al., "Rapid Chromatographic Technique for Preparative Separations with Moderate Resolution", *Journal of Organic Chemistry*, vol. 43, No. 14, pp. 2923-2925 (1978).

Takahaski, Katsuhiro et al., "Microbial Conversion of Saframycin A to 25-Dihydrosaframycin A and 21-Decyano-25-Dihydrosaframycin A (25-Dihydrosaframycin B) and Their Biological Activities", *The Journal of Antibiotics*, vol. XXXV, No. 2, pp. 196-202 (1982).

Takahaski, Katsuhiro, "New Antibiotics, Saframycins A, B, C, D and E", *The Journal of Antibiotics*, vol. XXX, No. 11, pp. 1015-1018 (1977).

Trowitzsch-Kienast, Wolfram et al., "Isolierung und Strukturaufklarung der Saframycine Mx 1 und Mx 2, neue antitumoraktive Antibiotika aus *Myxococcus xanthus*", *Liebigs Ann. Chem.*, vol. XXXV, pp. 475-481 (1988).

Witten, Jane L. et al., "Structures of Two Cockroach Neuropeptides Assigned by Fast Atom bombardment Mass Spectrometry", *Biochemical and Biophysical Research Communications*, vol. 124, No. 2, pp. 350-358 (1984).

Wright, Amy E. et al., "Antitumor Tetrahydroisoquinoline Alkaloids from the Colonial Ascidian *Ecteinascidia turbinata*", *The Journal of Organic Chemistry*, vol. 55, No. 15, pp. 4508-4512 (1990).

Yazawa, Katuskiyo et al., "Bioconversions of Saframycin A Specific to some Genera of Actinomycetes", *The Journal of Antibiotics*, vol. XXXV, No. 7, pp. 915-917 (1982).

Yazawa, Katsukiyo et al., "Isolation and Structural Elucidation of New Saframycins Y3, Yd-1, Yd-2, Ad-1, Y2b and Y2b-d", *The Journal of Antibiotics*; vol. XXXIX, No. 12, pp. 1639-1650 (1986).

Zmijewski, Milton J., Jr. et al., "The in vitro Interaction of Naphthyridinomycin with Deoxyribonucleic Acids", *Chemico-Biological Interations*, vol. 52, No. 3, pp. 361-375 (1985).

Martinez et al., "Phthalascidin, a synthetic antitumor agent with potency and mode of action comparable to ecteinascidin 743", Proc. Natl. Acad. Sci., USA, vol. 96, pp. 3496-3501, Mar. 1999.

* cited by examiner

SYNTHETIC PROCESS FOR THE MANUFACTURE OF AN ECTEINASCHIDIN COMPOUND

CROSS REFERENCE TO RELATED APPLICATIONS

This application is a continuation of U.S. application Ser. No. 10/257,856, filed Mar. 31, 2003, now abandoned which is the National Stage of International Application No.: PCT/GB01/02120, filed on May 15, 2001, which claims the benefit of International Application No.: PCT/GB00/01852 filed on May 15, 2000. The contents of these prior applications are incorporated herein by reference in their entireties.

The present invention relates to synthetic processes, and in particular it relates to synthetic processes for producing ecteinascidin compounds.

BACKGROUND OF THE INVENTION

European Patent 309,477 relates to ecteinascidins 729, 743, 745, 759A, 759B and 770. The ecteinascidin compounds are disclosed to have antibacterial and other useful properties. Ecteinascidin 743 is now undergoing clinical trials as an antitumour agent.

Ecteinascidin 743 has a complex tris(tetrahydroisoquinolinephenol) structure of the following formula (I):

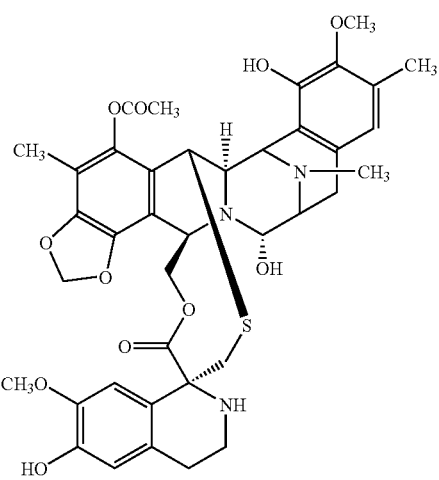

It is currently prepared by isolation from extracts of the marine tunicate *Ecteinascidin turbinata*. The yield is low, and alternative preparative processes have been sought.

A synthetic process for producing ecteinascidin compounds is described in U.S. Pat. No. 5,721,362, see also WO 9812198 which is incorporated herein by reference in full. The claimed method is long and complicated, there being 38 Examples each describing one or more steps in the synthetic sequence to arrive at ecteinascidin 743.

In the known synthetic process, a 1,4 bridge is formed using a 1-labile, 10-hydroxy, 18-protected hydroxy, di-6,8-en-5-one fused ring compound. As shown in Example 33, a compound (13) is converted to compound (14):

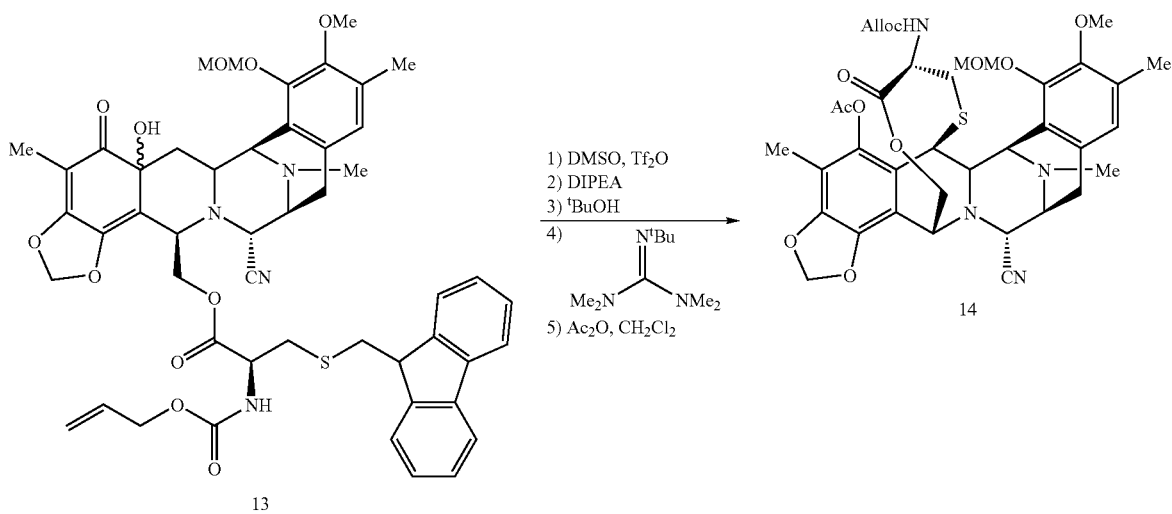

According to the known synthetic process, a spiroquinoline is then formed in the 1,4 bridge by the steps of Examples 34 to 36, and the 18-MOM protecting group is removed to give ecteinascidin 770 which can then be converted to ecteinascidin 743.

Claim 25 of U.S. Pat. No. 5,721,362 is directed at an intermediate phenol compound of a given formula (11), which we refer to also as Intermediate 11 or Int-11. It has the following bis(tetrahydroisoquinolinephenol) structure (II):

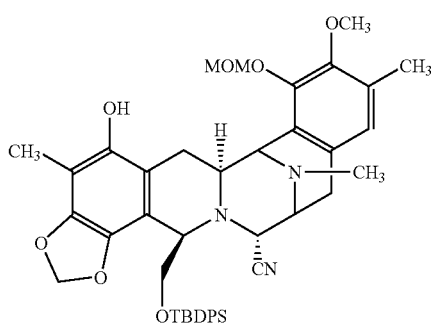

where MOM is a methoxymethyl substituent and TBDPS is a tert-butyldiphenylsilyl substituent.

From Intermediate 11 it is possible to synthesise another interesting antitumour agent, phthalascidin, see Proc. Natl. Acad. Sci. USA, 96, 3496-3501, 1999. Phthalascidin is a bis(tetrahydroisoquinolinephenol) derivative of formula (III):

In ecteinascidins 743 and 770, the 1,4 bridge has the structure of formula (IV):

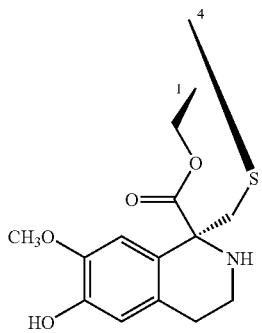

Other known ecteinascidins include compounds with a different bridged cyclic ring system, such as occurs in ecteinascidin 722 and 736, where the bridge has the structure of formula (V):

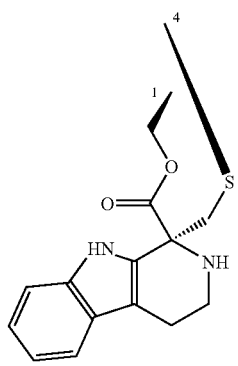

ecteinascidins 583 and 597, where the bridge has the structure of formula (VI):

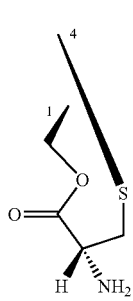

and ecteinascidin 594 and 596, where the bridge has the structure of formula (VII):

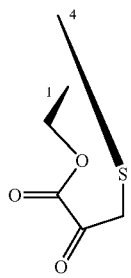

The complete structure for these and related compounds is given in J. Am. Chem. Soc. (1996) 118, 9017-9023. This article is incorporated by reference.

Other literature on the ecteinasdin compounds includes: Corey, E. J., J. Am. Chem. Soc., 1996, 118 pp. 9202-9203; Rinehart, et al., Journal of Natural Products, 1990, "Bioactive Compounds from Aquatic and Terrestrial Sources", vol. 53, pp. 771-792; Rinehart et al., Pure and Appl. Chem., 1990, "Biologically active natural products", vol 62, pp. 1277-1280; Rinehart, et al., J. Org. Chem., 1990, "Ecteinascidins 729, 743, 745, 759A, 759B, and 770: potent Antitumour Agents from the Caribbean Tunicate Ecteinascidia turninata", vol. 55, pp. 4512-4515; Wright et al., J. Org. Chem., 1990, "Antitumour Tetrahydroisoquinoline Alkaloids from the Colonial ascidian Ecteinascidia turbinata", vol. 55, pp. 4508-4512; Sakai et al., Proc. Natl. Acad. Sci. USA 1992, "Additional anitumor ecteinascidins from a Caribbean tunicate: Crystal structures and activities in vivo", vol. 89, 11456-11460; Science 1994, "Chemical Prospectors Scour the Seas for Promising Drugs", vol. 266, pp. 1324; Koenig, K. E., "Asymmetric Synthesis", ed. Morrison, Academic Press, Inc., Orlando, Fla., 1985, p. 71; Barton, et al., J. Chem Soc. Perkin Trans., 1, 1982, "Synthesis and Properties of a Series of Sterically Hindered Guanidine bases", pp. 2085; Fukuyama et al., J. Am. Chem. Soc., 1982, "Stereocontrolled Total Synthesis of (+)-Saframycin B", vol. 104, pp. 4957; Fukuyama et al., J. Am. Chem. Soc., 1990, "Total Synthesis of (+)-Saframycin A", vol. 112, p. 3712; Saito, et al., J. Org. Chem., 1989, "Synthesis of Saframycins. Preparation of a Key tricyclic Lactam Intermediate to Saframycin A", vol. 54, 5391; Still, et al., J. Org. Chem., 1978, "Rapid Chromatographic Technique for Preparative Separations with Moderate Resolution", vol. 43, p. 2923; Kofron, W. G.; Baclawski, L. M., J. Org. Chem., 1976, vol. 41, 1879; Guan et al., J. Biomolec. Struc. & Dynam., vol. 10, pp. 793-817 (1993); Shamma et al., "Carbon-13 NMR Shift Assignments of Amines and Alkaloids", p. 206 (1979); Lown et al., Biochemistry, 21, 419-428 (1982); Zmijewski et al., Chem. Biol. Interactions, 52, 361-375 (1985); Ito, CRC Crit. Rev. Anal. Chem., 17, 65-143 (1986); Rinehart et al., "Topics in Pharmaceutical Sciences 1989", pp. 613-626, D. D. Breimer, D. J. A. Cromwelin, K. K. Midha, Eds., Amsterdam Medical Press B. V., Noordwijk, The Netherlands (1989); Rinehart et al., "Biological Mass Spectrometry", 233-258 eds. Burlingame et al., Elsevier Amsterdam (1990); Guan et al., Jour. Biomolec. Struct. & Dynam., vol. 10 pp. 793-817 (1993); Nakagawa et al., J. Am. Chem. Soc, 111: 2721-2722 (1989); Lichter et al., "Food and Drugs from the Sea Proceedings" (1972), Marine Technology Society, Washington, D.C. 1973, 117-127; Sakai et al., J. Am. Chem. Soc., 1996, 118, 9017; Garcia-Rocha et al., Brit. J. Cancer, 1996, 73: 875-883; and Pommier et al., Biochemistry, 1996, 35: 13303-13309.

Further compounds are known which lack a bridged cyclic ring system. They include the bis(tetrahydroisoquinoline-quinone) antitumor-antimicrobial antibiotics safracins and saframycins, and the marine natural products renieramicins and xestomycin isolated from cultured microbes or sponges. They all have a common dimeric tetrahydroisoquinoline carbon framework. These compounds can be classified into four types, types I to IV, with respect to the oxidation pattern of the aromatic rings.

Type I, dimeric isoquinolinequinones, is a system of formula (VIII) most commonly occurring in this class of compounds, see the following table I.

TABLE I

Structure of Type I Saframycin Antibiotics.

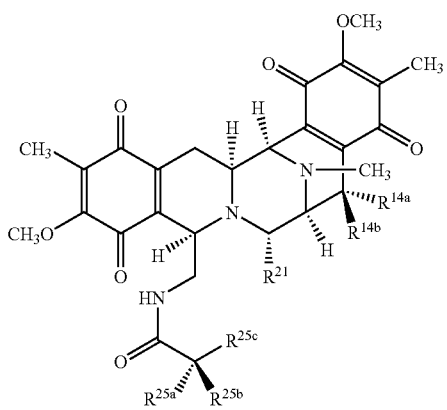

| Compound | $R^{14a}$ | $R^{14b}$ | $R^{21}$ | $R^{25a}$ | $R^{25b}$ | $R^{25c}$ |
|---|---|---|---|---|---|---|
| saframycin A | H | H | CN | O | O | $CH_3$ |
| saframycin B | H | H | H | O | O | $CH_3$ |
| saframycin C | H | $OCH_3$ | H | O | O | $CH_3$ |
| saframycin G | H | OH | CN | O | O | $CH_3$ |
| saframycin H | H | H | CN | OH | $CH_2COCH_3$ | $CH_3$ |
| saframycin S | H | H | OH | O | O | $CH_3$ |
| saframycin $Y_3$ | H | H | CN | $NH_2$ | H | $CH_3$ |
| saframycin $Yd_1$ | H | H | CN | $NH_2$ | H | $C_2H_5$ |
| saframycin $Ad_1$ | H | H | CN | O | O | $C_2H_5$ |
| saframycin $Yd_2$ | H | H | CN | $NH_2$ | H | H |
| saframycin $Y_{2b}$ | H | $Q^b$ | CN | $NH_2$ | H | $CH_3$ |
| saframycin $Y_{2b-d}$ | H | $Q^b$ | CN | $NH_2$ | H | $C_2H_5$ |
| saframycin $AH_2$ | H | H | CN | $H^a$ | $OH^a$ | $CH_3$ |
| saframycin $AH_2Ac$ | H | H | CN | H | OAc | $CH_3$ |
| saframycin $AH_1$ | H | H | CN | $OH^a$ | $H^a$ | $CH_3$ |

TABLE I-continued

Structure of Type I Saframycin Antibiotics.

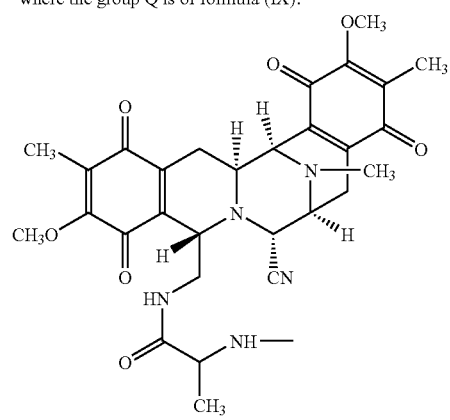

| Compound | $R^{14a}$ | $R^{14b}$ | $R^{21}$ | $R^{25a}$ | $R^{25b}$ | $R^{25c}$ |
|---|---|---|---|---|---|---|
| saframycin AH$_1$Ac | H | H | CN | OAc | H | CH$_3$ |
| saframycin AR$_3$ | H | H | H | H | OH | CH$_3$ |

[a]assignments are interchangeable.
[b]where the group Q is of formula (IX):

Type I aromatic rings are seen in saframycins A, B and C; G and H; and S isolated from *Streptomyces lavendulae* as minor components. A cyano derivative of saframycin A, called cyanoquinonamine, is known from Japanese Kokai JP-A2 59/225189 and 60/084,288. Saframycins Y$_3$, Yd$_1$, Ad$_1$, and Yd$_2$ were produced by *S. lavendulae* by directed biosynthesis, with appropriate supplementation of the culture medium. Saframycins Y$_{2b}$ and Y$_{2b\text{-}d}$ dimers formed by linking the nitrogen on the C-25 of one unit to the C-14 of the other, have also been produced in supplemented culture media of *S. lavendulae*. Saframycins AR$_1$ (=AH$_2$,), a microbial reduction product of saframycin A at C-25 produced by *Rhodococcus amidophilus*, is also prepared by nonstereoselective chemical reduction of saframycin A by sodium borohydride as a 1:1 mixture of epimers followed by chromatographic separation [the other isomer AH$_1$ is less polar]. The further reduction product saframycin AR$_3$, 21-decyano-25-dihydro-saframycin A, (=25-dihydrosaframycin B) was produced by the same microbial conversion. Another type of microbial conversion of saframycin A using a *Nocardia* species produced saframycin B and further reduction by a *Mycobacterium* species produced saframycin AH$^1$Ac. The 25-O-acetates of saframycin AH$_2$ and AH$_1$ have also been prepared chemically for biological studies.

Type I compounds of formula (X) have also been isolated from marines sponges, see Table II.

TABLE II

Structures of Type I Compounds from Marine Sponges.

|  | Substituents | | | |
|---|---|---|---|---|
|  | $R^{14a}$ | $R^{14b}$ | $R^{21}$ | R |
| renieramycin A | OH | H | H | —C(CH$_3$)═CH—CH$_3$ |
| renieramycin B | OC$_2$H$_5$ | H | H | —C(CH$_3$)═CH—CH$_3$ |
| renieramycin C | OH | O | O | —C(CH$_3$)═CH—CH$_3$ |
| renieramycin D | OC$_2$H$_5$ | O | O | —C(CH$_3$)═CH—CH$_3$ |
| renieramycin E | H | H | OH | —C(CH$_3$)═CH—CH$_3$ |
| renieramycin F | OCH$_3$ | H | OH | —C(CH$_3$)═CH—CH$_3$ |
| xestomycin | OCH$_3$ | H | H | —CH$_3$ |

Renieramycins A-D were isolated from the antimicrobial extract of a sponge, a *Reniera* species collected in Mexico, along with the biogenetically related monomeric isoquinolines renierone and related compounds. The structure of renieramycin A was initially assigned with inverted stereochemistry at C-3, C-11, and C-13. However, careful examination of the $^1$H NMR data for new, related compounds renieramycins E and F, isolated from the same sponge collected in Palau, revealed that the ring junction of renieramycins was identical to that of saframycins. This result led to the conclusion that the formerly assigned stereochemistry of renieramycins A to D must be the same as that of saframycins.

Xestomycin was found in a sponge, a *Xestospongia* species collected from Sri Lancan waters.

Type II compounds of formula (XI) with a reduced hydroquinone ring include saframycins D and F, isolated from *S. lavendulae*, and saframycins Mx-1 and Mx-2, isolated from *Myxococcus xanthus*. See table III.

TABLE III

Type II Compounds

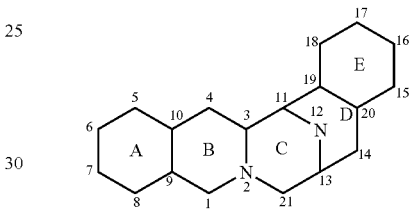

Substituents

| Compound | $R^{14a}$ | $R^{14b}$ | $R^{21}$ | $R^{25a}$ | $R^{25b}$ | $R^{25c}$ |
|---|---|---|---|---|---|---|
| saframycin D | O | O | H | O | O | $CH_3$ |
| saframycin F | O | O | CN | O | O | $CH_3$ |
| saframycin Mx-1 | H | $OCH_3$ | OH | H | $CH_3$ | $NH_2$ |
| saframycin Mx-2 | H | $OCH_3$ | H | H | $CH_3$ | $NH_2$ |

The type III skeleton is found in the antibiotics safracins A and B, isolated from cultured *Pseudomonas fluorescens*. These antibiotics of formula (XII) consist of a tetrahydroisoquinoline-quinone subunit and a tetrahydroisoquninolinephenol subunit.

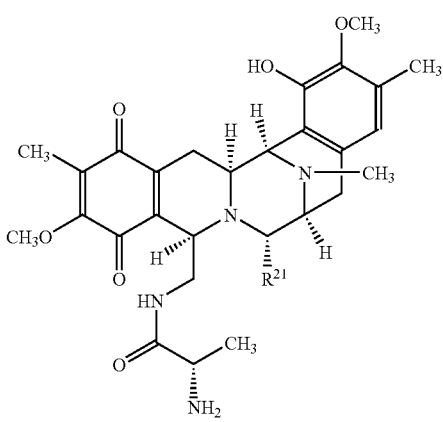

where $R^{21}$ is —H in safracin A and is —OH in safracin B.

Saframycin R, the only compound classified as the Type IV skeleton, was also isolated from *S. lavendulae*. This compound of formula (XIII), consisting of a hydroquinone ring with a glycolic ester sidechain on one of the phenolic oxygens, is conceivably a pro-drug of saframycin A because of its moderate toxicity.

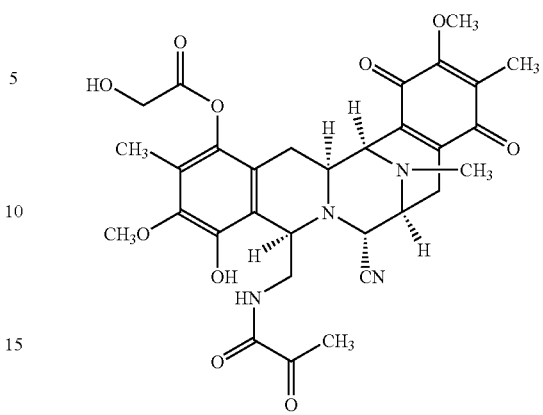

All these known compounds have a fused system of five rings (A) to (E) as shown in the following structure of formula (XIV):

The rings A and E are phenolic in the ecteinascidins and some other compounds, while in other compounds, notably the saframycins, the rings A and E are quinolic. In the known compounds, the rings B and D are tetrahydro, while ring C is perhydro.

OBJECT OF THE INVENTION

The need remains for alternative synthetic routes to the ecteinascidin compounds and related compounds. Such synthetic routes may provide more economic paths to the known antitumour agents, as well as permitting preparation of new active compounds.

SUMMARY OF THE INVENTION

This invention relates to synthetic processes for the formation of intermediates, derivatives and related structures of ecteinascidin or other tetrahydroisoquinolinephenol compounds.

In one aspect, the present invention provides a process for preparing an ecteinascidin product with a spiroamine-1,4-bridge. The process involving forming a 1,4 bridge using a 1-labile, 10-hydroxy, 18-protected hydroxy, di-6,8-en-5-one fused ring compound, where the fused ring is the formula (XIV). In the present invention, the C-18 protection is removed before spiroamine introduction.

Suitable starting materials for the new synthetic processes include compounds related to the natural bis(tetrahydroisoquinoline) alkaloids. Such starting materials may be prepared either from the different classes of saframycin and safracin antibiotics available from different culture broths as detailed in WO 0069862 or by other synthetic or biochemical processes. In this respect, WO 0069862 is incorporated herein in full by reference. The present PCT application claims priority from application PCT/GB 00/01852 which was published as WO 0069862. We incorporate that text by reference to the extent that there is disclosure therein which is not in the present specification.

PREFERRED EMBODIMENTS OF THE INVENTION

In one particular aspect, the present invention is directed at the use of the compound Intermediate 21 in a number of new synthetic processes for the preparation of ecteinascidin 743 and related compounds,

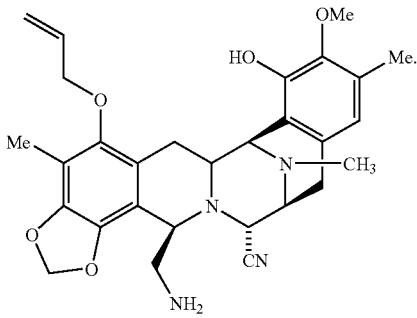

The Intermediate 21 has a 5-allyloxy group, where the allyl group serves to protect the 5-hydroxy group. It will be understood that other protecting groups can easily be employed, and that the present invention extends generally to the use of other such 5-protected hydroxy compounds.

Formation of Ecteinascidin 743 and Related Compounds

In general, the conversion of Intermediate 21, or a related compound, to an ecteinascidin product involves the following key transformations:

(a) Conversion of the $NH_2$ to OH by reaction, for example with sodium nitrite in acetic acid.
(b) E-ring phenol protection.
(c) Esterification by protecting the primary 1-hydroxy function with a protected cysteine sidechain.
(d) Deprotection of allyl group and oxidation.
(e) Creation of the bridged ring by cyclization reaction.
(f) Deprotections of E-ring phenol and the cysteine moiety
(g) Quinoline Introduction by Trans-amination and Petter Spengler reactions.

The high functionality of the intermediate compounds necessitates the use of protecting groups for the E-ring phenol and for the cysteine sidechain in order to prevent unwanted side reactions.

As such, a number of alternative intermediates can be generated dependent on the particular selection of protecting groups.

Different possible sequences are possible for combining these transformations dependent primarily on the protecting groups selected for the phenol ring and for the amine of the cysteine sidechain.

The total number of synthetic transformations is also a function of the protecting groups selected.

By way of illustration, the use of different combinations of protecting groups is described below for six typical routes for the preparation of ET-743 from Intermediate 21, also referred to herein as SF21.

| Route | Phenol Protection | Cysteine Protection | Number of steps |
| --- | --- | --- | --- |
| 1 | MOM | Boc | 12 |
| 2 | MEM | Boc | 10 |
| 3 | MEM | Cbz | 11 |
| 4 | MOM | Alloc | 13 |
| 5 | MEM | Alloc | 13 |
| 6 | MOM | Cbz | 15 |

As the skilled artisan will readily appreciate, the reaction schemes described herein may be modified and/or combined in various ways, and the alternative sequences of steps and the compounds generated therefrom are part of this invention.

Additionally, the use of other protecting group strategies not detailed also part of this invention.

Process Details of Six Typical Synthetic Routes

Full reaction schemes for each route are in the following Schemes 1 to 6.

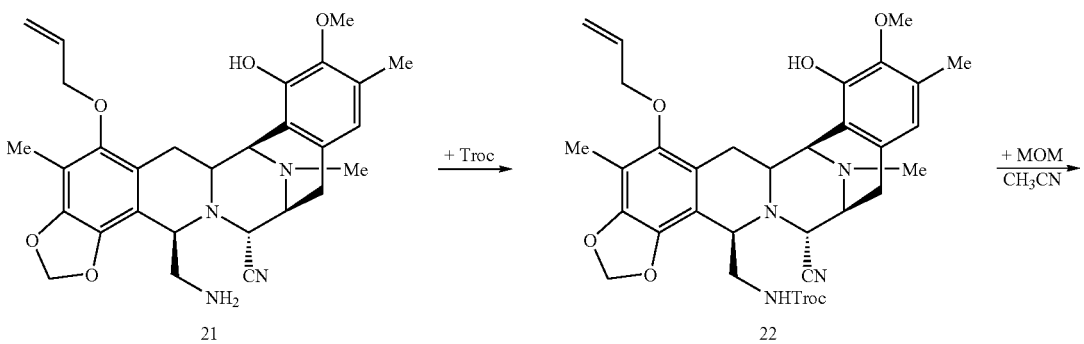

-continued
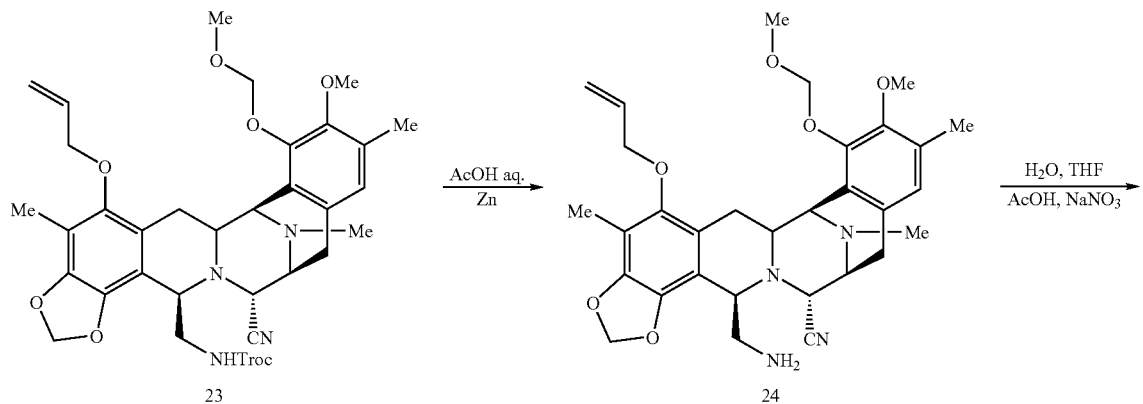
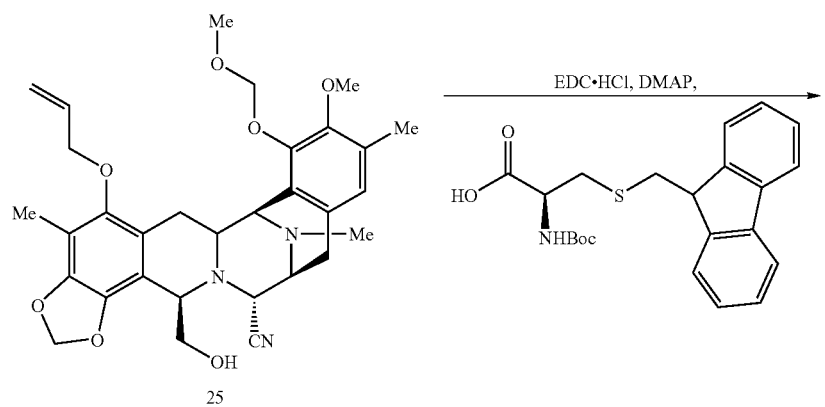
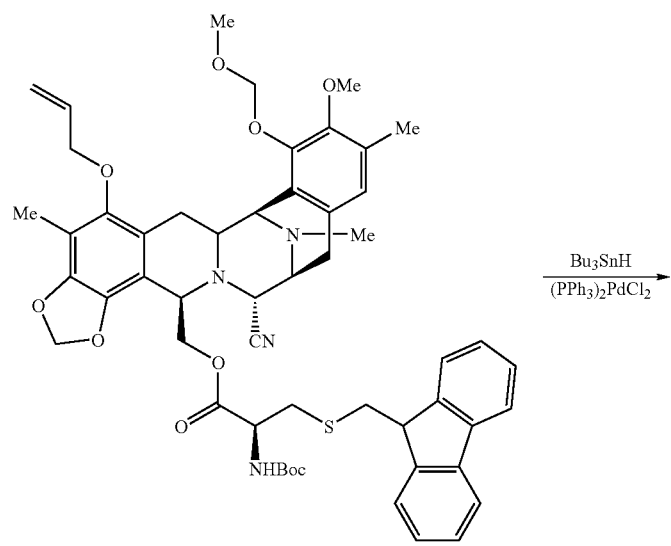

-continued
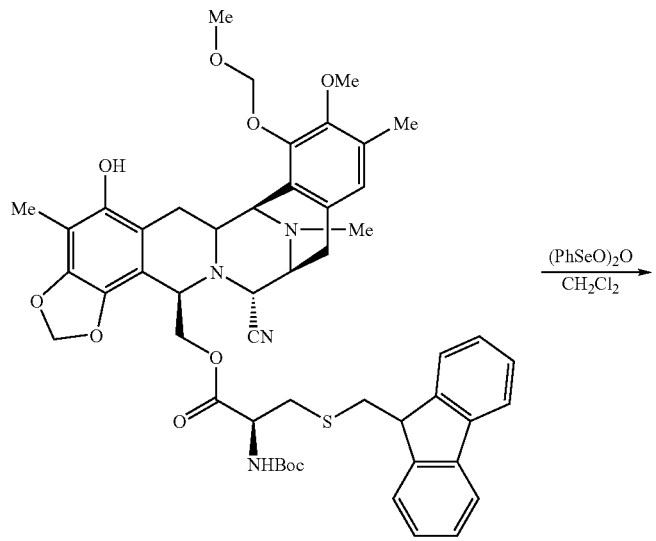
143
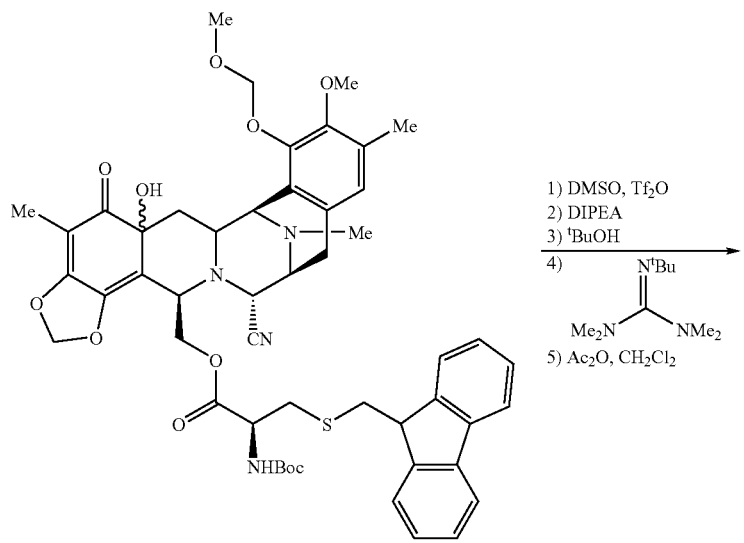
144
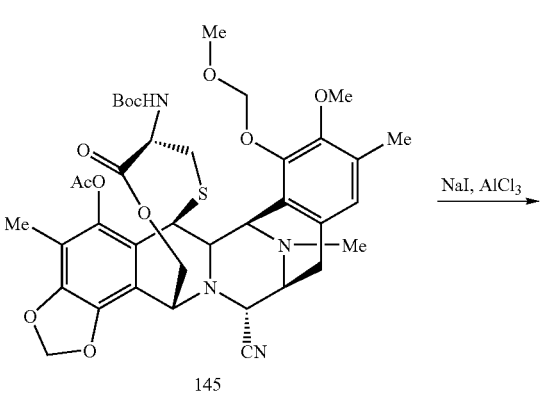
145

-continued
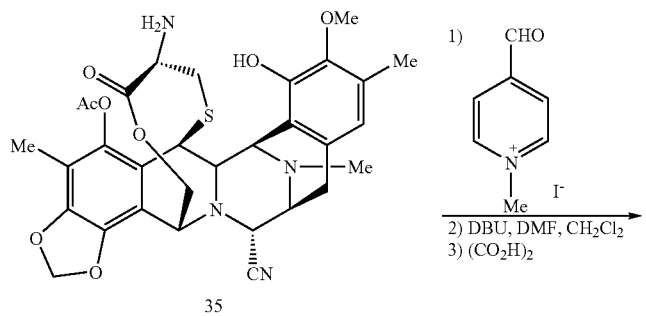
35
1) <image with CHO-pyridinium methiodide>
2) DBU, DMF, CH₂Cl₂
3) (CO₂H)₂
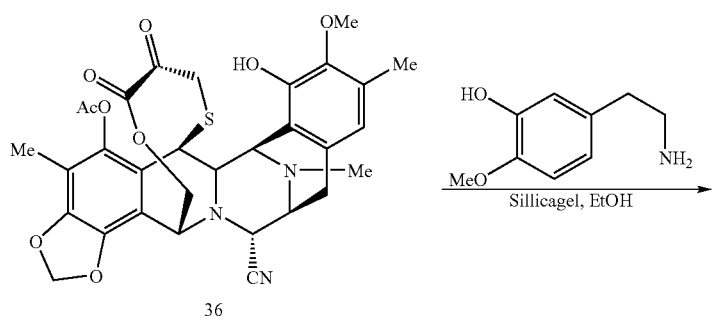
36
HO, MeO–C₆H₃–CH₂CH₂NH₂
―――――――――→
Sillicagel, EtOH
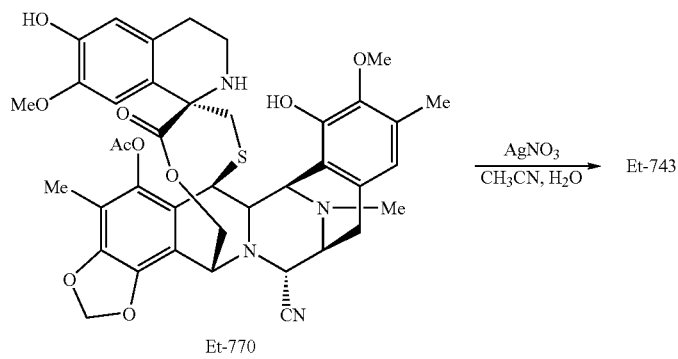
Et-770
AgNO₃
――――――→  Et-743
CH₃CN, H₂O
Scheme 2-ET-743: Hemisynthetic Alternative Route 2
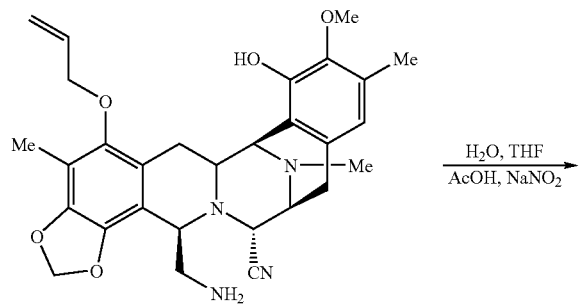
21
H₂O, THF
――――――→
AcOH, NaNO₂

-continued
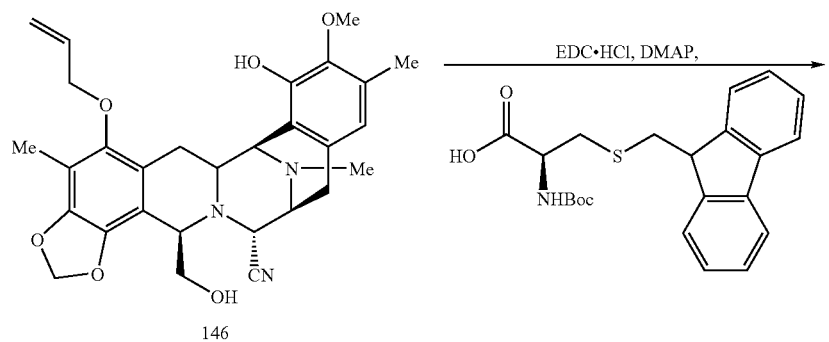
146
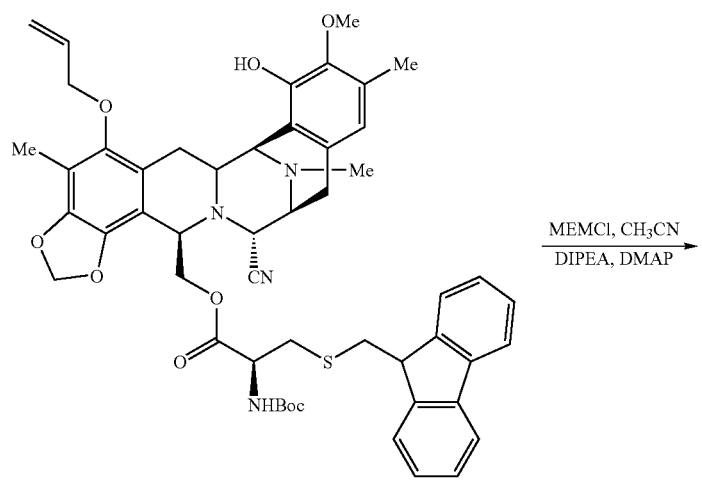
147
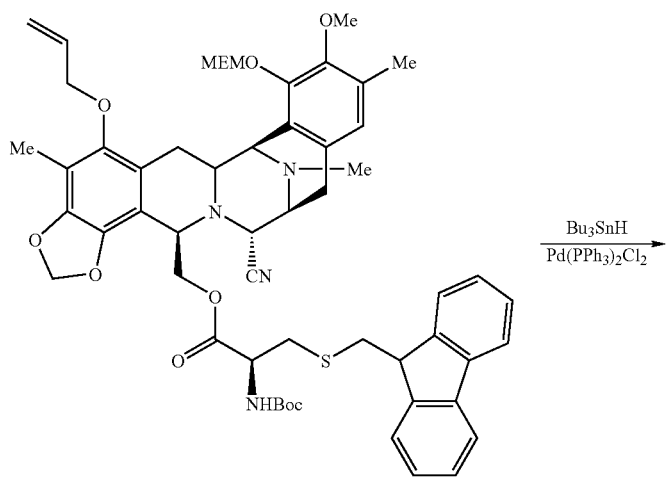
148

-continued
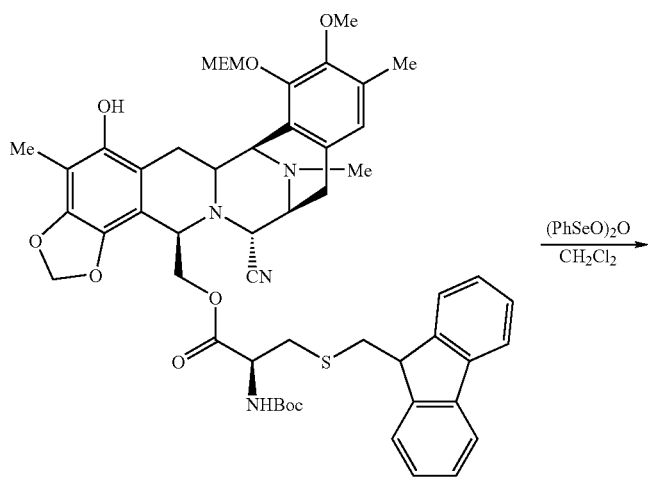
149
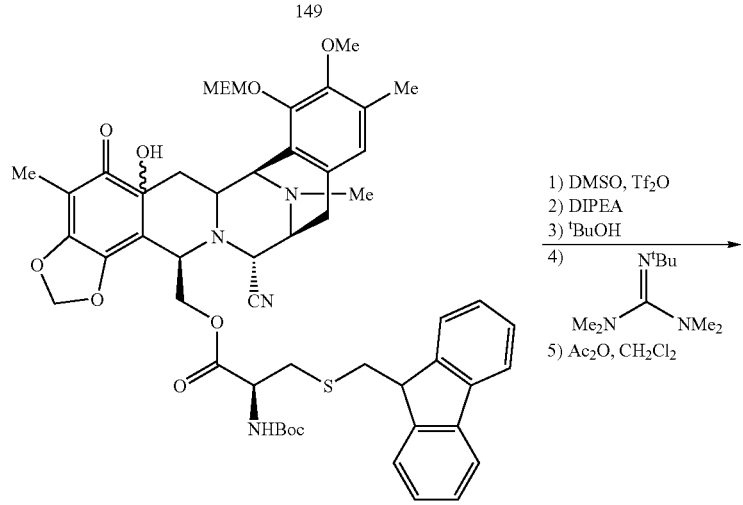
150
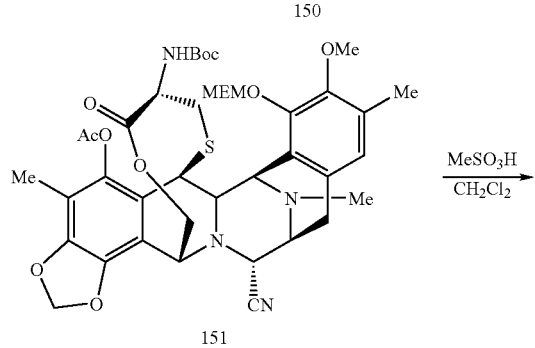
151
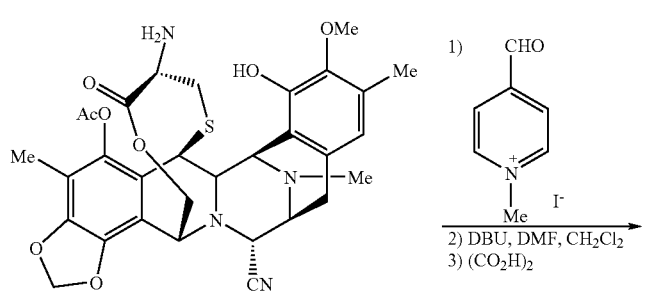
35

-continued
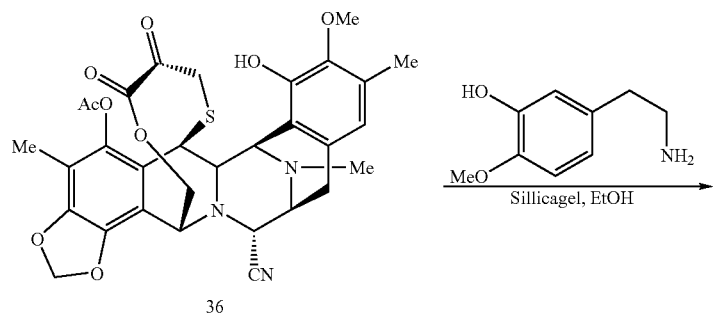
36
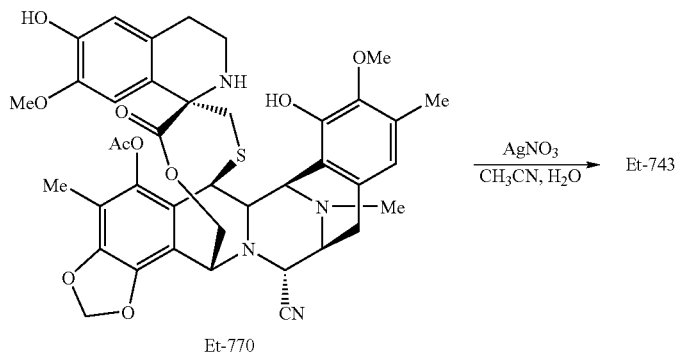
Et-770
Scheme 3-ET-743: Hemisynthetic Alternative Route 3
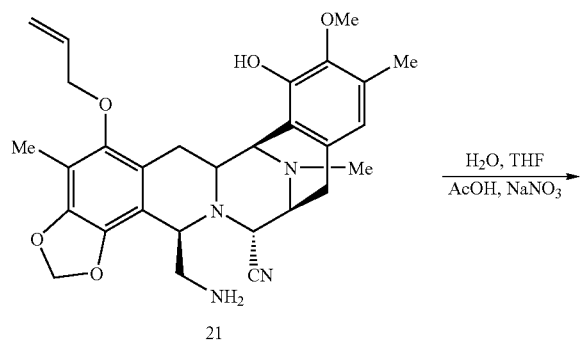
21
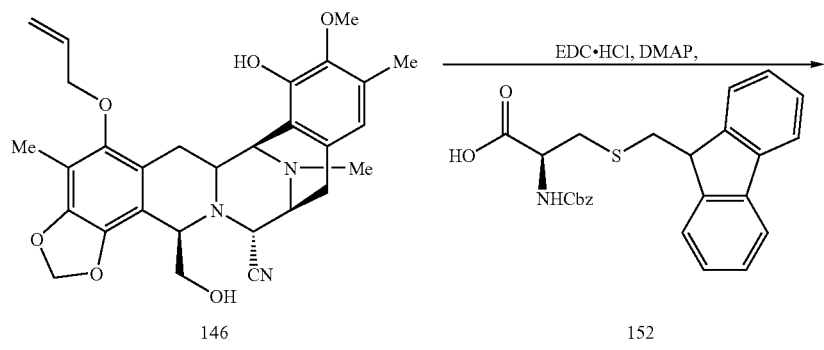
146 152

-continued
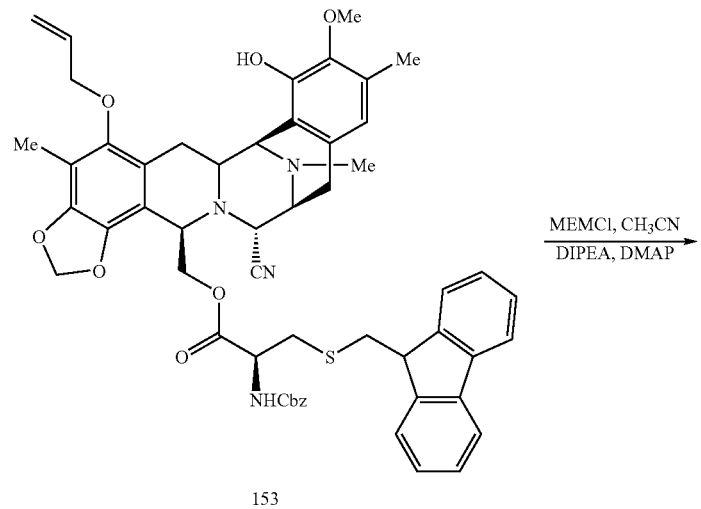
153
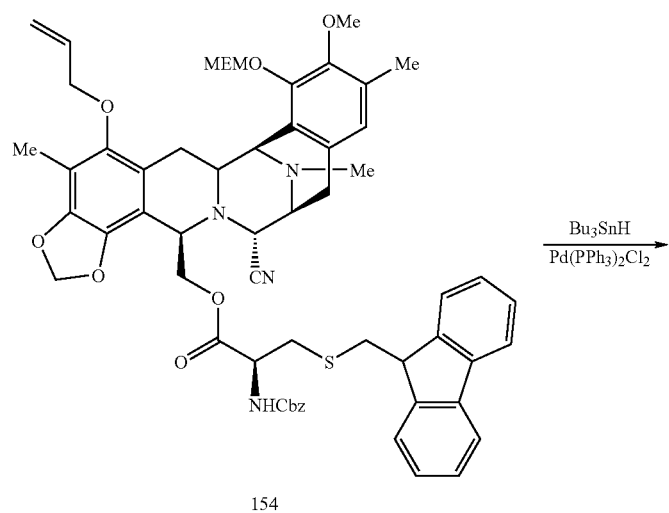
154
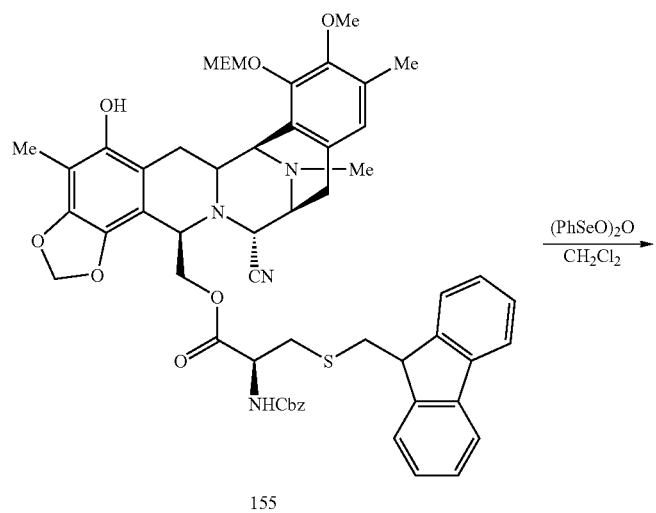
155

-continued
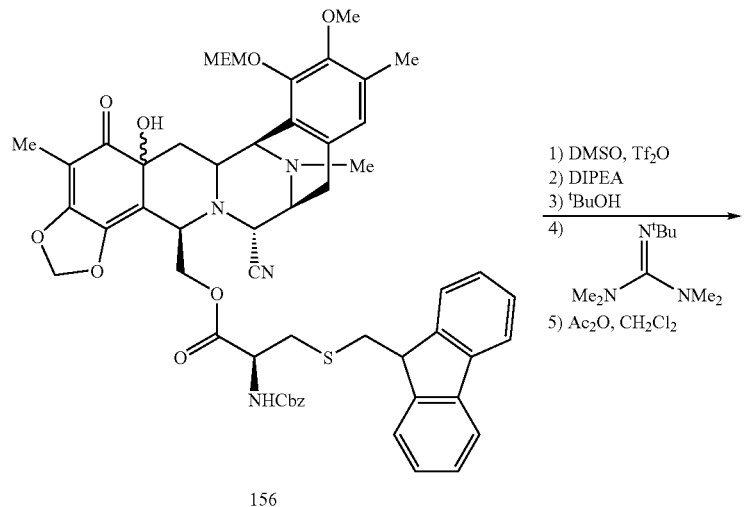
156
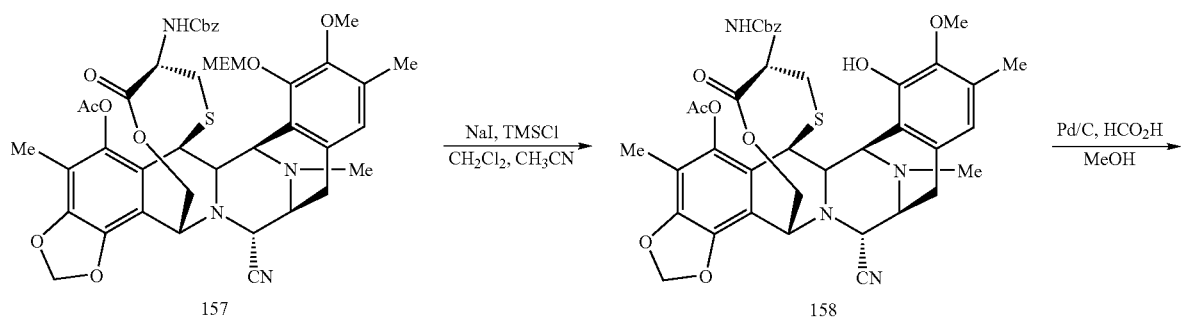
157 → 158
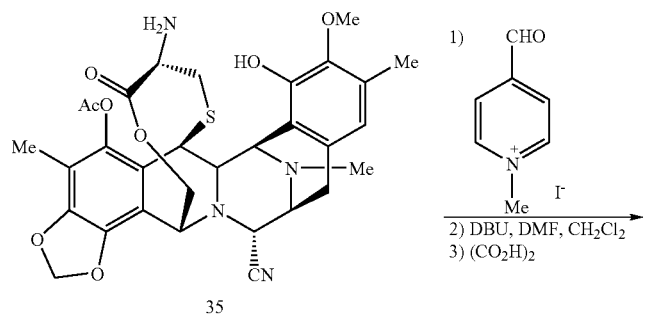
35
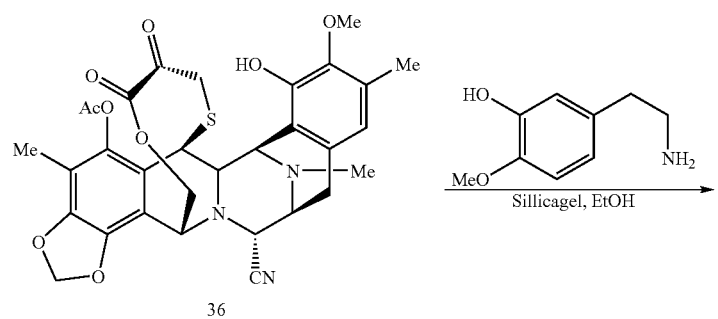
36

-continued
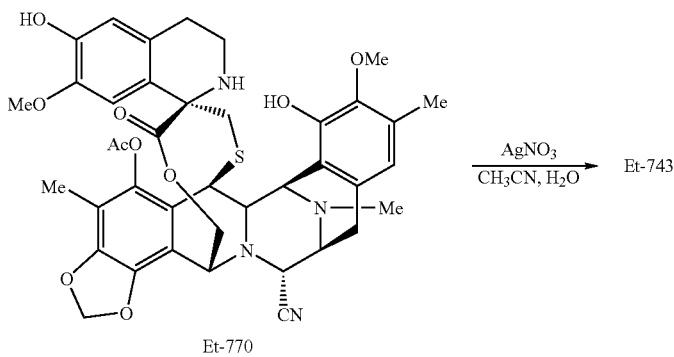
Et-770
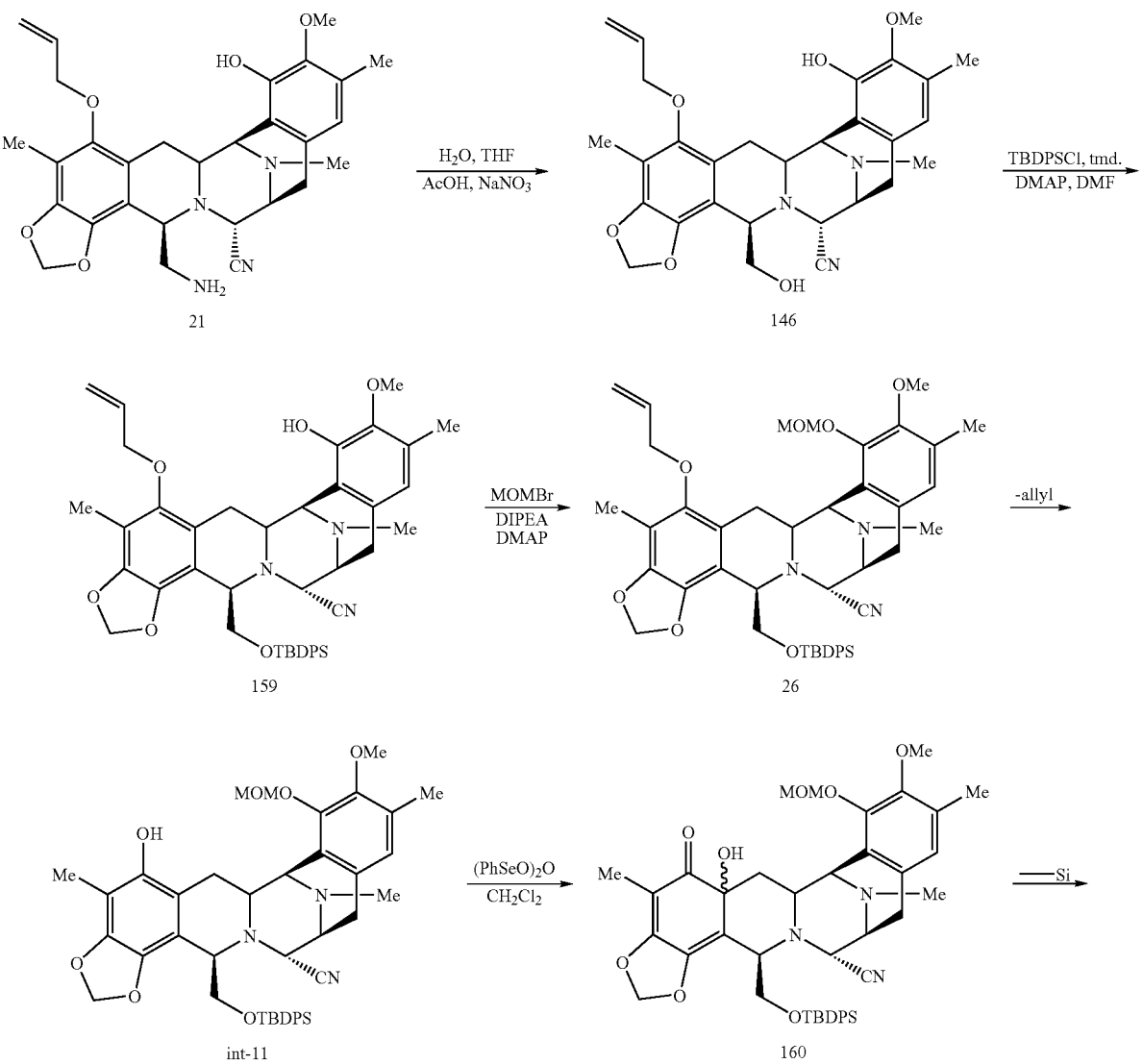
Scheme 4-ET-743: Hemisynthetic Alternative Route 4

-continued
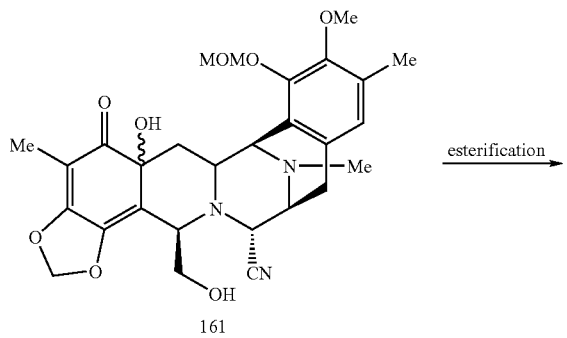
161
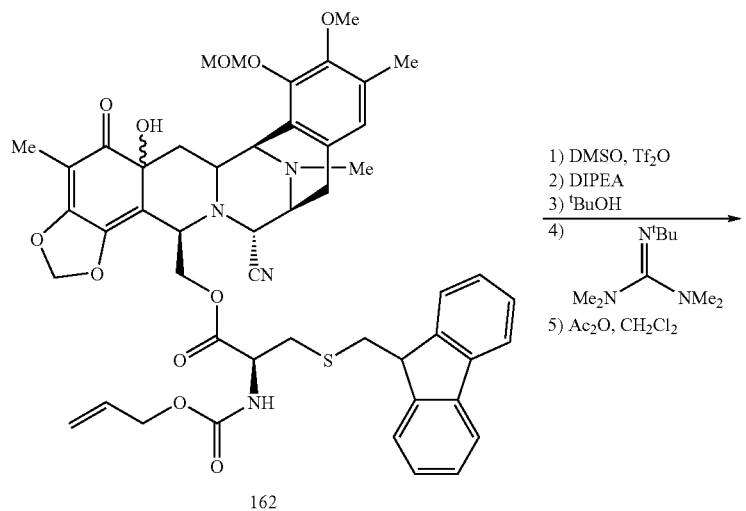
162
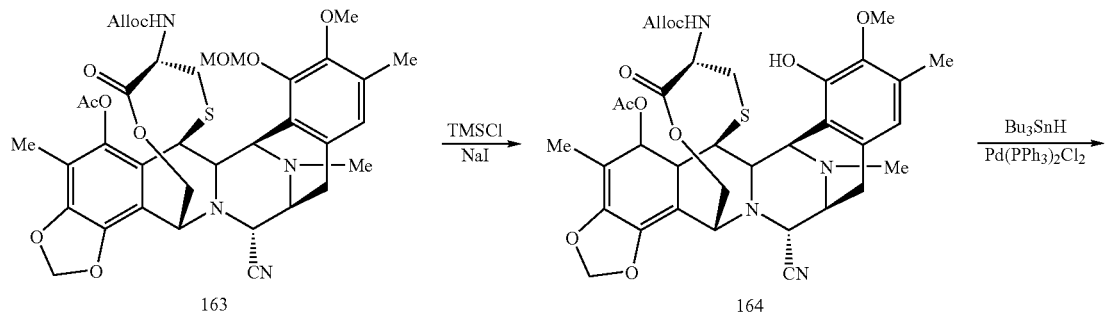
163 164
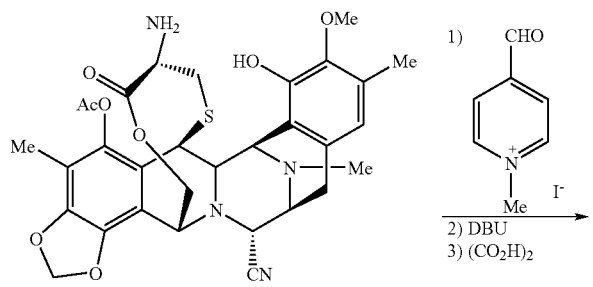
35

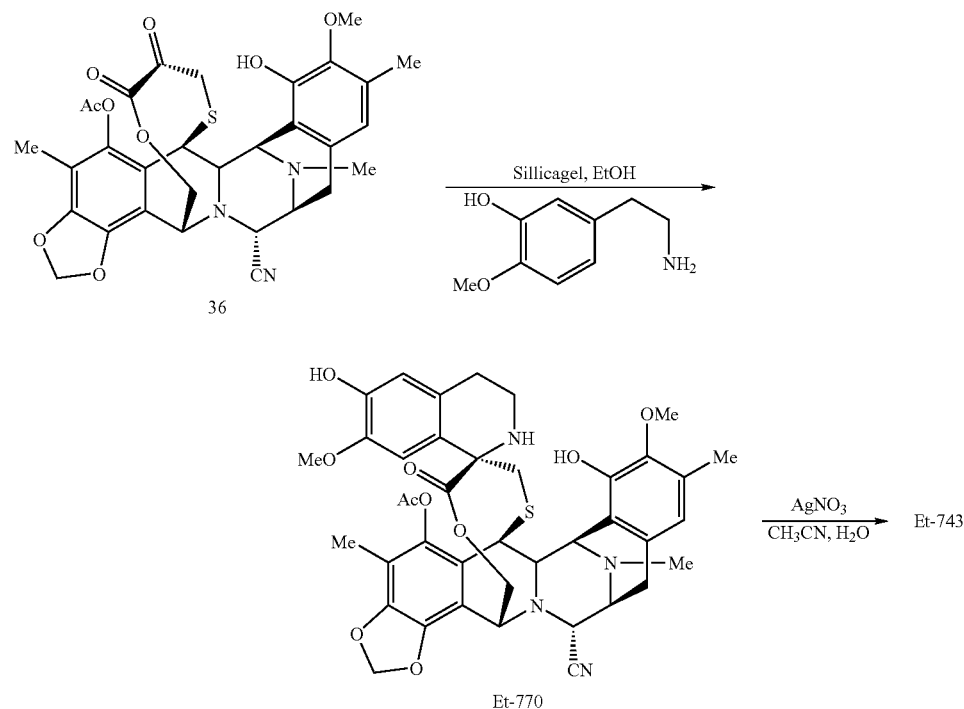
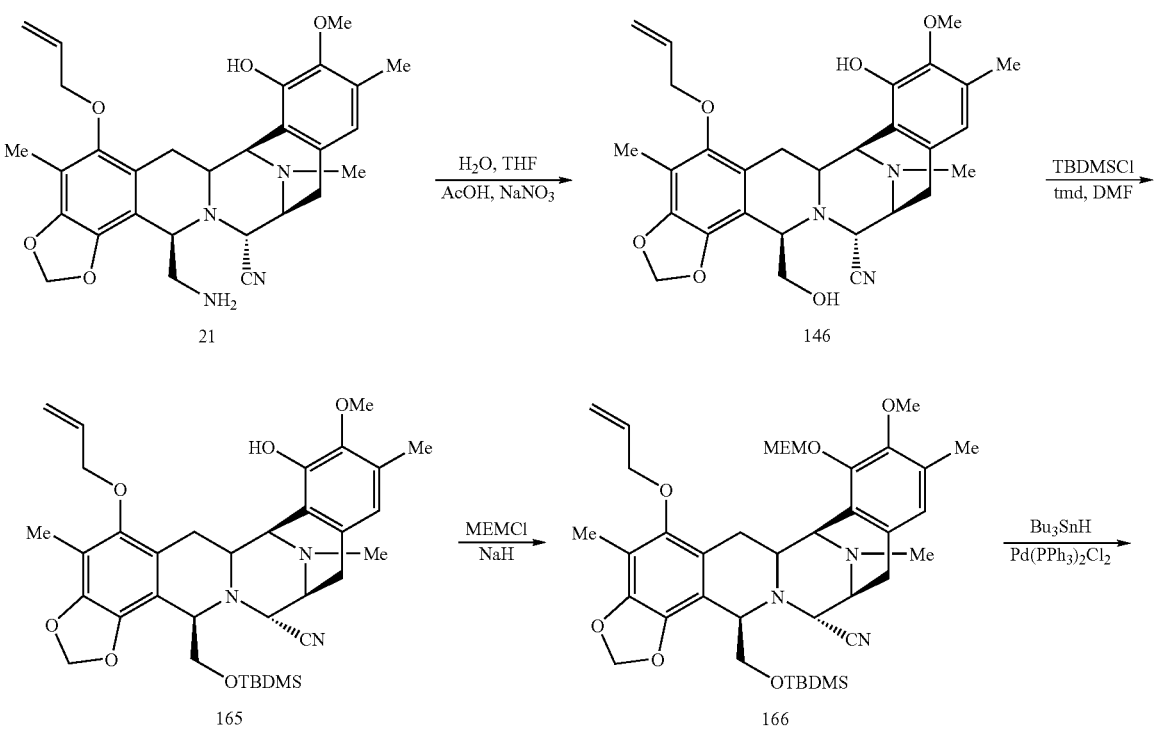
Scheme 5-ET-743: Hemisynthetic Alternative Route 5

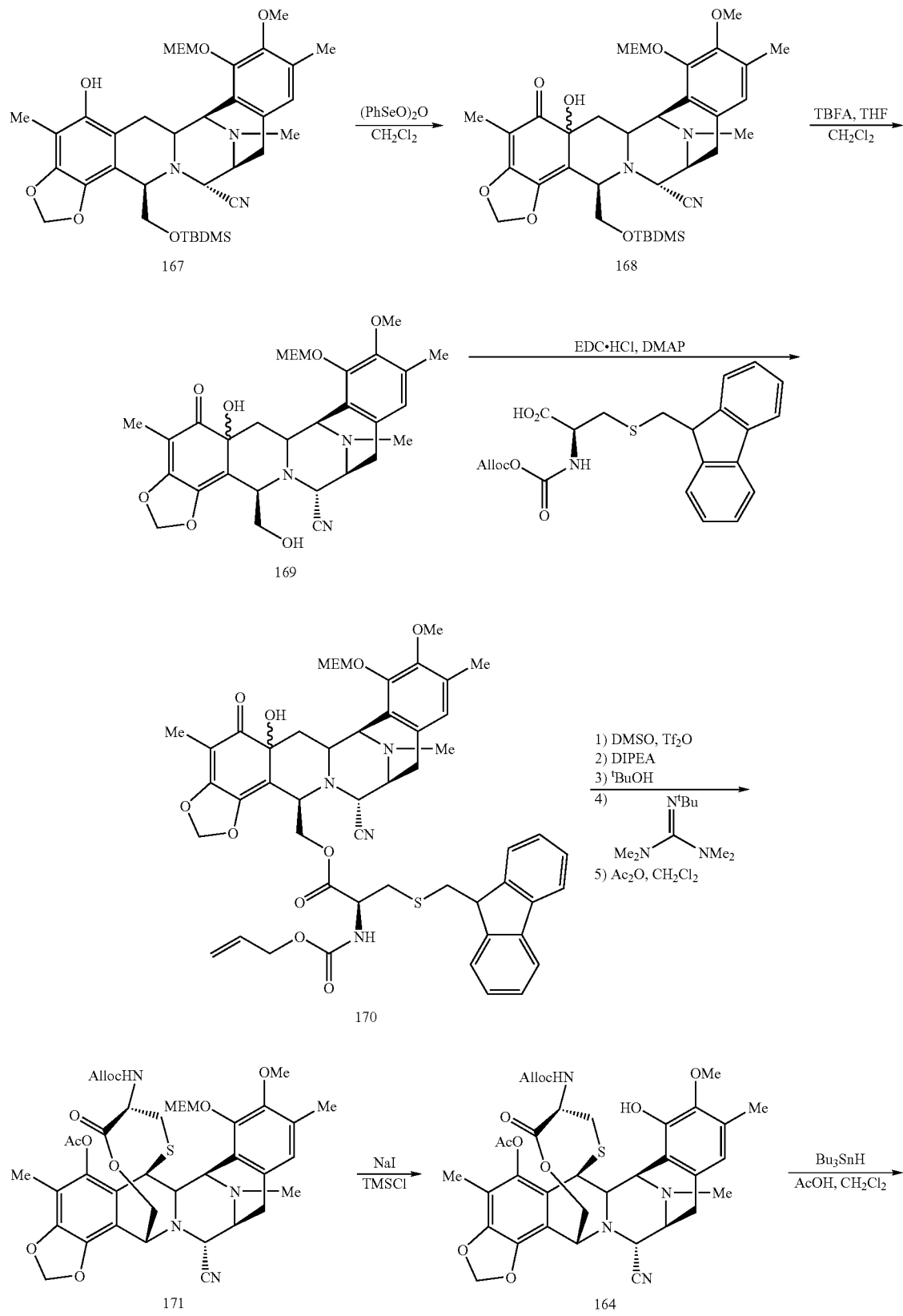

-continued
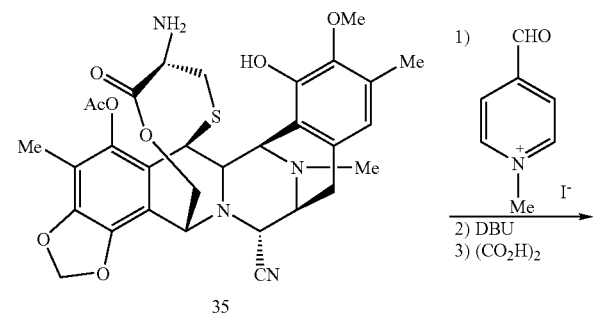
35
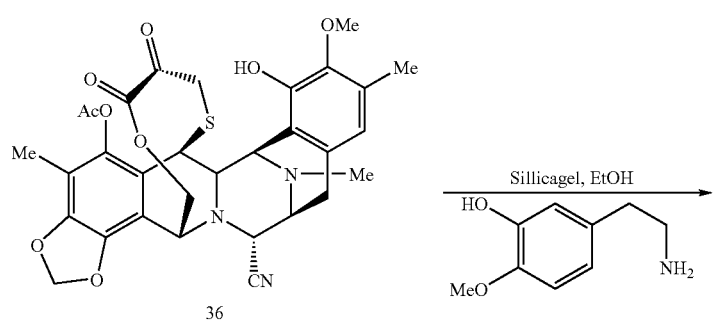
36
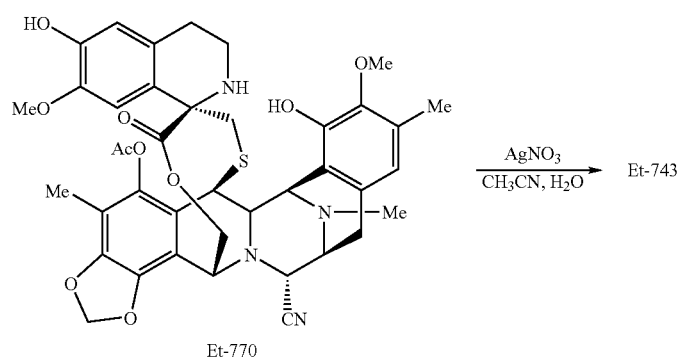
Et-770
→ Et-743
AgNO₃ / CH₃CN, H₂O
Scheme 6-ET-743 Hemisynthetic Alternative Route 6
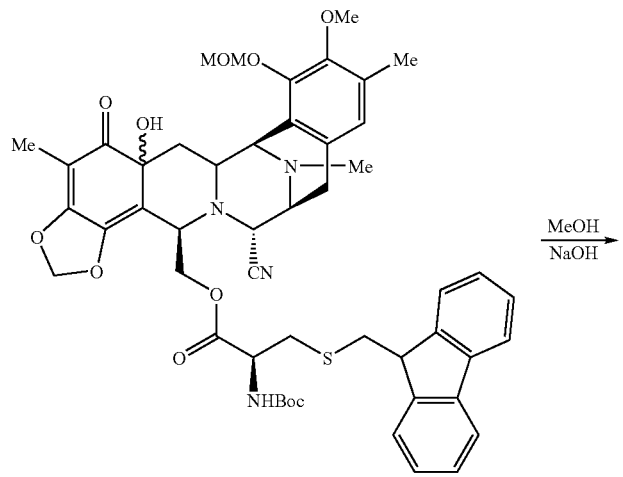
144
→ MeOH / NaOH -continued
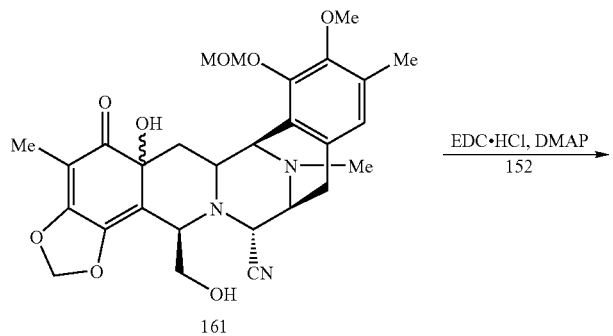
161
EDC·HCl, DMAP
152
→
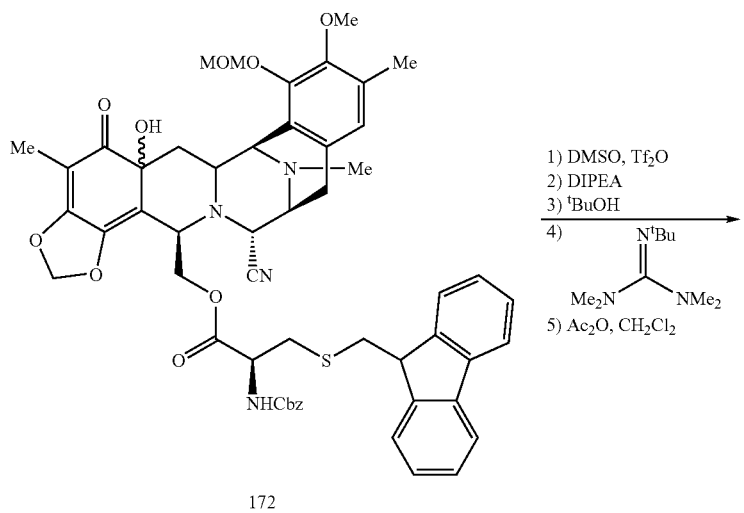
172
1) DMSO, Tf₂O
2) DIPEA
3) ᵗBuOH
4) Me₂N-C(=NᵗBu)-NMe₂
5) Ac₂O, CH₂Cl₂
→
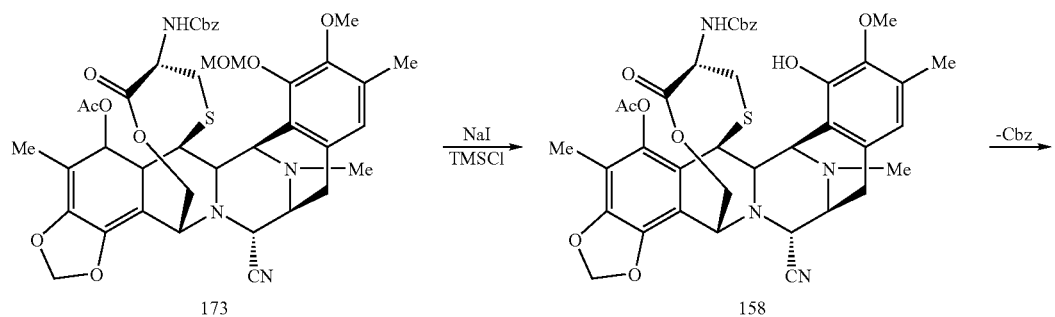
173
NaI
TMSCl
→
158
-Cbz
→
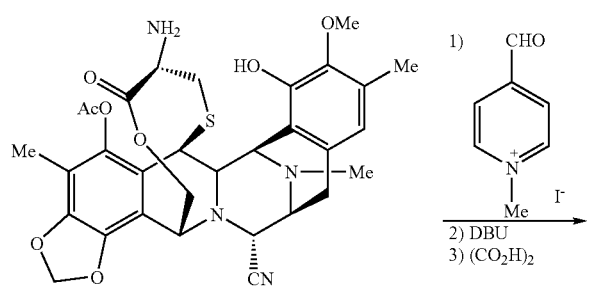
35
1) 4-pyridinecarboxaldehyde / N-methylpyridinium iodide
2) DBU
3) (CO₂H)₂
→

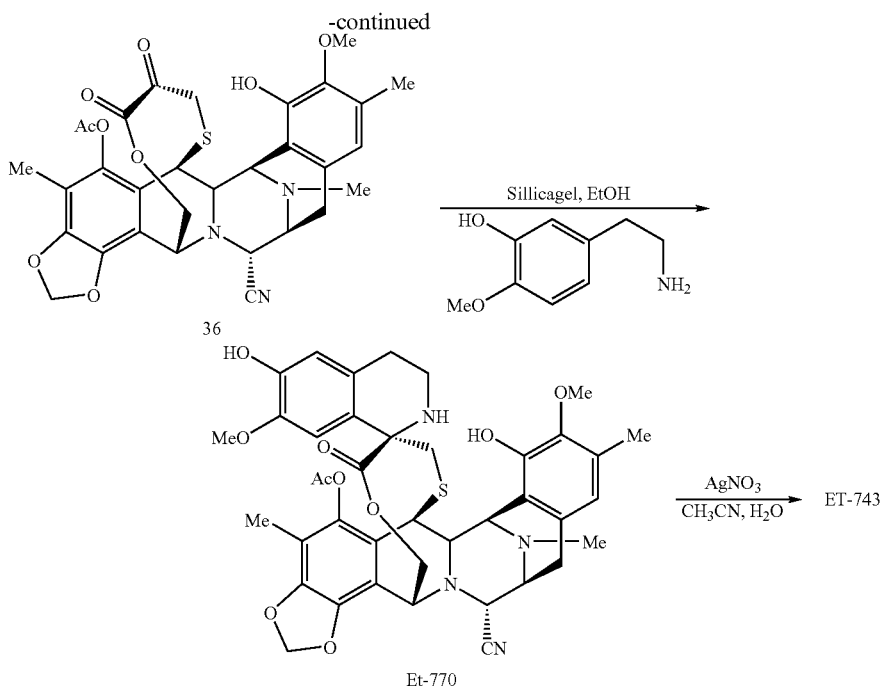

In route 1, protection of the E-ring phenol is achieved in three steps involving protection/deprotection of the amine of SF21 with Troc.

For routes 1 and 2, protection of the cysteine sidechain with Boc allows the phenol and cysteine groups to be deprotected in a single step rather than as two separate steps. For the rest of the routes, an additional deprotection step is required.

For route 2, Intermediate 25 is avoided through the use of the direct esterification methodology and the subsequent protection of the phenol with the MEM group.

In routes 2 and 3 protection of the E-ring phenol is delayed until after the diazotisation and esterification steps thereby allowing the phenol to be protected in a single step rather than by the three step sequence of route 1.

For routes 1, 2 and 3, direct esterification of the primary alcohol with the cysteine derivative eliminates the unproductive protection/deprotection steps of the primary alcohol with a silyl group (routes 4 and 5) thereby shortening the sequence by two steps.

Route 6 only contemplates herein the last steps from intermediate 161, which can be easily obtained from intermediate 21.

In routes 4 and 5 the primary alcohol produced by the initial diazotisation step is protected with silicon to allow selective protection of the E-ring phenol and avoiding intermediate 25. Following modification of the A-ring (deprotection/oxidation), the silicon group is removed and the primary alcohol esterified with the cysteine derivative.

These changes are a direct consequence of the problems that were found in the scale up of the route given in WO 0069862. As a result of these changes the overall route 2 is three steps shorter and potentially therefore more suitable and/or cheaper for routine manufacture.

Process Overview

Thus, in view of the routes 1 to 6, the present invention extends to a process for preparing an ecteinascidin product with a spiroamine-1,4-bridge, the process involving forming a 1,4 bridge using a 1-labile, 10-hydroxy, 18-protected hydroxy, di-6,8-en-5-one fused ring compound, wherein C-18 protection is removed before spiroamine introduction.

In one version of the process, the ecteinascidin product has a 21-hydroxy group, and the process includes converting a 21-cyano group to the 21-hydroxy group.

Typically the spiroamine is a spiroquinoline, especially the spiroquinoline of ecteinascidin 743.

In a preferred process the 18-protected group of the 1-labile, 10-hydroxy, 18-protected hydroxy, di-6,8-en-5-one fused ring compound is protected with: MOM, methoxymethyl; or MEM, methoxyethoxymethyl group.

Suitably the 1-labile group is an N-protected cysteinyloxymethylene group of the formula —$CH_2$—O—CO—CNHProt$^1$—$CH_2$—S—H.

In this formula Prot$^1$ is typically: Boc, t-butyloxycarbonyl; Troc, 2,2,2-trichloroethyloxycarbonyl; Cbz, benzyloxycarbonyl; or Alloc, allyloxycarbonyl.

With some embodiments of the process, Prot$^1$ is removed in the same step as C-18 protection.

The 1-labile group can be generated from a 1-substituent of the formula:

—$CH_2$—O—CO—CNHProt$^1$—$CH_2$—S-Prot$^2$.

In this formula, Prot$^2$ is typically Fm, 9-fluorenylmethyl.

A 1-substituent of the formula:

—$CH_2$—O—CO—CNHProt$^1$—$CH_2$—S-Prot$^2$ can be formed by esterification of a —$CH_2$—O—H substituent.

The esterification can be carried out before or after formation of the 10-hydroxy, di-6,8-en-5-one structure.

In one version, the claimed process starts from a 1-aminomethylene, 5-protected hydroxy, 7,8-dioxymethylene, 18-hydroxy, 21-cyano fused ring compound The 1-aminomethylene group can be temporarily protected to allow protection at the 18-hydroxy group, and the temporary protection removed.

Alternatively, the C-18 hydroxy group can be protected after formation of a 1-ester function.

In another variation, the 1-aminomethylene group is converted to a 1-hydroxymethylene group and the 1-hydroxymethylne group is temporarily protected, to allow protection at the 18-hydroxy group, and the temporary protection is removed.

The fused ring structure is suitably of the formula:

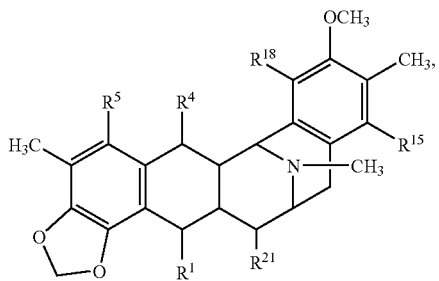

especially where $R^{15}$ is H. One or more or all of the remaining subsitituents can be as in ecteinascidin 743.

Hemisythesis

The invention permits the use of a known compound, safracin B, also referred to as quinonamine, in hemisynthetic synthesis.

More generally, the invention relates to a hemisynthetic process for the formation of intermediates, derivatives and related structures of ecteinascidin or other tetrahydroisoquinolinephenol compounds starting from natural bis(tetrahydroisoquinoline) alkaloids. Suitable starting materials for the hemi-synthetic process include the classes of saframycin and safracin antibiotics available from different culture broths, and also the classes of reineramicin and xestomycin compounds available from marine sponges.

A general formula (XV) for the starting compounds is as follows:

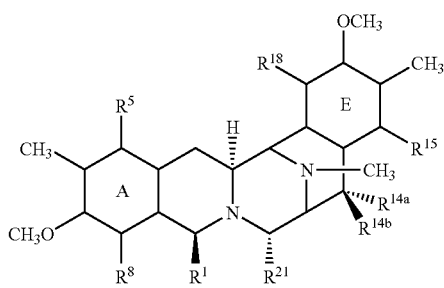

where:
$R^1$ is an amidomethylene group such as —CH²—NH—CO—CR$^{25a}$R$^{25b}$R$^{25c}$ where R$^{25a}$ and R$^{25b}$ form a keto group or one is —OH, —NH$_2$ or —OCOCH$_3$ and the other is —CH$_2$COCH$_3$, —H, —OH or —OCOCH$_3$, provided that when R$^{25a}$ is —OH or —NH$_2$ then R$^{25b}$ is not —OH, and R$^{25c}$ is —H, —CH$_3$ or —CH$_2$CH$_3$, or R$^1$ is an acyloxymethylene group such as —CH$_2$—O—CO—R, where R is —C(CH$_3$)=CH—CH$_3$ or —CH$_3$;

$R^5$ and $R^8$ are independently chosen from —H, —OH or —OCOCH$_2$OH, or $R^5$ and $R^8$ are both keto and the ring A is a p-benzoquinone ring; $R^{14a}$ and $R^{14b}$ are both —H or one is —H and the other is —OH, —OCH$_3$ or —OCH$_2$CH$_3$, or $R^{14a}$ and $R^{14b}$ together form a keto group;

$R^{15}$ and $R^{18}$ are independently chosen from —H or —OH, or $R^5$ and $R^8$ are both keto and the ring A is a p-benzoquinone ring; and $R^{21}$ is —OH or —CN.

A more general formula for these class of compounds is provided below:

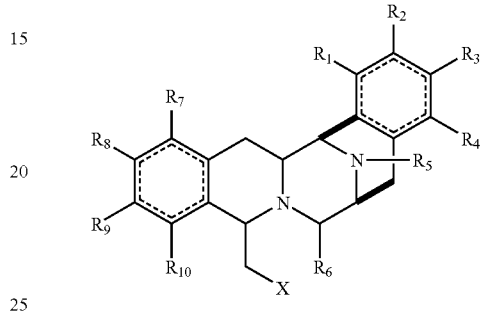

wherein the substituent groups defined by $R_1$, $R_2$, $R_3$, $R_4$, $R_5$, $R_6$, $R_7$, $R_8$, $R_9$, $R_{10}$ are each independently selected from the group consisting of H, OH, OCH$_3$, CN, =O, CH$_3$;

wherein X are the different amide or ester functionalities contained in the mentioned natural products;

wherein each dotted circle represents one, two or three optional double bonds.

Thus, according to the present invention, we now provide hemisynthetic routes for the production of intermediates including Intermediates 11 or 21 and thus for the production of the ecteinascidin compounds as well as phthalascidin and additional compounds. The hemisynthetic routes of the invention each comprise a number of transformation steps to arrive at the desired product. Each step in itself is a process in accordance with this invention. The invention is not limited to the routes that are exemplified, and alternative routes may be provided by, for example, changing the order of the transformation steps, as appropriate or by a change to the protecting groups used.

In particular, this invention involves the provision of a 21-cyano starting material of general formula (XVI):

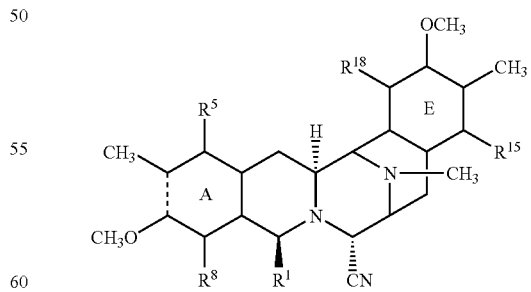

where $R^1$, $R^5$, $R^8$, $R^{14a}$, $R^{14b}$, $R^{15}$ and $R^{18}$ are as defined.

Other compounds of formula (XVI) with different substituents at the 21-position may also represent possible starting materials. In general, any derivative capable of production by nucleophilic displacement of the 21-hydroxy group of compounds of formula (XV) wherein $R^{21}$ is a hydroxy group cis a candidate. Examples of suitable 21-substituents include but are not limited to:

a mercapto group;

an alkylthio group (the alkyl group having from 1 to 6 carbon atoms);

an arylthio group (the aryl group having from 6 to 10 carbon atoms and being unsubstituted or substituted by from 1 to 5 substituents selected from, for example, alkyl group having from 1 to 6 carbon atoms, alkoxy groups having from 1 to 6 carbon atoms, halogen atoms, mercapto groups and nitro groups);

an amino group;

a mono-or dialkylamino (the or each alkyl group having from 1 to 6 carbon atoms);

a mono-or diarylamino group (the or each aryl group being as defined above in relation to arylthio groups);

an α-carbonylalkyl group of formula —$C(R^a)(R^b)$—$C(=O)$ $R^c$, where $R^a$ and $R^b$ are selected from hydrogen atoms, alkyl groups having from 1 to 20 carbon atoms, aryl groups (as defined above in relation to arylthio groups) and aralkyl groups (in which an alkyl group having from 1 to 4 carbon atoms is substituted by an aryl group a defined above in relation to arylthio groups), with the proviso that one of $R^a$ and $R^b$ is a hydrogen atom;

$R^c$ is selected from a hydrogen atom, an alkyl group having from 1 to 20 carbon atoms, aryl groups (as defined above in relation to arylthio groups), an aralkyl group (in which an allyl group having from 1 to 4 carbon atoms is substituted by an aryl group a defined above in relation to arylthio groups), an alkoxy group having from 1 to 6 carbon atoms, an amino group or a mono- or dialkylamino group as defined above.

Thus, in a more general aspect, the present invention relates to processes where the first step is to form a 21-deriviative using a nucleophilic reagent. We refer to such compounds as 21-Nuc compounds.

The presence of the 21-cyano group is required for some of the end-products, notably ecteinascidin 770 and phthalascidin, while for other end-products it acts as a protecting group which can readily be converted to another substituent, such as the 21-hydroxy group of ecteinascidin 743 or of 21-hydroxyphthalascidin. The adoption of the 21-cyano compound as the starting material effectively stabilises the molecule during the ensuing synthetic steps, until it is optionally removed. Other 21-Nuc compounds can offer this and other advantages.

In one important aspect, the present invention consists in the use of a 21-cyano compound of the general formula (XVI) in the preparation of a bis- or tris-(tetrahydroisoquinolinephenol) compounds. Products which may be prepared include intermediates such as Intermediate 11 or 21, and the ecteinascidins, as well as new and known compounds of related structure.

Preferred starting materials include those compounds of formula (XV) or (XVI) where $R^{14a}$ and $R^{14b}$ are both hydrogen. Preferred starting materials also include compounds of formula (XV) or (XVI) where $R^{15}$ is hydrogen. Furthermore, the preferred starting materials include compounds of formula (XV) or (XVI) where ring E is a phenolic ring. Preferred starting materials further include compounds of formula (XV) or (XVI) where at least one, better at least two or three of $R^5$, $R^8$, $R^{15}$ and $R^{18}$ is not hydrogen.

Examples of suitable starting materials for this invention include saframycin A, saframycin B, saframycin C, saframycin G, saframycin H, saframycin S, saframycin $Y_3$, saframycin $Yd_1$, saframycin $Ad_1$, saframycin $Yd_2$, saframycin $AH_2$, saframycin $AH_2Ac$, saframycin $AH_1$, saframycin $AH_1Ac$, saframycin $AR_3$, renieramycin A, renieramycin B, renieramycin C, renieramycin D, renieramycin E, renieramycin F, xestomycin, saframycin D, saframycin F, saframycin Mx-1, saframycin Mx-2, safracin A, safracin B and saframycin R. Preferred starting materials have a cyano group in position 21, for the group $R^{21}$.

In a particularly preferred aspect, the invention involves a hemisynthetic process wherein the transformation steps are applied to safracin B:

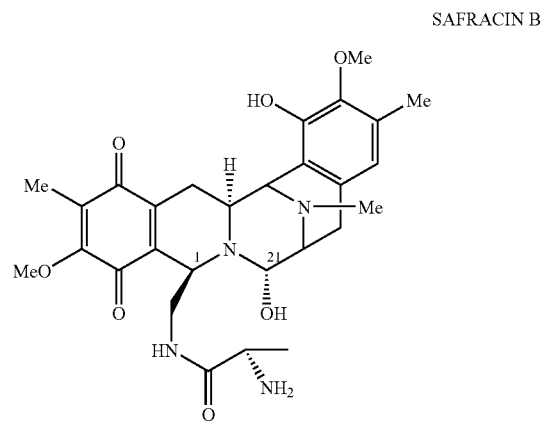

SAFRACIN B

Safracin B presents a ring system closely related to the ecteinascidins. This compound has the same pentacycle structure and the same substitution pattern in the right-hand aromatic ring, ring E. Also, safracin B presents very close similarities to some of the synthetic intermediates in the total synthesis of ET-743, particularly to the intermediates 11 or 21. Such intermediate can be transformed into Et-743 using a well established method. Synthetic conversion of safracin B into intermediates 11 or 21 will therefore provide an hemisynthetic method to obtain ET-743.

Thus, we provide Intermediates 11 or 21 made from this compound safracin B, and compounds derived from Intermediate 11 or 21, particularly ecteinascidin compounds. We further provide phthalascidin made from safracin B. The invention also relates to use of safracin B in the production of Intermediates 11 or 21, ecteinascidin compounds and the other intermediates of the invention. The invention also relates to compounds described herein derived from the other suggested starting materials, and use of those compounds in the production of such compounds.

The more preferred starting materials of this invention have a 21-cyano group. The currently most preferred compound of the present invention is the compound of Formula 2. This compound is obtained directly from safracin B and is considered a key intermediate in the hemisynthetic process.

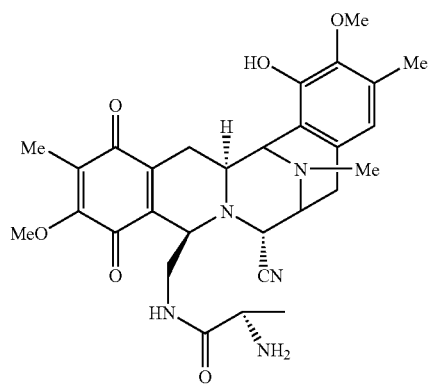

compound 2

In a related aspect, we provide cyanosafracin B by fermentation of a safracin B-producing strain of *Pseudomonas fluorescens*, and working up the cultured broth using cyanide ion. The preferred strain of *Pseudomonas fluorescens* is strain A2-2, FERM BP-14, which is employed in the procedure of EP 055,299. A suitable source of cyanide ion is potassium cyanide. In a typical work-up, the broth is filtered and excess cyanide ion is added. After an appropriate interval of agitation, such as 1 hour, the pH is rendered alkaline, say pH 9.5, and an organic extraction gives a crude extract which can be further purified to give the cyanosafracin B.

For the avoidance of doubt, the stereochemistries indicated in this patent specification are based on our understanding of the correct stereochemistry of the natural products. To the extent that an error is discovered in the assigned stereochemistry, then the appropriate correction needs to be made in the formulae given throughout in this patent specification. Furthermore, to the extent that the syntheses are capable of modification, this invention extends to stereoisomers.

The products of this invention are typically of the formula (XVIIb):

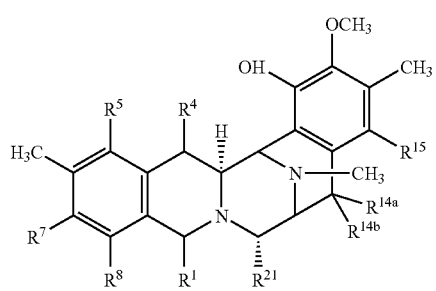

where
$R^1$ and $R^4$ together form a group of formula (IV), (V) (VI) or (VII):

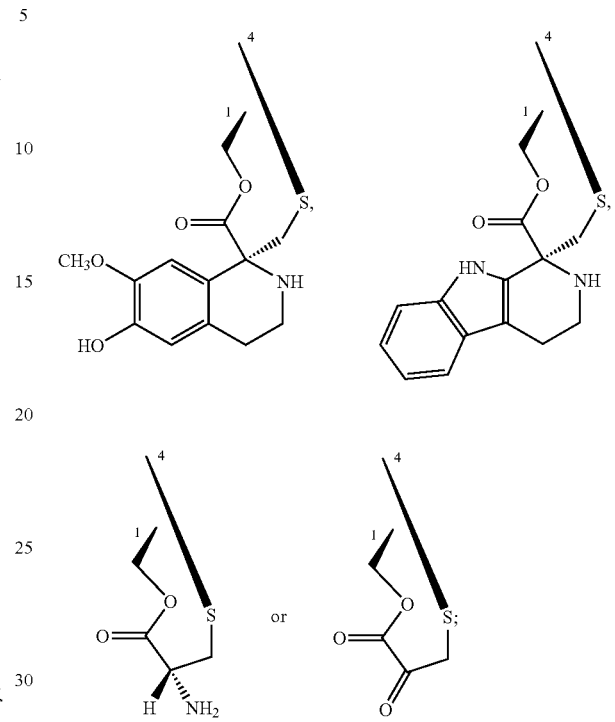

$R^5$ is —H or —OH;
$R^7$ and $R^8$ together form a group —O—$CH_2$—O—;
$R^{14a}$ and $R^{14b}$ are both —H or one is —H and the other is —OH, —$OCH_3$ or —$OCH_2CH_3$, or $R^{14a}$ and $R^{14b}$ together form a keto group; and
$R^{15}$ is —H or —OH;
$R^{21}$ is —H, —OH or —CN;

and derivatives including acyl derivatives thereof especially where $R^5$ is acetyloxy or other acyloxy group of up to 4 carbon atoms.

In the formula (XVIIb), $R^1$ typically with $R^4$ forms a group (IV) or (V). The group $R^{18}$ is usually protected. Usually $R^{21}$ is cyano.

Preferably $R^{14a}$ and $R^{14b}$ are hydrogen. Preferably $R^{15}$ is hydrogen. The O-acyl derivatives are suitably aliphatic O-acyl derivatives, especially acyl derivatives of 1 to 4 carbon atoms, and typically an O-acetyl group, notably at the 5-position.

Suitable protecting groups for phenols and hydroxy groups include ethers and esters, such as alkyl, alkoxyalkyl, aryloxyalkyl, alkoxyalkoxyalkyl, alkylsilylalkoxyalkyl, alkylthioalkyl, arylthioalkyl, azidoalkyl, cyanoalkyl, chloroalkyl, heterocyclic, arylacyl, haloarylacyl, cycloalkylalkyl, alkenyl, cycloalkyl, alyklarylalkyl, alkoxyarylalkyl, nitroarylalkyl, haloarylalkyl, alkylaminocarbonylarylalkyl, alkylsulfinylarylalky, alkylsilyl and other ethers, and arylacyl, aryl alkyl carbonate, aliphatic carbonate, alkylsulfinylarlyalkyl carbonate, alkyl carbonate, aryl haloalkyl carbonate, aryl alkenyl carbonate, aryl carbamate, alkyl phosphinyl, alkylphosphinothioyl, aryl phosphinothioyl, aryl alkyl sulphonate and other esters. Such groups may optionally be substituted with the previously mentioned groups in $R^1$.

Suitable protecting groups for amines include carbamates, amides, and other protecting groups, such as alkyl, arylalkyl, sulpho- or halo-arylalkyl, haloalkyl, alkylsilylalkyl, arylalkyl, cycloalkylalkyl, alkylarylalkyl, heterocyclylalkyl, nitroarylalkyl, acylaminoalkyl, nitroaryldithioarylalkyl, dicycloalkylcarboxamidoalkyl, cycloalkyl, alkenyl, arylalkenyl, nitroarylalkenyl, heterocyclylalkenyl, heterocyclyl, hydroxyheterocyclyl, alkyldithio, alkoxy- or halo- or alkylsulphinyl arylalkyl, hetercyclylacyl, and other carbamates, and alkanoyl, haloalkanoyl, arylalkanoyl, alkenoyl, heterocyclylacyl, aroyl, arylaroyl, haloaroyl, nitroaroyl, and other amides, as well as alkyl, alkenyl, alkylsilylalkoxyalkyl, alkoxyalkyl, cyanoalkyl, heterocyclyl, alkoxyarylalkyl, cycloalkyl, nitroaryl, arylalkyl, alkoxy- or hydroxy-arylalkyl, and many other groups. Such groups may optionally be substituted with the previously mentioned groups in $R^1$.

Examples of such protecting groups are given in the following tables.

| | abbreviation |
|---|---|
| protection for —OH group | |
| ethers | |
| methyl | |
| methoxymethyl | MOM |
| benzyloxymethyl | BOM |
| methoxyethoxymethyl | MEM |
| 2-(trimethylsilyl)ethoxymethyl | SEM |
| methylthiomethyl | MTM |
| phenylthiomethyl | PTM |
| azidomethyl | |
| cyanomethyl | |
| 2,2-dichloro-1,1-difluoroethyl | |
| 2-chloroethyl | |
| 2-bromoethyl | |
| tetrahydropyranyl | THP |
| 1-ethoxyethyl | EE |
| phenacyl | |
| 4-bromophenacyl | |
| cyclopropylmethyl | |
| allyl | |
| propargyl | |
| isopropyl | |
| cyclohexyl | |
| t-butyl | |
| benzyl | |
| 2,6-dimethylbenzyl | |
| 4-methoxybenzyl | MPM or PMB |
| o-nitrobenzyl | |
| 2,6-dichlorobenzyl | |
| 3,4-dichlorobenzyl | |
| 4-(dimethylamino)carbonylbenzyl | |
| 4-methylsufinylbenzyl | Msib |
| 9-anthrylmethyl | |
| 4-picolyl | |
| heptafluoro-p-tolyl | |
| tetrafluoro-4-pyridyl | |
| trimethylsilyl | TMS |
| t-butyldimethylsilyl | TBDMS |
| t-butyldiphenylsilyl | TBDPS |
| triisopropylsilyl | TIPS |
| esters | |
| aryl formate | |
| aryl acetate | |
| aryl levulinate | |
| aryl pivaloate | ArOPv |
| aryl benzoate | |
| aryl 9-fluorocarboxylate | |
| aryl methyl carbonate | |
| 1-adamantyl carbonate | |
| t-butyl carbonate | BOC-OAr |
| 4-methylsulfinylbenzyl carbonate | Msz-Oar |

-continued

| | abbreviation |
|---|---|
| 2,4-dimethylpent-3-yl carbonate | Doc-Oar |
| aryl 2,2,2-trichloroethyl carbonate | |
| aryl vinyl carbonate | |
| aryl benzyl carbonate | |
| aryl carbamate | |
| dimethylphosphinyl | Dmp-OAr |
| dimethylphosphinothioyl | Mpt-OAr |
| diphenylphosphinothioyl | Dpt-Oar |
| aryl methanesulfonate | |
| aryl toluenesulfonate | |
| aryl 2-formylbenzenesulfonate | |
| protection for the —NH$_2$ group | |
| carbamates | |
| methyl | |
| ethyl | |
| 9-fluorenylmethyl | Fmoc |
| 9-(2-sulfo)fluroenylmethyl | |
| 9-(2,7-dibromo)fluorenylmethyl | |
| 17-tetrabenzo[a,c,g,i]fluorenylmethyl | Tbfmoc |
| 2-chloro-3-indenylmethyl | Climoc |
| benz[f]inden-3-ylmethyl | Bimoc |
| 2,7-di-t-butyl[9-(10,10-dioxo-10,10,10-tetrahydrothioxanthyl)]methyl | DBD-Tmoc |
| 2,2,2-trichloroethyl | Troc |
| 2-trimethylsilylethyl | Teoc |
| 2-phenylethyl | hZ |
| 1-(1-adamantyl)-1-methylethyl | Adpoc |
| 2-chlooethyl | |
| 1,1-dimethyl-2-chloroethyl | |
| 1,1-dimethyl-2-bromoethyl | |
| 1,1-dimethyl-2,2-dibromoethyl | DB-t-BOC |
| 1,1-dimethyl-2,2,2-trichloroethyl | TCBOC |
| 1-methyl-1-(4-biphenyl)ethyl | Bpoc |
| 1-(3,5-di-t-butylphenyl)-1-1-methylethyl | t-Burmeoc |
| 2-(2'-and 4'-pyridyl)ethyl | Pyoc |
| 2,2-bis(4'-nitrophenyl)ethyl | Bnpeoc |
| n-(2-pivaloylamino)-1,1-dimethylethyl | |
| 2-[(2-nitrophenyl)dithio]-1-phenylethyl | NpSSPeoc |
| 2-(n,n-dicyclohexylcarboxamido)ethyl | |
| t-butyl | BOC |
| 1-adamantyl | 1-Adoc |
| 2-adamantyl | 2-Adoc |
| vinyl | Voc |
| allyl | Aloc or Alloc |
| 1-isopropylallyl | Ipaoc |
| cinnamyl | Coc |
| 4-nitrocinnamyl | Noc |
| 3-(3'-pyridyl)prop-2-enyl | Paloc |
| 8-quinolyl | |
| n-hydroxypiperidinyl | |
| alkyldithio | |
| benzyl | Cbz or Z |
| p-methoxybenzyl | Moz |
| p-nitrobenzyl | PNZ |
| p-bromobenzyl | |
| p-chlorobenzyl | |
| 2,4-dichlorobenzyl | |
| 4-methylsulfinylbenzyl | Msz |
| 9-anthrylmethyl | |
| diphenylmethyl | |
| phenothiazinyl-(10)-carbonyl | |
| n'-p-toluenesulfonylaminocarbonyl | |
| n'-phenylaminothiocarbonyl | |
| amides | |
| formamide | |
| acetamide | |
| chloroacetamide | |
| trifluoroacetamide | TFA |
| phenylacetamide | |
| 3-phenylpropanamide | |
| pent-4-enamide | |
| picolinamide | |
| 3-pyridylcarboxamide | |
| benzamide | |

-continued

| | abbreviation |
|---|---|
| p-phenylbenzamide | |
| n-phthalimide | |
| n-tetrachlorophthalimide | TCP |
| 4-nitro-n-phthalimide | |
| n-dithiasuccinimide | Dts |
| n-2,3-diphenylmaleimide | |
| n-2,5-dimethylpyrrole | |
| n-2,5-bis(triisopropylsiloxyl)pyrrole | BIPSOP |
| n-1,1,4,4-tetramethyldisiliazacyclopentante adduct | STABASE |
| 1,1,3,3-tetramethyl-1,3-disilaisoindoline | BSB |
| special —NH protective groups | |
| n-methylamine | |
| n-t-butylamine | |
| n-allylamine | |
| n-[2-trimethylsilyl)ethoxy]methylamine | SEM |
| n-3-acetoxypropylamine | |
| n-cyanomethylamine | |
| n-(1-isopropyl-4-nitro-2-oxo-3-pyrrolin-3-yl)amine | |
| n-2,4-dimethoxybenzylamine | Dmb |
| 2-azanorbornenes | |
| n-2,4-dinitrophenylamine | |
| n-benzylamine | Bn |
| n-4-methoxybenzylamine | MPM |
| n-2,4-dimethoxybenzylamine | DMPM |
| n-2-hydroxybenzylamine | Hbn |
| n-(diphenylmethyl)amino | DPM |
| n-bis(4-methoxyphenyl)methylamine | |
| n-5-dibenzosuberylamine | DBS |
| n-triphenylmethylamine | Tr |
| n-[(4-methoxyphenyl)diphenylmethyl]amino | MMTr |
| n-9-phenylflurenylamine | Pf |
| n-ferrocenylmethylamine | Fcm |
| n-2-picolylamine n'-oxide | |
| n-1,1-dimethylthiomethyleneamine | |
| n-benzylideneamine | |
| n-p-methoxybenzylideneamine | |
| n-diphenylmethyleneamine | |
| n-(5,5-dimethyl-3-oxo-1-cyclohexenyl)amine | |
| n-nitroamine | |
| n-nitrosoamine | |
| diphenylphosphinamide | Dpp |
| dimethylthiophosphinamide | Mpt |
| diphenylthiophosphinamide | Ppt |
| dibenzyl phosphoramidate | |
| 2-nitrobenzenesulfenamide | Nps |
| n-1-(2,2,2-trifluoro-1,1-diphenyl)ethylsufenamide | TDE |
| 3-nitro-2-pyridinesulfenamide | Npys |
| p-toluenesulfonamide | Ts |
| benzenesulfonamide | |

Particular ecteinascidin products of this invention include compounds of the formula (XVIII):

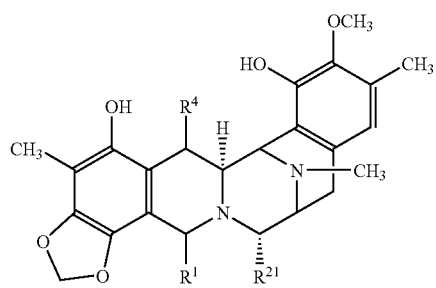

where $R^1$ and $R^4$ form a group of formula (IV), (V), (VI) or (VII):

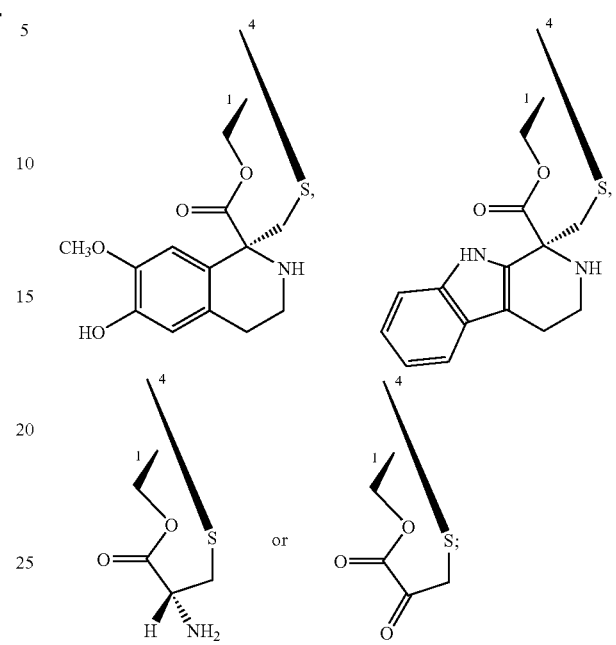

more particularly a group (I or (V);
$R^{21}$ is —H, —OH or —CN, more particularly —OH or —CN;

and acyl derivatives thereof, more particularly 5-acyl derivatives including the 5-acetyl derivative.

In general, the conversion of the 21-cyano starting compound to an ecteinascidin product of, for example, formula (XVIII) involves:

a) conversion if necessary of a quinone system for the ring E into the phenol system
b) conversion if necessary of a quinone system for the ring A into the phenol system;
c) conversion of the phenol system for the ring A into the methylenedioxyphenol ring;
d) formation of the bridged spiro ring system of formula (IV), (VI) or (VII) across the 1-position and 4-position in ring B; and
e) derivatisation as appropriate, such as acylation.

Step (a), conversion if necessary of a quinone system for the ring E into the phenol system, can be effected by conventional reduction procedures. A suitable reagent system is hydrogen with a palladium-carbon catalyst, though other reducing systems can be employed.

Step (b), conversion if necessary of a quinone system for the ring A into the phenol system is analogous to step (a), and more detail is not needed.

Step (c), conversion of the phenol system for the ring A into the methylenedioxyphenol ring, can be effected in several ways, possibly along with step (b). For example, a quinone ring A can be demethylated in the methoxy substituent at the 7-position and reduced to a dihydroquinone and trapped with a suitable electrophilic reagent such as $CH_2Br_2$, $BrCH_2Cl$, or a similar divalent reagent directly yielding the methylenedioxy ring system, or with a divalent reagent such as thiocarbonyldiimidazol which yields a substituted methylenedioxy ring system which can be converted to the desired ring.

Step (d) is typically effected by appropriate substitution at the 1-position with a bridging reagent that can assist formation of the desired bridge, forming an exendo quinone methide at the 4-position and allowing the methide to react with the 1-substituent to bring about the bridged structure. Preferred bridging reagents are of formula (XIX)

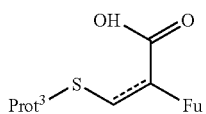

where Fu indicates a protected functional group, such as a group —NHProt$^{4a}$, Prot$^3$ is a protecting group, and the dotted line shows an optional double bond.

Suitably the methide is formed by first introducing a hydroxy group at the 10-position at the junction of rings A and B to give a partial structure of formula (XX):

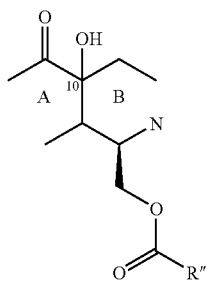

or more preferably a partial structure of formula (XXI):

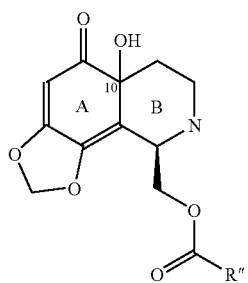

where the group R" is chosen for the desired group of formula (IV), (V), (VI) or, (VII). For the first two such groups, the group R" typically takes the form —CHFu-CH$_2$—SProt$^3$. The protecting groups can then be removed and modified as appropriate to give the desired compound.

A typical procedure for step (d) is provided in U.S. Pat. No. 5,721,362 incorporated by reference. Particular reference is made to the passage at column 8, step (l) and Example 33 of the US patent, and related passages.

Derivatisation in step (e) can include acylation, for instance with a group R$^a$—CO—, where R$^a$ can be various groups such as alkyl, alkoxy, alkylene, arylalkyl, arylalkylene, amino acid acyl, or heterocyclyl, each optionally substituted with halo, cyano, nitro, carboxyalkyl, alkoxy, aryl, aryloxy, heterocyclyl, heterocyclyloxy, alkyl, amino or substituted amino. Other acylating agents include isothiocyanates, such as aryl isothiocyanates, notably phenyl isocyanate. The alkyl, alkoxy or alkylene groups of R$^a$ suitably have 1 to 6 or 12 carbon atoms, and can be linear, branched or cyclic. Aryl groups are typically phenyl, biphenyl or naphthyl. Heterocyclyl groups can be aromatic or partially or completely unsaturated and suitably have 4 to 8 ring atoms, more preferably 5 or 6 ring atoms, with one or more heteroatoms selected from nitrogen, sulphur and oxygen.

Without being exhaustive, typical R$^a$ groups include alkyl, haloalkyl, alkoxyalkyl, haloalkoxyalkyl, arylalkylene, haloalkylarylakylene, acyl, haloacyl, arlyalkyl, alkenyl and amino acid. For example, R$^a$—CO— can be acetyl, trifluoroacetyl, 2,2,2-trichloroethoxycarbonyl, isovalerylcarbonyl, trans-3-(trifluoromethyl)cinnamoylcarbonyl, heptafluorobutyrylcarbonyl, decanoylcarbonyl, trans-cinnamoylcarbonyl, butyrylcarbonyl, 3-chloropropyonylcarbonyl, cinnamoylcarbonyl, 4-methylcinnamoylcarbonyl, hydrocinnamoylcarbonyl, or transhexenoylcarbonyl, or alanyl, arginyl, aspartyl, asparagyl, cystyl, glutamyl, glutaminyl, glycyl, histidyl, hydroxyprolyl, isoleucyl, leucyl, lysyl, methionyl, phenylalanyl, prolyl, seryl, threonyl, thyronyl, tryptophyl, tyrosyl, valyl, as well as other less common amino acid acyl groups, as well as phthalimido and other cyclic amides. Other examples may be found among the listed protecting groups. Compounds wherein —CO—R$^a$ is derived from an amino acid and include an amino group can themselves form acyl derivatives. Suitable N-acyl commands include dipeptides which in turn can form N-acyl derivatives.

By way of illustration, it is now feasible to transform cyanosafracin B compound of formula 2 into ET-743 resulting in a shorter and more straightforward way to make ET-743 than methods previously described.

The retrosynthetic analysis to make ET-743 using compound 29 is depicted in scheme I.

Scheme I

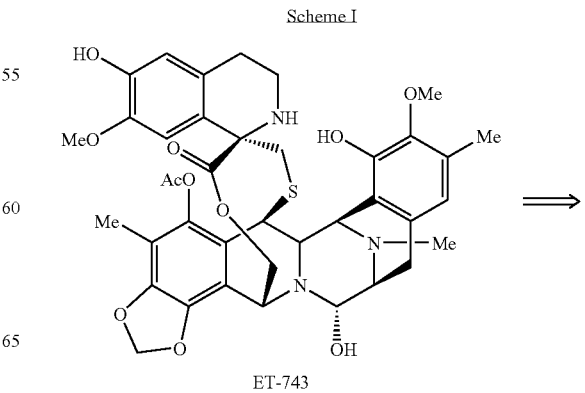

ET-743

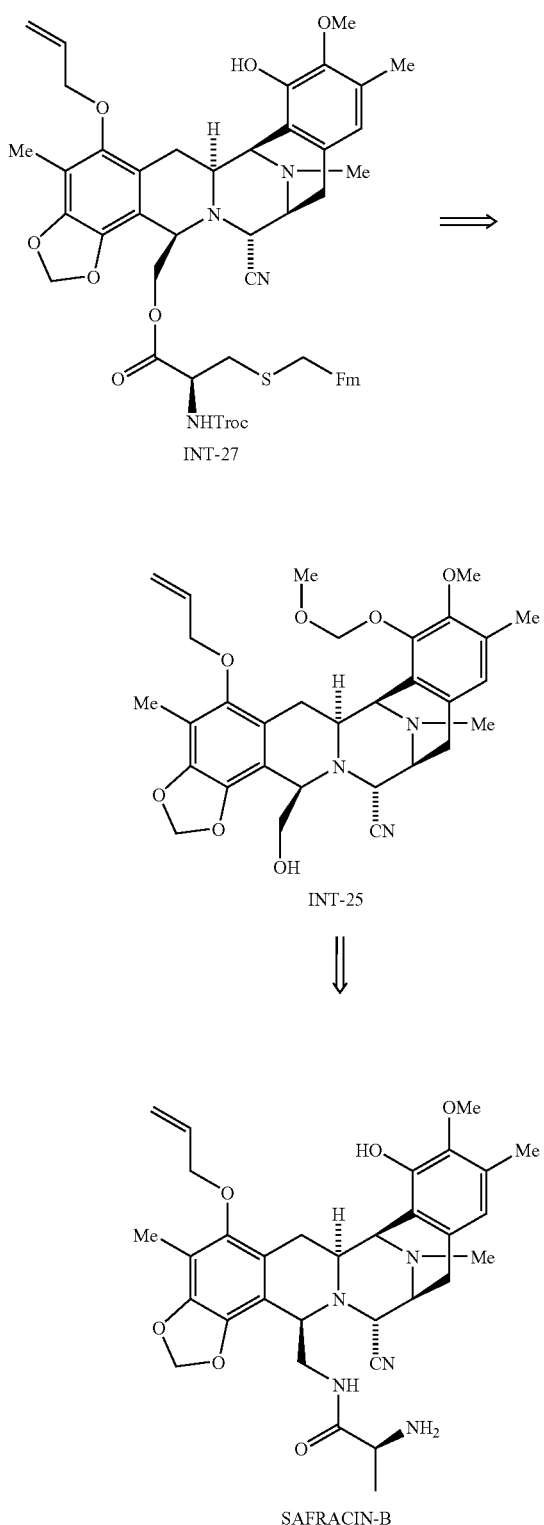

SAFRACIN-B

Following the above scheme I it is possible to obtain ET-743 in 21 linear steps. This method transforms cyanosafracin B into intermediate 25 through a sequence of reactions that involves essentially (1) removal of methoxy group placed in ring A, (2) reduction of ring A and formation of methylene-dioxy group in one pot, (3) hydrolysis of amide function placed over carbon 1, (4) transformation of the resulting amine group into hydroxyl group. Furthermore the method avoids protection and de-protection of the primary alcohol function at the position 1 in ring B of compound 25 using directly a cysteine residue 29 to form intermediate 27. Cysteine derivative 29 is protected in the amino group with β-β-β-trichloroethoxycarbonyl protecting group in order to have compatibility with the existing allyl and MOM groups. Intermediate 27 is directly oxidized and cycled. These circumstances, together with a different de-protecting strategy in the later stages of the synthesis makes the route novel and more amenable to industrial development than the process of U.S. Pat. No. 5,721,362.

The conversion of the 2-cyano compound into Intermediate 25 usually involves the following steps (see scheme II):

formation of the protected compound of Formula 14 by reacting 2 with tert-butoxycarbonyl anhydride;

converting of 14 into the di-protected compound of Formula 15 by reacting with bromomethylmethyl ether and diisopropylethylamine in acetonitrile;

selectively elimination of the methoxy group of the quinone system in 15 to obtain the compound of Formula 16 by reacting with a methanolic solution of sodium hydroxide;

transforming of 16 into the methylene-dioxy compound of Formula 18 by employing the next preferred sequence: (1) quinone group of compound 16 is reduced with 10% Pd/C under hydrogen atmosphere; (2) the hydroquinone intermediate is converted into the methylenedioxy compound of Formula 17 by reacting with bromochloromethane and caesium carbonate under hydrogen atmosphere; (3) 17 is transformed into the compound of Formula 18 by protecting the free hydroxyl group as a $OCH_2R$ group. This reaction is carried out with $BrCH_2R$ and caesium carbonate, where R can be aryl, $CH=CH_2$, OR' etc.

elimination of the tert-butoxycarbonyl and the methyloxymethyl protecting groups of 18 to afford the compound of Formula 19 by reacting with a solution of HCl in dioxane. Also this reaction is achieved by mixing 18 with a solution of trifluoroacetic acid in dichloromethane;

formation of the thiourea compound of Formula 20 by reacting 19 with phenylisothiocyanate;

converting compound of Formula 20 into the amine compound of Formula 21 by reacting with a solution of hydrogen chloride in dioxane;

transforming compound of Formula 21 into the N-Troc derivative 22 by reacting with trichloroethyl chloroformate and pyridine;

formation of the protected hydroxy compound of Formula 23 by reacting 22 with bromomethylmethyl ether and diisopropylethylamine;

transforming compound of Formula 23 into the N—H derivative 24 by reacting with acetic acid and zinc;

conversion of compound of Formula 24 into the hydroxy compound of Formula 25 by reaction with sodium nitrite in acetic acid. Alternatively, it can be used nitrogen tetroxide in a mixture of acetic acid and acetonitrile followed by treatment with sodium hydroxide. Also, it can be used sodium nitrite in a mixture of acetic anhydride-acetic acid, followed by treatment with sodium hydroxide.

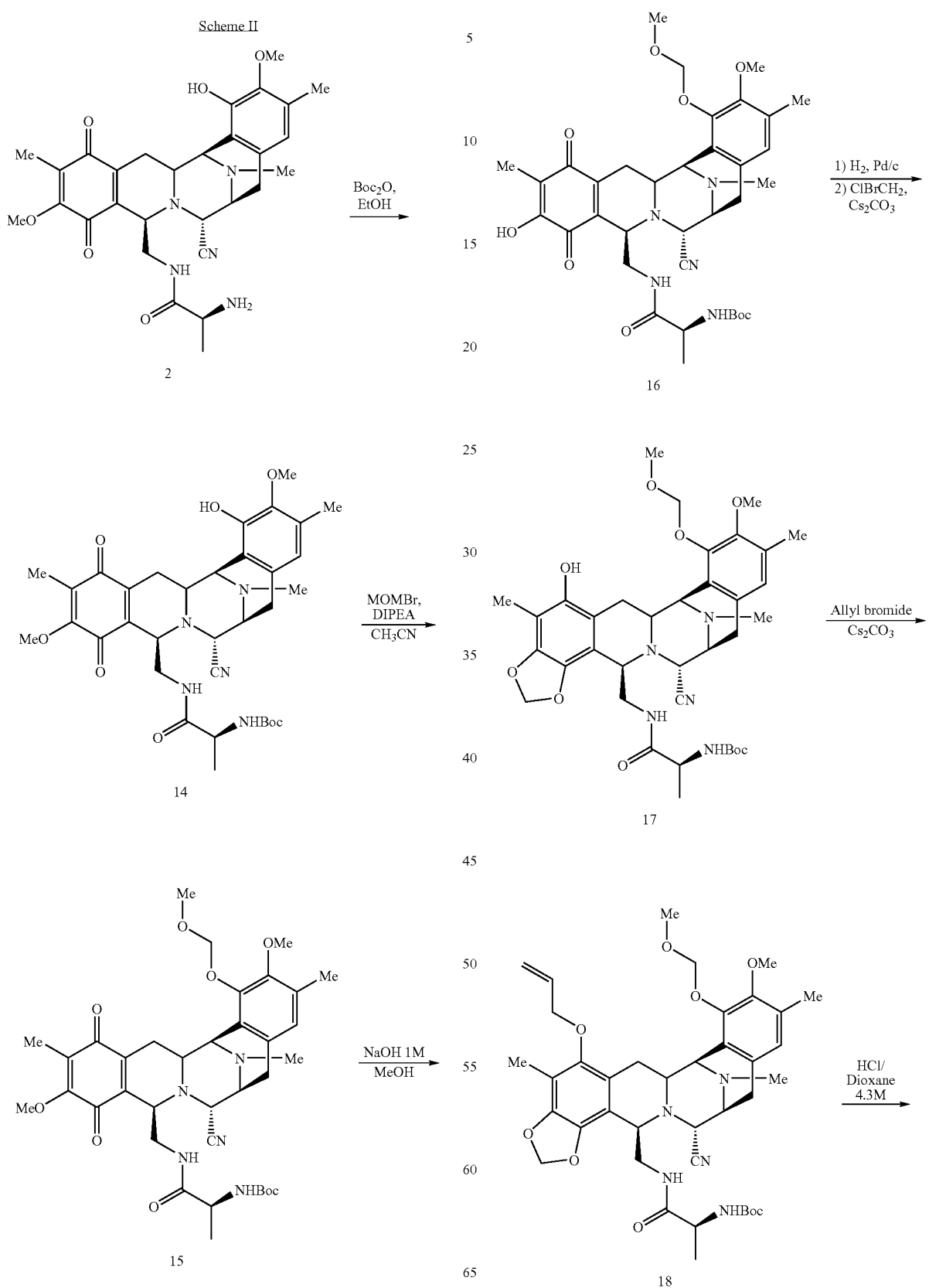

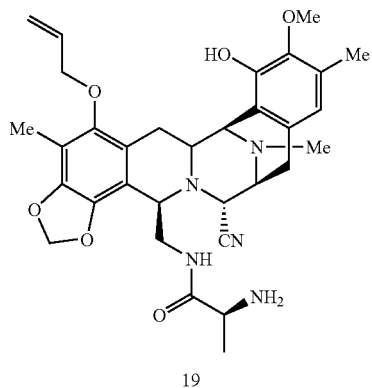
19
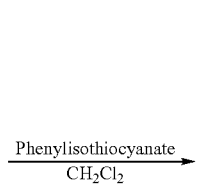
Phenylisothiocyanate
CH$_2$Cl$_2$
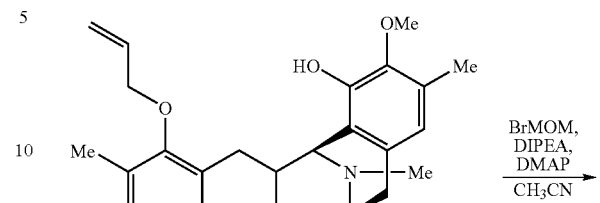
22
BrMOM,
DIPEA,
DMAP
CH$_3$CN
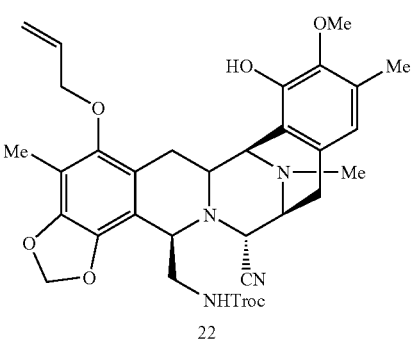
23
AcOH aq.
Zn
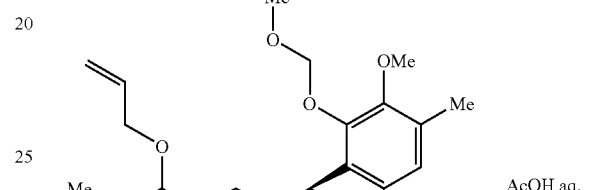
24
H$_2$O, THF,
AcOH
NaNO$_3$
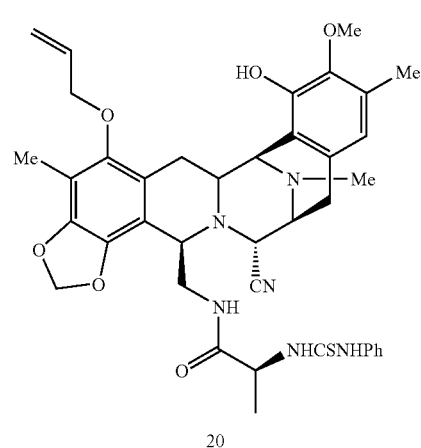
20
HCl/
Dioxane
4.3M
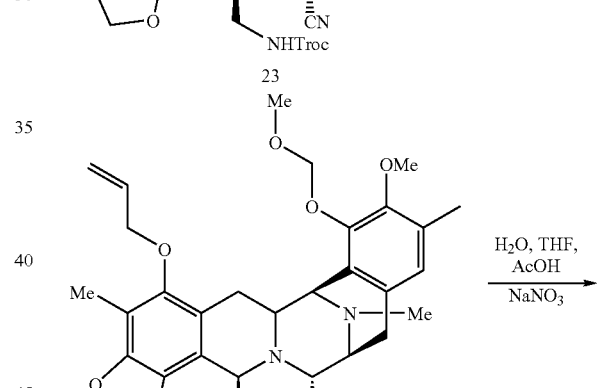
25
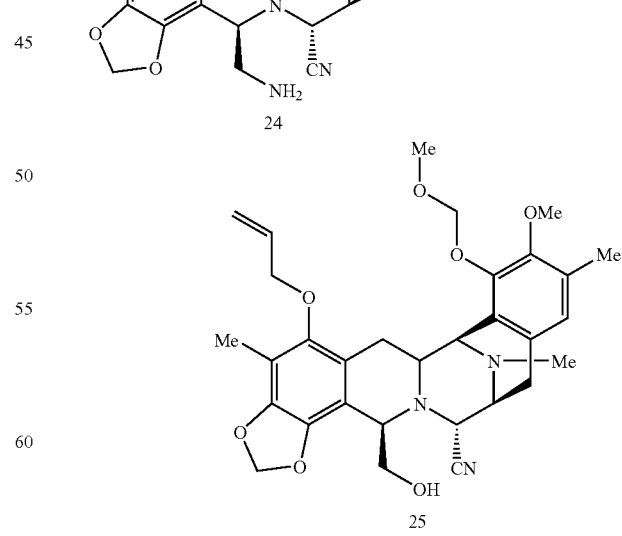
21
ClTroc,
pyr.,
CH$_2$Cl$_2$ The conversion of the Intermediate 25 compound into ET-743 using cysteine derivative 29 usually involves the following steps (see scheme III):
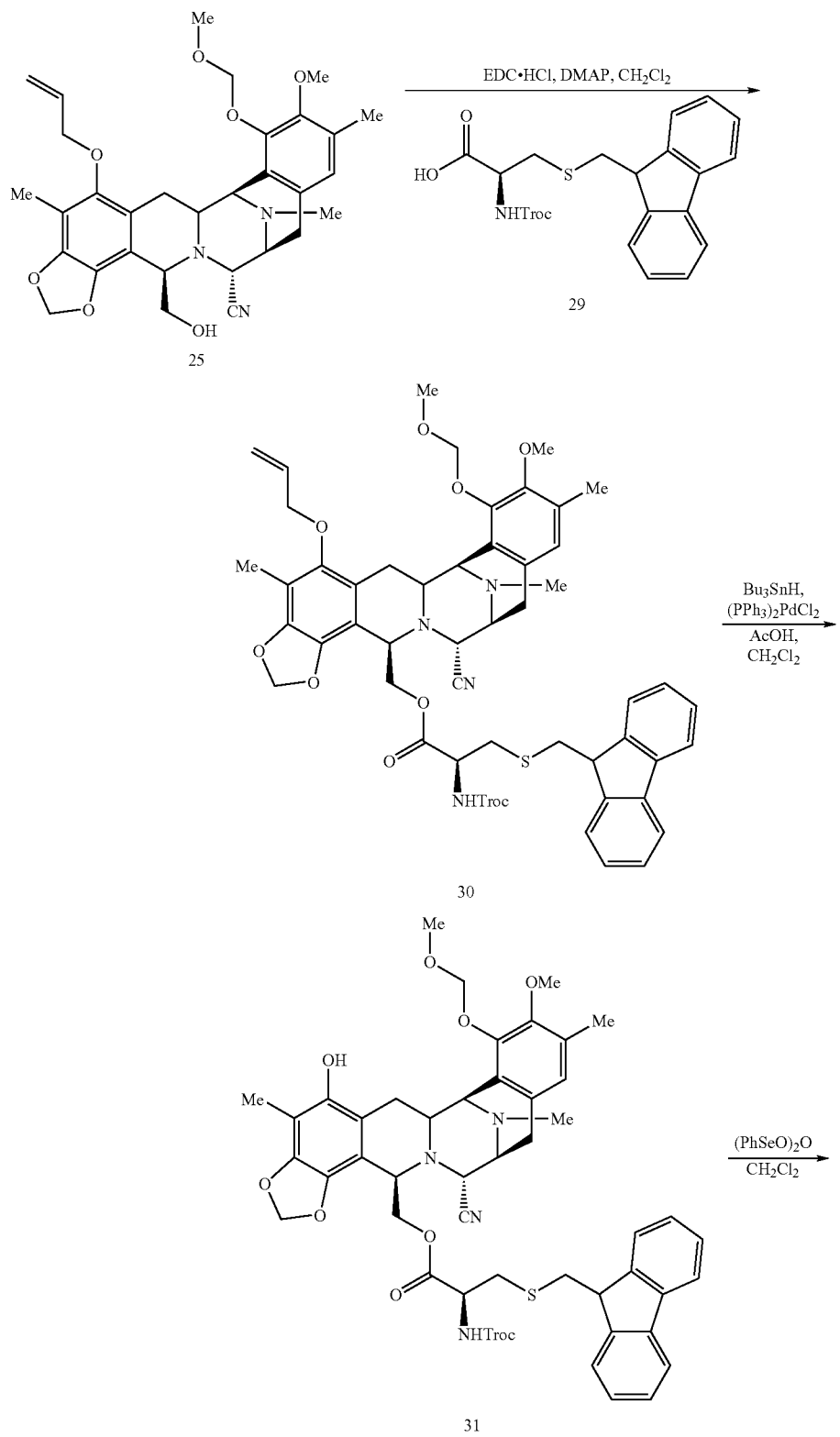

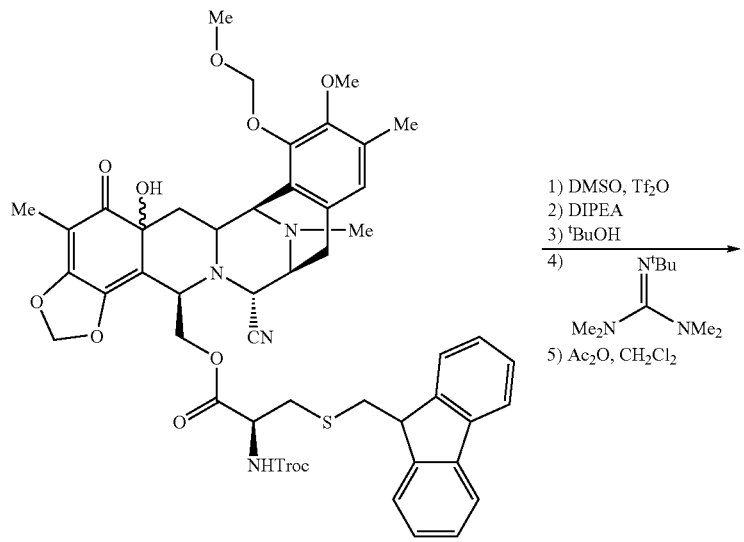
32
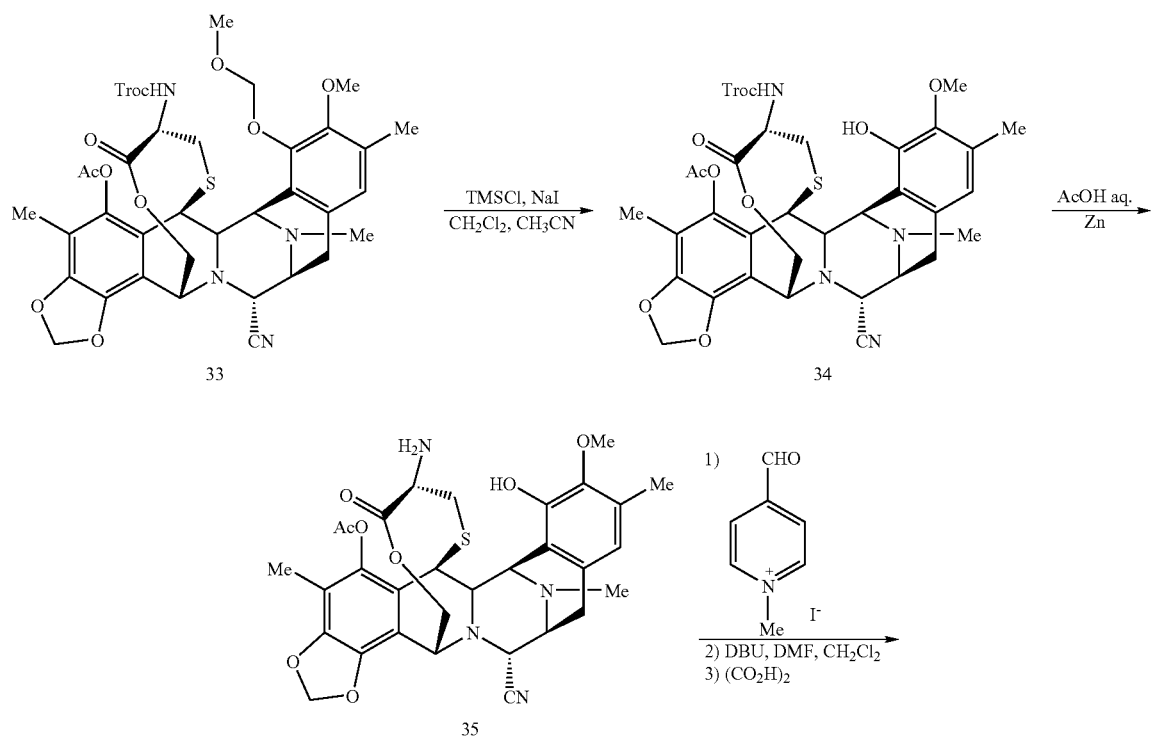
33     34
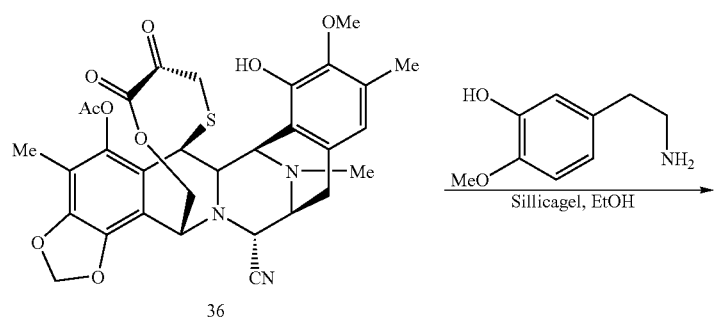
35
36

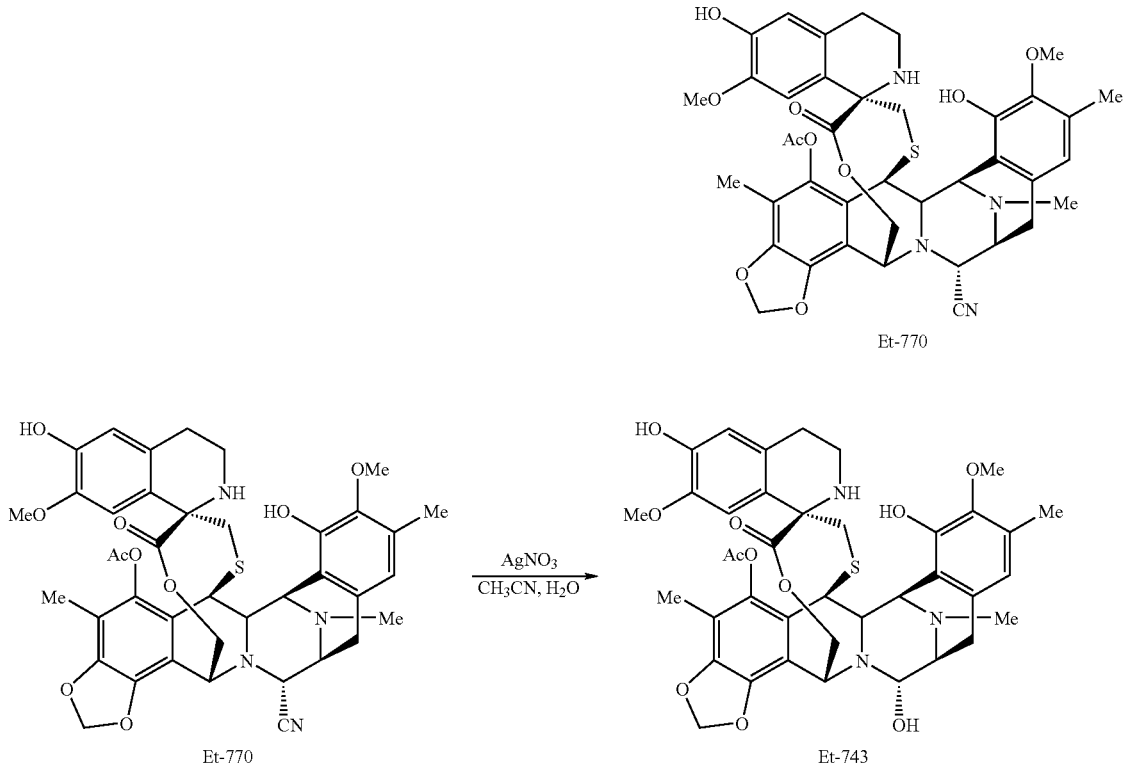

Et-770

Et-770 → (AgNO₃, CH₃CN, H₂O) → Et-743 transforming compound of formula 24 into the derivative 30 by protecting the primary hydroxyl function with (S)-N-2,2,2-tricloroethoxycarbonyl-S-(9H-fluoren-9-ylmethyl)cysteine 29;

converting the protected compound of formula 30 into the phenol derivative 31 by cleavage of the allyl group with tributyltin hydride and dichloropalladium-bis (triphenylphosphine);

transforming the phenol compound of Formula 31 into compound of formula 32 by oxidation with benzeneseleninic anhydride at low temperature;

transforming the hydroxy compound of formula 32 into the lactone 33 by the following sequence: (1) Reacting compound of formula 32 with 2 eq. of triflic anhydride and 5 eq. of DMSO. (2) followed by reaction with 8 eq. of diisopropylethylamine. (3) followed by reaction with 4 eq of t-butyl alcohol (4) followed by reaction with 7 eq of 2-tert-Butyl-1,1,3,3, tetramethylguanidine (5) followed by reaction with 10 eq of acetic anhydride;

transforming the lactone compound 33 into hydroxyl compound 34 by removal of MOM protecting group with TMSI;

cleaving the N-trichloroethoxycarbonyl group of the compound of formula 34 into compound 35 by reaction with Zn/AcOH;

transforming the amino compound 35 into the corresponding α-keto lactone compound 36 by reaction with N-methylpyridinium carboxaldehyde chloride followed by DBU;

forming ET-770 by reacting compound of Formula 36 with 3-hydroxy-4-methoxyphenylethylamine;

transforming ET-770 into ET-743 by reaction with silver nitrate in a mixture of AcN/H₂O.

Formation of Intermediate 11 and Related Intermediates

The retrosynthetic analysis is described in the following sequence.

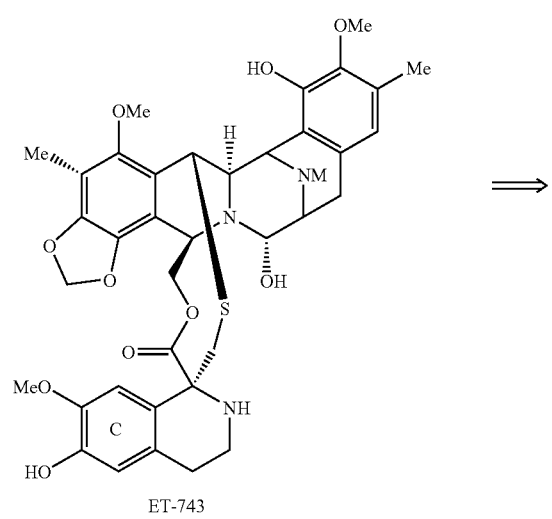

ET-743

-continued

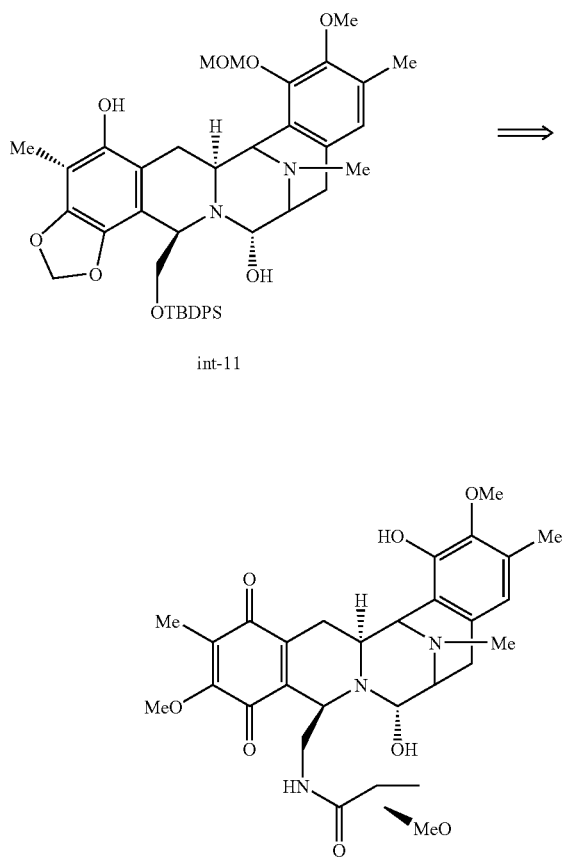

int-11

In the present invention, a key class of intermediate includes Intermediate 11 and has the general formula (XXI):

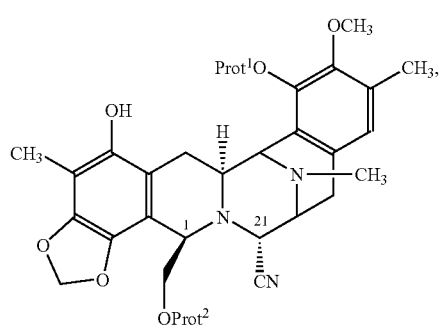

where Prot¹ and Prot² are hydroxy protecting groups, preferably different. For Intermediate 11 itself, the group Prot¹ is a methoxymethyl group, and Prot² is a t-butyldiphenylsilyl group.

The conversion of the 21-cyano compound to Intermediate 11 or a related intermediate of formula (X) usually involves the following steps:

a) conversion if necessary of a quinone system for the ring E into the phenol system
b) formation of the —OProt¹ group at the 18-position, in ring E;
c) formation of the —CH$_2$—OProt² group at the 1-position, in ring B; and
d) conversion if necessary of a quinone system for the ring A into the phenol system;
e) conversion of the phenol system for the ring A into the methylenedioxyphenol ring.

Step (b), formation of the —OProt¹ group at the 18-position in ring E, is a typical protection reaction for a phenol group, and no special comments need to be made. Appropriate conditions are chosen depending on the nature of the protecting group. The other steps are similar to the other reactions.

Step (b), formation of the —CH$_2$—OProt² group at the 1-position in ring B, is normally carried out by forming a group —CH$_2$NH$_2$ at the 1-position and then converting the amine function to a hydroxy function and protecting. Thus, where the starting material has a group R¹ which is —CH²—NH—CO—CR$^{25a}$R$^{25b}$R$^{25c}$ then it is matter of removing the N-acyl group. Where the starting material has a group R¹ which is —CH$_2$—O—CO—R then no change may be needed for an ecteinascidin product where the substituent R¹ is the same. For other products, it is matter of removing the O-acyl group. Various procedures are available for such de-acylations. In one variation, the deacylation and conversion to a hydroxy function are performed in one step. Thereafter, the hydroxy group can be acylated or otherwise converted to give the appropriate R¹ group.

U.S. Pat. No. 5,721,362 describe synthetic methods to make ET-743 through a long multistep synthesis. One of the Intermediates of this synthesis is Intermediate 11. Using cyanosafracin B as starting material it is possible to reach Intermediate 11 providing a much shorter way to make such Intermediate and therefor improving the method to make ET-743

Cyanosafracin B can be converted into Intermediate 25 by the methods described above. From Intermediate 25 is possible to reach Intermediate 11 using the following steps, see scheme VII.

formation of the protected hydroxy compound of Formula 26 by reacting 25 with tert-butyldiphenylsilyl chloride in the presence of a base;

final cleavage of the allyl group with tributyltin hydride and dichloropalladium-bis (triphenylphosphine) in 26 that leads to the formation of the intermediate 11.

Scheme VII

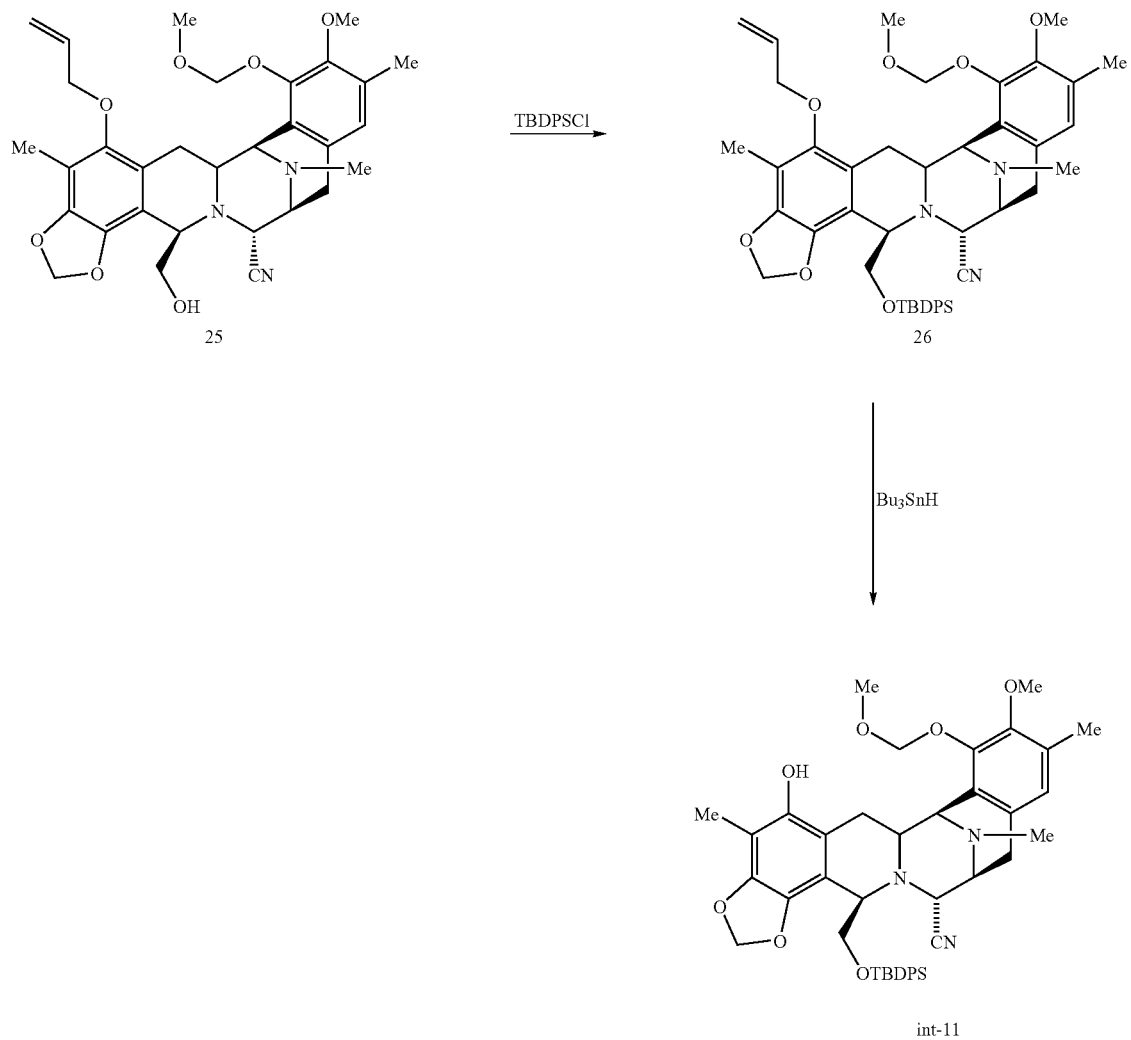

One embodiment of the synthetic process of the present invention to transform safracin B into intermediate 11 is a modification and extension of Scheme VIII and comprises the sequential steps of: stereospecifically converting the compound Safracin B to the compound of Formula 2 by selective replacement of OH by CN by reacting with KCN in acid media;

forming the thiourea compound of Formula 3 by reacting compound of Formula 2 with phenyl isothiocyanate;

converting the thiourea compound of Formula 3 into the acetamide of Formula 5 by an hydrolysis in acid media followed by addition of acetic anhydride; The intermediate amine compound of Formula 4 can be isolated by quenching the hydrolysis in acid media with sodium bicarbonate, but this intermediate is highly unstable, and is transformed quickly into a five member cyclic imine, named compound 6;

forming the protected compound of Formula 7 by reacting with bromomethylmethyl ether and diisopropylethylamine in dichloromethane;

selectively de-methylating the methoxy group of the quinone system of compound of Formula 7 into the compound of Formula 8 by reacting with methanolic solution of sodium hydroxide;

transforming the compound of Formula 8 into methylenedioxy-compound of Formula 9 by the preferred following sequence: (1) quinone group of compound 8 is reduced with 10% Pd/C under hydrogen atmosphere; (2) the hydroquinone intermediate is converted into the methylenedioxy compound of Formula 9 by reacting with bromochloromethane and cesium carbonate under hydrogen atmosphere; (3) compound of Formula 9 is transformed into compound of Formula 10 by protecting the free hydroxyl group as a $OCH_2R$ group, by reacting with $BrCH_2R$ and cesium carbonate, where R can be aryl, $CH=CH_2$, OR' etc.;

converting the acetamide group of compound of Formula 10 into the corresponding hydroxyl group of Formula 25 by reaction with nitrogen tetroxide in a mixture of acetic acid and acetic acetate followed by treatment with sodium hydroxide; alternatively can be used sodium nitrite in a mixture of acetic anhydride acetic acid, followed by treatment with sodium hydroxide; alternatively the acetamide group of compound of Formula 10 can be converted into the primary amine group by reacting with hydrazine or with Boc$_2$O, DMAP followed by hydrazine; such primary amine can be converted into the corresponding hydroxyl group (compound of Formula 25) by an oxidative conversion of the primary amine into the corresponding aldehyde with 4-formyl-1-methylpyridinium benzenesulphonate or other pyridinium ion, followed by DBU or other base treatment and further hydrolization, and followed by the reduction of the aldehyde to the corresponding hydroxyl group with lithium aluminium hydride or other reducing agent;

forming the protected compound of Formula 26 by reacting with t-butyldiphenylsilyl chloride and dimethylaminopyridine in dichloromethane (Scheme VII);

transforming the silylated compound of Formula 26 into the intermediate 11 by deprotection of the OCH$_2$R protecting group, by reacting under reductive conditions or acid conditions. Typical procedures are with palladium black under hydrogen atmosphere, or aqueous TFA, or tributyltin hydride and dichlorobis (triphenylphosphine palladium).

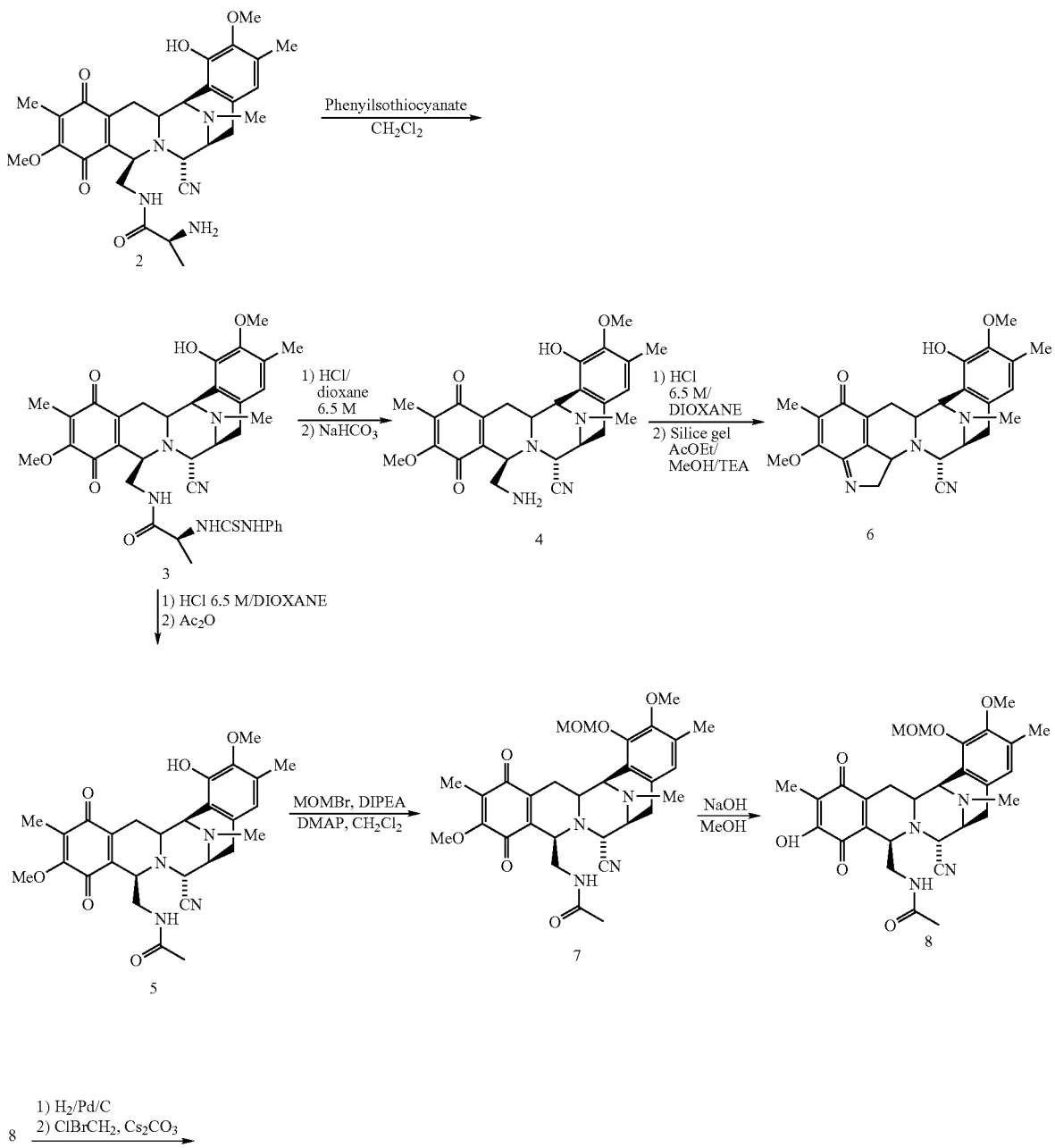

-continued
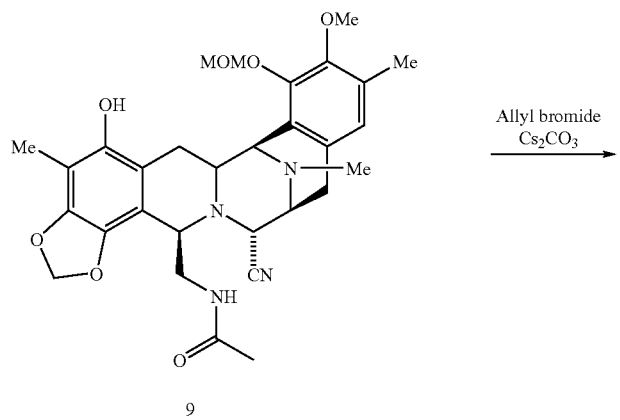
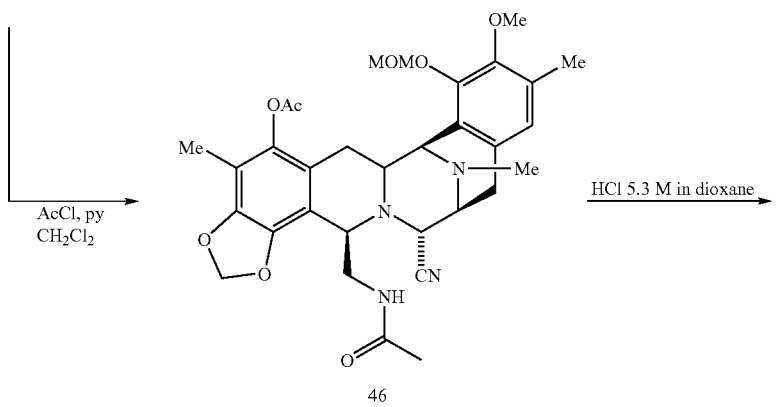
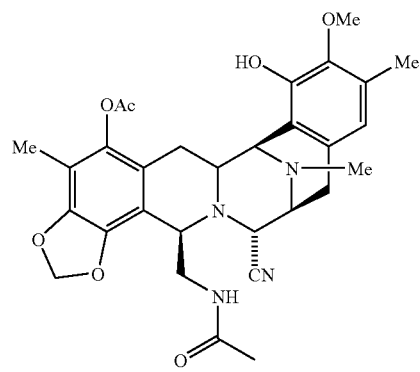

In yet another preferred modification, the cyano compound of Formula 2 can be transformed into Intermediate 11 using an extension of the scheme II, involving the further steps of:

formation of the protected hydroxy compound of Formula 26 by reacting 25 with tert-butyldiphenylsilyl chloride in the presence of a base;

final cleavage of the allyl group with tributyltin hydride and dichloropalladium-bis (triphenylphosphine) in 26 that leads to the formation of the intermediate 11.

Thus, by these and other routes, it is possible to transform cyanosafracin B into a number of intermediates and derivatives with potential antitumor therapeutic activity. These intermediates can be made starting from already described compounds, or using alternative routes.

Novel Intermediate Compounds

In the light of the preceding explanations, it can be seen that the present invention provides novel intermediate compounds. Depending on ring A, the intermediates are of formula (XXIIa):

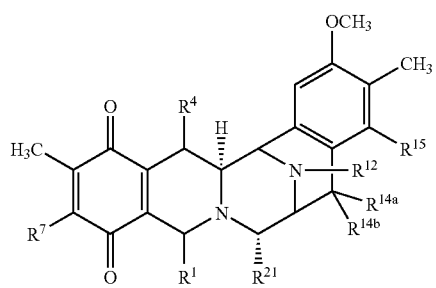

or of formula (XXIIb):

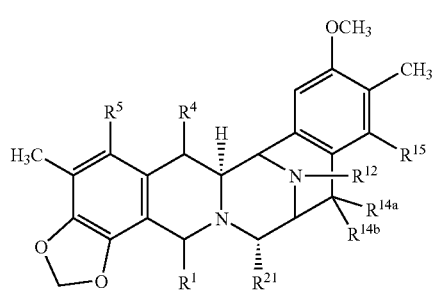

where:
$R^1$ is —CH$_2$NH$_2$ or —CH$_2$OH, or a protected or derivatised version of such a group and $R^4$ is —H; or $R^{1a}$ and $R^4$ together form a group of formula (IV), (V), (VI) or (VII):

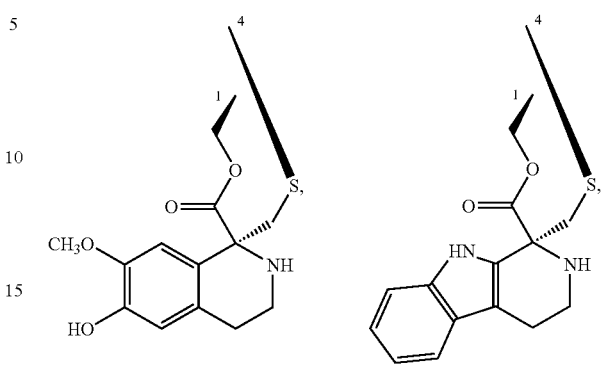

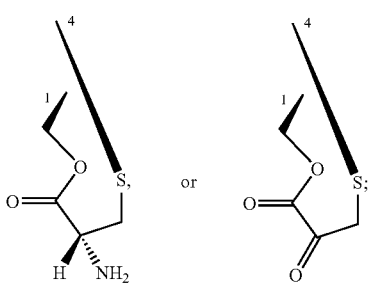

$R^5$ is —OH or a protected or derivatised version of such a group;

$R^{14a}$ and $R^{14b}$ are both —H or one is —H and the other is —OH or a protected or derivatised version of such a group, —OCH$_3$ or —OCH$_2$CH$_3$, or $R^{14a}$ and $R^{14b}$ together form a keto group;

$R^{12}$ is —H—, —CH$_3$— or —CH$_2$CH$_3$—;

$R^{15}$ is —H, —OH or a protected or derivatised version of such a group; and $R^{18}$ is —OH or a protected or derivatised version of such a group.

In one embodiment, preferably at least of $R^1$, $R^5$, $R^{14a}$, $R^{14b}$, $R^{15}$ or $R^{18}$ is a protected or derivatised group.

In one variation of this invention, the group $R^1$ is not a tert-butyldiphenylsilyl substituent and/or the group $R^{18}$ is not a methoxymethyl group.

Preferably $R^1$ is —CH$_2$NH$_2$ or —CH$_2$OH, or a protected or derivatised version of such a group and $R^4$ is —H; or $R^{1a}$ and $R^4$ together form a group:

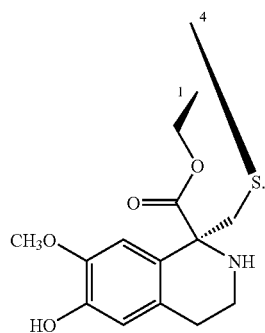

Preferably $R^{14a}$ and $R^{14b}$ are both —H.

One preferred class of intermediates includes the compound which we identify as compound 25, of formula:

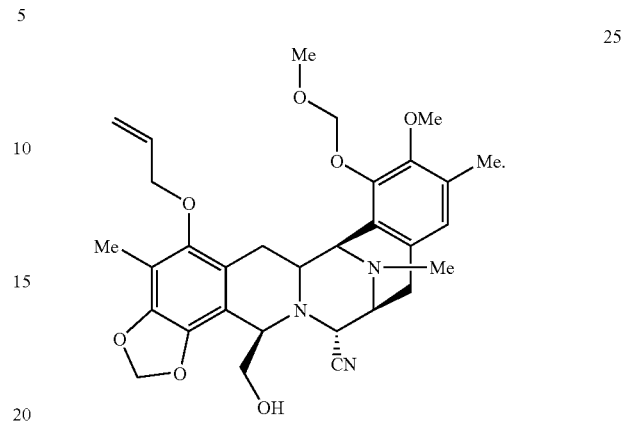

The preferred class is thus of the general formula where the group MOM is replaced by any other protecting group.

Other preferred intermediates includes the compounds which we identify as compound 45 and 43 (Scheme IX).

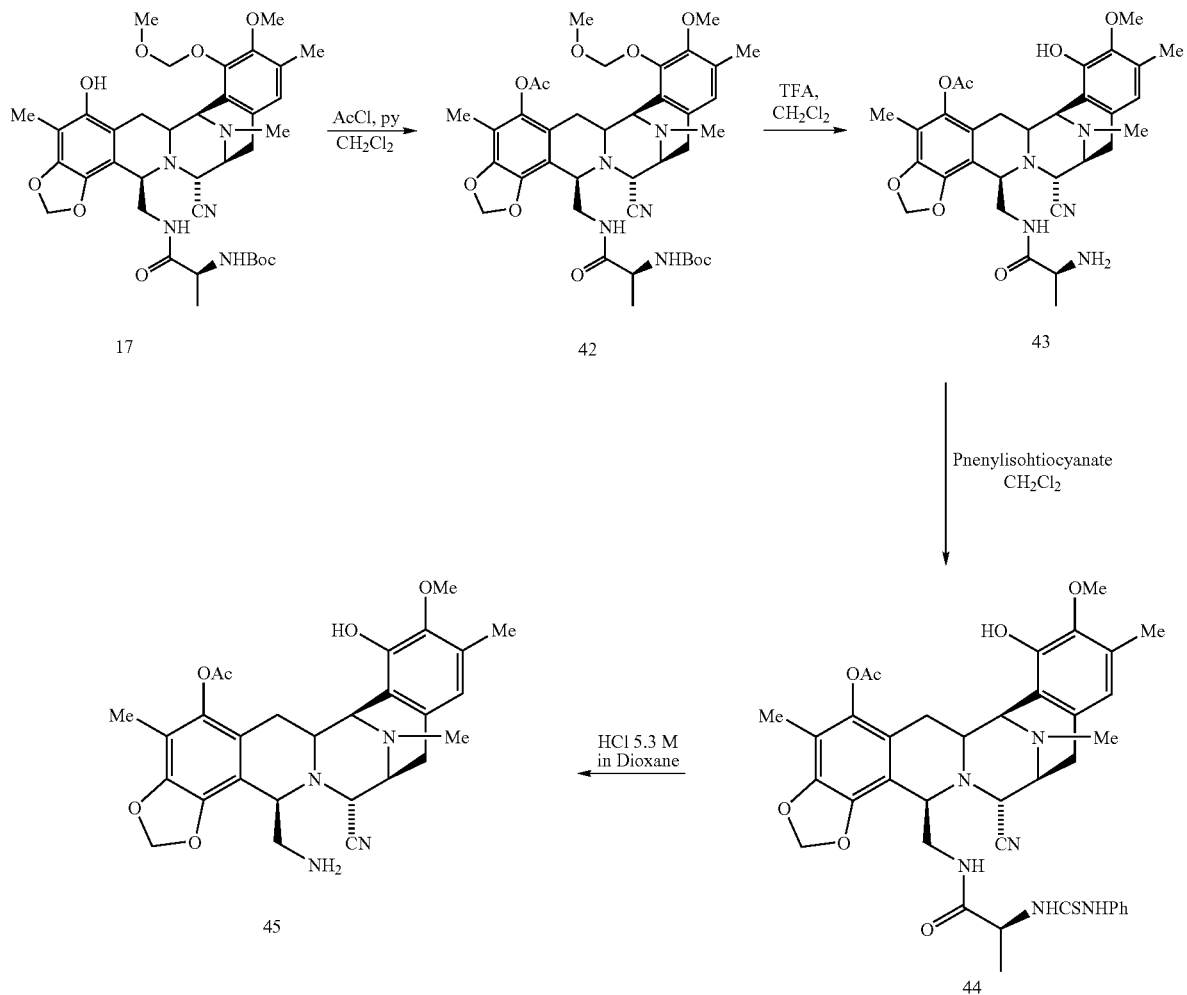

Other N-acyl derivatives may readily be made from compound 45 and are an important part of this invention. Suitable acyl groups include those previously mentioned. The corresponding 21-hydroxy compounds are also useful and are among the active compounds which we have found.

Novel Active Compounds

We have additionally found that certain of the compounds of the invention which we initially prepared as intermediates have exceptional activity in the treatment of cancers, such as leukaemias, lung cancer, colon cancer, kidney cancer and melanoma.

Thus, the present invention provides a method of treating any mammal, notably a human, affected by cancer which comprises administering to the affected individual a therapeutically effective amount of a compound of the invention, or a pharmaceutical composition thereof.

The present invention also relates to pharmaceutical preparations, which contain as active ingredient a compound or compounds of the invention, as well as the processes for their preparation.

Examples of pharmaceutical compositions include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

Administration of the compounds or compositions of the present invention may be by any suitable method, such as intravenous infusion, oral preparations, intraperitoneal and intravenous administration. We prefer that infusion times of up to 24 hours are used, more preferably 2-12 hours, with 2-6 hours most preferred. Short infusion times which allow treatment to be carried out without an overnight stay in hospital are especially desirable. However, infusion may be 12 to 24 hours or even longer if required. Infusion may be carried out at suitable intervals of say 2 to 4 weeks. Pharmaceutical compositions containing compounds of the invention may be delivered by liposome or nanosphere encapsulation, in sustained release formulations or by other standard delivery means.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds and compositions of this invention may be used with other drugs to provide a combination therapy. The other drugs may form part of the same composition, or be provided as a separate composition for administration at the same time or a different time. The identity of the other drug is not particularly limited, and suitable candidates include:

a) drugs with antimitotic effects, especially those which target cytoskeletal elements, including microtubule modulators such as taxane drugs (such as taxol, paclitaxel, taxotere, docetaxel), podophylotoxins or vinca alkaloids (vincristine, vinblastine);
b) antimetabolite drugs such as 5-fluorouracil, cytarabine, gemcitabine, purine analogues such as pentostatin, methotrexate);
c) alkylating agents such as nitrogen mustards (such as cyclophosphamide or ifosphamide);
d) drugs which target DNA such as the antracycline drugs adriamycin, doxorubicin, pharmorubicin or epirubicin;
e) drugs which target topoisomerases such as etoposide;
f) hormones and hormone agonists or antagonists such as estrogens, antiestrogens (tamoxifen and related compounds) and androgens, flutamide, leuprorelin, goserelin, cyprotrone or octreotide;
g) drugs which target signal transduction in tumour cells including antibody derivatives such as herceptin;
h) alkylating drugs such as platinum drugs (cis-platin, carbonplatin, oxaliplatin, paraplatin) or nitrosoureas;
i) drugs potentially affecting metastasis of tumours such as matrix metalloproteinase inhibitors;
j) gene therapy and antisense agents;
k) antibody therapeutics;
l) other bioactive compounds of marine origin, notably the didemnins such as aplidine;
m) steroid analogues, in particular dexamethasone;
n) anti-inflammatory drugs, in particular dexamethasone; and
o) anti-emetic drugs, in particular dexamethasone.

The present invention also extends to the compounds of the invention for use in a method of treatment, and to the use of the compounds in the preparation of a composition for treatment of cancer.

Cytotoxic Activity

Cell Cultures. Cells were maintained in logarithmic phase of growth in Eagle's Minimum Essential Medium, with Earle's Balanced Salts, with 2.0 mM L-glutamine, with non-essential amino acids, without sodium bicarbonate (EMEM/neaa); supplemented with 10% Fetal Calf Serum (FCS), $10^{-2}$ M sodium bicarbonate and 0.1 g/l penicillin-G+streptomycin sulfate.

A simple screening procedure has been carried out to determine and compare the antitumour activity of these compounds, using an adapted form of the method described by Bergeron et al (1984). The tumour cell line employed have been P-388 (suspension culture of a lymphoid neoplasm from DBA/2 mouse), A-549 (monolayer culture of a human lung carcinoma), HT-29 (monolayer culture of a human colon carcinoma) and MEL-28 (monolayer culture of a human melanoma).

P-388 cell were seeded into 16 mm wells at $1 \times 10^4$ cells per well in 1 ml aliquots of MEM 5FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humid atmosphere, an approximately $IC_{50}$ was determined by comparing the growth in wells with drug to the growth in wells control.

A-549, HT-29 and MEL-28 were seeded into 16 mm wells at $2 \times 10^4$ cells per well in 1 ml aliquots of MEM 10FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humid atmosphere, the wells were stained with 0.1% Crystal Violet. An approximately $IC_{50}$ was determined by comparing the growth in wells with drug to the growth in wells control.

1. Raymond J. Bergeron, Paul F. Cavanaugh, Jr., Steven J. Kline. Robert G. Hughes, Jr., Gary T. Elliot and Carl W. Porter. Antineoplastic and antiherpetic activity of spermidine catecholamide iron chelators. *Biochem. Bioph. Res. Comm.* 1984, 121(3), 848-854.

2. Alan C. Schroeder, Robert G. Hughes, Jr. and Alexander Bloch. Effects of Acyclic Pyrimidine Nucleoside Analoges. *J. Med. Chem.* 1981, 24 1078-1083.
Cytotoxic Activity
| Compound | IC$_{50}$ (µM) | | | | | |
|---|---|---|---|---|---|---|
| | P-388 | A-549 | HT-29 | MEL-28 | CV-1 | DU-145 |
| 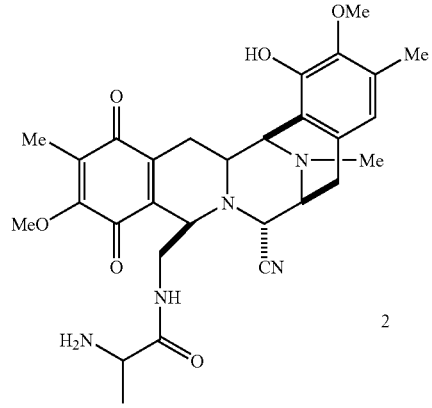 2 | 0.009 | 0.018 | 0.018 | 0.018 | 0.023 | |
| 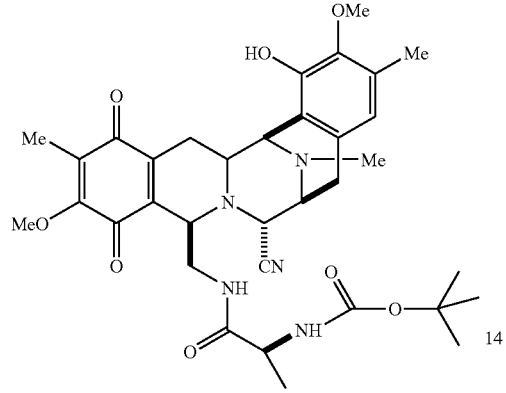 14 | 0.15 | >0.15 | 0.15 | >0.15 | | |
| 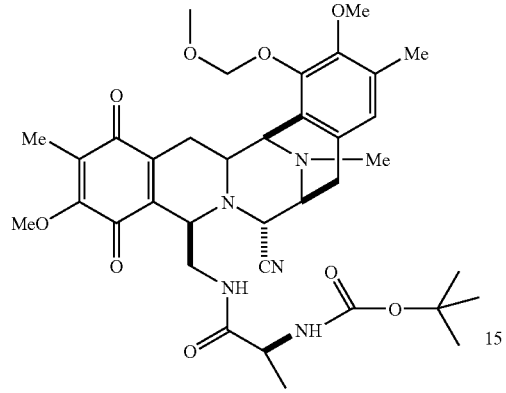 15 | 1.44 | 1.44 | 1.44 | 1.44 | | |

-continued
| Compound | IC₅₀ (μM) | | | | | |
|---|---|---|---|---|---|---|
| | P-388 | A-549 | HT-29 | MEL-28 | CV-1 | DU-145 |
| 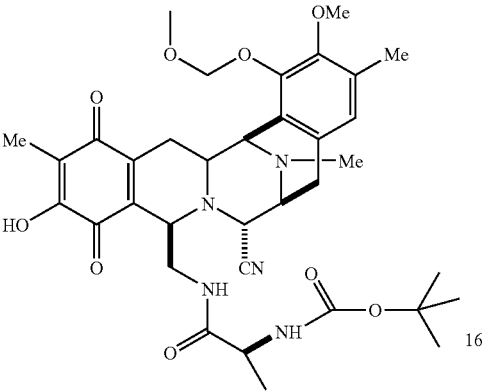 16 | >1.5 | >1.5 | >1.5 | >1.5 | | |
| 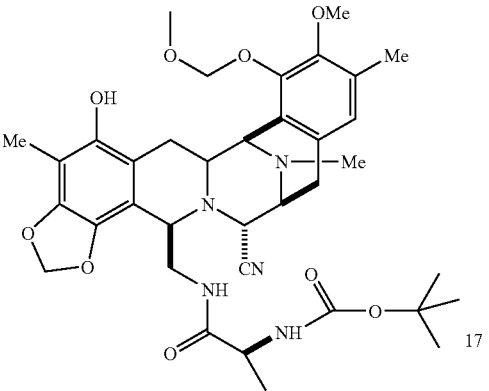 17 | 1.4 | 1.4 | 1.4 | 1.4 | | |
| 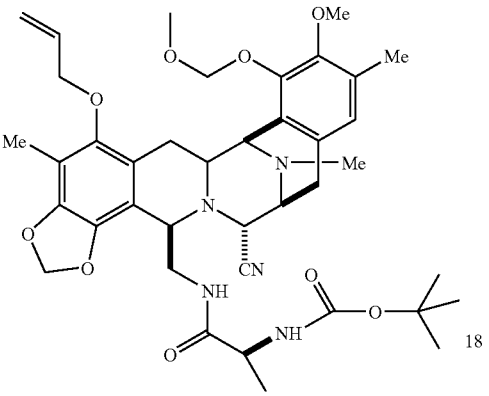 18 | 0.01 | 0.01 | 0.01 | 0.01 | | |

-continued
| Compound | IC$_{50}$ (μM) | | | | | |
|---|---|---|---|---|---|---|
| | P-388 | A-549 | HT-29 | MEL-28 | CV-1 | DU-145 |
| 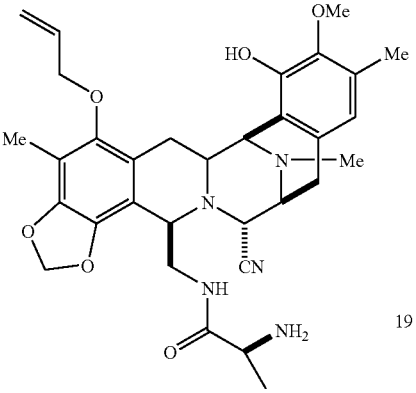 19 | 0.08 | 0.16 | 0.01 | 0.16 | | |
| 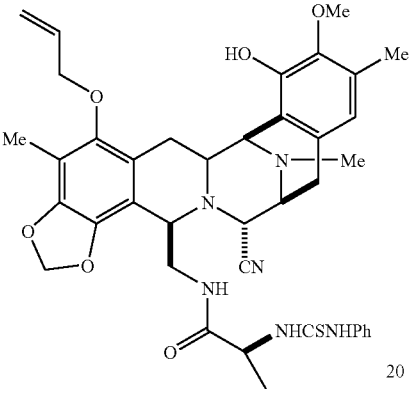 20 | 0.01 | 0.01 | 0.01 | 0.01 | | |
| 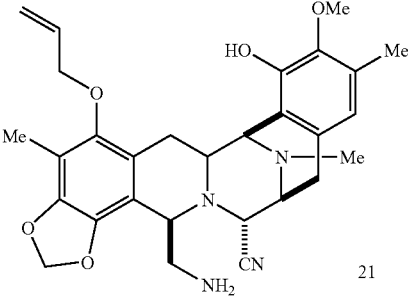 21 | 0.019 | 0.019 | 0.019 | 0.019 | | |
| 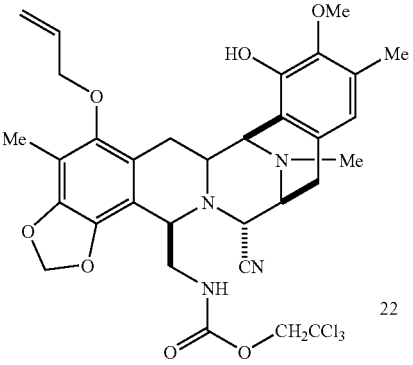 22 | 0.014 | 0.014 | 0.014 | 0.014 | 0.014 | 0.014 |

-continued

| Compound | IC$_{50}$ (μM) | | | | | |
|---|---|---|---|---|---|---|
| | P-388 | A-549 | HT-29 | MEL-28 | CV-1 | DU-145 |
| 23 | 0.13 | 0.13 | 0.13 | 0.13 | 0.13 | 0.13 |
| 24 | 0.18 | 1.8 | 1.8 | 1.8 | 1.8 | 1.8 |
| 25 | 0.2 | 0.2 | 0.2 | 0.2 | 0.2 | 0.2 |
| 35 | 0.008 | 0.008 | 0.008 | 0.008 | | |

| Compound | IC$_{50}$ (μM) | | | | | |
|---|---|---|---|---|---|---|
| | P-388 | A-549 | HT-29 | MEL-28 | CV-1 | DU-145 |
| 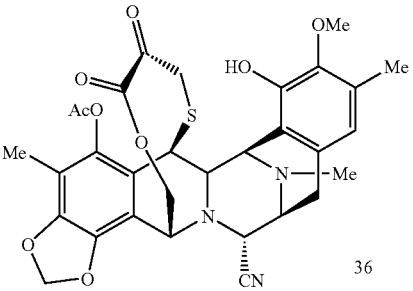 36 | 0.01 | 0.01 | 0.01 | 0.01 | | |
| 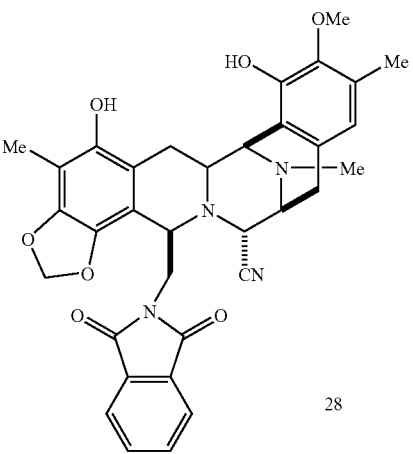 28 | 0.001 | 0.001 | 0.001 | 0.001 | 0.001 | 0.001 |
| 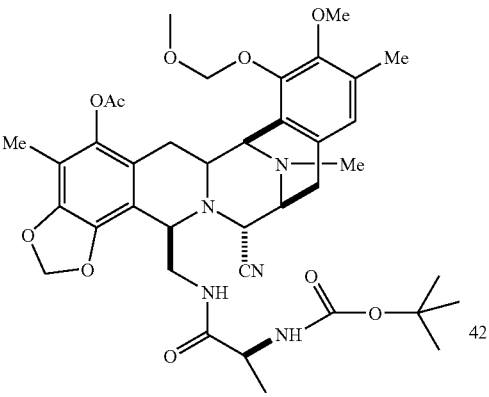 42 | 0.13 | 0.13 | 0.13 | 0.13 | | 0.13 |
| 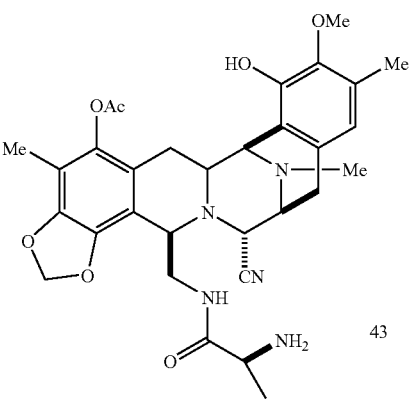 43 | 0.008 | 0.016 | 0.008 | 0.008 | | 0.016 |

-continued
| Compound | IC$_{50}$ (μM) | | | | | |
|---|---|---|---|---|---|---|
| | P-388 | A-549 | HT-29 | MEL-28 | CV-1 | DU-145 |
| 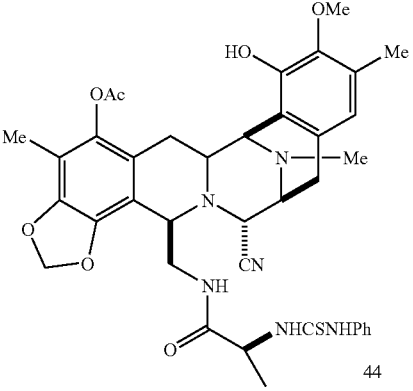 44 | 0.001 | 0.001 | 0.001 | 0.001 | | 0.001 |
| 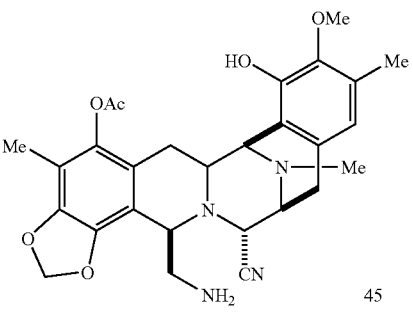 45 | 0.01 | 0.01 | 0.01 | 0.01 | | 0.01 |
| 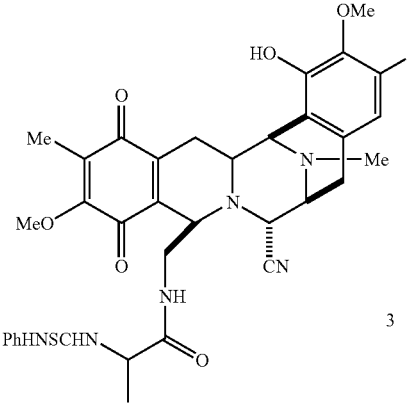 3 | 0.015 | 0.015 | 0.015 | 0.015 | 0.018 | |
| 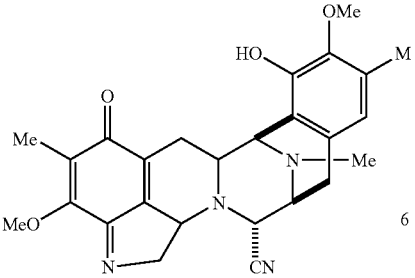 6 | 2.171 | 2.171 | 2.171 | 2.171 | 2.171 | |

| Compound | IC$_{50}$ (μM) | | | | | |
|---|---|---|---|---|---|---|
| | P-388 | A-549 | HT-29 | MEL-28 | CV-1 | DU-145 |
| 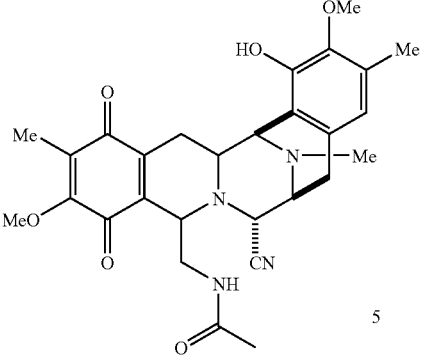 5 | 0.005 | 0.005 | 0.005 | 0.005 | | |
| 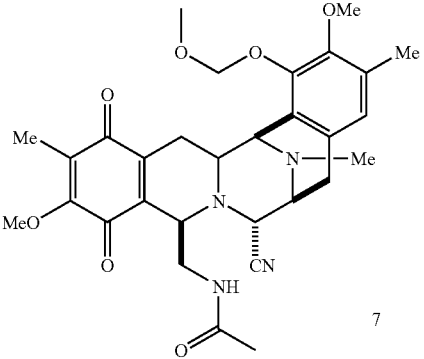 7 | 0.22 | 0.22 | 0.22 | 0.22 | 0.22 | |
| 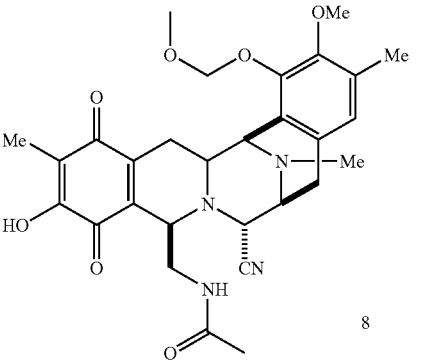 8 | >9 | >18.1 | >18.1 | >18.1 | >18.1 | |
| 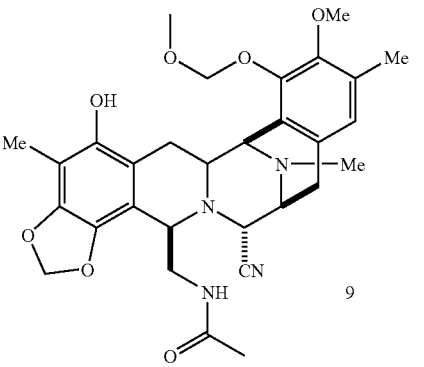 9 | >1.77 | >1.77 | >1.77 | >1.77 | | >1.77 |

-continued
| Compound | IC$_{50}$ (μM) | | | | | |
|---|---|---|---|---|---|---|
| | P-388 | A-549 | HT-29 | MEL-28 | CV-1 | DU-145 |
| 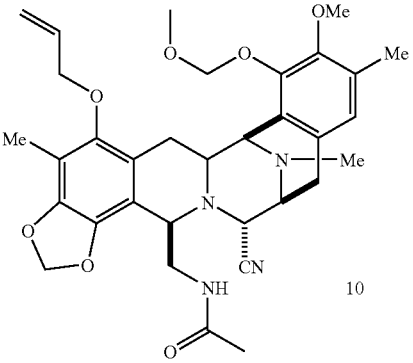 10 | >1.65 | >1.65 | >1.65 | >1.65 | | >1.65 |
| 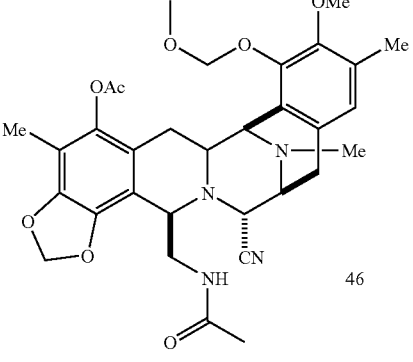 46 | 0.016 | 0.016 | 0.016 | 0.016 | | 0.016 |
| 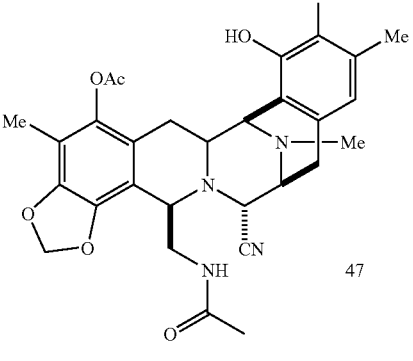 47 | 0.001 | 0.001 | 0.001 | 0.001 | | 0.001 |
| 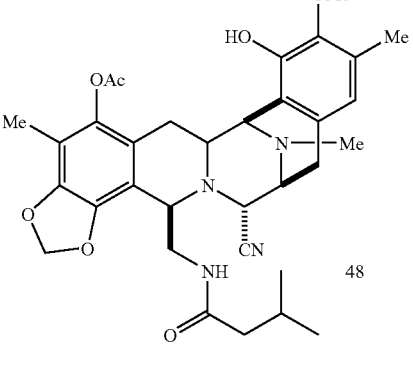 48 | 0.0008 | 0.001 | 0.0008 | 0.0008 | | 0.001 |

-continued

| Compound | IC$_{50}$ (μM) | | | | | |
|---|---|---|---|---|---|---|
| | P-388 | A-549 | HT-29 | MEL-28 | CV-1 | DU-145 |
| 49 | 0.007 | 0.007 | 0.007 | 0.007 | | 0.007 |
| 50 | 0.0001 | 0.0001 | 0.0001 | 0.0001 | | 0.0001 |
| 51 | 0.0001 | 0.0001 | 0.0001 | 0.0001 | | 0.0001 |

-continued
| Compound | IC$_{50}$ ($\mu$M) | | | | | |
|---|---|---|---|---|---|---|
| | P-388 | A-549 | HT-29 | MEL-28 | CV-1 | DU-145 |
| 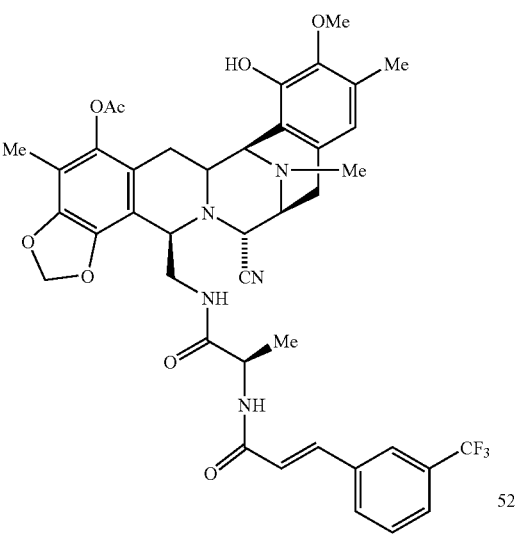 52 | 0.001 | 0.001 | 0.001 | 0.001 | | 0.001 |
| 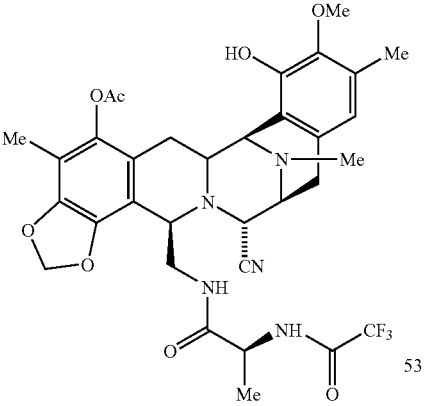 53 | 0.0001 | 0.0001 | 0.0001 | 0.0001 | | 0.0001 |
| 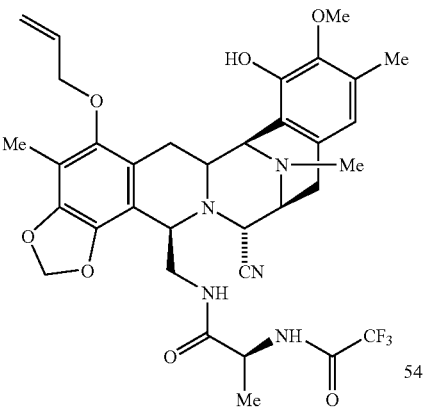 54 | 0.001 | 0.001 | 0.001 | 0.001 | | 0.001 |

| Compound | IC₅₀ (μM) | | | | | |
|---|---|---|---|---|---|---|
| | P-388 | A-549 | HT-29 | MEL-28 | CV-1 | DU-145 |
| 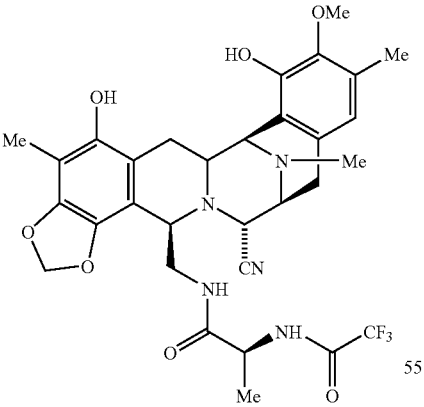 55 | 0.01 | 0.01 | 0.01 | 0.01 | | 0.01 |
| 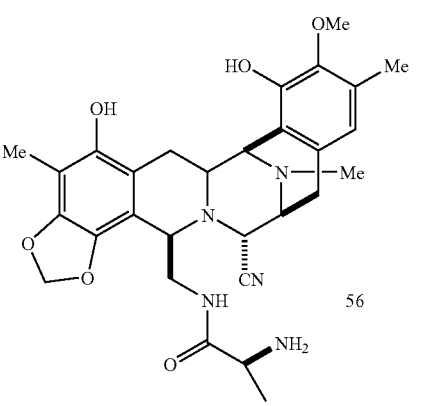 56 | 0.18 | 0.9 | 0.18 | 0.8 | | 0.9 |
| 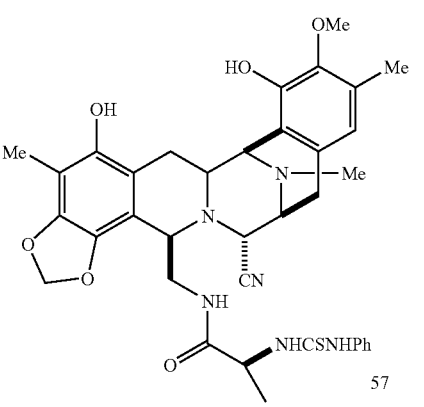 57 | 0.14 | 0.14 | 0.14 | 0.14 | | 0.14 |

-continued
| Compound | IC$_{50}$ (μM) | | | | | |
|---|---|---|---|---|---|---|
| | P-388 | A-549 | HT-29 | MEL-28 | CV-1 | DU-145 |
| 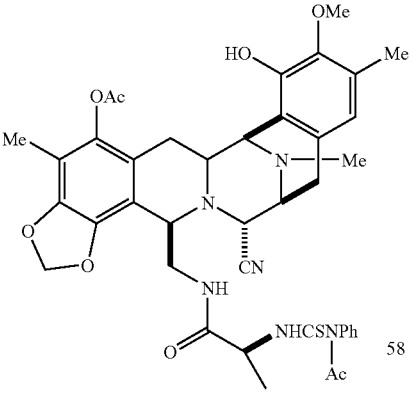 58 | 0.001 | 0.001 | 0.001 | 0.001 | | 0.001 |
| 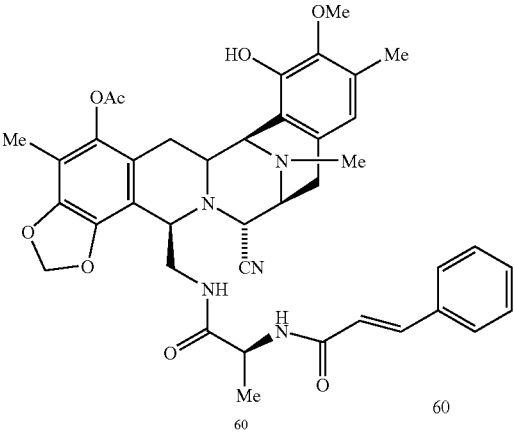 60 | 0.001 | 0.001 | 0.0005 | 0.001 | | 0.0005 |
| 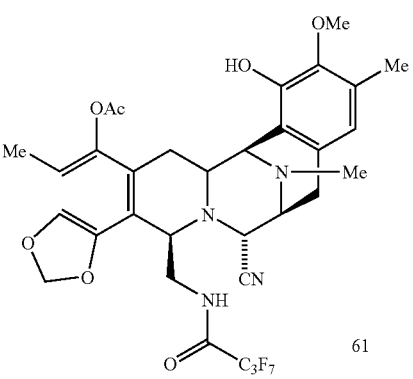 61 | 0.001 | 0.001 | 0.001 | 0.001 | | 0.001 |

-continued
| Compound | IC$_{50}$ (μM) | | | | | |
|---|---|---|---|---|---|---|
| | P-388 | A-549 | HT-29 | MEL-28 | CV-1 | DU-145 |
| 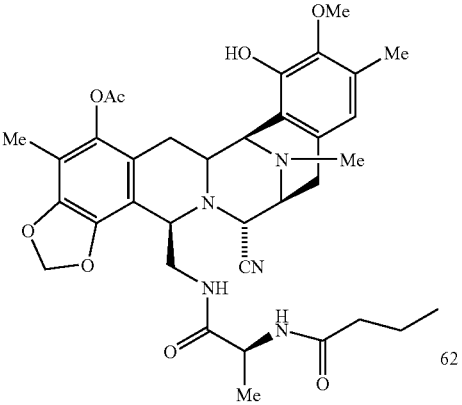 62 | 0.001 | 0.001 | 0.0005 | 0.0005 | | 0.001 |
| 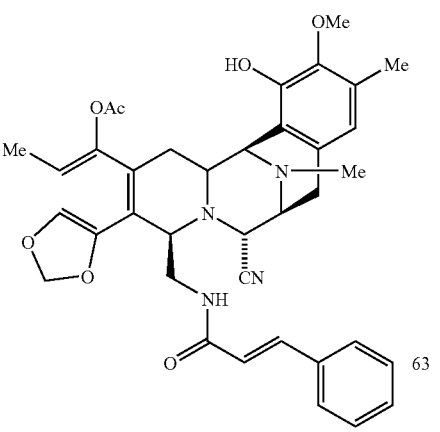 63 | 0.0001 | 0.0001 | 0.0001 | 0.0001 | | 0.0001 |
| 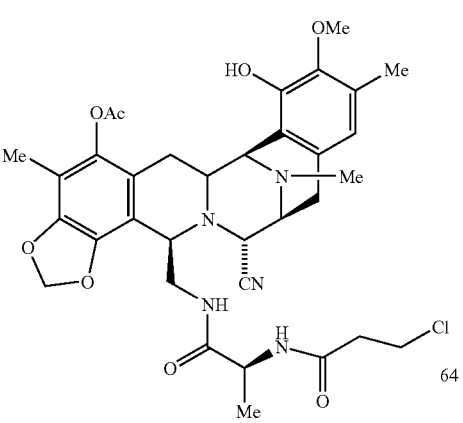 64 | 0.001 | 0.001 | 0.001 | 0.001 | | 0.001 |

-continued
| Compound | IC$_{50}$ (μM) | | | | | |
|---|---|---|---|---|---|---|
| | P-388 | A-549 | HT-29 | MEL-28 | CV-1 | DU-145 |
| 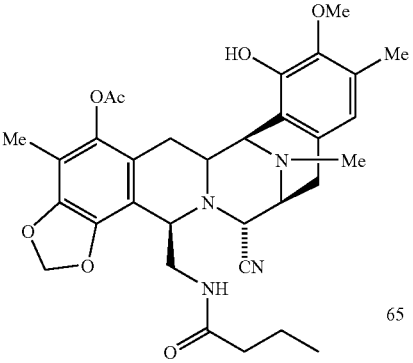 65 | 0.0001 | 0.0005 | 0.0001 | 0.0001 | | 0.0005 |
| 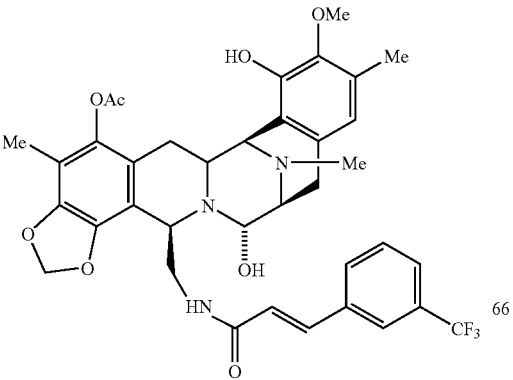 66 | 0.0001 | 0.0001 | 0.0001 | 0.0001 | | 0.0001 |
| 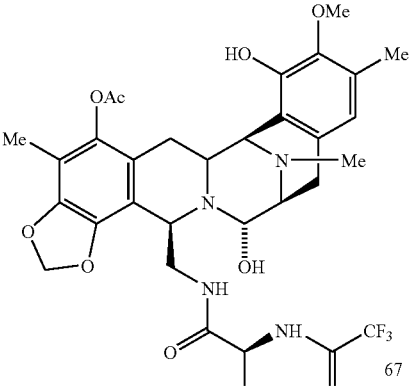 67 | 0.0001 | 0.0001 | 0.0001 | 0.0001 | | 0.0001 |

-continued
| Compound | IC$_{50}$ (μM) | | | | | |
|---|---|---|---|---|---|---|
| | P-388 | A-549 | HT-29 | MEL-28 | CV-1 | DU-145 |
| 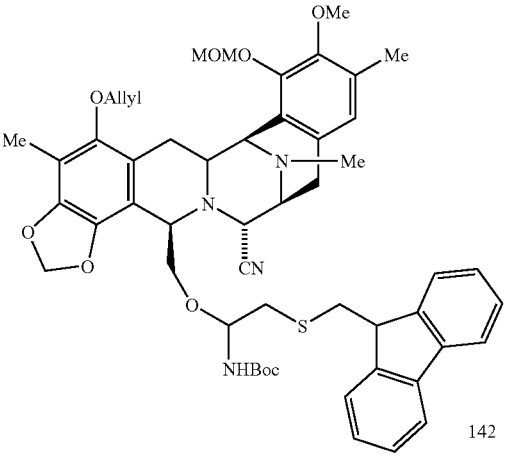
142 | | >1 | >1 | | | |
| 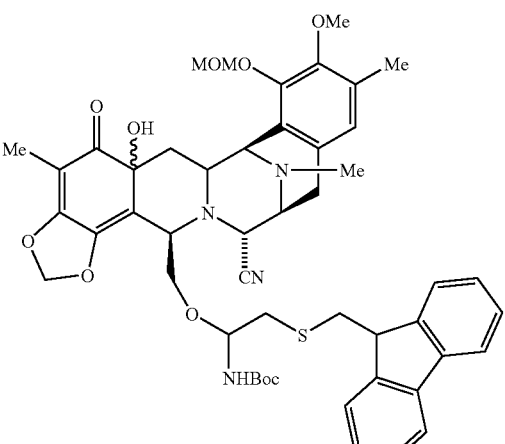
144 | | >1 | >1 | | | |
| 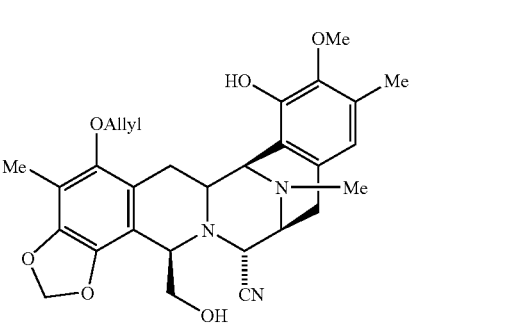
146 | 0.19 | 0.19 | 0.19 | 0.19 | | |

-continued
| | IC₅₀ (μM) | | | | | |
|---|---|---|---|---|---|---|
| Compound | P-388 | A-549 | HT-29 | MEL-28 | CV-1 | DU-145 |
| 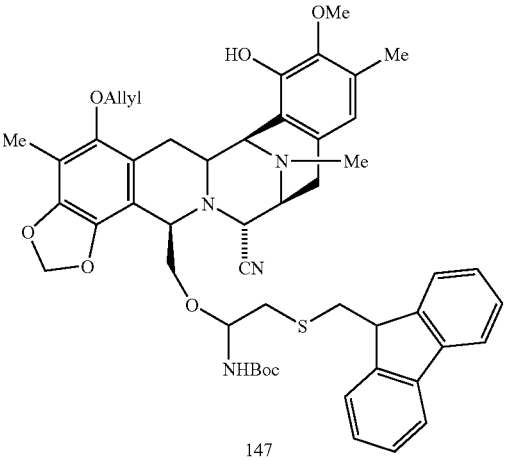 147 | | 0.0055 | 0.0055 | | | |
| 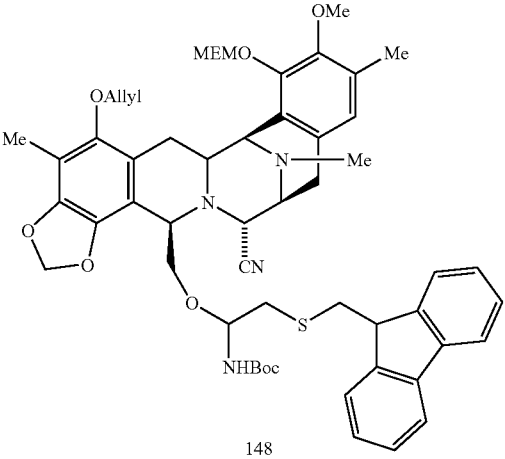 148 | | >1 | >1 | | | |
| 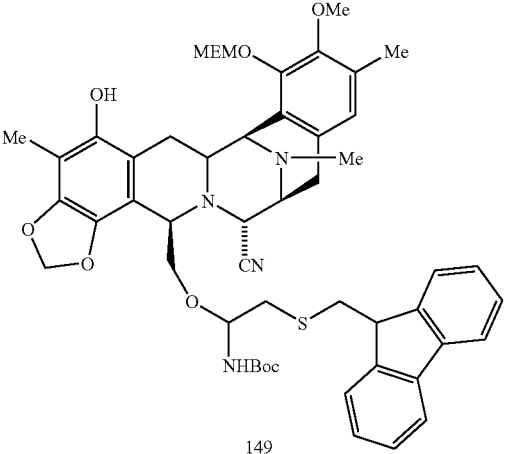 149 | | 0.01 | 0.01 | | | |

-continued

| Compound | IC₅₀ (μM) | | | | | |
|---|---|---|---|---|---|---|
| | P-388 | A-549 | HT-29 | MEL-28 | CV-1 | DU-145 |
| 150 | 0.051 | 0.051 | | | | |
| 151 | 0.012 | 0.012 | | | | |
| 153 | 0.11 | 0.11 | | | | |

-continued
| Compound | IC₅₀ (μM) | | | | | |
|---|---|---|---|---|---|---|
| | P-388 | A-549 | HT-29 | MEL-28 | CV-1 | DU-145 |
| 154 | >1 | >1 | | | | |
| 156 | >1 | >1 | | | | |
| 157 | 0.59 | 0.59 | | | | |
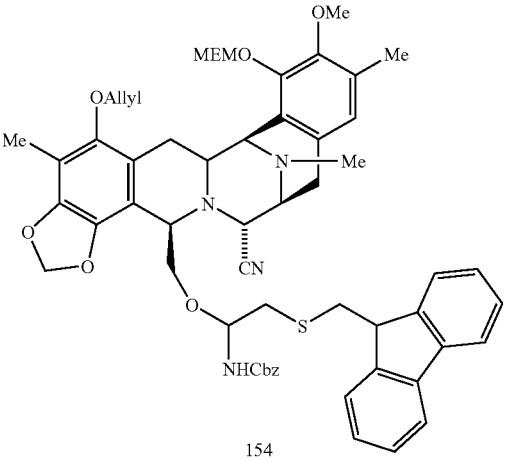
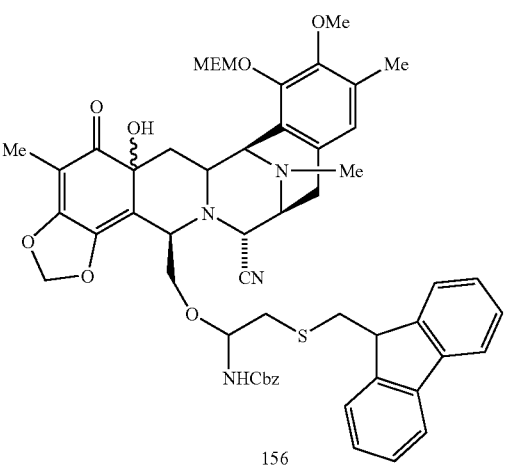
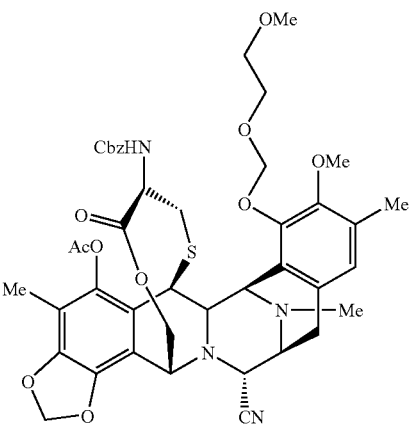

-continued

| Compound | IC$_{50}$ (μM) | | | | | |
|---|---|---|---|---|---|---|
| | P-388 | A-549 | HT-29 | MEL-28 | CV-1 | DU-145 |
| 158 | | 0.0013 | 0.0013 | | | |
| 164 | | 0.00015 | 0.00015 | | | |
| 165 | | >1 | >1 | | | |
| 166 | | >1 | >1 | | | |

-continued

| Compound | IC₅₀ (µM) | | | | | |
|---|---|---|---|---|---|---|
| | P-388 | A-549 | HT-29 | MEL-28 | CV-1 | DU-145 |
| 167 | | >1 | >1 | | | |
| 168 | | >1 | >1 | | | |
| 169 | | >1 | >1 | | | |
| 170 | | >1 | >1 | | | |

-continued
| Compound | IC$_{50}$ (µM) | | | | | |
|---|---|---|---|---|---|---|
| | P-388 | A-549 | HT-29 | MEL-28 | CV-1 | DU-145 |
| 171 | | 0.012 | 0.012 | | | |
| 172 | | >1 | >1 | | | |
| 173 | | 0.062 | 0.062 | | | |
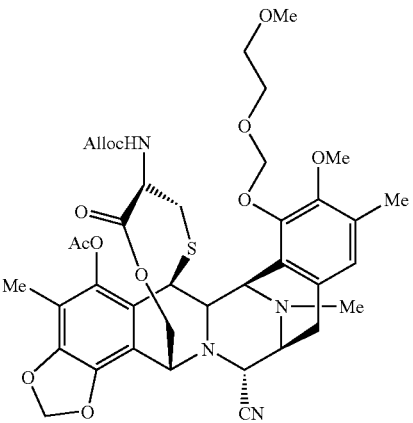
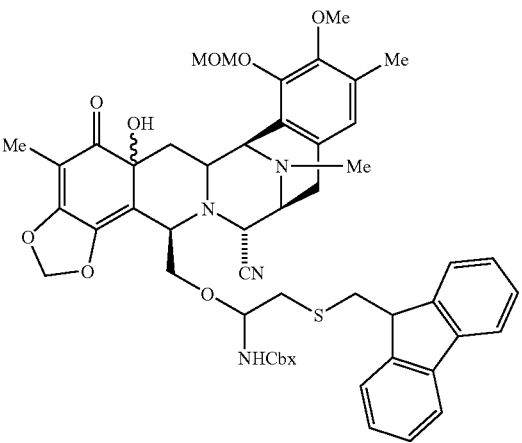
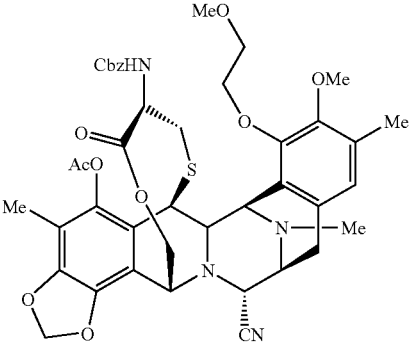

The active compounds of this invention thus include compounds with the 10-hydroxy group and the 1-labile group.

An important method of this invention includes the reaction:

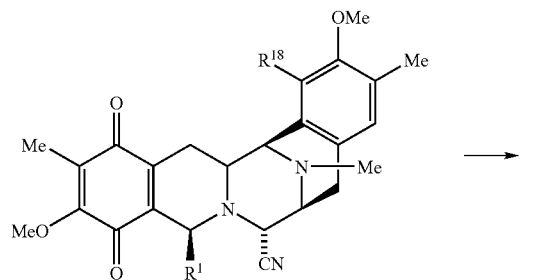

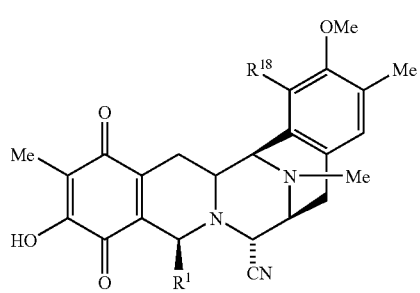

Another important method of this invention includes the reaction:

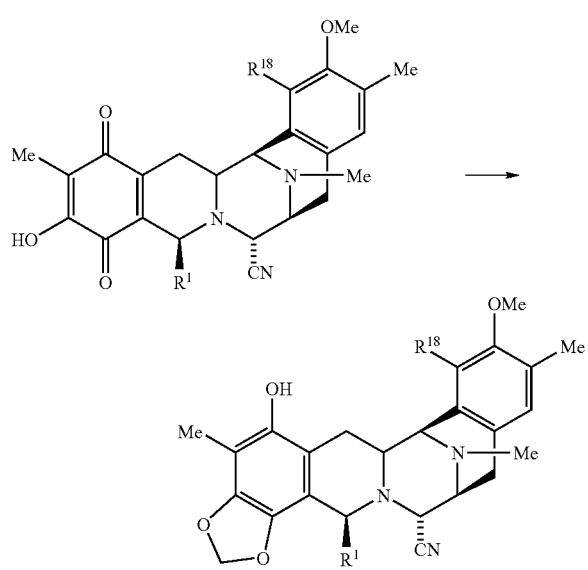

Another important method of this invention includes the reaction includes the reaction where a group $R^1$ is aminomethylene is converted to a hydroxymethylene group.

Another important method of this invention includes the reaction wherein a compound with a group $R^1$ which is hydroxymethylene is reacted with a reagent of the formula (XIX)

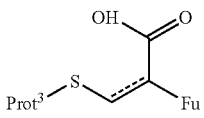

where Fu indicates a protected functional group, $Prot^3$ is a protecting group, and the dotted line shows an optional double bond.

Another important method of this invention includes the reaction for preparing a 21-cyano compound of formula (XVI) which comprises reacting a compound of formula (XV):

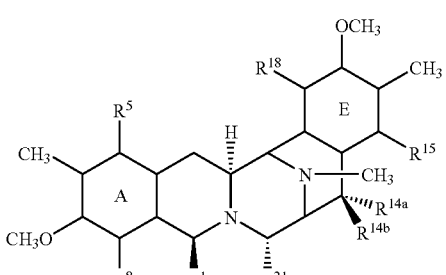

where $R^1$, $R^5$, $R^8$, $R^{14a}$, $R^{14b}$, $R^{15}$ and $R^{18}$ are as defined and $R^{21}$ is a hydroxy group, with a source of cyanide ion, to give the desired 21-cyano compound.

In addition, processes using other nucleophile-containing compounds, to produce similar compounds of formula (XVI) wherein the 21-position is protected by another nucleophilic group, a 21-Nuc group, are also envisaged. For example, a 21-Nuc compound of formula (XVI) with an alkylamino substituent at the 21-position can be produced by reacting the compound of formula (XV) wherein $R^{21}$ is a hydroxy group with a suitable alkylamine. A 21-Nuc compound of formula (XVI) with an alkylthio substituent at the 21-position can also be produced by reacting the compound of formula (XV) wherein $R^{21}$ is a hydroxy group with a suitable alkanethiol. Alternatively, a 21-Nuc compound of formula (XVI) with an □-carbonylalkyl substituent at the 21-position can be produced by reacting the compound of formula (XV) wherein $R^{21}$ is a hydroxy group with a suitable carbonyl compound, typically in the presence of a base. Other synthetic routes are available for other 21-Nuc compounds.

Another important reaction of this invention involves treatment of a 21-cyano product of this invention to form a 21-hydroxy compound. Such compounds have interesting in vivo properties.

EXAMPLES

The present invention is illustrated by the following examples.

Example 1

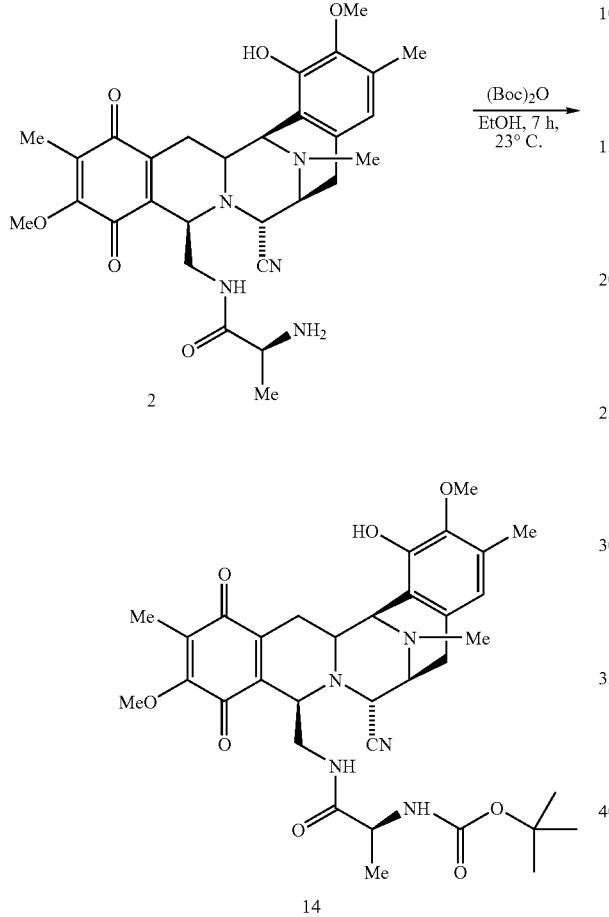

To a solution of 2 (21.53 g, 39.17 mmol) in ethanol (200 ml), tert-butoxycarbonyl anhydride (7.7 g, 35.25 mmol) was added and the mixture was stirred for 7 h at 23° C. Then, the reaction was concentrated in vacuo and the residue was purified by flash column chromatography (SiO$_2$, hexane:ethyl acetate 6:4) to give 14 (20.6 g, 81%) as a yellow solid.

Rf: 0.52 (ethyl acetate:CHCl$_3$ 5:2).

$^1$H NMR (300 MHz, CDCl$_3$): δ 6.49 (s, 1H), 6.32 (bs, 1H), 5.26 (bs, 1H), 4.60 (bs, 1H), 4.14 (d, J=2.4 Hz, 1H), 4.05 (d, J=2.4 Hz, 1H), 3.94 (s, 3H), 3.81 (d, J=4.8 Hz, 1H), 3.7 (s, 3H), 3.34 (br d, J=7.2 Hz, 1H), 3.18-3.00 (m, 5H), 2.44 (d, J=18.3 Hz, 1H), 2.29 (s, 3H), 2.24 (s, 3H), 1.82 (s, 3H), 1.80-1.65 (m, 1H), 1.48 (s, 9H), 0.86 (d, J=5.7 Hz, 3H)

$^{13}$C NMR (75 MHz, CDCl$_3$): δ 185.5, 180.8, 172.7, 155.9, 154.5, 147.3, 143.3, 141.5, 135.3, 130.4, 129.2, 127.5, 120.2, 117.4, 116.9, 80.2, 60.7, 60.3, 58.5, 55.9, 55.8, 54.9, 54.4, 50.0, 41.6, 40.3, 28.0, 25.3, 24.0, 18.1, 15.6, 8.5.

ESI-MS m/z: Calcd. for C$_{34}$H$_{43}$N$_5$O$_8$: 649.7. Found (M+H)$^+$: 650.3.

Example 2

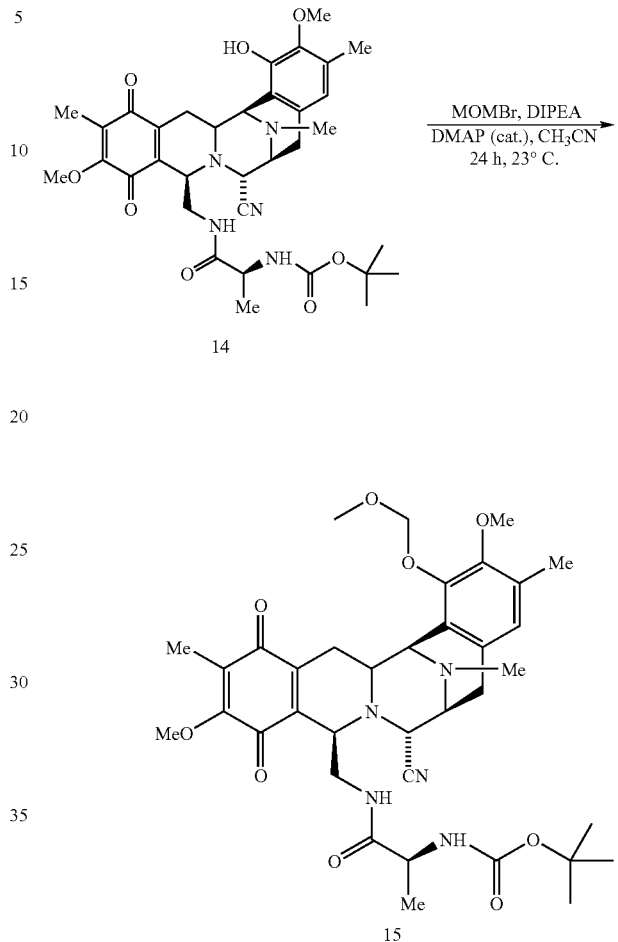

To a stirred solution of 14 (20.6 g, 31.75 mmol) in CH$_3$CN (159 ml), diisopropylethylamine (82.96 ml, 476.2 mmol), methoxymethylene bromide (25.9 ml, 317.5 mmol) and dimethylaminopyridine (155 mg, 1.27 mmol) were added at 0° C. The mixture was stirred at 23° C. for 24 h. The reaction was quenched at 0° C. with aqueous 0.1N HCl (750 ml) (pH=5), and extracted with CH$_2$Cl$_2$ (2×400 ml). The organic phase was dried (sodium sulphate) and concentrated in vacuo. The residue was purified by flash column chromatography (SiO$_2$, gradient hexane:ethyl acetate 4:1 to hexane:ethyl acetate 3:2) to give 15 (17.6 g, 83%) as a yellow solid.

Rf: 0.38 (hexane:ethyl acetate 3:7).

$^1$H NMR (300 MHz, CDCl$_3$): δ 6.73 (s, 1H), 5.35 (bs, 1H), 5.13 (s, 2H), 4.50 (bs, 1H), 4.25 (d, J=2.7 Hz, 1H), 4.03 (d, J=2.7 Hz, 1H), 3.97 (s, 3H), 3.84 (bs, 1H), 3.82-3.65 (m, 1H), 3.69 (s, 3H), 3.56 (s, 3H), 3.39-3.37 (m, 1H), 3.20-3.00 (m, 5H), 2.46 (d, J=18 Hz, 1H), 2.33 (s, 3H), 2.23 (s, 3H), 1.85 (s, 3H), 1.73-1.63 (m, 1H), 1.29 (s, 9H), 0.93 (d, J=5.1 Hz, 3H)

$^{13}$C NMR (75 MHz, CDCl$_3$): δ 185.4, 180.9, 172.4, 155.9, 154.5, 149.0, 148.4, 141.6, 135.1, 131.0, 129.9, 127.6, 124.4, 123.7, 117.3, 99.1, 79.3, 60.7, 59.7, 58.4, 57.5, 56.2, 55.9, 55.0, 54.2, 50.0, 41.5, 39.9, 28.0, 25.2, 24.0, 18.1, 15.6, 8.5.

ESI-MS m/z: Calcd. for C$_{36}$H$_{47}$N$_5$O$_9$: 693.8. Found (M+H)$^+$: 694.3.

Example 3

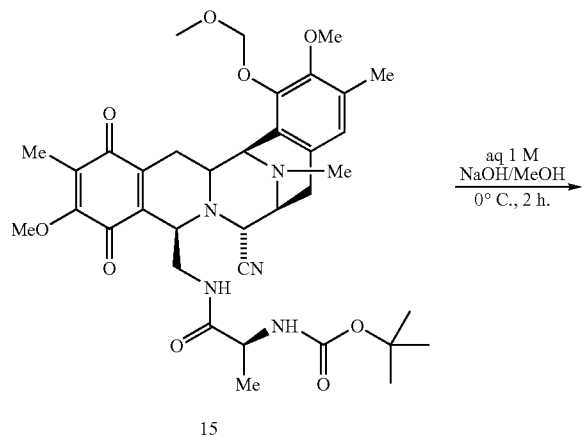

To a flask containing 15 (8 g, 1.5 ml) in methanol (1.6 l) an aqueous solution of 1M sodium hydroxide (3.2 l) was added at 0° C. The reaction was stirred for 2 h at this temperature and then, quenched with 6M HCl to pH=5. The mixture was extracted with ethyl acetate (3×1l) and the combined organic layers were dried over sodium sulphate and concentrated in vacuo. The residue was purified by flash column chromatography (SiO$_2$, gradient CHCl$_3$ to CHCl$_3$:ethyl acetate 2:1) to afford 16 (5.3 mg, 68%).

Rf: 0.48 (CH$_3$CN:H$_2$O 7:3, RP-C18)

$^1$H NMR (300 MHz, CDCl$_3$): δ 6.73 (s, 1H), 5.43 (bs, 1H), 5.16 (s, 2H), 4.54 (bs, 1H), 4.26 (d, J=1.8 Hz, 1H), 4.04 (d, J=2.7 Hz 1H), 3.84 (bs, 1H), 3.80-3.64 (m, 1H), 3.58 (s, 3H), 3.41-3.39 (m, 1H), 3.22-3.06 (m, 5H), 2.49 (d, J=18.6 Hz 1H), 2.35 (s, 3H), 2.30-2.25 (m, 1H), 2.24 (s, 3H), 1.87 (s, 3H), 1.45-1.33 (m, 1H), 1.19 (s, 9H), 1.00 (br d, J=6.6 Hz 3H)

$^{13}$C NMR (75 MHz, ☐CDCl$_3$): δ 184.9, 180.9, 172.6, 154.7, 151.3, 149.1, 148.6, 144.7, 132.9, 131.3, 129.8, 124.5, 123.7, 117.3, 116.8, 99.1, 79.4, 59.8, 58.6, 57.7, 56.2, 55.6, 54.9, 54.5, 50.1, 41.6, 40.1, 28.0, 25.3, 24.4, 18.1, 15.7, 8.0.

ESI-MS m/z: Calcd. for C$_{35}$H$_{45}$N$_5$O$_9$: 679.7. Found (M+H)$^+$: 680.3.

Example 4

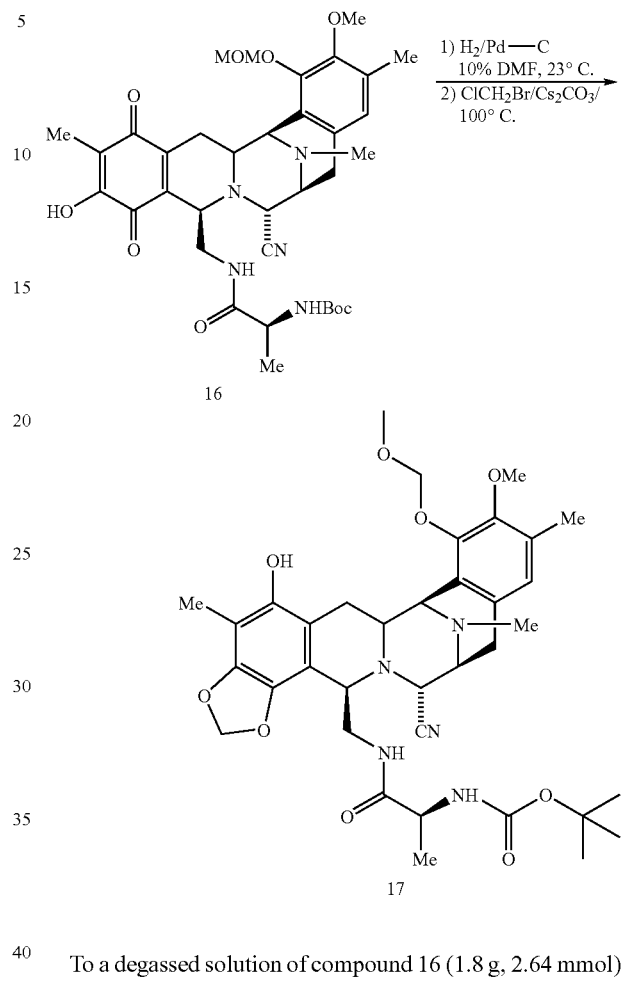

To a degassed solution of compound 16 (1.8 g, 2.64 mmol) in DMF (221 ml) 10% Pd/C (360 mg) was added and stirred under H$_2$ (atmospheric pressure) for 45 min. The reaction was filtered through celite under argon, to a flask containing anhydrous Cs$_2$CO$_3$ (2.58 g, 7.92 mmol). Then, bromochloromethane (3.40 ml 52.8 mmol), was added and the tube was sealed and stirred at 100° C. for 2 h. The reaction was cooled, filtered through a pad of celite and washed with CH$_2$Cl$_2$. The organic layer was concentrated and dried (sodium sulphate) to afford 17 as a brown oil that was used in the next step with no further purification.

Rf: 0.36 (hexane:ethyl acetate 1:5, SiO$_2$).

$^1$H NMR (300 MHz, CDCl$_3$): δ 6.68 (s, 1H), 6.05 (bs, 1H), 5.90 (s, 1H), 5.79 (s, 1H), 5.40 (bs, 1H), 5.31-5.24 (m, 2H), 4.67 (d, J=8.1 Hz, 1H), 4.19 (d, J=2.7 Hz, 1H), 4.07 (bs, 1H), 4.01 (bs, 1H), 3.70 (s, 3H), 3.67 (s, 3H), 3.64-2.96 (m, 5H), 2.65 (d, J=18.3 Hz, 1H), 2.33 (s, 3H), 2.21 (s, 3H), 2.04 (s, 3H), 2.01-1.95 (m, 1H), 1.28 (s, 9H), 0.87 (d, J=6.3 Hz, 3H)

$^{13}$C NMR (75 MHz, CDCl$_3$): δ 172.1, 162.6, 154.9, 149.1, 145.7, 135.9, 130.8, 130.7, 125.1, 123.1, 117.8, 100.8, 99.8, 76.6, 59.8, 59.2, 57.7, 57.0, 56.7, 55.8, 55.2, 49.5, 41.6, 40.1, 36.5, 31.9, 31.6, 29.7, 28.2, 26.3, 25.0, 22.6, 18.2, 15.8, 14.1, 8.8.

ESI-MS m/z: Calcd. for C$_{36}$H$_{47}$N$_5$O$_9$: 693.34. Found (M+H)$^+$: 694.3.

Example 5

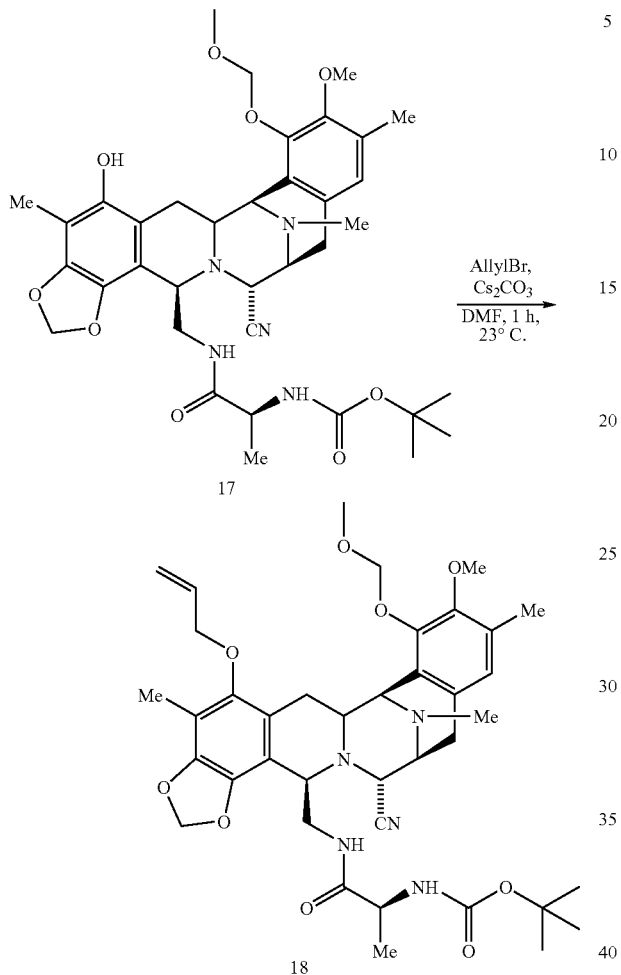

To a flask containing a solution of 17 (1.83 g, 2.65 mmol) in DMF (13 ml), Cs$_2$CO$_3$ (2.6 g, 7.97 mmol), and allyl bromide (1.15 ml, 13.28 mmol) were added at 0° C. The resulting mixture was stirred at 23° C. for 1 h. The reaction was filtered through a pad of celite and washed with CH$_2$Cl$_2$. The organic layer was dried and concentrated (sodium sulphate). The residue was purified by flash column chromatography (SiO$_2$, CHCl$_3$:ethyl acetate 1:4) to afford 18 (1.08 mg, 56%) as a white solid.

Rf: 0.36 (CHCl$_3$:ethyl acetate 1:3).

$^1$H NMR (300 MHz, CDCl$_3$): δ 6.70 (s, 1H), 6.27-6.02 (m, 1H), 5.94 (s, 1H), 5.83 (s, 1H), 5.37 (dd, J$_1$=1.01 Hz, J$_2$=16.8 Hz, 1H), 5.40 (bs, 1H), 5.25 (dd, J$_1$=1.0 Hz, J$_2$=10.5 Hz, 1H), 5.10 (s, 2H), 4.91 (bs, 1H), 4.25-4.22 (m, 1H), 4.21 (d, J=2.4 Hz, 1H), 4.14-4.10 (m, 1H), 4.08 (d, J=2.4 Hz, 1H), 4.00 (bs, 1H), 3.70 (s, 3H), 3.59 (s, 3H), 3.56-3.35 (m, 2H), 3.26-3.20 (m, 2H), 3.05-2.96 (dd, J$_1$=8.1 Hz, J$_2$=18 Hz, 1H), 2.63 (d, J=18 Hz, 1H), 2.30 (s, 3H), 2.21 (s, 3H), 2.09 (s, 3H), 1.91-1.80 (m, 1H), 1.24 (s, 9H), 0.94 (d, J=6.6 Hz, 3H)

$^{13}$C NMR (75 MHz, CDCl$_3$): δ 172.0, 154.8, 148.8, 148.6, 148.4, 144.4, 138.8, 133.7, 130.9, 130.3, 125.1, 124.0, 120.9, 117.8, 117.4, 112.8, 112.6, 101.1, 99.2, 73.9, 59.7, 59.3, 57.7, 56.9, 56.8, 56.2, 55.2, 40.1, 34.6, 31.5, 28.1, 26.4, 25.1, 22.6, 18.5, 15.7, 14.0, 9.2.

ESI-MS m/z: Calcd. for C$_{39}$H$_{51}$N$_5$O$_9$: 733.4. Found (M+H)$^+$: 734.4.

Example 6

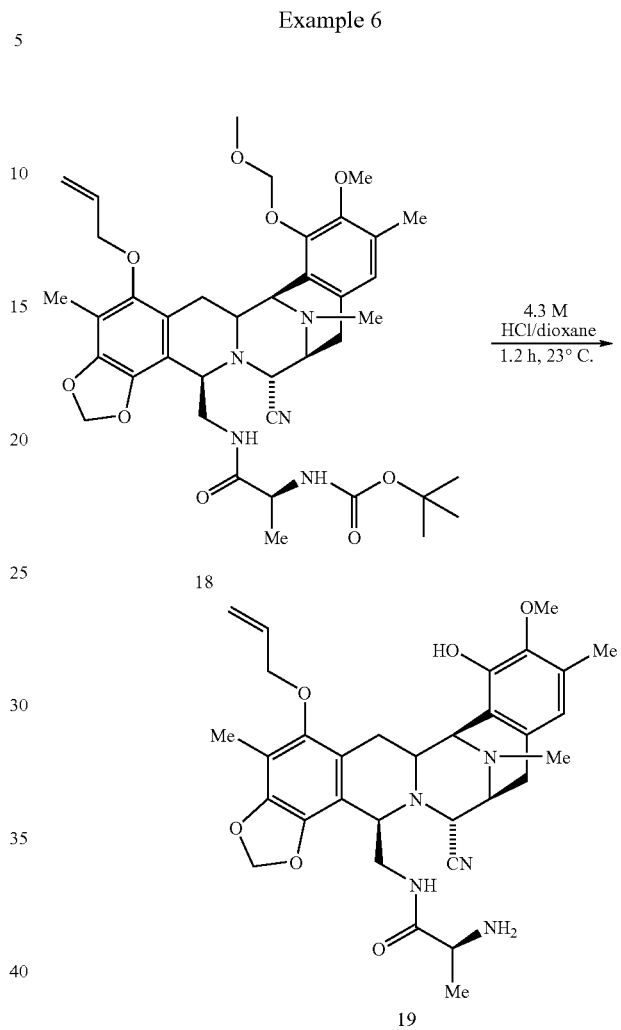

To a solution of 18 (0.1 g, 0.137 mmol) in dioxane (2 ml), 4.2M HCl/dioxane (1.46 ml) was added and the mixture was stirred for 1.2 h at 23° C. The reaction was quenched at 0° C. with sat. Aqueous sodium bicarbonate (60 ml) and extracted with ethyl acetate (2×70 ml). The organic layers were dried (sodium sulphate) and concentrated in vacuo to afford 19 (267 mg, 95%) as a white solid that was used in subsequent reactions with no further purification.

Rf: 0.17 (ethyl acetate:methanol 10:1, SiO$_2$)

$^1$H NMR (300 MHz, CDCl$_3$): δ 6.49 (s, 1H), 6.12-6.00 (m, 1H), 5.94 (s, 1H), 5.86 (s, 1H), 5.34 (dd, J=1.0 Hz, J=17.4 Hz, 1H), 5.25 (dd, J=1.0 Hz, J-10.2 Hz, 1H), 4.18-3.76 (m, 5H), 3.74 (s, 3H), 3.71-3.59 (m, 1H), 3.36-3.20 (m, 4H), 3.01-2.90 (m, 1H), 2.60 (d, J=18.0 Hz, 1H), 2.29 (s, 3H), 2.24 (s, 3H), 2.11 (s, 3H), 1.97-1.86 (m, 1H), 0.93 (d, J=8.7 Hz, 3H)

$^{13}$C NMR (75 MHz, CDCl$_3$): δ 175.5, 148.4, 146.7, 144.4, 142.4, 138.9, 133.7, 131.3, 128.3, 120.8, 117.9, 117.4, 113.8, 112.4, 101.1, 74.2, 60.5, 59.1, 56.5, 56.1, 56.3, 56.0, 55.0, 50.5, 41.6, 39.5, 29.5, 26.4, 24.9, 21.1, 15.5, 9.33.

ESI-MS m/z: Calcd. for C$_{32}$H$_{39}$N$_5$O$_6$: 589. Found (M+H)$^+$: 590.

Example 7

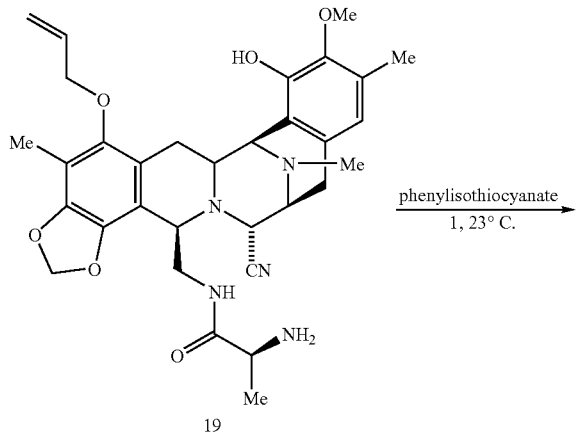

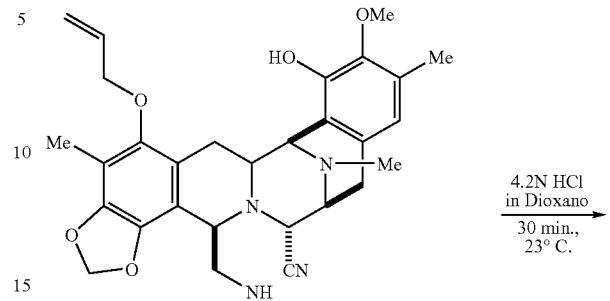

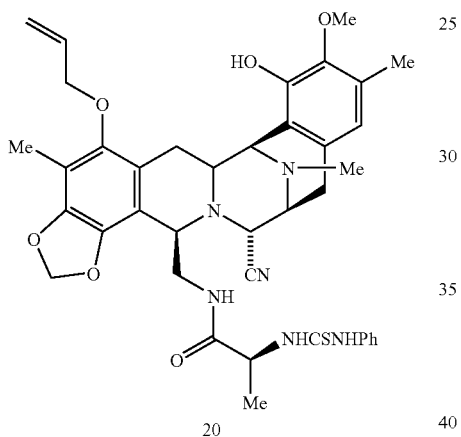

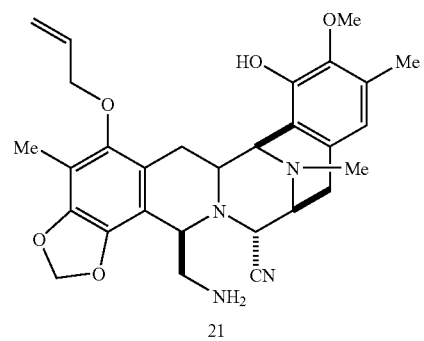

To a solution of 19 (250 mg, 0.42 mmol) in CH$_2$Cl$_2$ (1.5 mmol), phenyl isothiocyanate (0.3 ml, 2.51 mmol) was added and the mixture was stirred at 23° C. for 1 h. The reaction was concentrated in vacuo and the residue was purified by flash column chromatography (SiO$_2$, gradient Hexane to 5:1 hexane:ethyl acetate) to afford 20 (270 mg, 87%) as a white solid.

Rf: 0.56 (CHCl$_3$:ethyl acetate 1:4).

$^1$H NMR (300 MHz, CDCl$_3$): δ 8.00 (bs, 1H), 7.45–6.97 (m, 4H), 6.10 (s, 1H), 6.08–6.00 (m, 1H), 5.92 (s, 1H), 5.89 (s, 1H), 5.82 (s, 1H), 5.40 (dd, J=1.5 Hz, J=17.1 Hz, 1H), 3.38 (bs, 1H), 5.23 (dd, J=1.5 Hz, J=10.5 Hz, 1H), 4.42–4.36 (m, 1H), 4.19–4.03 (m, 5H), 3.71 (s, 3H), 3.68–3.17 (m, 4H), 2.90 (dd, J=7.8 Hz, J=18.3 Hz, 1H), 2.57 (d, J=18.3 Hz, 1H), 2.25 (s, 3H), 2.12 (s, 3H), 2.10 (s, 3H), 1.90 (dd, J=12.3 Hz, J=16.5 Hz, 1H), 0.81 (d, J=6.9 Hz, 3H).

$^{13}$C NMR (75 MHz, CDCl$_3$): δ 178.4, 171.6, 148.6, 146.8, 144.3, 142.7, 138.7, 136.2, 133.6, 130.7, 129.8, 126.6, 124.2, 124.1, 120.9, 120.5, 117.7, 117.4, 116.7, 112.6, 112.5, 101.0, 74.0, 60.6, 59.0, 57.0, 56.2, 56.1, 55.0, 53.3, 41.4, 39.7, 26.3, 24.8, 18.3, 15.5, 9.2.

ESI-MS m/z: Calcd. for C$_{39}$H$_{44}$N$_6$O$_6$S: 724.8 Found (M+H)$^+$: 725.3.

Example 8

To a solution of 20 (270 mg, 0.37 mmol) in dioxane (1 ml), 4.2N HCl/dioxane (3.5 ml) was added and the reaction was stirred at 23° C. for 30 min. Then, ethyl acetate (20 ml) and H$_2$O (20 ml) were added and the organic layer was decanted. The aqueous phase was basified with saturated aqueous sodium bicarbonate (60 ml) (pH=8) at 0° C. and then, extracted with CH$_2$Cl$_2$ (2×50 ml). The combined organic extracts were dried (sodium sulphate), and concentrated in vacuo. The residue was purified by flash column chromatography (SiO$_2$, ethyl acetate:methanol 5:1) to afford compound 21 (158 mg, 82%) as a white solid.

Rf: 0.3 (ethyl acetate:methanol 1:1).

$^1$H NMR (300 MHz, CDCl$_3$): δ 6.45 (s, 1H), 6.12–6.03 (m, 1H), 5.91 (s, 1H), 5.85 (s, 1H), 5.38 (dd, J$_1$=1.2 Hz, J$_2$=17.1 Hz, 1H), 5.24 (dd, J$_1$=1.2 Hz, J$_2$=10.5 Hz, 1H), 4.23–4.09 (m, 4H), 3.98 (d, J=2.1 Hz, 1H), 3.90 (bs, 1H), 3.72 (s, 3H), 3.36–3.02 (m, 5H), 2.72–2.71 (m, 2H), 2.48 (d, J=18.0 Hz, 1H), 2.33 (s, 3H), 2.22 (s, 3H), 2.11 (s, 3H), 1.85 (dd, J$_1$=11.7 Hz, J$_2$=15.6 Hz, 1H)).

$^{13}$C NMR (75 MHz, CDCl$_3$): δ 148.4, 146.7, 144.4, 142.8, 138.8, 133.8, 130.5, 128.8, 121.5, 120.8, 118.0, 117.5, 116.9, 113.6, 112.2, 101.1, 74.3, 60.7, 59.9, 58.8, 56.6, 56.5, 55.3, 44.2, 41.8, 29.7, 26.5, 25.7, 15.7, 9.4.

ESI-MS m/z: Calcd. for C$_{29}$H$_{34}$N$_4$O$_5$: 518.3. Found (M+H)$^+$: 519.2.

Example 9

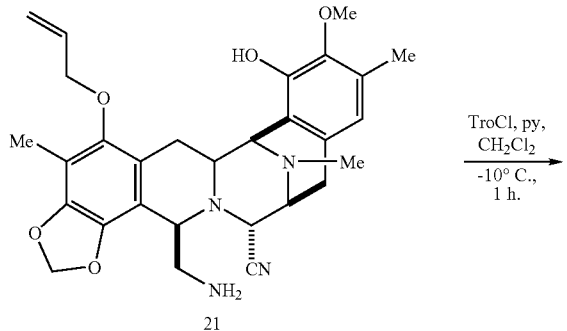

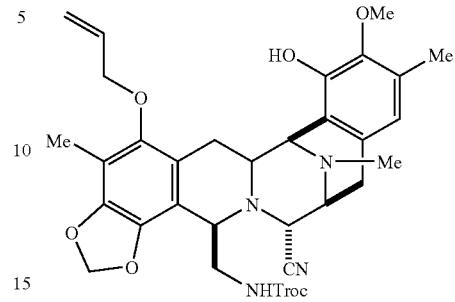

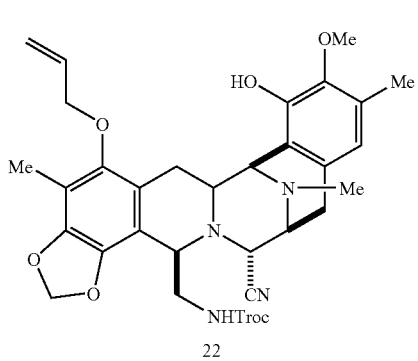

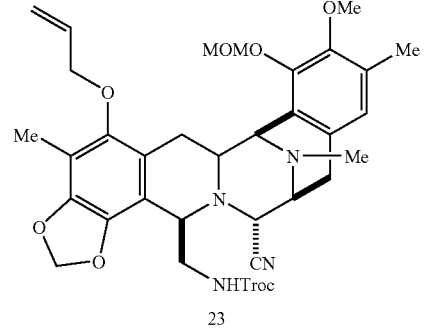

Example 10

To a solution of 21 (0.64 g, 1.22 mmol) in $CH_2Cl_2$ (6.13 ml), pyridine (0.104 ml, 1.28 mmol) and 2,2,2-trichloroethyl chloroformate (0.177 ml, 1.28 mmol) were added at −10° C. The mixture was stirred at this temperature for 1 h and then, the reaction was quenched by addition of 0.1N HCl (10 ml) and extracted with $CH_2Cl_2$ (2×10 ml). The organic layer was dried over sodium sulphate and concentrated in vacuo. The residue was purified by flash column chromatography ($SiO_2$; (hexane:ethyl acetate 1:2) to afford 22 (0.84 g, 98%) as a white foam solid.

Rf: 0.57 (ethyl acetate:methanol 5:1).

$^1$H NMR (300 MHz, $CDCl_3$): δ 6.50 (s, 1H), 6.10-6.00 (m, 1H), 6.94 (d, J=1.5 Hz, 1H), 5.87 (d, J=1.5 Hz, 1H), 5.73 (bs, 1H), 5.37 (dq, $J_1$=1.5 Hz, $J_2$=17.1 Hz, 1H), 5.26 (dq, $J_1$=1.8 Hz, $J_2$=10.2 Hz, 1H), 4.60 (d, J=12 Hz, 1H), 4.22-4.10 (m, 4H), 4.19 (d, J=12 Hz, 1H), 4.02 (m, 2H), 3.75 (s, 3H), 3.37-3.18 (m, 5H), 3.04 (dd, $J_1$=8.1 Hz, $J_2$=18 Hz, 1H), 2.63 (d, J=18 Hz, 1H), 2.31 (s, 3H), 2.26 (s, 3H), 2.11 (s, 3H), 1.85 (dd, $J_1$=12.3 Hz, $J_2$=15.9 Hz, 1H).

$^{13}$C NMR (75 MHz, $CDCl_3$) δ 154.3, 148.5, 146.7, 144.5, 142.8, 139.0, 133.8, 130.7, 128.7, 121.3, 120.8, 117.8, 117.7, 116.8, 112.7, 101.2, 77.2, 74.3, 60.7, 59.9, 57.0, 56.4, 55.3, 43.3, 41.7, 31.6, 26.4, 25.3, 22.6, 15.9, 14.1, 9.4.

ESI-MS m/z: Calcd. for $C_{32}H_{35}Cl_3N_4O_7$: 694.17. Found (M+H)$^+$: 695.2.

To a solution of 22 (0.32 g, 0.46 mmol) in $CH_3CN$ (2.33 ml), diisopropylethylamine (1.62 ml, 9.34 mmol), bromomethyl methyl ether (0.57 ml, 7.0 mmol) and dimethylaminopyridine (6 mg, 0.046 mmol) were added at 0° C. The mixture was heated at 30° C. for 10 h. Then, the reaction was diluted with dichloromethane (30 ml) and poured in an aqueous solution of HCl at pH=5 (10 ml). The organic layer was dried over sodium sulphate and the solvent was eliminated under reduced pressure to give a residue which was purified by flash column chromatography ($SiO_2$, hexane:ethyl acetate 2:1) to afford 23 (0.304 g, 88%) as a white foam solid.

Rf: 0.62 (hexane:ethyl acetate 1:3).

$^1$H NMR (300 MHz, $CDCl_3$): δ 6.73 (s, 1H), 6.10 (m, 1H), 5.94 (d, J=1.5 Hz, 1H), 5.88 (d, J=1.5 Hz, 1H), 5.39 (dq, $J_1$=1.5 Hz, $J_2$=17.1 Hz, 1H), 5.26 (dq, $J_1$=1.8 Hz, $J_2$=10.2 Hz, 1H), 5.12 (s, 2H), 4.61 (d, J=12 Hz, 1H), 4.55 (t, J=6.6 Hz, 1H), 4.25 (d, J=12 Hz, 1H), 4.22-4.11 (m, 4H), 4.03 (m, 2H), 3.72 (s, 3H), 3.58 (s, 3H), 3.38-3.21 (m, 5H), 3.05 (dd, $J_1$=8.1 Hz, $J_2$=18 Hz, 1H), 2.65 (d, J=18 Hz, 1H), 2.32 (s, 3H), 2.23 (s, 3H), 2.12 (s, 3H), 1.79 (dd, $J_1$=12.3 Hz, $J_2$=15.9 Hz, 1H);

$^{13}$C NMR (75 MHz, $CDCl_3$) δ 154.3, 148.6, 148.4, 144.5, 139.0, 133.6, 130.6, 130.1, 125.07, 124.7, 124.0, 121.1, 117.7, 112.6, 101.2, 99.2, 77.2, 74.4, 74.1, 59.8, 59.8, 57.7, 57.0, 56.8, 56.68, 55.3, 43.2, 41.5, 26.4, 25.2, 15.9, 9.3.

ESI-MS m/z: Calcd. for $C_{34}H_{39}Cl_3N_4O_8$: 738.20. Found (M+H)$^+$: 739.0.

Example 11

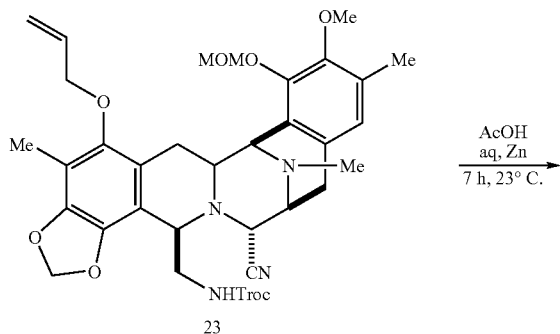

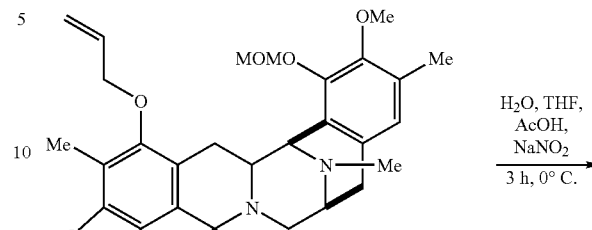

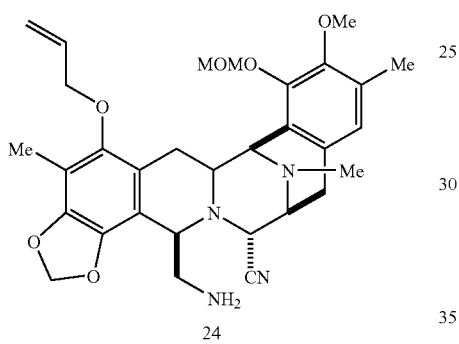

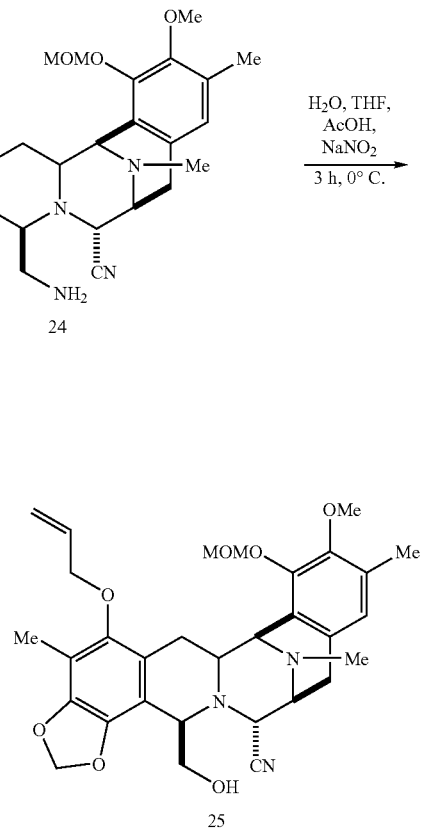

Example 12

To a suspension of 23 (0.304 g, 0.41 mmol) in 90% aqueous acetic acid (4 ml), powder zinc (0.2 g, 6.17 mmol) was added and the reaction was stirred for 7 hour at 23° C. The mixture was filtered through a pad of celite which was washed with $CH_2Cl_2$. The organic layer was washed with an aqueous sat. solution of sodium bicarbonate (pH=9) (15 ml) and dried over sodium sulphate. The solvent was eliminated under reduced pressure to give 24 (0.191 g, 83%) as a white solid.

Rf: 0.3 (ethyl acetate:methanol 5:1).

$^1$H NMR (300 MHz, $CDCl_3$): δ 6.68 (s, 1H), 6.09 (m, 1H), 5.90 (d, J=1.5 Hz, 1H), 5.83 (d, J=1.5 Hz, 1H), 5.39, (dq, $J_1$=1.5 Hz, $J_2$=17.1 Hz, 1H), 5.25 (dq, $J_1$=1.5 Hz, $J_2$=10.2 Hz, 1H), 5.10 (s, 2H), 4.22-4.09 (m, 3H), 3.98 (d, J=2.4 Hz, 1H), 3.89 (m, 1H), 3.69 (s, 3H), 3.57 (s, 3H), 3.37-3.17 (m, 3H), 3.07 (dd, $J_1$=8.1 Hz, $J_2$=18 Hz, 1H), 2.71 (m, 2H), 2.48 (d, J=18 Hz, 1H), 2.33 (s, 3H), 2.19 (s, 3H), 2.17 (s, 3H), 1.80 (dd, $J_1$=12.3 Hz, $J_2$=15.9 Hz, 1H)

$^{13}$C NMR (75 MHz, $CDCl_3$): δ 148.5, 148.2, 144.3, 138.7, 133.7, 130.7, 129.9, 125.0, 123.9, 121.3, 117.9, 117.5, 113.6, 112.0, 101.0, 99.2, 74.0, 59.8, 59.7, 58.8, 57.6, 57.0, 56.2, 55.2, 44.2, 41.5, 31.5, 26.4, 25.6, 22.5, 16.7, 14.0, 9.2.

ESI-MS m/z: Calcd. for $C_{31}H_{38}N_4O_6$: 562.66. Found $(M+H)^+$: 563.1.

To a solution of 24 (20 mg, 0.035 mmol), in $H_2O$ (0.7 mmol) and THF (0.7 mmol), $NaNO_2$ (12 mg, 0.17 mmol) and 90% aqueous AcOH (0.06 ml) were added at 0° C. and the mixture was stirred at 0° C. for 3 h. After dilution with $CH_2Cl_2$ (5 ml), the organic layer was washed with water (1 ml), dried over sodium sulphate and concentrated in vacuo.

The residue was purified by flash column chromatography ($SiO_2$, hexane:ethyl acetate 2:1) to afford 25 (9.8 mg, 50%) as a white solid.

Rf: 0.34 (hexane:ethyl acetate 1:1).

$^1$H NMR (300 MHz, $CDCl_3$): δ 6.71 (s, 1H), 6.11 (m, 1H), 5.92 (d, J=1.5 Hz, 1H), 5.87 (d, J=1.5 Hz, 1H), 5.42 (dq, $J_1$=1.5 Hz, $J_2$=17.1 Hz, 1H), 5.28 (dq, $J_1$=1.5 Hz, $J_2$=10.2 Hz, 1H), 5.12 (s, 2H), 4.26-4.09 (m, 3H), 4.05 (d, J=2.4 Hz, 1H), 3.97 (t, J=3.0 Hz, 1H), 3.70 (s, 3H), 3.67-3.32 (m, 4H), 3.58 (s, 3H), 3.24 (dd, $J_1$=2.7 Hz, $J_2$=15.9 Hz, 1H), 3.12 (dd, $J_1$=8.1 Hz, $J_2$=18.0 Hz, 1H), 2.51 (d, J=18 Hz, 1H), 2.36 (s, 3H), 2.21 (s, 3H), 2.12 (s, 3H), 1.83 (dd, $J_1$=12.3 Hz, $J_2$=15.9 Hz, 1H)

$^{13}$C NMR (75 MHz, $CDCl_3$) δ 148.7, 148.4, 138.9, 133.7, 131.1, 129.4, 125.1, 123.9, 120.7, 117.6, 117.5, 113.2, 112.3, 101.1, 99.2, 74.0, 63.2, 59.8, 59.7, 57.9, 57.7, 57.0, 56.5, 55.2, 41.6, 29.6, 26.1, 25.6, 22.6, 15.7, 9.2.

ESI-MS m/z: Calcd. for $C_{31}H_{37}N_3O_7$: 563.64. Found $(M+H)^+$: 564.1.

Example 13

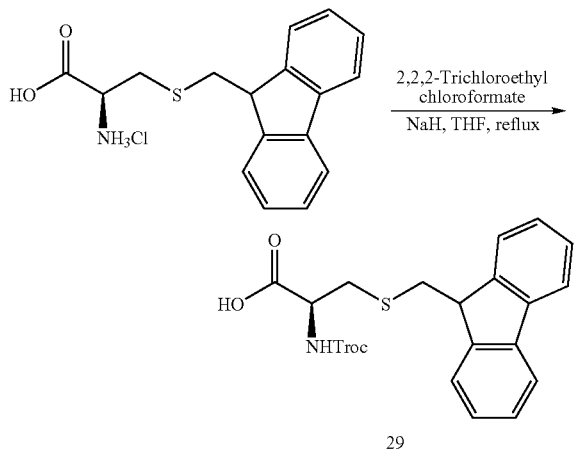

The starting material (2.0 g, 5.90 mmol) was added to a suspension of sodium hydride (354 mg, 8.86 mmol) in THF (40 ml) at 23° C., following the suspension was treated with allyl chloroformate (1.135 ml, 8.25 mmol) at 23° C. and then refluxed for 3 hours. The suspension was cooled, filtered off, the solid washed with ethyl acetate (100 ml), and the filtrate was concentrated. The oil crude was ground with hexane (100 ml) and kept at 4° C. overnight. After, the solvent was decanted and the light yellow slurry was treated with $CH_2Cl_2$ (20 ml), and precipitated with hexane (100 ml). After 10 minutes, the solvent was decanted again. The operation was repeated until appearing a white solid. The white solid was filtered off and dried to afford compound 29 (1.80 g, 65%) as a white solid.

$^1$H-NMR (300 MHz, CDCl$_3$): δ 7.74 (d, J=7.5 Hz, 2H), 7.62 (d, J=6.9 Hz, 2H), 7.33 (t, J=7.5 Hz, 2H), 7.30 (t, J=6.3 Hz, 2H), 5.71 (d, J=7.8 Hz, 1H), 4.73 (d, J=7.8 Hz, 2H), 4.59 (m, 1H), 4.11 (t, J=6.0 Hz, 1H), 3.17 (dd, J=6.0 Hz, J=2.7 Hz, 2H), 3.20 (dd, J=5.4 Hz, J=2.1 Hz, 2H).

$^{13}$C-NMR (75 MHz, CDCl$_3$): δ 173.6, 152.7, 144.0, 139.7, 137.8, 126.0, 125.6, 123.4, 118.3, 73.4, 52.4, 45.5, 35.8, 33.7.

ESI-MS m/z: Calcd. for $C_{20}H_{18}Cl_3NO_4S$: 474.8. Found (M+Na)$^+$: 497.8

Example 14

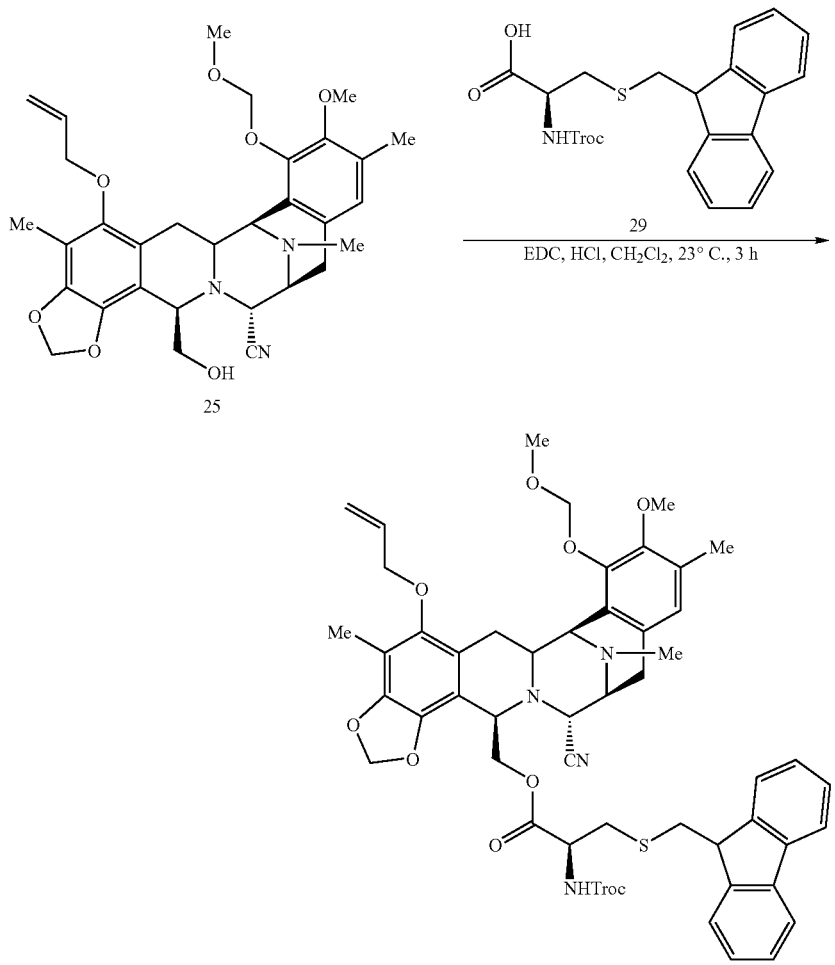

A mixture of compound 25 (585 mg, 1.03 mmol) and compound 29 (1.47 mg, 3.11 mmol) were azeotroped with anhydrous toluene (3×0.10 ml). To a solution of 25 and 29 in anhydrous $CH_2Cl_2$ (40 ml) was added DMAP (633 mg, 5.18 mmol) and EDC-HCl (994 mg, 5.18 mmol) at 23° C. The reaction mixture was stirred at 23° C. for 3 hours. The mixture was partitioned with saturated aqueous solution of sodium bicarbonate (50 ml) and the layers were separated. The aqueous layer was washed with $CH_2Cl_2$ (50 ml). The combined organic layers were dried over sodium sulphate, filtered and concentrated. The crude was purified by flash column chromatography (ethyl acetate/hexane 1:3) to obtain 30 (1.00 g, 95%) as a pale cream yellow solid.

$^1$H-NMR (300 MHz, CDCl$_3$): δ 7.72 (m, 2H), 7.52 (m, 2H), 7.38 (m, 2H), 7.28 (m, 2H), 6.65 (s, 1H), 6.03 (m, 1H), 5.92 (d, J=1.5 Hz, 1H), 5.79 (d, J=1.5 Hz, 1H), 5.39 (m, 1H), 5.29 (dq, J=10.3 Hz, J=1.5 Hz, 1H), 5.10 (s, 2H), 4.73 (d, J=11.9 Hz, 1H), 4.66 (d, J=11.9 Hz, 1H), 4.53 (m, 1H), 4.36-3.96 (m, 9H), 3.89 (t, J=6.4 Hz, 1H), 3.71 (s, 3H), 3.55 (s, 3H), 3.33 (m, 1H), 3.20 (m, 2H), 2.94 (m, 3H), 2.59 (m, 1H), 2.29 (s, 3H), 2.23 (s, 3H), 2.02 (s, 3H), 1.83 (dd, J=16.0 Hz, J=11.9 Hz, 1H).

$^{13}$C-NMR (75 MHz, CDCl$_3$): δ 169.7, 154.0, 148.8, 148.4, 145.7, 144.5, 140.9, 139.0, 133.7, 130.9, 130.6, 127.6, 127.0, 124.8, 124.6, 124.1, 120.8, 119.9, 118.2, 117.7, 117.3, 112.7, 112.1, 101.3, 99.2, 74.7, 73.9, 64.4, 59.8, 57.7, 57.0, 56.8, 55.4, 53.3, 46.7, 41.4, 36.5, 34.7, 31.5, 26.4, 24.9, 22.6, 15.7, 14.0, 9.1

ESI-MS m/z: Calcd. for $C_{51}H_{53}Cl_3N_4O_{10}S$: 1020.4. Found (M+H)$^+$: 1021.2

Example 15

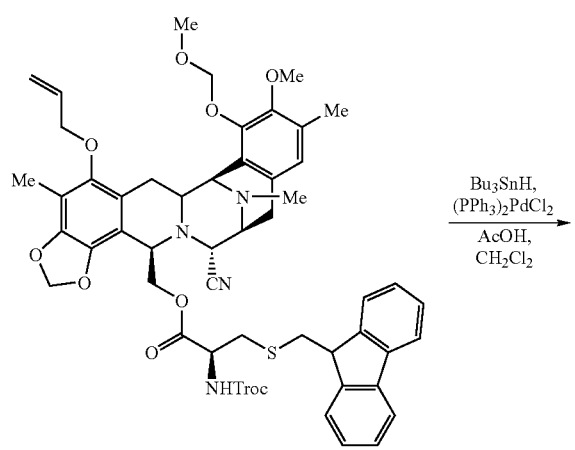

30

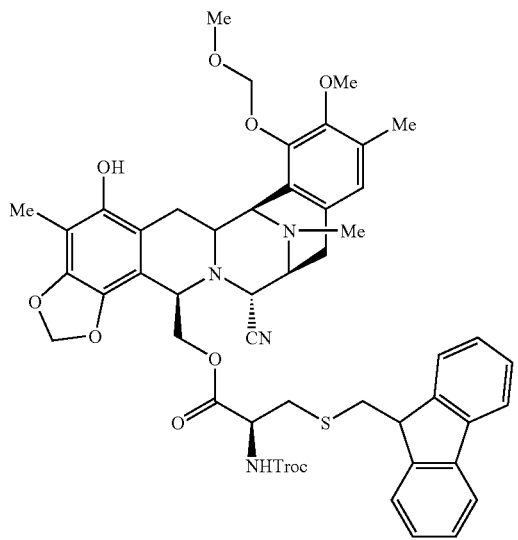

31

To a solution of 30 (845 mg, 0.82 mmol), acetic acid (500 mg, 8.28 mmol) and (PPh$_3$)$_2$PdCl$_2$ (29 mg, 0.04 mmol) in anhydrous CH$_2$Cl$_2$ 20 ml at 23° C. was added, dropwise, Bu$_3$SnH (650 mg, 2.23 mmol). The reaction mixture was stirred at this temperature for 15 min., bubbling was. The crude was quenched with water (50 ml) and extracted with CH$_2$Cl$_2$ (3×50 ml). The organic layers were dried over sodium sulphate, filtered and concentrated. The crude was purified by flash column chromatography (ethyl acetate/hexane in gradient from 1:5 to 1:3) to obtain compound 31 (730 mg, 90%) as a pale cream yellow solid.

$^1$H-NMR (300 MHz, CDCl$_3$): δ 7.72 (m, 2H), 7.56 (m, 2H), 7.37 (m, 2H), 7.30 (m, 2H), 6.65 (s, 1H), 5.89 (s, 1H), 5.77 (s, 1H), 5.74 (s, 1H), 5.36 (d, J=5.9 Hz, 1H), 5.32 (d, J=5.9 Hz, 1H), 5.20 (d, J=9.0, 1H), 4.75 (d, J=12.0 Hz, 1H), 4.73 (m, 1H), 4.48 (d, J=11.9 Hz, 1H), 4.08 (m, 4H), 3.89 (m, 1H), 3.86, (t, J=6.2 Hz, 1H), 3.70 (s, 3H), 3.69 (s, 3H), 3.38 (m, 1H), 3.25 (m, 1H), 3.02-2.89 (m, 4H), 2.67 (s, 1H), 2.61 (s, 1H), 2.51 (dd, J=14.3 Hz, J=4.5 Hz, 1H), 2.29 (s, 3H), 2.23 (s, 3H), 1.95 (s, 3H), 1.83 (m, 1H).

$^{13}$C-NMR (75 MHz, CDCl$_3$): δ 168.2, 152.5, 148.1, 146.2, 144.4, 144.3, 143.3, 139.6, 134.6, 129.7, 129.6, 126.2, 125.6, 123.4, 123.3, 121.6, 118.5, 116.3, 110.7, 110.2, 105.1, 99.4, 98.5, 75.2, 73.3, 61.7, 58.4, 57.9, 56.3, 56.1, 55.1, 54.7, 53.9, 51.9, 45.2, 40.1, 35.6, 33.3, 24.8, 23.3, 14.5, 7.3.

ESI-MS m/z: Calcd. for $C_{48}H_{49}Cl_3N_4O_{10}S$: 980.3. Found (M+H)$^+$: 981.2

Example 16

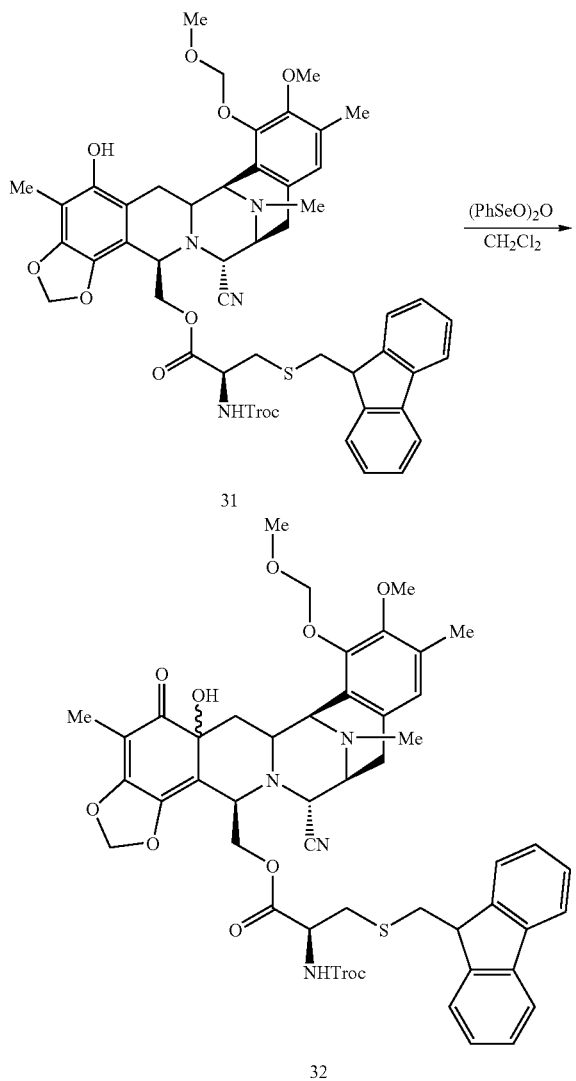

To a solution of 31 (310 mg, 0.32 mmol), in anhydrous CH$_2$Cl$_2$ (15 ml) at −10° C. was added a solution of benzeneseleninic anhydride 70% (165 mg, 0.32 mmol), in anhydrous CH$_2$Cl$_2$ (7 ml), via cannula, keeping the temperature at −10° C. The reaction mixture was stirred at −10° C. for 5 min. A saturated solution of sodium bicarbonate (30 ml) was added at this temperature. The aqueous layer was washed with more CH$_2$Cl$_2$ (40 ml). The organic layers were dried over sodium sulphate, filtered and concentrated. The crude was purified by flash column chromatography (ethyl acetate/hexane in gradient from 1:5 to 1:1) to obtain 32 (287 mg, 91%, HPLC: 91.3%) as a pale cream yellow solid and as a mixture of two isomers (65:35) which were used in the next step.

$^1$H-NMR (300 MHz, CDCl$_3$): δ (Mixture of isomers) 7.76 (m, 4H), 7.65 (m, 4H), 7.39 (m, 4H), 7.29 (m, 4H), 6.62 (s, 1H), 6.55 (s, 1H), 5.79-5.63 (m, 6H), 5.09 (s, 1H), 5.02 (d, J=6.0 Hz, 1H), 4.99 (d, J=6.0 Hz, 1H), 4.80-4.63 (m, 6H), 4.60 (m, 1H), 4.50 (m, 1H), 4.38 (d, J=12.8 Hz, J=7.5 Hz, 1H), 4.27 (dd, J=12.8 Hz, J=7.5 Hz, 1H), 4.16-3.90 (m, 10H), 3.84 (s, 3H), 3.62 (s, 3H), 3.50 (s, 3H), 3.49 (s, 3H), 3.33-2.83 (m, 14H), 2.45-2.18 (m, 2H), 2.21 (s, 6H), 2.17 (s, 6H), 1.77 (s, 6H), 1.67 (m, 2H).

$^{13}$C-NMR (75 MHz, CDCl$_3$): δ (Mixture of isomers) 168.6, 168.4, 158.6, 154.8, 152.8, 152.5, 147.3, 147.2, 146.8, 144.1, 144.0, 140.8, 139.7, 137.1, 129.8, 129.3, 128.4, 128.7, 126.5, 125.5, 123.7, 123.6, 123.5, 123.4, 122.2, 121.3, 118.3, 115.8, 115.5, 110.2, 106.9, 103.5, 103.2, 100.1, 99.6, 97.9, 97.7, 93.8, 73.4, 70.9, 69.2, 64.9, 62.5, 59.3, 58.9, 58.4, 56.7, 56.3, 56.2, 55.4, 55.2, 55.1, 54.9, 54.7, 54.3, 54.1, 53.8, 52.8, 45.5, 40.5, 40.0, 39.8, 35.8, 35.5, 33.9, 33.7, 30.1, 28.8, 24.2, 24.1, 21.2, 14.5, 14.4, 12.7, 6.0, 5.7.

ESI-MS m/z: Calcd. for C$_{48}$H$_{49}$Cl$_3$N$_4$O$_{11}$S: 996.3. Found (M+H)$^+$: 997.2

Example 17

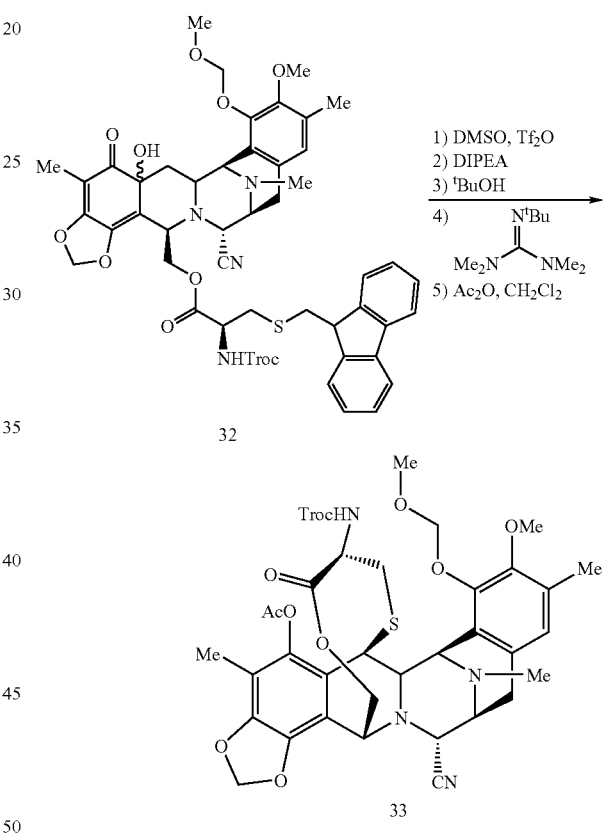

The reaction flask was flamed twice, purged vacuum/Argon several times and kept under Argon atmosphere for the reaction. To a solution of DMSO (39.1 ml, 0.55 mmol, 5 equivalents.) in anhydrous CH$_2$Cl$_2$ (4.5 ml) was dropwise added triflic anhydride (37.3 ml, 0.22 mmol, 2 equivalents.) at −78° C. The reaction mixture was stirred at −78° C. for 20 minutes, then a solution of 32 (110 mg, 0.11 mmol, HPLC: 91.3%) in anhydrous CH$_2$Cl$_2$ (1 ml, for the main addition and 0.5 ml for wash) at −78° C. was added, via cannula. During the addition the temperature was kept at −78° C. in both flasks and the colour changed from yellow to brown. The reaction mixture was stirred at −40° C. for 35 minutes. During this period of time the solution was turned from yellow to dark green. After this time, $^i$Pr$_2$NEt (153 ml, 0.88 mmol, 8 equivalents.) was dropwise added and the reaction mixture was kept at 0° C. for 45 minutes, the colour of the solution turned to brown during this time. Then t-butanol (41.6 ml, 0.44 mmol, 4 equivalents.) and 2-'Butyl-1,1,3,3-tetramethylguanidine (132.8 ml, 0.77 mmol, 7 equivalents.) were dropwise added and the reaction mixture was stirred at 23° C. for 40 minutes. After this time, acetic anhydride (104.3 ml, 1.10 mmol, 10 equivalents.) was dropwise added and the reaction mixture was kept at 23° C. for 1 hour more. Then the reaction mixture was diluted with $CH_2Cl_2$ (20 ml) and washed with aqueous saturated solution of $NH_4Cl$ (50 ml), sodium bicarbonate (50 ml), and sodium chloride (50 ml). The combined organic layers were dried over sodium sulphate, filtered and concentrated. The residue was purified by flash column chromatography (eluent:ethyl acetate/hexane gradient from 1:3 to 1:2) to afford compound 33 (54 mg, 58%) as a pale yellow solid.

$^1$H-NMR (300 MHz, CDCl$_3$): δ 6.85 (s, 1H), 6.09 (s, 1H), 5.99 (s, 1H), 5.20 (d, J=5.8 Hz, 1H), 5.14 (d, J=5.3 Hz, 1H), 5.03 (m, 1H), 4.82 (d, J=12.2, 1H), 4.63 (d, J=12.0 Hz, 1H), 4.52 (m, 1H), 4.35-4.17 (m, 4H), 3.76 (s, 3H), 3.56 (s, 3H), 3.45 (m, 2H), 2.91 (m, 2H), 2.32 (s, 3H), 2.28 (s, 3H), 2.21 (s, 3H), 2.12 (m, 2H), 2.03 (s, 3H).

$^{13}$C-NMR (75 MHz, CDCl$_3$): δ 168.5, 167.2, 152.7, 148.1, 147.1, 144.5, 139.6, 139.1, 130.5, 129.0, 123.7, 123.5, 123.3, 118.8, 116.5, 112.1, 100.6, 97.8, 73.3, 60.5, 59.4, 59.2, 58.3, 57.6, 57.4, 56.1, 53.3, 53.1, 40.6, 40.0, 31.0, 22.2, 18.9, 14.4, 8.1.

ESI-MS m/z: Calcd. for $C_{36}H_{39}Cl_3N_4O_{11}S$: 842.1. Found $(M+H)^+$: 843.1

Example 18

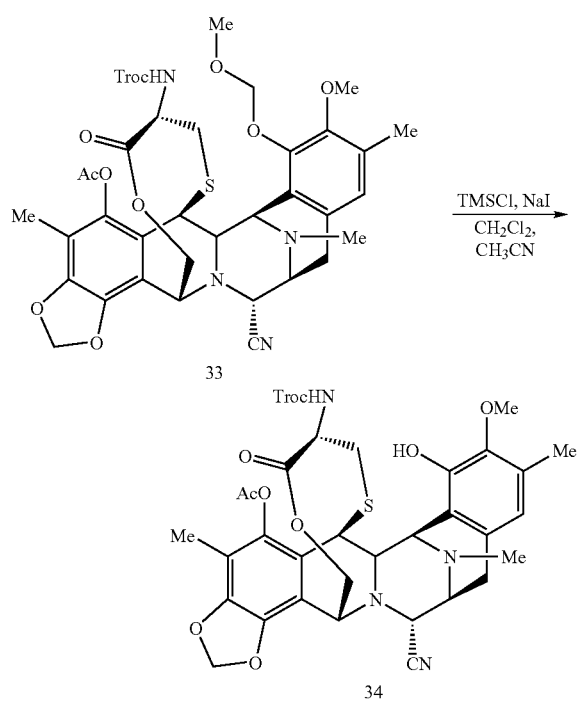

To a solution of 33 (12 mg, 0.014 mmol) in dry dichloromethane (1.2 ml) and HPLC grade acetonitrile (1.2 ml) was added at 23° C. sodium iodide (21 mg, 0.14 mmol) and freshly distilled (over calcium hydride at atmospheric pressure) trimethylsilyl chloride (15.4 mg, 0.14 mmol). The reaction mixture turned to orange colour. After 15 min the solution was diluted with dichloromethane (10 ml) and was washed with a freshly aqueous saturated solution of $Na_2S_2O_4$ (3×10 ml). The organic layer was dried over sodium sulphate, filtered and concentrated. It was obtained compound 34 (13 mg, quantitative) as pale yellow solid which was used without further purification.

$^1$H-NMR (300 MHz, CDCl$_3$): δ 6.85 (s, 1H), 6.09 (s, 1H), 5.99 (s, 1H), 5.27 (d, J=5.8 Hz, 1H), 5.14 (d, J=5.3 Hz, 1H), 5.03 (d, J=11.9 Hz, 1H), 4.82 (d, J=12.2, 1H), 4.63 (d, J=13.0 Hz, 1H), 4.52 (m, 1H), 4.34 (m, 1H), 4.27 (bs, 1H), 4.18 (m, 2H), 3.76 (s, 3H), 3.56 (s, 3H), 3.44 (m, 1H), 3.42 (m, 1H), 2.91 (m, 2H), 2.32 (s, 3H), 2.28 (s, 3H), 2.21 (s, 3H), 2.03 (s, 3H).

ESI-MS m/z: Calcd. for $C_{34}H_{35}N_4O_{10}S$: 798.1. Found $(M+H)^+$: 799.1

Example 19

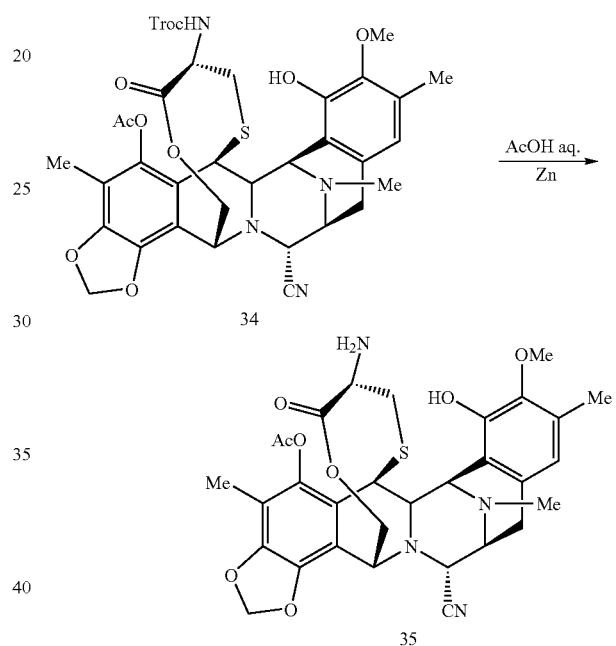

To a solution of 34 (13 mg, 0.016 mmol) in a mixture of acetic acid/$H_2O$ (90:10, 1 ml) was added powder Zinc (5.3 mg, 0.081 mmol) at 23° C. The reaction mixture was heated at 70° C. for 6 h. After this time, was cooled to 23° C., diluted with $CH_2Cl_2$ (20 ml) and washed with aqueous saturated solution of sodium bicarbonate (15 ml) and aqueous solution of Et$_3$N (15 ml). The organic layer was dried over sodium sulphate, filtered and concentrated. The residue was purified by flash column chromatography with Silica-NH$_2$ (eluent: ethyl acetate/hexane gradient from 0:100 to 50:50) to afford compound 35 (6.8 mg, 77% for two steps) as a pale yellow solid.

$^1$H-NMR (300 MHz, CDCl$_3$): δ 6.51 (s, 1H), 6.03 (dd, J=1.3 Hz, J=26.5 Hz, 2H), 5.75 (bs, 1H), 5.02 (d, J=11.6 Hz, 1H), 4.52 (m, 1H), 4.25 (m, 2H), 4.18 (d, J=2.5 Hz, 1H), 4.12 (dd, J=1.9 Hz, J=11.5 Hz, 1H), 3.77 (s, 3H), 3.40 (m, 2H), 3.26 (t, J=6.4 Hz, 1H), 2.88 (m, 2H), 2.30-2.10 (m, 2H), 2.30 (s, 3H), 2.28 (s, 3H), 2.18 (s, 3H), 2.02 (s, 3H).

$^{13}$C-NMR (75 MHz, CDCl$_3$): δ 174.1, 168.4, 147.8, 145.4, 142.9, 140.8, 140.1, 131.7, 130.2, 129.1, 128.3, 120.4, 118.3, 117.9, 113.8, 111.7, 101.7, 61.2, 59.8, 59.2, 58.9, 54.4, 53.8, 54.4, 41.3, 41.5, 34.1, 23.6, 20.3, 15.5, 9.4.

ESI-MS m/z: Calcd. for $C_{31}H_{34}N_4O_8S$: 622.7. Found $(M+H)^+$: 623.2.

Example 20

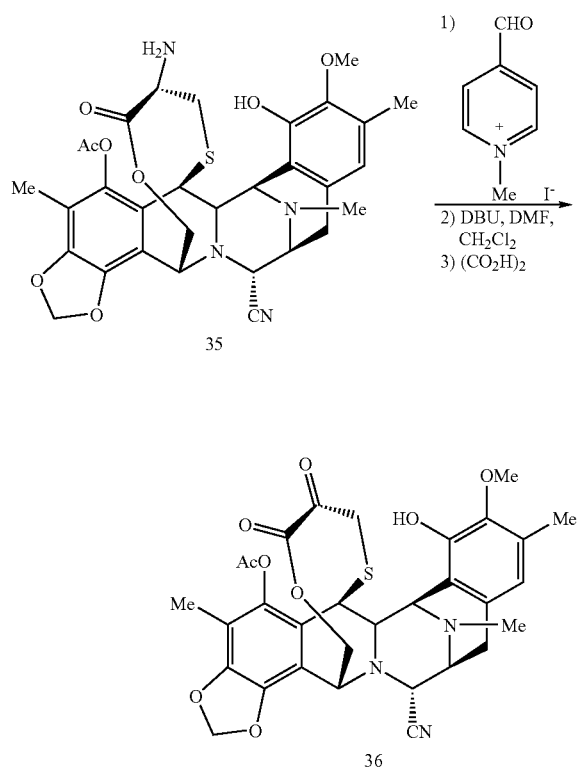

A solution of N-methylpyridine-4-carboxaldehyde iodide (378 mg, 1.5 mmol) in anhydrous DMF (5.8 mL) was treated with anhydrous toluene (2×10 mL) to eliminate the amount of water by azeotropic removal of the toluene. A solution of 35 (134 mg, 0.21 mmol), previously treated with anhydrous toluene (2×10 mL), in anhydrous $CH_2Cl_2$ (distilled over $CaH_2$, 7.2 mL) was added, via cannula, at 23° C. to this orange solution. The reaction mixture was stirred at 23° C. for 4 hours. After this time DBU (32.2 □L, 0.21 mmol) was dropwise added at 23° C. and it was stirred for 15 minutes at 23° C. A freshly aqueous saturated solution of oxalic acid (5.8 mL) was added to the reaction mixture and was stirred for 30 minutes at 23° C. Then the reaction mixture was cooled to 0° C. and $NaHCO_3$ was portionwise added followed by addittion of aqueous saturated solution of $NaHCO_3$. The mixture was extracted with $Et_2O$. $K_2CO_3$ was added to the aqueous layer and it was extrated with $Et_2O$. The combined organic layers were dried over $MgSO_4$ and the solvent was removed under reduced pressure. The crude was purified by flash column chromatography (AcOEt/hexane from 1/3 to 1/1) to afford compound 36 (77 mg, 57%) as pale yellow solid.

$^1$H-NMR (300 MHz, $CDCl_3$): δ 6.48 (s, 1H), 6.11 (d, J=1.3 Hz, 1H), 6.02 (d, J=1.3 Hz, 1H), 5.70 (bs, 1H), 5.09 (d, J=11.3 Hz, 1H), 4.66 (bs, 1H), 4.39 (m, 1H), 4.27 (d, J=5.6 Hz, 1H), 4.21 (d, J=10.5 Hz, 1H), 4.16 (d, J=2.6 Hz, 1H), 3.76 (s, 3H), 3.54 (d, J=5.1 Hz, 1H), 3.42 (d, 3=8.5 Hz, 1H), 2.88-2.54 (m, 3H), 2.32 (s, 3H), 2.24 (s, 3H), 2.14 (s, 3H), 2.04 (s, 3H). $^{13}$C-NMR (75 MHz, $CDCl_3$): δ 186.7, 168.5, 160.5, 147.1, 146.4, 142.9, 141.6, 140.7, 130.4, 129.8, 121.7 (2C), 120.0, 117.8, 117.1, 113.5, 102.2, 61.7, 61.4, 60.3, 59.8, 58.9, 54.6, 41.6, 36.9, 29.7, 24.1, 20.3, 15.8, 14.1, 9.6.

ESI-MS m/z: Calcd. for $C_{31}H_{31}N_3O_9S$: 621.7. Found $(M+H)^+$: 622.2

Example 21

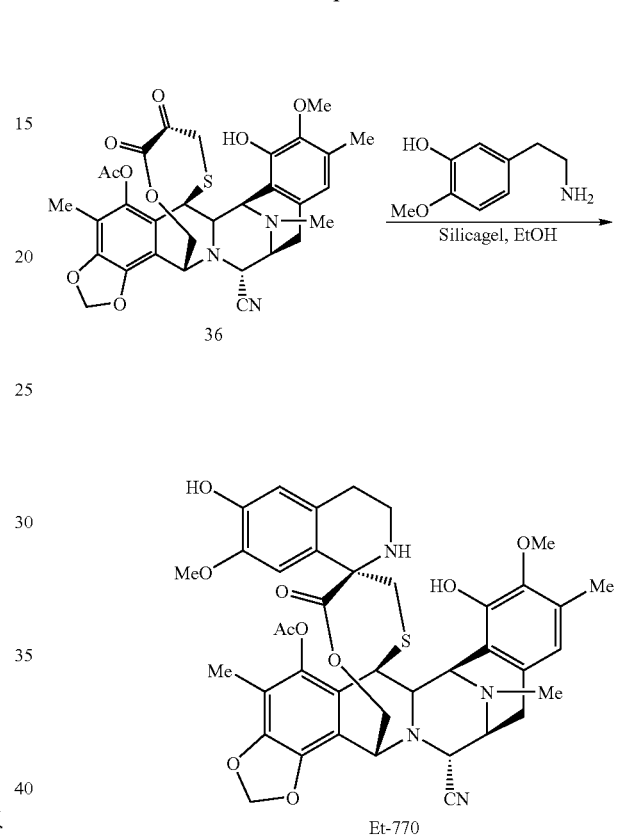

To a solution of 36 (49 mg, 0.08 mmol) and 2-[3-hydroxy-4-methoxyphenyl]ethylamine (46.2 mg, 0.27 mmol) in ethanol (2.5 ml) was added silica gel (105 mg) at 23° C. The reaction mixture was stirred at 23° C. for 14 h. It was diluted with hexane and poured into a column of chromatography (ethyl acetate/hexane from 1/3 to 1/1) to afford Et-770 (55 mg, 90%) as a pale yellow solid.

$^1$H-NMR (300 MHz, $CDCl_3$): δ 6.60 (s, 1H), 6.47 (s, 1H), 6.45 (s, 1H), 6.05 (s, 1H), 5.98 (s, 1H), 5.02 (d, J=111.4 Hz, 1H), 4.57 (bs, 1H), 4.32 (bs, 1H), 4.28 (d, J=5.3 Hz, 1H), 4.18 (d, J=2.5 Hz, 1H), 4.12 (dd, J=2.1 Hz, J=11.5 Hz, 1H), 3.78 (s, 3H), 3.62 (s, 3H), 3.50 (d, J=5.0 Hz, 1H), 3.42 (m, 1H), 3.10 (ddd, $J_1$=4.0 Hz, $J_2$=10.0 Hz, $J_3$=11.0 Hz, 1H), 2.94 (m, 2H), 2.79 (m, 1H), 2.61 (m, 1H), 2.47 (m, 1H), 2.35 (m, 1H), 2.32 (s, 3H), 2.27 (s, 3H), 2.20 (s, 3H), 2.09 (m, 1H), 2.04 (s, 3H).

ESI-MS m/z: Calcd. for $C_{40}H_{42}N_4O_{10}S$: 770.7. Found $(M+H)^+$: 771.2

Example 22

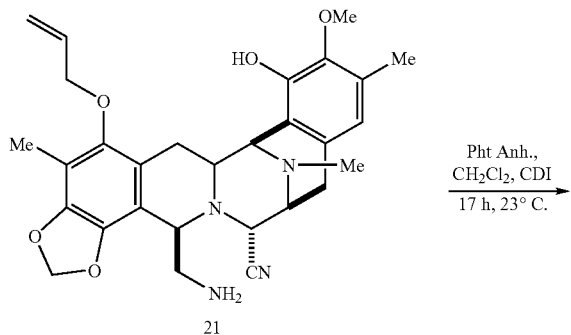

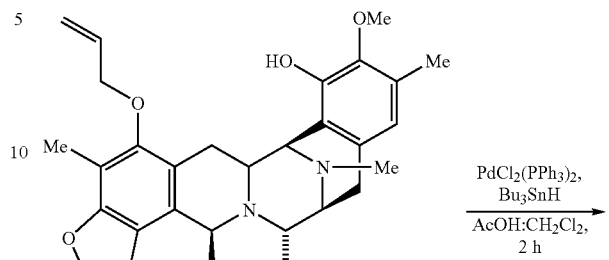

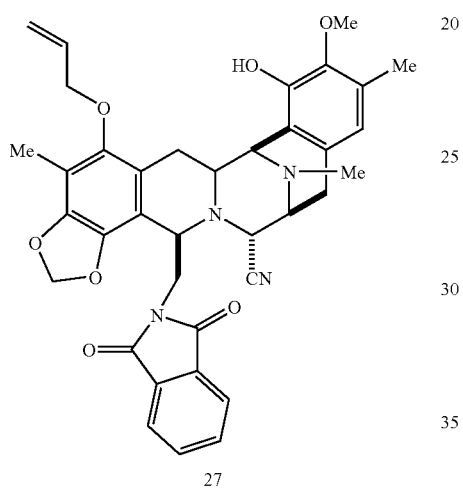

To a solution of 21 (22 mg, 0.042 mmol) in CH$_2$Cl$_2$ (0.8 ml) was added phthalic anhydride (6.44 mg, 0.042 mmol) and the reaction mixture was stirred for 2 h at 23° C. Then, carbonyldiimidazole (1 mg, 0.006 mmol) was added and the mixture was stirred at 23° C. for 7 h. Then, carbonyldiimidazole (5.86 mg, 0.035 ml) was added and the reaction was stirred at 23° C. for an additional 17 h. The solution was diluted with CH$_2$Cl$_2$ (15 ml) and washed with 0.1 N HCl (15 ml). The organic layer was dried over sodium sulphate, filtered, and the solvent was eliminated under reduced pressure. The residue was purified by flash column chromatography (SiO$_2$, hexane:ethyl acetate 2:1) to afford 27 (26.4 mg, 96%) as a white solid.

Rf: 0.58 (ethyl acetate).

$^1$H NMR (300 MHz, CDCl$_3$): δ 7.73-7.64 (m, 4H), 6.40 (s, 1H), 6.12-6.01 (m, 1H), 5.63 (s, 1H), 5.58 (d, J=1.5 Hz, 1H), 5.37 (dd, J$_1$=1.8 Hz, J$_2$=17.4 Hz), 5.23 (dd, J$_1$=1.8 Hz, J$_2$=10.5 Hz, 1H), 5.12 (d, J=1.5 Hz, 1H), 4.22-4.15 (m, 3H), 4.08 (d, J=1.8 Hz, 1H), 3.68 (s, 3H), 3.59-3.55 (m 2H), 3.35 (d, J=8.1 Hz, 1H), 3.27-3.16 (m, 2H), 3.05 (dd, J$_1$=8.1 Hz, J$_2$=18.3 Hz, 1H), 2.64 (d, J=18.0 Hz, 1H), 2.30 (s, 3H), 2.24 (s, 3H), 2.09 (s, 3H), 1.80 (dd, J$_1$=11.4 Hz, J$_2$=15 Hz, 1H);

$^{13}$C NMR (75 MHz, CDCl$_3$): δ 167.7, 148.9, 146.4, 144.2, 142.6, 139.5, 134.0, 133.5, 132.0, 131.0, 128.3, 123.0, 121.3, 120.9, 118.1, 117.5, 116.8, 113.6, 112.4, 100.8, 74.5, 60.6, 60.5, 57.7, 56.6, 55.6, 55.5, 42.3, 41.7, 26.6, 25.5, 15.9, 9.46.

ESI-MS m/z: Calcd. for C$_{37}$H$_{35}$N$_4$O$_7$: 648.79. Found (M+H)$^+$: 649.3.

Example 23

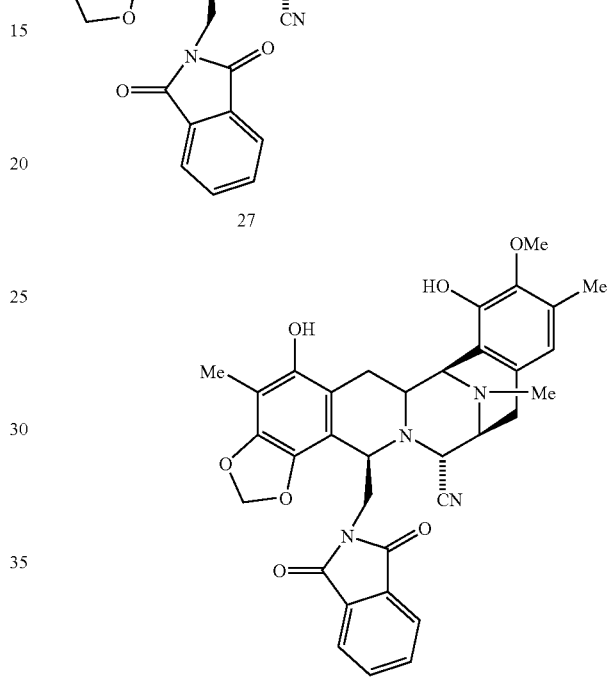

To a solution of 27 (26 mg, 0.041 mmol) in CH$_2$Cl$_2$ (11 ml), acetic acid (11 ml), (PPh$_3$)$_2$PdCl$_2$ (2.36 mg) and Bu$_3$SnH (28 ml, 0.10 mmol) were added at 23° C. After stirring at that temperature for 2 h the reaction was poured into a pad of flash column (SiO$_2$, gradient Hex to hexane:ethyl acetate 2:1) to afford 28 (24.7 mg, 99%) as a white solid.

Rf: 0.33 (hexane:ethyl acetate 2:1).

$^1$H NMR (300 MHz, CDCl$_3$): δ 7.75-7.70 (m, 2H), 7.69-7.65 (m, 2H), 6.39 (s, 1H), 5.82 (bs, 1H), 5.50 (d, J=1.5 Hz, 1H), 5.0 (d, J=1.5 Hz, 1H), 4.45 (bs, 1H), 4.23-4.19 (m, 2H), 4.10-4.09 (m, 1H), 3.73 (s, 3H), 3.60-3.48 (m, 2H), 3.36-3.33 (m, 1H), 3.26-3.20 (m, 1H), 3.14-3.08 (m, 1H), 3.98 (d, J=14.4 Hz, 1H), 2.61 (d, J=18.3 Hz, 1H), 2.30 (s, 3H), 2.23 (s, 3H), 2.06 (s, 3H), 1.85 (dd, J$_1$=12 Hz, J$_2$=15.3 Hz);

$^{13}$C NMR (75 MHz, CDCl$_3$): δ 167.8, 146.4, 145.1, 143.9, 142.7, 137.1, 133.5, 131.9, 130.8, 128.4, 122.9, 120.8, 118.0, 116.8, 114.0, 113.4, 106.4, 100.4, 60.6, 60.5, 57.8, 56.6, 55.5, 55.2, 42.6, 41.5, 25.6, 25.5, 15.8, 8.9.

ESI-MS m/z: Calcd. for C$_{34}$H$_{32}$N$_4$O$_7$: 608.6. Found (M+H)$^+$: 609.2.

Example 24

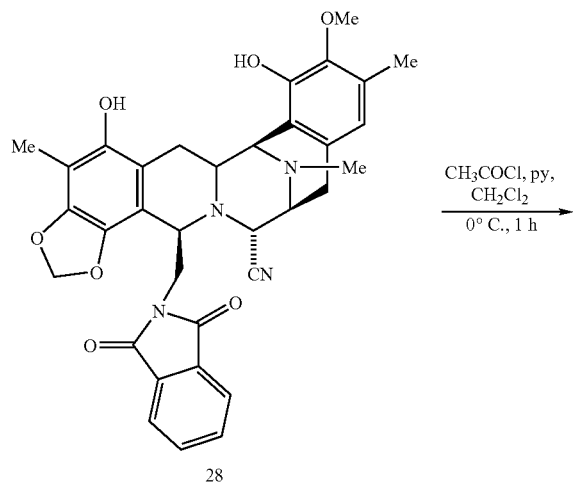

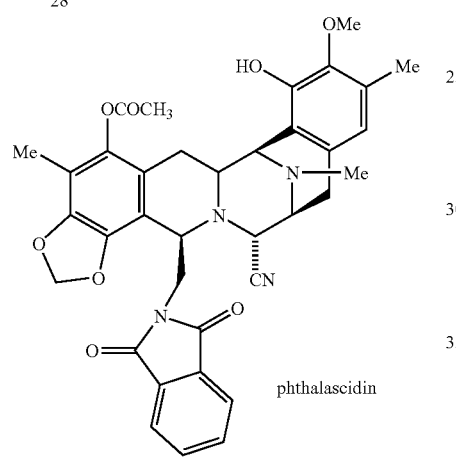

To a solution of 28 (357 mg, 0.058 mmol) in CH$_2$Cl$_2$ (3 ml), acetyl chloride (41.58 ml, 0.58 mmol) and pyridine (47.3 ml, 0.58 ml) were added at 0° C. The reaction mixture was stirred for 1 h and then, the solution was diluted with CH$_2$Cl$_2$ (15 ml) and washed with 0.1 N HCl (15 ml). The organic layer was dried over sodium sulphate, filtered, and the solvent was eliminated under reduced pressure. The residue was purified by flash column chromatography (RP-18, CH$_3$CN:H$_2$O 60:40) to afford phthalascidin (354 mg, 94%) as a white solid.

Rf: 0.37 (CH$_3$CN:H$_2$O 7:3, RP-18).

$^1$H NMR (300 MHz, CDCl$_3$): δ 7.72-7.68 (m, 2H), 7.67-7.63 (m, 2H), 6.38 (s, 1H), 5.69 (d, J=1.2 Hz, 1H), 5.64 (d, J=1.2 Hz, 1H), 5.30 (bs, 1H), 4.25-4.21 (m, 2H), 4.02 (d, J=2.1 Hz, 1H), 3.64-3.62 (m, 5H), 3.33 (d, J=8.4 Hz, 1H), 3.21-3.16 (m, 1H), 3.02 (dd, J$_1$=8.1 Hz, J$_2$=18 Hz, 1H), 2.76 (dd, J$_1$=1.8 Hz, J$_2$=15.6 Hz, 1H), 2.63 (d, J=17.7 Hz, 1H), 2.29 (s, 3H), 2.28 (s, 3H), 2.21 (s, 3H), 2.0 (s, 3H), 1.73 (dd, J$_1$=12.0 Hz, J$_2$=15.3 Hz, 1H))

$^{13}$C NMR (75 MHz, CDCl$_3$): δ 168.5, 167.6, 146.2, 144.2, 142.5, 141.0, 140.5, 133.4, 131.8, 130.7, 128.2, 120.9, 120.8, 117.9, 116.4, 113.6, 101.1, 60.4, 60.0, 57.0, 56.3, 55.6, 55.4, 41.6, 41.5, 26.5, 25.2, 20.2, 15.7, 9.4.

ESI-MS m/z: Calcd. for C$_{36}$H$_{34}$N$_4$O$_8$: 650. Found (M+H)$^+$: 651.2.

Example 25

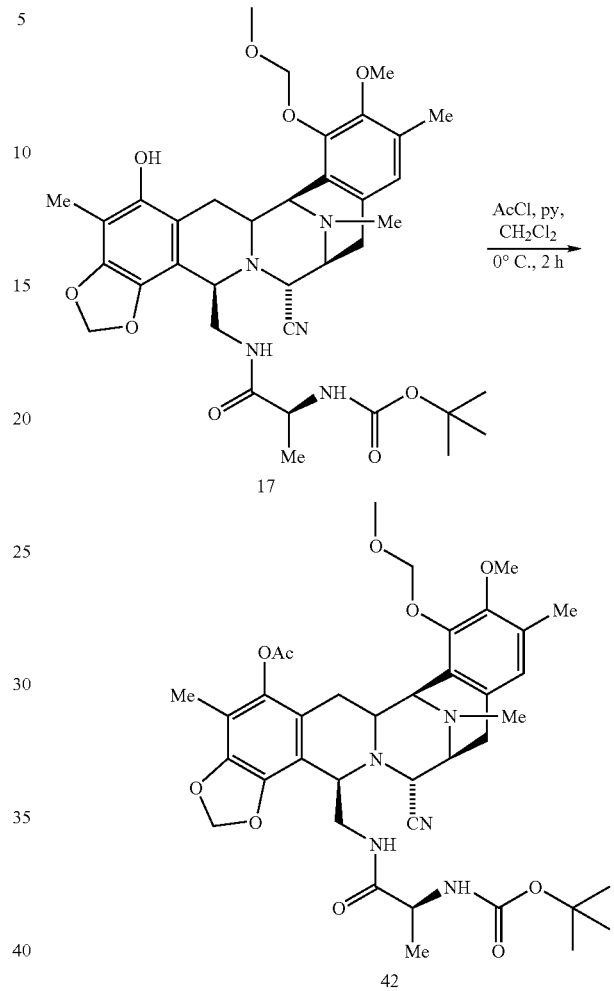

To a solution of 17 (300 mg, 0.432 mmol) in CH$_2$Cl$_2$ (2 ml), acetyl chloride (30.7 ml, 0.432 mmol) and pyridine (34.9 ml, 0.432 mmol) were added at 0° C. The reaction mixture was stirred for 2 h at that temperature and then, the solution was diluted with CH$_2$Cl$_2$ (15 ml) and washed with 0.1 N HCl (15 ml). The organic layer was dried over sodium sulphate, filtered, and the solvent was eliminated under reduced pressure to afford 42 (318 mg, 100%) as a white solid that was used in subsequent reactions with no further purification.

Rf: 0.5 (ethyl acetate:methanol 5:1).

$^1$H NMR (300 MHz, CDCl$_3$). δ 6.66 (s, 1H), 5.93 (d, J=1.2 Hz, 1H), 5.83 (d, J=1.2 Hz, 1H), 5.42 (t, J=6.6 Hz, 1H), 5.07 (d, J=5.7 Hz, 1H), 4.98 (d, J=5.7 Hz, 1H), 4.16 (d, J=1.8 Hz, 1H), 4.11 (d, J=2.7 Hz, 1H), 3.98 (bs, 1H), 3.73-3.61 (m, 2H), 3.64 (s, 3H), 3.52-3.48 (m, 1H), 3.50 (s, 3H), 3.33 (d, J=9.6 Hz, 1H), 3.17-3.14 (m, 1H), 2.97-2.87 (m, 1H), 2.75-2.70 (d, J=16.8 Hz, 1H), 2.26 (s, 6H), 2.16 (s, 3H), 1.96 (s, 3H), 1.70 (dd, J$_1$=11.7 Hz, J$_2$=15.6 Hz, 1H), 1.33 (s, 9H), 0.59 (d, J=6.0 Hz, 3H).

$^{13}$C NMR (75 MHz, CDCl$_3$)): δ 172.0, 168.3, 162.3, 148.2, 144.4, 140.4, 140.2, 130.9, 130.5, 125.3, 123.4, 120.8, 117.6, 112.7, 111.7, 101.4, 99.1, 79.2, 59.5, 58.8, 57.5, 57.4, 56.4, 55.5, 55.0, 41.3, 39.0, 28.2, 26.4, 24.6, 19.9, 18.4, 15.4, 9.1.

ESI-MS m/z: Calcd. for C$_{38}$H$_{49}$N$_5$O$_{10}$: 735.82. Found (M+H)$^+$: 736.3.

Example 26

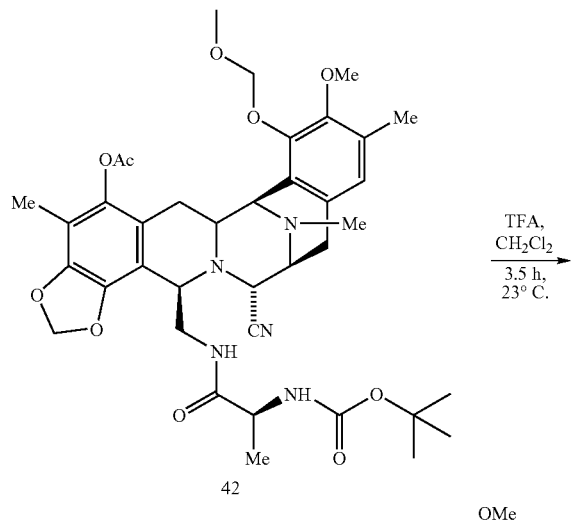

To a solution of 42 (318 mg, 0.432 mmol) in CH$_2$Cl$_2$ (2.16 mmol), trifluoroacetic acid (1.33 ml, 17.30 mmol) was added and the reaction mixture was stirred for 3.5 h at 23° C. The reaction was quenched at 0° C. with saturated aqueous sodium bicarbonate (60 ml) and extracted with CH$_2$Cl$_2$ (2×70 ml). The combined organic layers were dried (sodium sulphate) and concentrated in vacuo. The residue was purified by flash column chromatography (SiO$_2$, ethyl acetate:methanol 20:1) to afford 43 (154 mg, 60%) as a white solid.

Rf: 0.22 (ethyl acetate:methanol 5:1).

$^1$H NMR (300 MHz, CDCl$_3$). δ 6.47 (s, 1H), 6.22 (bs, 1H), 5.95 (d, J=1.2 Hz, 1H), 5.88 (d, J=1.2 Hz, 1H), 4.08-4.06 (m, 2H), 4.01 (bs, 1H), 3.69 (s, 3H), 3.49 (d, J=3.6 Hz, 1H), 3.33 (d, J=8.1 Hz, 1H), 3.26-3.22 (m, 1H), 2.95 (dd, J$_1$=8.1 Hz, J$_2$=18 Hz, 1H), 2.80-2.76 (m, 2H), 2.58 (d, J=18 Hz, 1H), 2.29 (s, 3H), 2.27 (s, 3H), 2.21 (s, 3H), 1.96 (s, 3H), 1.77 (dd, J$_1$=12.3 Hz, J$_2$=15.6 Hz, 1H), 0.90 (d, J=6.9 Hz, 3H).

$^{13}$C NMR (75 MHz, CDCl$_3$)): δ 174.8, 169.0, 146.8, 144.4, 142.8, 140.5, 140.2, 131.1, 128.8, 120.8, 120.5, 117.1, 112.9, 111.6, 101.5, 60.3, 59.0, 56.5, 56.3, 55.6, 55.1, 50.2, 41.6, 39.5, 26.8, 26.3, 24.9, 20.2, 15.4, 9.2.

ESI-MS m/z: Calcd. for C$_{31}$H$_{37}$N$_5$O$_7$: 591.65. Found (M+H)$^+$: 592.3.

Example 27

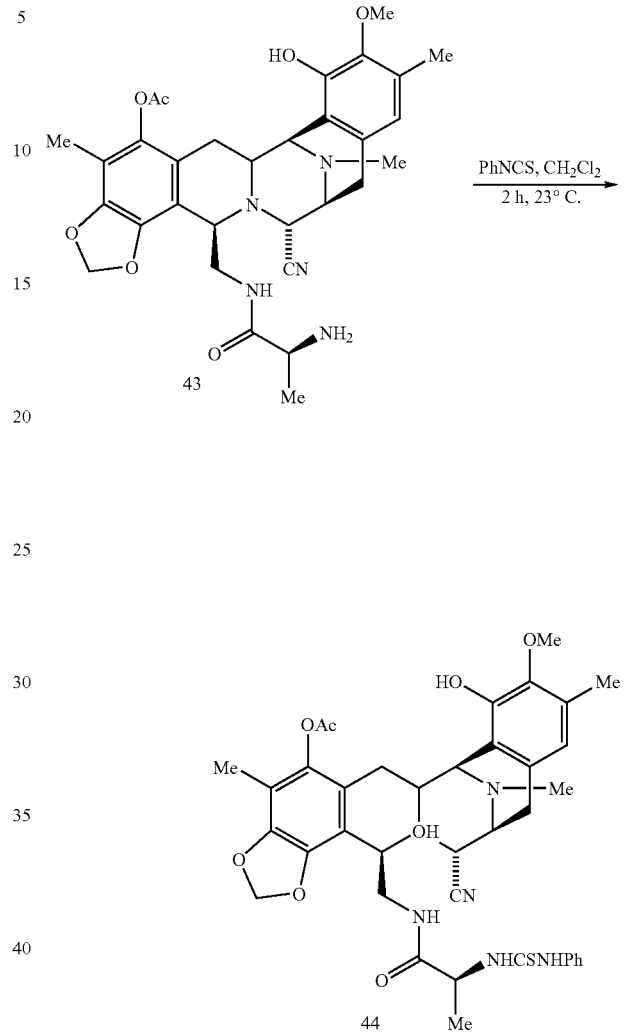

To a solution of 43 (154 mg, 0.26 mmol) in CH$_2$Cl$_2$ (1.3 ml), phenyl isothiocyanate (186 ml, 1.56 mmol) was added and the mixture was stirred at 23° C. for 2 h. The reaction was concentrated in vacuo and the residue was purified by flash column chromatography (SiO$_2$, gradient Hexane to hexane: ethyl acetate 1:1) to afford 44 (120 mg, 63%) as a white solid.

Rf: 0.41 (ethyl acetate:methanol 5:1).

$^1$H NMR (300 MHz, CDCl$_3$). δ 8.17 (s, 1H), 7.49-7.44 (m, 3H), 7.31-7.24 (m, 3H), 7.05 (d, J=6.9 Hz, 1H), 5.98 (d, J=1.2 Hz, 1H), 5.87 (d, J=1.2 Hz, 1H), 5.52 (bs, 1H), 4.54 (t, J=6.6 Hz, 1H), 4.15 (d, J=2.1 Hz, 1H), 4.03 (d, J=2.7 Hz, 2H), 3.80 (bs, 1H), 3.66 (s, 3H), 3.40 (bs, 1H), 3.32 (d, J=7.8 Hz, 1H), 3.16 (d, J=11.7 Hz, 1H), 2.82-2.61 (m, 3H), 2.29 (s, 3H), 2.20 (s, 3H), 2.01 (s, 3H), 1.99 (s, 3H), 1.80 (dd, J$_1$=12.0 Hz, J$_2$=15.9 Hz, 1H), 0.62 (d, J=6.0 Hz, 3H).

$^{13}$C NMR (75 MHz, CDCl$_3$) δ 178.5, 171.9, 168.7, 146.7, 144.5, 142.6, 140.6, 140.3, 136.3, 131.0, 129.9, 128.9, 126.7, 124.4, 120.9, 120.6, 117.7, 116.6, 112.7, 111.9, 101.4, 60.4, 58.7, 57.5, 56.1, 55.7, 55.1, 53.3, 41.4, 38.8, 26.3, 24.4, 20.2, 18.1, 15.3, 9.2.

ESI-MS m/z: Calcd. for C$_{38}$H$_{42}$N$_6$O$_7$S: 726.3. Found (M+H)$^+$: 727.3.

Example 28

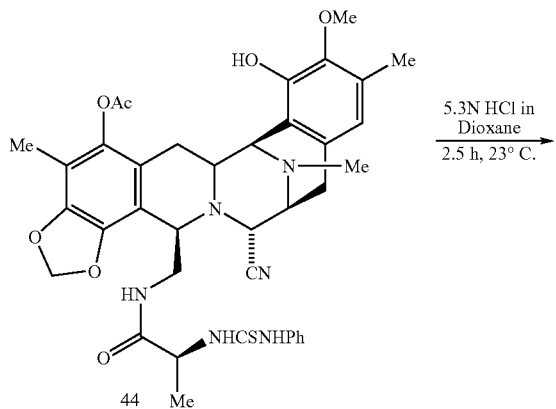

To a solution of 44 (120 mg, 0.165 mmol) in dioxane (0.9 ml), 5.3N HCl/dioxane (1.8 ml) was added and the reaction was stirred at 23° C. for 2.5 h. Then, CH$_2$Cl$_2$ (10 ml) and H$_2$O (5 ml) were added to this reaction and the organic layer was decanted. The aqueous phase was basified with saturated aq sodium bicarbonate (20 ml) (pH=8) at 0° C. and then, extracted with CH$_2$Cl$_2$ (2×15 ml). The combined organic extracts were dried (sodium sulphate), and concentrated in vacuo to afford 45 (75 mg, 87%) as a white solid that was used in subsequent reactions with no further purification.

Rf: 0.23 (ethyl acetate:methanol 5:1).

$^1$H NMR (300 MHz, CDCl$_3$): δ 6.43 (s, 1H), 5.94 (d, J=1.2 Hz, 1H), 5.87 (d, J=1.2 Hz, 1H), 4.10 (d, J=2.1 Hz, 1H), 3.98 (d, J=2.4 Hz, 1H), 3.91 (bs, 1H), 3.69 (s, 3H), 3.34-3.25 (m, 2H), 3.05 (dd, J$_1$=1.8 Hz, J$_2$=8.1 Hz, 1H), 2.80-2.73 (m, 3H), 2.46 (d, J=18 Hz, 1H), 2.30 (s, 3H), 2.28 (s, 3H), 2.20 (s, 3H), 1.98 (s, 3H), 1.79 (dd, J$_1$=12.6 Hz, J$_2$=16.2 Hz, 1H);

$^{13}$C NMR (75 MHz, CDCl$_3$): δ 168.7, 146.7, 144.4, 142.9, 140.4, 130.4, 128.9, 121.1, 120.8, 117.8, 116.8, 113.6, 111.5, 101.4, 67.6, 60.5, 59.8, 58.4, 56.6, 55.8, 55.3, 43.6, 41.8, 31.3, 25.6, 20.2, 15.6, 9.2.

ESI-MS m/z: Calcd. for C$_{28}$H$_{32}$N$_4$O$_6$: 520.58. Found (M+H)$^+$: 521.3.

Example 29

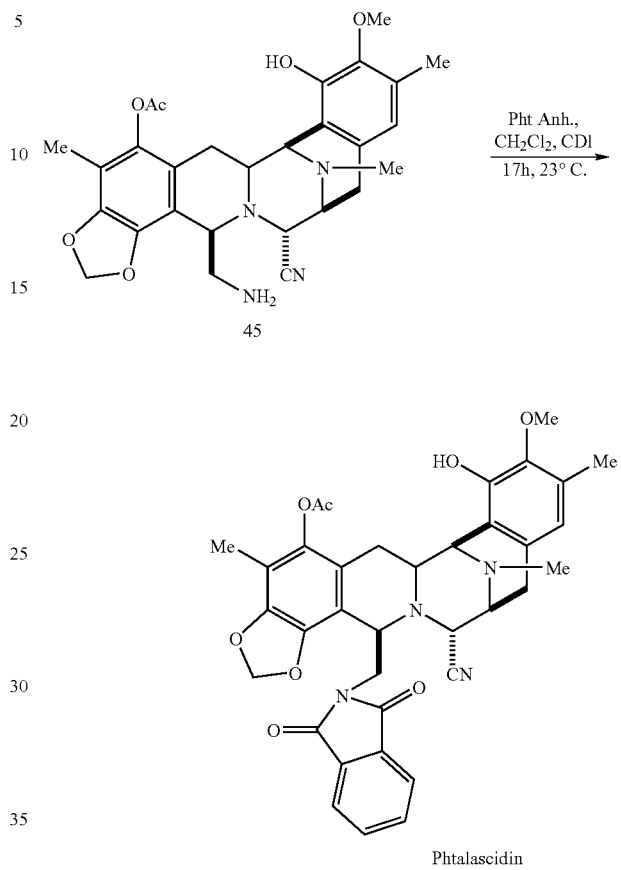

To a solution of 45 (10 mg, 0.02 mmol) in CH$_2$Cl$_2$ (0.4 ml) was added phthalic anhydride (2.84 mg, 0.02 mmol) and the reaction mixture was stirred for 2 h at 23° C. Then, carbonyldiimidazole (0.5 mg, 0.003 mmol) was added and the mixture was stirred at 23° C. for 7 h. Then, carbonyldiimidazole (2.61 mg, 0.016 mmol) was added and the reaction was stirred at 23° C. for an additional 17 h. The solution was diluted with CH$_2$Cl$_2$ (10 ml) and washed with 0.1 N HCl (5 ml). The organic layer was dried over sodium sulphate, filtered, and the solvent was eliminated under reduced pressure. The residue was purified by flash column chromatography (RP-18, CH$_3$CN:H$_2$O 60:40) to afford phthalascidin (11.7 mg, 93%) as a white solid.

Rf: 0.37 (CH$_3$CN:H$_2$O 7:3, RP-18).

$^1$H NMR (300 MHz, CDCl$_3$): δ 7.72-7.68 (m, 2H), 7.67-7.63 (m, 2H), 6.38 (s, 1H), 5.69 (d, J=1.2 Hz, 1H), 5.64 (d, J=1.2 Hz, 1H), 5.30 (bs, 1H), 4.25-4.21 (m, 2 h), 4.02 (d, J=2.1 Hz, 1H), 3.64-3.62 (m, 5H), 3.33 (d, J=8.4 Hz, 1H), 3.21-3.16 (m, 1H), 3.02 (dd, J$_1$=8.1 Hz, J$_2$=18 Hz, 1H), 2.76 (dd, J$_1$=1.8 Hz, J$_2$=15.6 Hz, 1H), 2.63 (d, J=17.7 Hz, 1H), 2.29 (s, 3H), 2.28 (s, 3H), 2.21 (s, 3H), 2.0 (s, 3H), 1.73 (dd, J$_1$=12.0 Hz, J$_2$=15.3 Hz, 1H)).

$^{13}$C NMR (75 MHz, CDCl$_3$): δ 168.5, 167.6, 146.2, 144.2, 142.5, 141.0, 140.5, 133.4, 131.8, 130.7, 128.2, 120.9, 120.8, 117.9, 116.4, 113.6, 101.1, 60.4, 60.0, 57.0, 56.3, 55.6, 55.4, 41.6, 41.5, 26.5, 25.2, 20.2, 15.7, 9.4.

ESI-MS m/z: Calcd. for C$_{36}$H$_{34}$N$_4$O$_8$: 650. Found (M+H)$^+$: 651.2.

Example 30

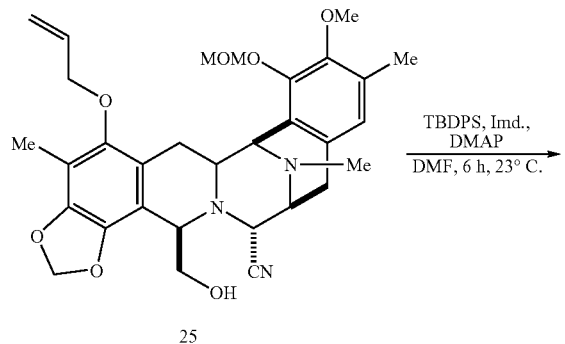

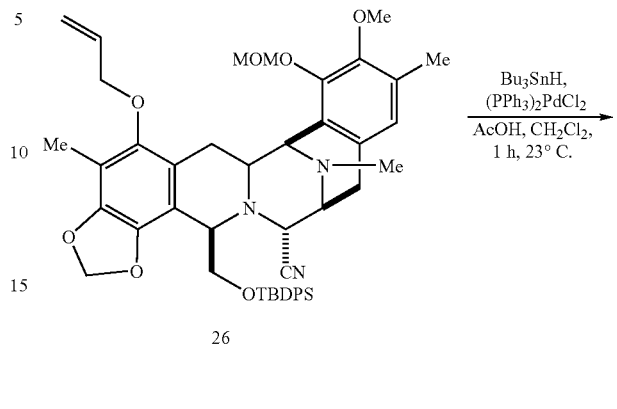

Example 31

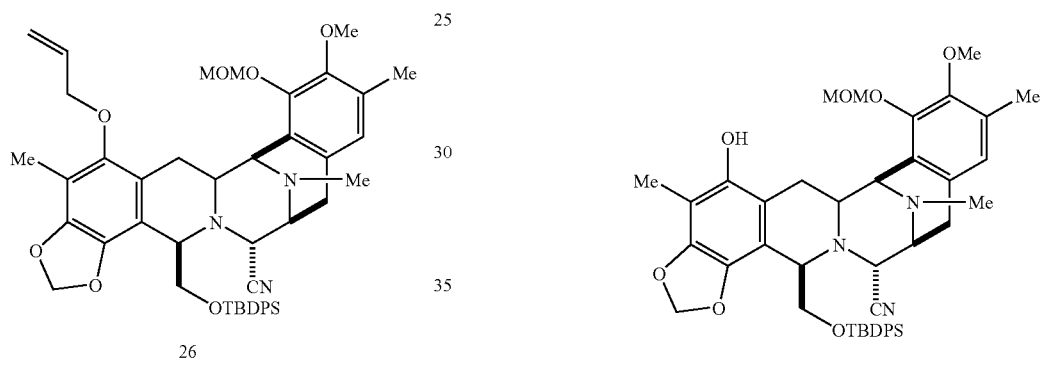

To a solution of 25 (18 mg, 0.032 mmol) in DMF (0.05 ml), cat. DMAP (0.5 mg, 0.004 mmol), imidazole (5 mg, 0.08 mmol) and tert-Butyldiphenylsilyl chloride (12.5 ml, 0.048 mmol) were added at 0° C. and the reaction mixture was stirred for 6 h at 23° C. Water (10 ml) was added at 0° C. and the aqueous phase was extracted with hexane:ethyl acetate 1:10 (2×10 mmol). The organic layer was dried (sodium sulphate), filtered, and the solvent was removed under reduced pressure. The crude was purified by flash column chromatography ($SiO_2$, hexane:ethyl acetate 3:1) to afford 26 (27 mg, 88%) as a white solid.

Rf: 0.29 (hexane:ethyl acetate 3:1).

$^1$H NMR (300 MHz, $CDCl_3$) δ 7.61-7.58 (m, 2 h), 7.42-7.28 (m, 8H), 6.71 (s, 1H), 6.19-6.02 (m, 1H), 5.78 (d, J=1.2 Hz, 1H), 5.64 (d, J=1.2 Hz, 1H), 5.40 (dd, $J_1$=1.2 Hz, $J_2$=17.1 Hz, 1H), 5.27 (dd, $J_1$=1.2 Hz, $J_2$=10.2 Hz, 1H), 5.13 (s, 2 h), 4.45 (d, J=2.4 Hz, 1H), 4.24 (d, J=2.1 Hz, 1H), 4.17-4.06 (m, 3H), 3.75 (s, 3H), 3.64 (dd, $J_1$=2.4 Hz, $J_2$=9.9 Hz, 1H), 3.59 (s, 3H), 3.42-3.21 (m, 4H), 3.10 (dd, $J_1$=8.1 Hz, $J_2$=17.7 Hz, 1H), 2.70 (d, J=17.7 Hz, 1H), 2.33 (s, 3H), 2.26 (s, 3H), 2.11 (s, 3H), 2.08-1.89 (m, 1H), 0.87 (s, 9H);

$^{13}$C NMR (75 MHz, $CDCl_3$): δ 148.5, 148.3, 148.1, 144.0, 139.0, 135.6, 135.4, 133.8, 133.1, 132.6, 130.5, 130.3, 129.6, 129.4, 127.5, 127.4, 125.1, 124.3, 121.6, 118.5, 117.5, 112.9, 111.7, 100.8, 99.2, 74.0, 67.7, 61.5, 59.6, 59.0, 57.7, 57.1, 55.4, 41.6, 29.6, 26.6, 25.5, 18.8, 15.8, 9.2.

ESI-MS m/z: Calcd. for $C_{47}H_{55}N_3O_7Si$: 801.3. Found (M+H)$^+$: 802.3.

To a solution of 26 (7 mg, 0.0087 mmol) in $CH_2Cl_2$ (0.15 ml), acetic acid (2.5 ml, 0.044 mmol), $(PPh_3)_2PdCl_2$ (0.5 mg, 6.96×10$^{-4}$ mmol) and $Bu_3SnH$ (3.5 ml, 0.013 mmol) were added at 23° C. The reaction mixture was stirred at that temperature for 1 h. The solution was diluted with a mixture of hexane:ethyl acetate 5:1 (0.5 ml) and poured into a pad of flash column ($SiO_2$, gradient 5:1 to 1:1 hexane:ethyl acetate) affording ET-11 (5 mg, 75%) as a white solid.

Rf: 0.36 (hexane:ethyl acetate 1:5, silica).

$^1$H NMR (300 MHz, $CDCl_3$): δ 7.56 (m, 2 h), 7.41-7.25 (m, 8H), 6.67 (s, 1H), 5.72 (d, J=1.0 Hz, 1H), 5.58 (d, J=1.0 Hz, 1H), 5.51 (s, 1H), 5.38 (d, J=5.75 Hz, 1H), 5.16 (d, J=5.7 Hz, 1H), 4.57 (d, J=2.9 Hz, 1H), 4.21 (m, 1H), 4.09 (m, 1H), 3.72 (s, 3H), 3.71 (s, 3H), 3.68 (dd, $J_1$=2.1 Hz, $J_2$=10.4 Hz, 1H), 3.38-3.26 (m, 3H), 3.11 (dd, $J_1$=2.5 Hz, $J_2$=15.7 Hz, 1H), 3.01 (dd, $J_1$=8.9 Hz, $J_2$=17.9 Hz, 1H), 2.70 (d, J=17.9 Hz, 1H), 2.31 (s, 3H), 2.25 (s, 3H), 2.06 (s, 3H), 1.89 (dd, $J_1$=12.1 Hz, $J_2$=15.7 Hz, 1H), 0.9 (s, 9H).);

$^{13}$C NMR (75 MHz, $CDCl_3$): δ 149.0, 147.4, 145.3, 144.3, 136.3, 135.7, 135.4, 133.2, 130.9, 130.5, 129.6, 129.5, 127.5, 125.0, 118.6, 112.5, 112.1, 105.7, 100.5, 99.8, 68.5, 61.5, 59.7, 58.8, 57.7, 56.9, 56.5, 55.4, 41.7, 26.6, 26.2, 25.5, 18.9, 15.8, 14.2, 8.7.

ESI-MS m/z: Calcd. for $C_{44}H_{51}N_3O_7Si$: 761. Found (M+H)$^+$: 762.

Example 32

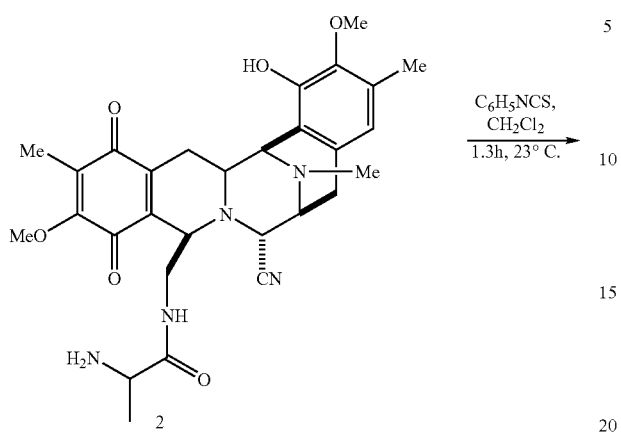

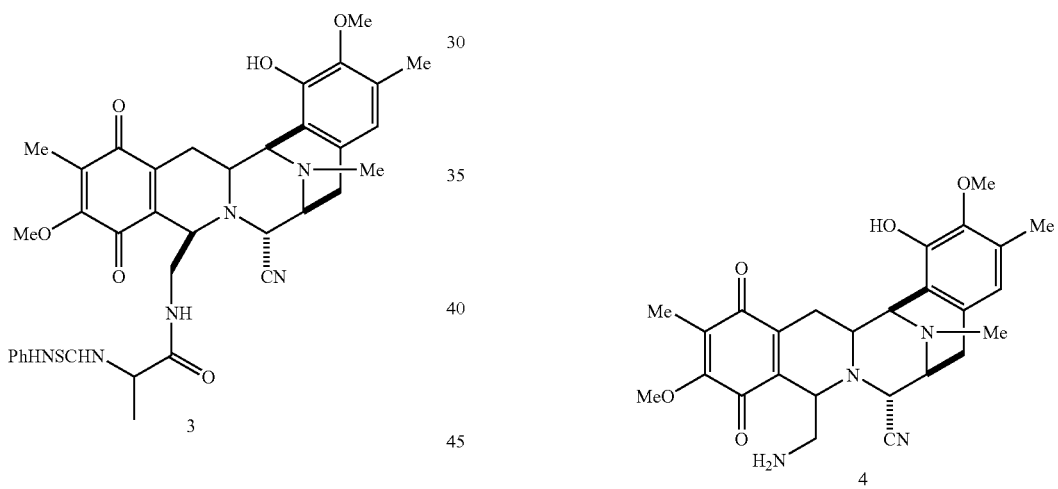

A solution of 2 (3.0 g, 5.46 mmol) and phenyl isothiocyanate (3.92 mL, 32.76 mmol) in CH$_2$Cl$_2$ (27 ml) was stirred at 23° C. for 1.5 h. The reaction mixture was partitioned between CH$_2$Cl$_2$ (10 ml) and H$_2$O (5 ml). The organic layer was dried over sodium sulphate, filtered and concentrated. The residue was purified by flash column chromatography (SiO$_2$, gradient Hex to 2:3 hexane:ethyl acetate) to give 3 (3.29 g, 88%) as a yellow solid.

Rf: 0.27 (ACN:H$_2$O 3:2, RP-C18);

$^1$H NMR (300 MHz, CDCl$_3$): δ 7.77 (bs, 1H), 7.42-7.11 (m, 5H), 6.65 (d, 1H), 6.29 (s, 1H), 5.6-5.5 (m, 1H), 4.19-4.14 (m, 2 h), 4.08 (d, 1H), 3.92 (s, 3H), 3.87-3.65 (m, 6H), 3.77 (s, 3H), 3.37-2.98 (m, 8H), 2.50 (d, 1H), 2.31 (s, 3H), 2.20 (s, 3H), 1.96 (d, 1H), 1.87 (s, 3H), 1.81-1.75 (m, 1H), 0.96 (d, 3H);

$^{13}$C NMR (75 MHz, CDCl$_3$): δ 185.7, 180.9, 178.9, 172.0, 155.7, 147.1, 143.2, 142.4, 136.0, 135.1, 130.5, 129.9, 129.3, 128.5, 126.9, 124.4, 120.2, 117.4, 116.3, 77.1, 60.9, 58.6, 56.2, 55.8, 55.0, 54.6, 53.5, 41.7, 40.3, 25.1, 24.5, 18.4, 15.8, 8.7

ESI-MS m/z: Calcd. for C$_{36}$H$_{40}$N$_6$O$_6$S: 684.8. Found (M+H)$^+$: 685.2.

Example 33

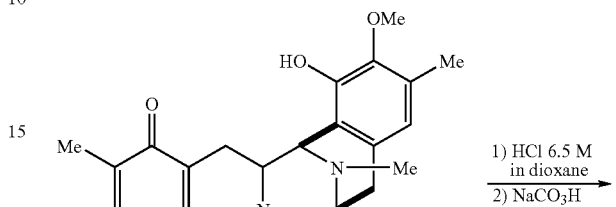

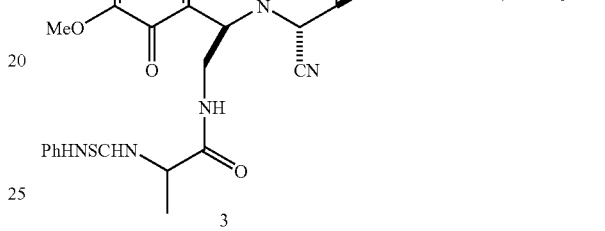

A solution of 3 (0.143 g, 0.208 mmol) in 6.5 M HCl/dioxane (150 ml) was stirred at 23° C. for 6 h. Then, toluene (3 ml) was added to this reaction and the organic layer was decanted. The residue was partitioned between saturated aqueous sodium bicarbonate (3 ml) and CHCl$_3$ (3×3 ml) The organic layers were dried and concentrated to afford title compound as a mixture of 4 and 6 (4:6 90:10) which slowly cyclizes to 6 on standing.

Rf: 0.4 (ethyl acetate:methanol 5:1, silica);

$^1$H NMR (300 MHz, CDCl$_3$): δ 6.45 (s, 1H), 4.16 (m, 1H), 4.02 (d, 1H), 3.96 (s, 3H), 3.79 (m, 2 h), 3.75 (s, 3H), 3.35 (m, 1H), 3.20-3.00 (m, 3H), 2.87 (d, 1H), 2.75 (d, 1H), 2.43 (d, 1H), 2.34 (s, 3H), 2.30 (s, 3H), 1.93 (s, 3H), 1.72-1.5 (m, 3H).

ESI-MS m/z: Calcd. for C$_{26}$H$_{30}$N$_4$O$_5$: 478.5. Found (M+H)$^+$: 479.2

Example 34

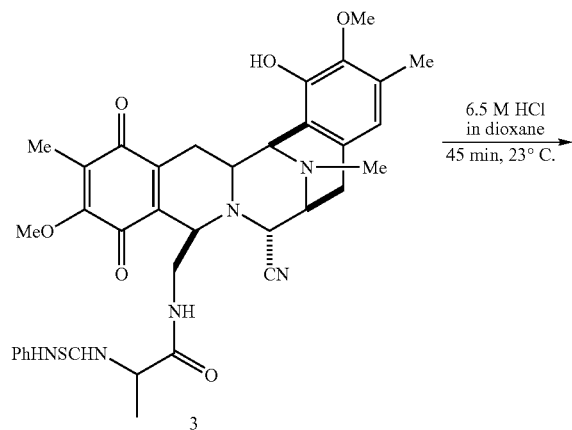

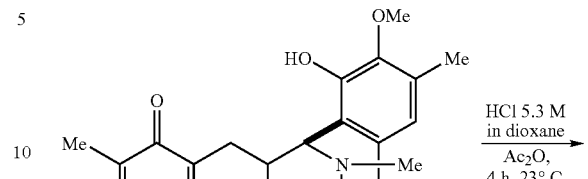

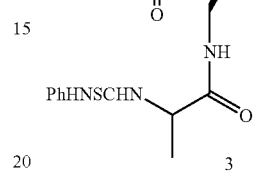

A solution of 3 (0.143 g, 0.208 mmol) in 6.5M HCl/dioxane (150 ml) was stirred at 23° C. for 1 h. Evaporation of the solvent gave a residue which was purified by flash column chromatography (ethyl acetate/methanol/triethylamine 100:25:0.1) to give 6 (80 mg, 83%) as a yellow solid.

Rf: 0.26 (ACN:$H_2O$ 3:2, RP-C18);

$^1$H NMR (500 MHz, $CDCl_3$): δ 6.46 (s, 1H), 5.9 (bs, 1H) 4.67 (dd, J=18.3 Hz, J=7.8 Hz, 1H), 4.24 (d, 1H), 4.16 (s, 3H), 3.93 (d, J=2.7 Hz, 1H), 3.8 (m, 2 h), 3.77 (s, 3H), 3.45 (m, 2 h), 3.08 (dd, J=17.9 Hz, J=3.6 Hz, 1H), 2.78 (m, 1H), 2.55 (d, 1H), 2.3 (m, 1H), 2.3 (s, 3H), 2.28 (s, 3H), 1.90 (s, 3H);

$^{13}$C NMR (75 MHz, $CDCl_3$): δ 186.2, 162.1, 154.9, 146.9, 145.3, 143.0, 130.1, 129.4, 128.1, 125.0, 121.4, 116.4, 116.2, 66.6, 60.7, 60.7, 60.1, 59.6, 58.8, 55.6, 54.9, 41.9, 25.3, 24.7, 15.7, 8.9.

ESI-MS m/z: Calcd. for $C_{26}H_{28}N_4O_4$: 460.5. Found (M+H)$^+$: 461.1

Example 35

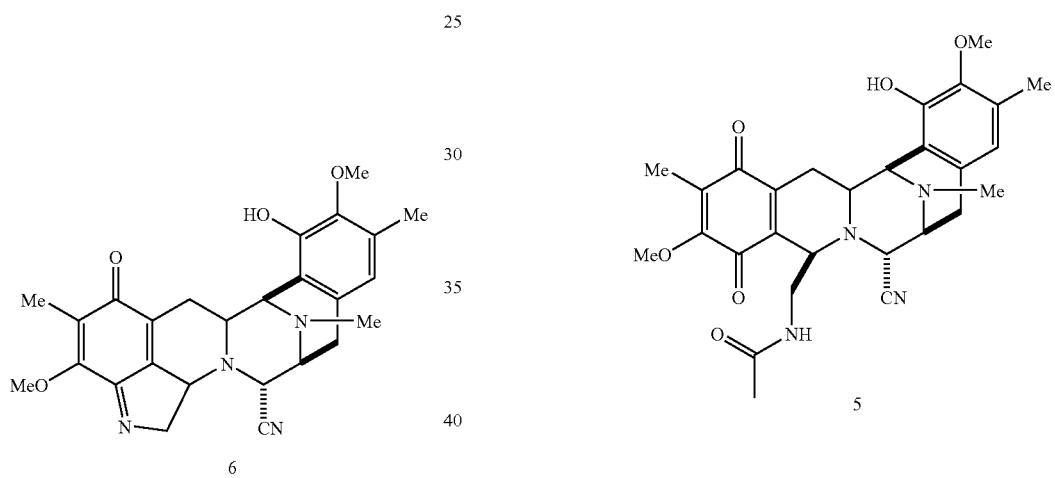

To a solution of 3 (2.38 g, 3.47 mmol) in dioxane (5 ml) 5.3M HCl in dioxane (34 ml) was added and the reaction was stirred at 23° C. for 45 minutes. Then $Ac_2O$ (51 ml, 539.5 mmol) was added and the mixture was stirred for 4 h. The reaction was cooled at 0° C. and partitioned between aqueous saturated $Na_2CO_3$ (300 ml) and ethyl acetate (300 ml) at this temperature. The organic phase was dried over sodium sulphate, filtered and concentrated. The residue was purified by flash column chromatography ($SiO_2$, gradient $CH_2Cl_2$ to $CH_2Cl_2$:ethyl acetate 1:2) to give 5 (1.75 g, 97%) as a yellow solid.

Rf: 0.53 (ACN:$H_2O$ 3:2, RP-C18);

$^1$H NMR (300 MHz, $CDCl_3$): δ 6.51 (s, 1H), 5.98 (bs, 1H), 4.84 (dd, 1H), 4.17 (d, 1H), 4.00 (d, 1H), 3.99 (s, 3H), 3.85 (bs, 1H), 3.81 (m, 1H), 3.74 (s, 3H), 3.70 (d, 1H), 3.23 (m, 1H), 3.11 (dd, 1H), 3.09 (m, 1H), 2.93 (m, 2 h), 2.44 (d, 1H), 3.67 (s, 3H), 2.25 (s, 3H), 1.70 (s, 3H), 1.60-1.50 (m, 2 h), 1.29 (s, 3H);

$^{13}$C NMR (75 MHz, $CDCl_3$): δ 185.9, 180.8, 169.9, 160.2, 156.2, 147.0, 143.1, 140.4, 136.1, 130.6, 129.6, 127.9, 120.4, 117.2, 61.0, 60.7, 58.6, 56.1, 55.7, 55.1, 54.3, 41.8, 41.1, 25.7, 23.9, 22.2, 15.7, 8.7.

ESI-MS m/z: Calcd. for $C_{28}H_{32}N_4O_6$: 520.6. Found (M+H)$^+$: 521.1

Example 36

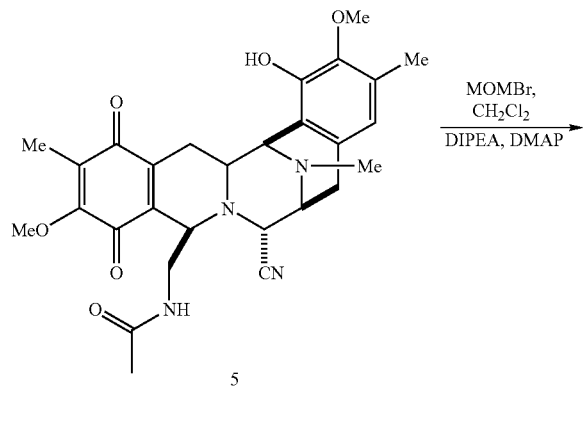
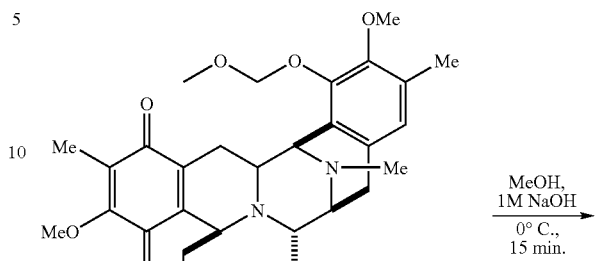
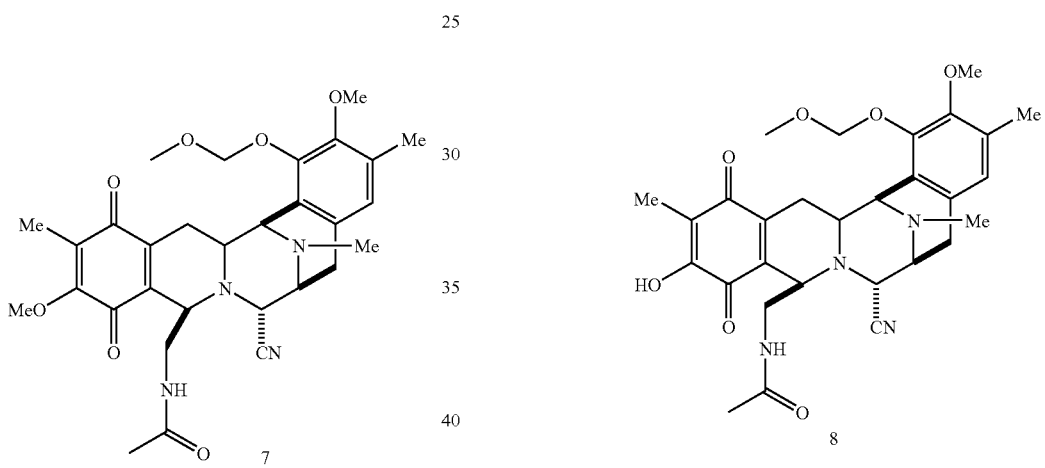

To a solution of 5 (1.75 g, 3.36 mmol) in CH$_2$Cl$_2$ (17 ml) diisopropylethylamine (11.71 ml, 67.23 mmol), DMAP (20 mg, 0.17 mmol) and bromomethyl methyl ether (4.11 ml, 50.42 mmol) were added at 0° C. After 6 h at 23° C. the reaction was partitioned between CH$_2$Cl$_2$ (50 ml) and aqueous saturated sodium bicarbonate (25 ml). The organic layer was dried over sodium sulphate and the solvent was eliminated under reduced pressure. The crude was purified by flash column chromatography (RP-18, CH$_3$CN/H$_2$O 1/1) to give 7 (1.32 g, 70%) as a yellow solid.

Rf: 0.34 (ACN:H$_2$O 2:3, RP-C18);

$^1$H NMR (300 MHz, CDCl$_3$): δ 6.74 (s, 1H), 5.14 (s, 2 h), 4.82 (m, 1H), 4.22 (d, 1H), 4.00 (s, 3H), 4.0 (m, 1H), 3.83 (m, 2 h), 3.7 (s, 3H), 3.58 (s, 3H), 3.4 (m, 1H), 3.2-2.95 (m, 6H), 2.43 (d, 1H), 2.37 (s, 3H), 2.22 (s, 3H), 1.89 (s, 3H), 1.5-1.4 (m, 2 h), 1.31 (s, 3H);

$^{13}$C NMR (75 MHz, CDCl$_3$): δ 185.9, 180.7, 169.6, 156.2, 148.9, 148.5, 140.3, 136.2, 131.3, 130.1, 127.7, 124.6, 123.7, 117.3, 99.5, 99.2, 60.9, 59.7, 58.8, 57.7, 56.4, 55.7, 55.0, 54.2, 51.0, 41.6, 41.0, 40.5, 25.5, 23.9, 22.3, 19.3, 15.6, 14.6, 8.6.

ESI-MS m/z: Calcd. for C$_{30}$H$_{36}$N$_4$O$_7$: 564.6. Found (M+H)$^+$: 565.3

Example 37

To a solution of 7 (0.37 g, 0.65 mmol) in methanol (74 ml) at 0° C. was added 1M sodium hydroxide (130 ml). The reaction was stirred for 15 minutes and then, quenched at 0° C. with 6M HCl to pH=5. The mixture was extracted with ethyl acetate (3×50 ml) and the combined organic layers were dried over sodium sulphate and concentrated in vacuo. The residue was purified by flash column chromatography (RP-C18 CH$_3$CN:H$_2$O 1/:1) to afford 8 (232 mg, 65%) as a yellow oil.

Rf: 0.5 (ACN:H$_2$O 3:2, RP-C18);

$^1$H NMR (300 MHz, CDCl$_3$): δ 6.75 (s, 1H), 5.15 (s, 2 h), 4.86 (m, 1H), 4.26 (d, 1H),), 4.01 (d, 1H), 3.88-3.81 (m, 2 h), 3.70 (s, 3H), 3.58 (s, 3H), 3.39 (m, 1H), 3.27-3.21 (m, 1H), 3.18-3.08 (m, 2 h), 3.03-2.97 (m, 1H) 2.47 (d, 1H), 2.37 (s, 3H), 2.22 (s, 3H), 1.90 (s, 3H), 1.57-1.46 (m, 2 h), 1.33 (s, 3H);

$^{13}$C NMR (75 MHz, ☐CDCl$_3$): 185.3, 180.6, 175.9, 170.1, 151.5, 148.9, 148.6, 143.3, 133.7, 131.5, 129.9, 124.7, 123.5, 117.1, 117.0, 99.2, 59.8, 58.7, 57.8, 56.3, 55.3, 54.9, 54.3, 41.5, 40.7, 29.6, 25.5, 24.4, 22.2, 20.7, 15.7, 8.0.

ESI-MS m/z: Calcd. for C$_{29}$H$_{34}$N$_4$O$_7$: 550.6. Found (M+H)$^+$: 551.2

Example 38

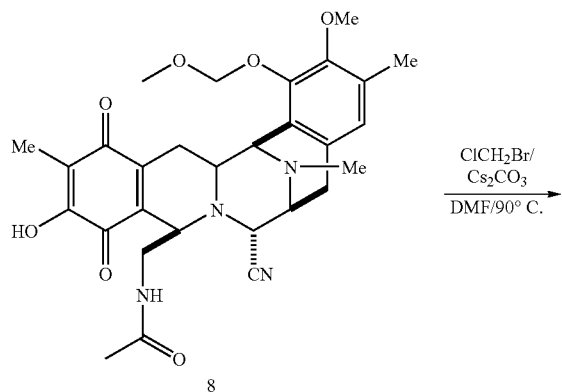

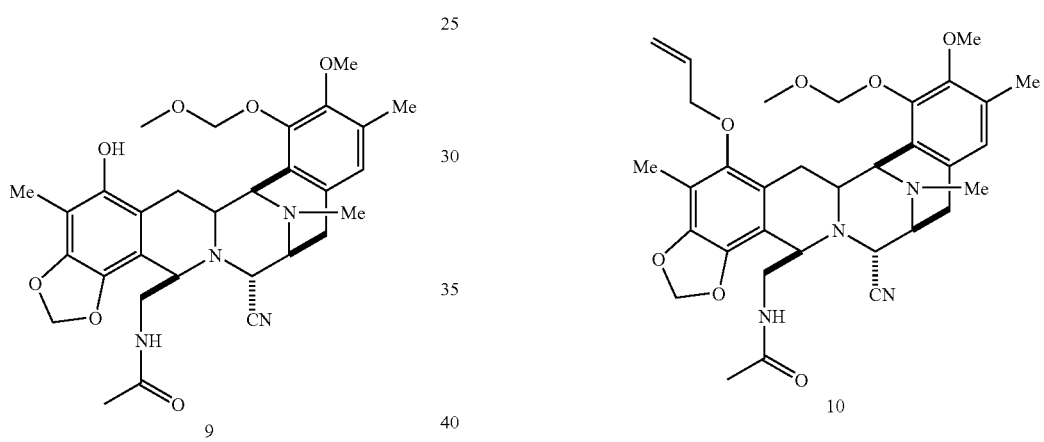

To a degassed solution of compound 8 (240 mg, 0.435 mmol) in DMF (30 ml) 10% Pd/C (48 mg) was added and the reaction was stirred under $H_2$ (atmospheric pressure.) for 1 h. The reaction was filtered through a pad of celite under Argon to a Schlenk tube, as a colourless solution, containing anhydrous $Cs_2CO_3$ (240 mg, 0.739 mmol). Then, bromochloromethane (0.566 ml, 8.71 mmol) was added. The tube was sealed and stirred at 90° C. for 3 h. The reaction was cooled and filtrated through celite and washed with $CH_2Cl_2$. The organic layer was concentrated and dried (sodium sulphate) to afford 9 as a brown oil that was used in the next step with no further purification.

Rf: 0.36 ($SiO_2$, hexane:ethyl acetate 1:5)

$^1$H NMR (300 MHz, $CDCl_3$): δ 6.71 (s, 3H), 5.89 (d, 1H), 5.81 (d, 1H), 5.63 (bs, 1H), 5.33 (d, 1H), 5.17 (d, 1H), 4.97 (m, 1H), 4.20 (d, 1H), 4.09 (m, 1H), 3.99 (m, 1H), 3.68 (m, 1H), 3.65 (s, 6H), 3.59-3.47 (m, 4H), 3.37-3.27 (m, 2 h), 3.14-2.97 (m, 2 h), 2.62 (d, 1H), 2.32 (s, 3H), 2.20 (s, 3H), 2.08 (s, 3H), 1.72 (m, 1H), 1.36 (s, 3H);

$^{13}$C NMR (75 MHz, $CDCl_3$): δ 169.8, 149.1, 147.4, 145.5, 136.2, 130.9, 130.8, 125.0, 122.9, 117.7, 112.6, 111.8, 106.4, 100.8, 99.8, 59.8, 58.9, 57.7, 56.6, 56.4, 55.5, 55.2, 41.6, 40.1, 29.6, 25.9, 25.0, 22.6, 15.6, 8.8.

ESI-MS m/z: Calcd. for $C_{30}H_{36}SiN_4O_7$: 564.6. Found $(M+H)^+$: 565.3.

Example 39

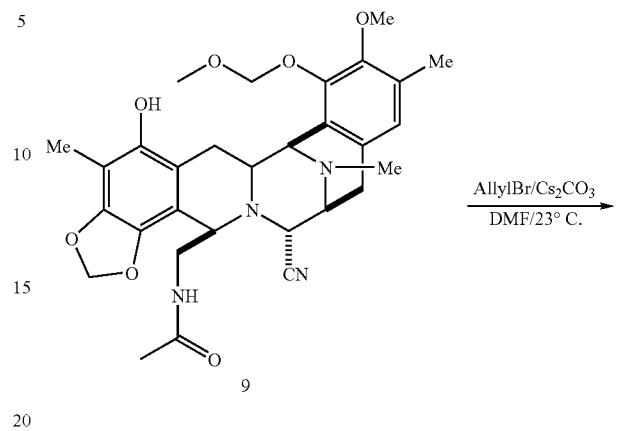

To a flask containing 9 (245 mg, 0.435 mmol) in DMF, (4 ml), cesium carbonate (425 mg, 1.30 mmol) and allyl bromide (376 ml, 4.35 mmol) were added at 0° C. and the mixture was stirred at 23° C. for 1 h. The reaction was filtered though a pad of celite and partitioned between $CH_2Cl_2$ (25 ml) and $H_2O$ (10 ml). The organic phase was dried (sodium sulphate) and concentrated at reduced pressure to afford a residue that was purified by flash column chromatography ($SiO_2$, $CHCl_3$: ethyl acetate 1:2) to give 10 as a yellow oil. (113 mg, 43%).

Rf: 0.36 (hexane:ethyl acetate 1:5)

$^1$H NMR (300 MHz, $CDCl_3$): δ 6.74 (s, 1H), 6.3-6.0 (m, 1H), 5.94 (d, 1H), 5.87 (d, 1H), 5.43-5.36 (m, 2 h), 5.22 (s, 2 h), 5.00 (m, 1H), 4.22 (m, 1H), 4.17-4.01 (m, 1H), 3.98 (m, 2 h), 3.71-3.67 (m, 1H), 3.69 (s, 3H), 3.62-3.51 (m, 3H), 3.58 (s, 3H), 3.39-3.37 (m, 1H), 3.31-3.26 (m, 3H), 3.09 (dd, 1H), 2.56 (d, 1H), 2.36 (s, 3H), 2.21 (s, 3H), 2.11 (s, 3H), 2.24-2.10 (m, 1H), 1.82-1.73 (m, 1H), 1.24 (bs, 3H)

$^{13}$C NMR (75 MHz, $CDCl_3$): δ 169.4, 148.8, 148.3, 139.1, 133.7, 130.9, 130.3, 125.2, 120.2, 117.7, 113.1, 112.6, 101.3, 99.3, 74.1, 59.7, 59.3, 57.8, 57.0, 56.1, 56.1, 55.2, 41.6, 41.0, 40.9, 29.7, 26.3, 22.5, 15.6, 9.3

ESI-MS m/z: Calcd. for $C_{33}H_{40}N_4O_7$: 604.7. Found $(M+H)^+$: 605.3.

Example 40

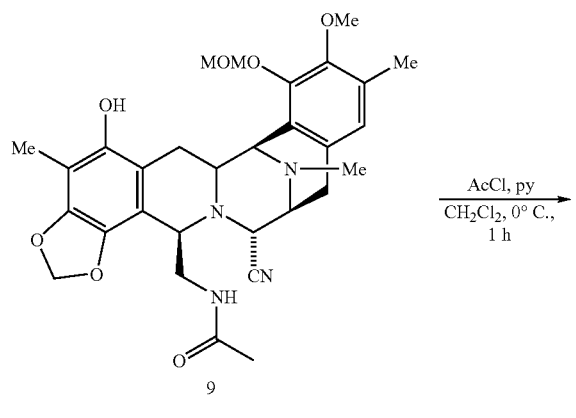

Example 41

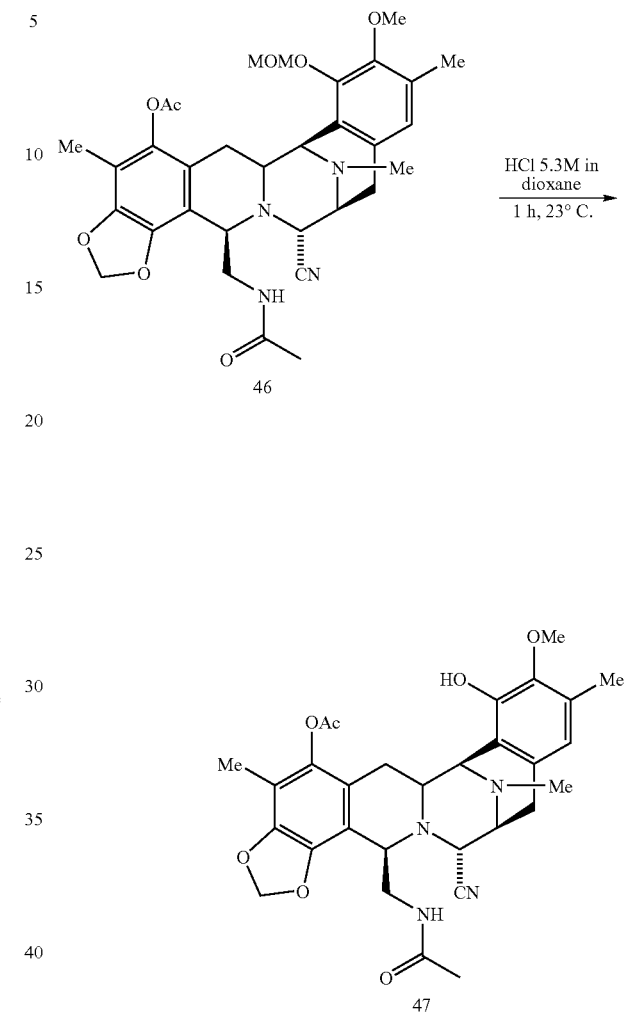

To a solution of 9 (22 mg, 0.039 mmol) in CH$_2$Cl$_2$ (0.2 ml), acetyl chloride (2.79 ml, 0.039 mmol) and pyridine (3.2 ml, 0.039 mmol) were added at 0° C. The reaction mixture was stirred for 1 h and then, the solution was diluted with CH$_2$Cl$_2$ (10 ml) and washed with 0.1 N HCl (5 ml). The organic layer was dried over sodium sulphate, filtered, and the solvent was eliminated under reduced pressure to afford 46 (22 mg, 93%) as a white solid.

Rf: 0.4 (hexane:ethyl acetate 1:5).

$^1$H NMR (300 MHz, CDCl$_3$) δ 6.74 (s, 1H), 5.97 (d, J=0.9 Hz, 1H), 5.91 (d, J=0.9 Hz, 1H), 5.12 (d, J=5.7 Hz, 2 h), 5.04 (d, J=5.7 Hz, 1H) 4.90 (t, J=6 Hz, 1H), 4.17 (d, J=2.7 Hz, 1H), 4.05 (d, J=2.7 Hz, 1H), 4.01 (bs, 1H), 3.71 (s, 3H), 3.57 (s, 3H), 3.50-3.44 (m, 2 h), 3.38-3.36 (m, 1H), 3.30-3.26 (m, 1H), 3.00 (dd, J$_1$=7.8 Hz, J$_2$=18.0 Hz, 1H), 2.79 (d, J=12.9 Hz, 1H), 2.60 (d, J=18.0 Hz, 1H), 2.35 (s, 3H), 2.32 (s, 3H), 2.21 (s, 3H), 2.00 (s, 3H), 1.68 (dd, J$_1$=11.7 Hz, J$_2$=15.6 Hz, 1H).

ESI-MS m/z: Calcd. for C$_{32}$H$_{38}$N$_4$O$_8$: 606.67. Found (M+H)$^+$: 607.3.

To a solution of 46 (8 mg, 0.013 mmol) in dioxane (0.1 ml), 5.3N HCl/dioxane (0.5 ml) was added and the reaction was stirred at 23° C. for 1 h. Then, the solution was diluted with CH$_2$Cl$_2$ (5 ml) and washed with 0.1 N HCl (3 ml). The organic layer was dried over sodium sulphate, filtered, and the solvent was eliminated under reduced pressure to afford 47 (5 mg, 70%) as a white solid.

Rf: 0.4 (hexane:ethyl acetate 1:5).

$^1$H NMR (300 MHz, CDCl$_3$). δ 6.51 (s, 1H), 5.97 (d, J=1.2 Hz, 1H), 5.91 (d, J=1.2 Hz, 1H), 4.97 (bs, 1H), 4.11 (bs, 1H), 4.04-4.02 (m, 2 h), 3.75 (s, 3H),), 3.65 (d, J=2.1 Hz, 2 h), 3.56-3.30 (m, 2 h), 3.04 (dd, J$_1$=7.5 Hz, J$_2$=18 Hz, 1H), 2.80 (d, J=14.4 Hz, 1H), 2.59 (d, J=18.3 Hz, 1H), 2.33 (s, 3H), 2.24 (s, 3H), 2.00 (s, 3H), 1.76 (dd, J$_1$=12.0 Hz, J$_2$=15.9 Hz, 1H), 1.33 (s, 3H), 1.25 (s, 3H).

ESI-MS m/z: Calcd. for C$_{30}$H$_{34}$N$_4$O$_7$: 562.61. Found (M+H)$^+$: 563.3.

Example 42

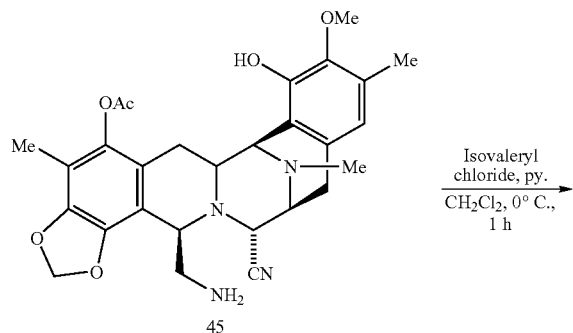

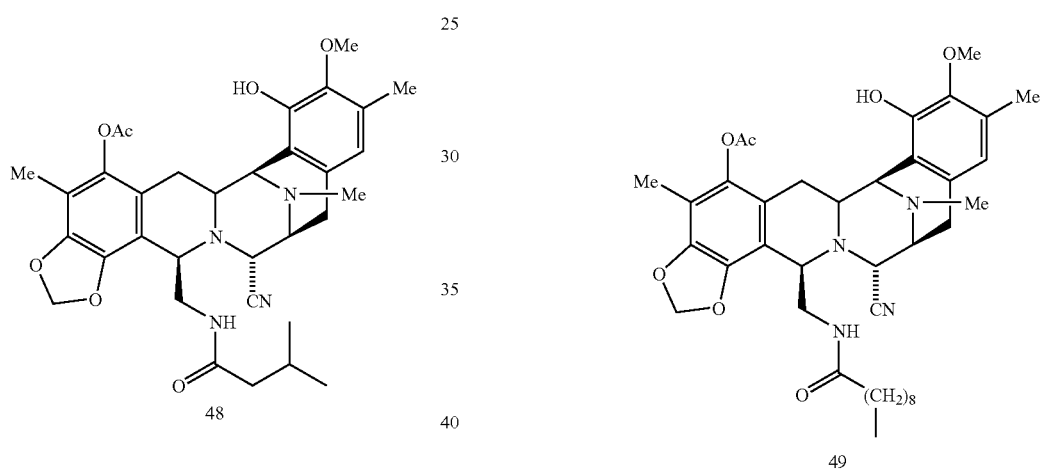

To a solution of 45 (10 mg, 0.0192 mmol) in CH$_2$Cl$_2$ (0.3 ml), isovaleryl chloride (2.34 ml, 0.0192 mmol) and pyridine (1.55 ml, 0.0192 mmol) were added at 0° C. The reaction mixture was stirred for 1 h and then, the solution was diluted with CH$_2$Cl$_2$ (5 ml) and washed with 0.1 N HCl (3 ml). The organic layer was dried over sodium sulphate, filtered, and the solvent was eliminated under reduced pressure. The residue was purified by flash column chromatography (SiO$_2$, Hex: ethyl acetate 1:2) to afford 48 (11 mg, 95%) as a white solid.

Rf: 0.12 (Hex:ethyl acetate 1:2).

$^1$H NMR (300 MHz, CDCl$_3$): δ 6.50 (s, 1H), 5.98 (d, J=1.5 Hz, 1H), 5.91(d, J=1.5 Hz, 1H), 5.75 (s, 1H), 5.02 (t, J=5.4 Hz, 1H), 4.10 (d, J=1.5 Hz, 1H), 4.06 (d, J=2.7 Hz, 1H), 4.02 (d, J=2.7 Hz, 1H), 3.77 (s, 3H), 3.76-3.71 (m, 1H), 3.86-3.28 (m, 3H), 3.04 (dd, J$_1$=8.1 Hz, J$_2$=18.3 Hz, 1H), 2.78 (d, J=15.9 Hz, 1H), 2.55 (d, J=18 Hz, 1H), 2.32 (s, 6H), 2.26 (s, 3H), 1.98 (s, 3H), 1.84-1.68 (m, 2 h), 1.36 (d, J=7.2 Hz, 2 h), 0.69 (d, J=6.6 Hz, 3H), 0.62 (d, J=6.6 Hz, 3H).

ESI-MS m/z: Calcd. for C$_{33}$H$_{40}$N$_4$O$_7$: 604.69. Found (M+H)$^+$: 605.3.

Example 43

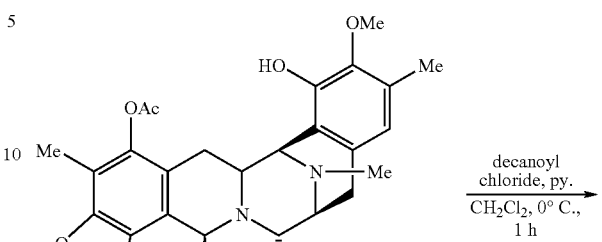

To a solution of 45 (10 mg, 0.0192 mmol) in CH$_2$Cl$_2$ (0.3 ml), isovaleryl chloride (3.98 ml, 0.0192 mmol) and pyridine (1.55 ml, 0.0192 mmol) were added at 0° C. The reaction mixture was stirred for 1 h and then, the solution was diluted with CH$_2$Cl$_2$ (5 ml) and washed with 0.1 N HCl (3 ml). The organic layer was dried over sodium sulphate, filtered, and the solvent was eliminated under reduced pressure. The residue was purified by flash column chromatography (SiO$_2$, Hex: ethyl acetate 1:2) to afford 49 (12.4 mg, 96%) as a white solid.

Rf: 0.7 (ethyl acetate:methanol 10:1).

$^1$H NMR (300 MHz, CDCl$_3$): δ 6.50 (s, 1H), 5.98 (d, J=1.5 Hz, 1H), 5.91 (d, J=1.5 Hz, 1H), 5.73 (s, 1H), 5.08 (t, J=5.4 Hz, 1H), 4.10 (d, J=1.5 Hz, 1H), 4.05 (m., 1H), 4.01 (m, 1H), 3.76 (s, 3H), 3.65-3.61 (m, 1H), 3.40-3.27 (m, 3H), 3.03 (dd, J$_1$=8.1 Hz, J$_2$=18.6 Hz, 1H), 2.78 (d, J=13.2 Hz, 1H), 2.57 (d, J=18.3 Hz, 1H), 2.32 (s, 3H), 2.31 (s, 3H), 2.25 (s, 3H), 1.99 (s, 3H), 1.79 (dd, J$_1$=12.0 Hz, J$_2$=16.5 Hz, 1H), 1.73-1.42 (m, 4H), 1.33-1.18 (m, 10H), 1.03 (m, 2 h), 0.87 (t, J=6.6 Hz, 3H).

ESI-MS m/z: Calcd. for C$_{38}$H$_{50}$N$_4$O$_7$: 674.83. Found (M+H)$^+$: 675.5.

Example 44

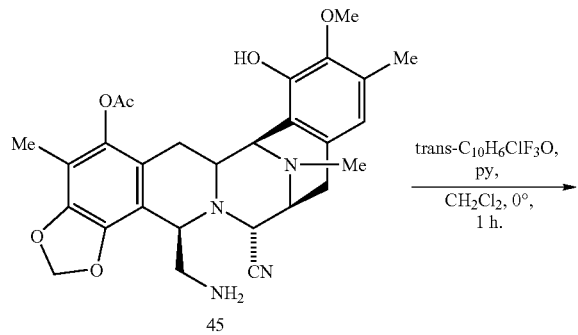

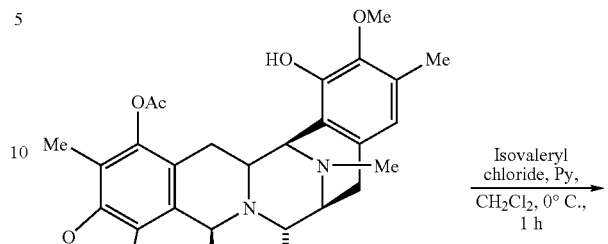

Example 45

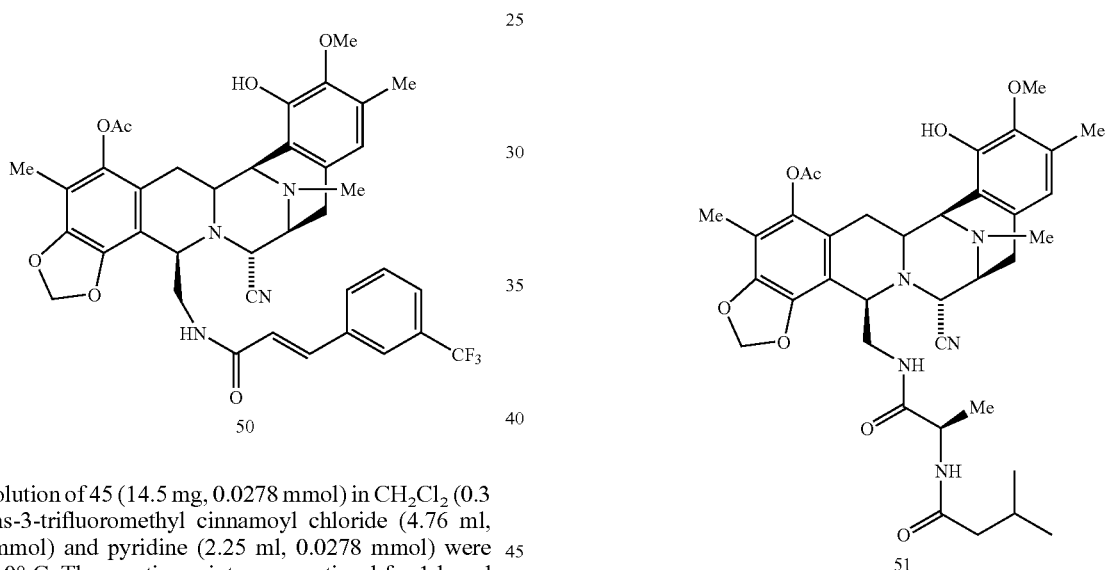

To a solution of 45 (14.5 mg, 0.0278 mmol) in $CH_2Cl_2$ (0.3 ml), trans-3-trifluoromethyl cinnamoyl chloride (4.76 ml, 0.0278 mmol) and pyridine (2.25 ml, 0.0278 mmol) were added at 0° C. The reaction mixture was stirred for 1 h and then, the solution was diluted with $CH_2Cl_2$ (5 ml) and washed with 0.1 N HCl (3 ml). The organic layer was dried over sodium sulphate, filtered, and the solvent was eliminated under reduced pressure. The residue was purified by flash column chromatography ($SiO_2$, Hex:ethyl acetate 1:1) to afford 50 (18.7 mg, 94%) as a white solid.

Rf: 0.64 (ethyl acetate:methanol 5:1).

$^1$H NMR (300 MHz, $CH_3OD$). δ 7.74-7.55 (m, 4H), 7.23 (d, J=16.0 Hz, 1H), 6.34 (s, 1H), 6.12 (d, J=16.0 Hz, 1H), 6.07 (d, J=0.9 Hz, 1H), 5.96 (d, J=0.9 Hz, 1H), 4.39 (d, J=2.4 Hz, 1H), 4.07-4.05 (m, 1H), 3.81 (bs, 1H), 3.46-3.51 (m, 3H), 3.42 (s, 3H), 3.09 (br d, J=12.0 Hz, 1H), 2.94-2.85 (m, 2 h), 2.74 (d, J=18.3 Hz, 1H), 2.38 (s, 3H), 2.23 (s, 3H), 2.02 (s, 3H), 1.80 (s, 3H), 1.84-1.75 (m, 1H).

$^{13}$C NMR (75 MHz, $CDCl_3$)): δ 168.7, 165.3, 146.5, 144.7, 142.6, 140.6, 138.0, 135.9, 131.0, 130.9, 129.1, 128.6, 125.8, 125.7, 124.5, 124.4, 122.7, 121.2, 117.8, 116.5, 113.0, 112.0, 101.7, 60.4, 59.1, 56.5, 56.4, 55.6, 55.3, 41.8, 40.3, 26.6, 25.1, 20.3, 15.4, 9.3.

ESI-MS m/z: Calcd. for $C_{38}H_{37}F_3N_4O_7$: 718.72. Found (M+H)$^+$: 719.3.

To a solution of 43 (33 mg, 0.0557 mmol) in $CH_2Cl_2$ (0.4 ml), isovaleryl chloride (6.79 ml, 0.0557 mmol) and pyridine (4.5 ml, 0.0557 mmol) were added at 0° C. The reaction mixture was stirred for 1 h and then, the solution was diluted with $CH_2Cl_2$ (5 ml) and washed with 0.1 N HCl (3 ml). The organic layer was dried over sodium sulphate, filtered, and the solvent was eliminated under reduced pressure. The residue was purified by flash column chromatography ($SiO_2$, Hex: ethyl acetate 1:2) to afford 51 (34 mg, 91%) as a white solid.

Rf: 0.09 (Hex:ethyl acetate 1:2).

$^1$H NMR (300 MHz, $CDCl_3$): δ 6.46 (s, 1H), 6.10 (bs, 1H), 5.99 (d, J=0.9 Hz, 1H), 5.90 (d, J=0.9 Hz, 1H), 5.30 (t, J=6.0 Hz, 1H), 4.10-4.05 (m, 3H), 3.81 (bs, 1H), 3.74 (s, 3H), 3.54 (bs, 1H), 3.38-3.36 (m, 1H), 3.29-3.21 (m, 1H), 3.00 (dd, $J_1$=8.0 Hz, $J_2$=18.0 Hz, 1H), 2.25 (s, 3H), 2.20 (s, 3H), 2.00 (s, 3H), 1.95-1.90 (m, 3H), 0.87 (d, J=6.6 Hz, 6H), 0.76 (d, J=6.0 Hz, 3H).

ESI-MS m/z: Calcd. for $C_{36}H_{45}N_5O_8$: 675.77. Found (M+H)$^+$: 676.3.

Example 46

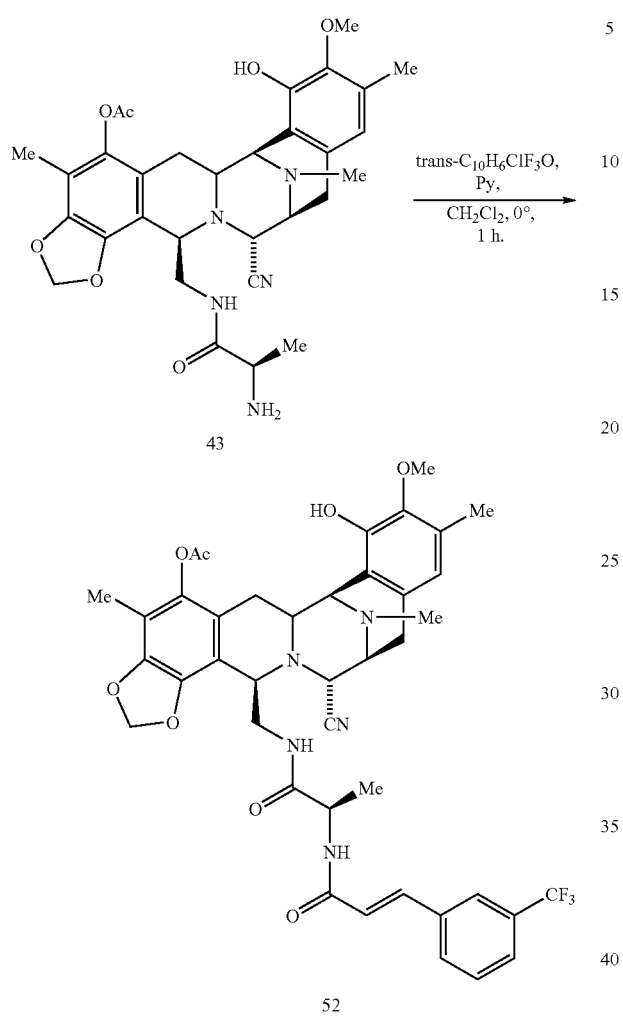

To a solution of 43 (33 mg, 0.0557 mmol) in CH$_2$Cl$_2$ (0.4 ml), trans-3-trifluoromethyl cinnamoyl chloride (9.52 ml, 0.0557 mmol) and pyridine (4.5 ml, 0.0557 mmol) were added at 0° C. The reaction mixture was stirred for 1 h and then, the solution was diluted with CH$_2$Cl$_2$ (5 ml) and washed with 0.1 N HCl (3 ml). The organic layer was dried over sodium sulphate, filtered, and the solvent was eliminated under reduced pressure. The residue was purified by flash column chromatography (SiO$_2$, Hex:ethyl acetate 1:2) to afford 52 (40 mg, 92%) as a white solid.

Rf: 0.21 (hexane:ethyl acetate 1:2).

$^1$H NMR (300 MHz, CD$_3$OD). δ 7.74-7.47 (m, 4H), 6.49 (s, 1H), 6.40 (d, J=15.6 Hz, 1H), 6.00 (d, J=1.5 Hz, 1H), 5.90 (d, J=1.5 Hz, 1H), 5.47 (t, J=6 Hz, 1H), 4.12-4.09 (m, 3H), 3.93 (bs, 1H), 3.71 (s, 3H), 3.59-3.58 (m, 1H), 3.38 (d, J=7.8 Hz, 1H), 3.29 (d, J=12.0 Hz, 1H), 3.00 (dd, J$_1$=8.1 Hz, J$_2$=18.3 Hz, 1H), 2.79-2.78 (m, 1H), 2.65 (d, J=18.3 Hz, 1H) 2.29 (s, 6H), 2.28 (s, 3H), 2.22 (s, 3H), 1.84-1.80 (m, 1H), 0.85-0.84 (m, 3H).

$^{13}$C NMR (75 MHz, CDCl$_3$) δ 171.9, 168.8, 164.4, 146.9, 144.6, 143.0, 140.5, 140.5, 139.3, 135.7, 131.1, 131.0, 129.4, 129.1, 126.0, 124.1, 124.0, 122.4, 121.1, 120.7, 120.6, 117.7, 116.9, 112.8, 112.0, 101.6, 60.6, 59.3, 57.1, 56.3, 55.9, 55.2, 49.0, 41.7, 49.9, 26.5, 25.1, 20.2, 18.4, 15.7, 9.3.

ESI-MS m/z: Calcd. for C$_{41}$H$_{42}$F$_3$N$_5$O$_8$: 789.8. Found (M+H)$^+$: 790.3.

Example 47

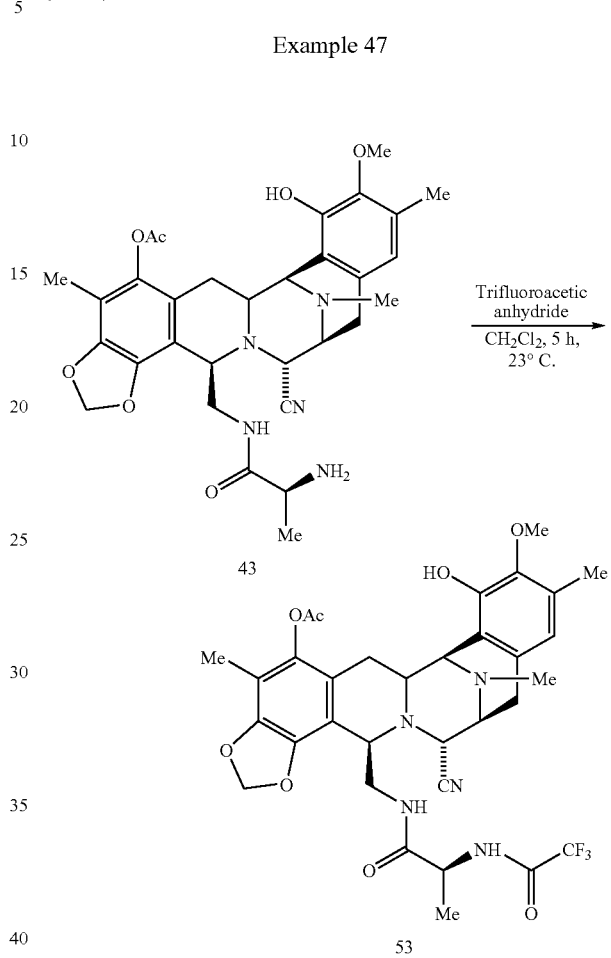

To a solution of 43 (10 mg, 0.0169 mmol) in CH$_2$Cl$_2$ (0.2 ml) trifluoroacetic anhydride (2.38 μl, 0.0169 mmol) was added at 23° C. The reaction mixture was stirred for 5 h and then, the solution was diluted with CH$_2$Cl$_2$ (5 ml) and washed with 0.1 N HCl (3 ml). The organic layer was dried over sodium sulphate, filtered, and the solvent was eliminated under reduced pressure. The residue was purified by flash column chromatography (SiO$_2$, Hex:ethyl acetate 3:2) to afford 53 (10.7 mg, 93%) as a white solid.

Rf: 0.57 (ethyl acetate:methanol 5:1).

$^1$H NMR (300 MHz, CDCl$_3$) δ 6.45 (s, 1H), 6.00 (d, J=1.2 Hz, 1H), 5.90 (d, J=1.2 Hz, 1H), 5.87 (bs, 1H), 5.32 (bs, 1H), 4.12(d, J=2.1 Hz, 1H), 4.08 (d, J=1.8 Hz, 1H), 3.78-3.56 (m, 3H), 3.72 (s, 3H), 3.40 (d, J=8.1 Hz, 1H), 3.25 (d, J=9.3 Hz, 1H), 3.00 (dd, J$_1$=8.4 Hz, J$_2$=18.0 Hz, 1H), 2.77 (dd, J$_1$=2.1 Hz, J$_2$=15.9 Hz, 1H), 2.68 (d, J=18.6 Hz, 1H), 2.30 (s, 3H), 2.28 (s, 3H), 2.22 (s, 3H), 2.00 (s, 3H), 1.75 (dd, J$_1$=11.4 Hz, J$_2$=15.9 Hz, 1H), 0.69 (d, J=6.3 Hz, 3H).

$^{13}$C NMR (75 MHz, CDCl$_3$) δ 170.1, 168.6, 156.0, 147.0, 144.6, 143.0, 140.6, 140.4, 131.0, 129.4, 120.9, 120.7, 117.6, 116.8, 112.4, 112.1, 101.6, 60.5, 59.0, 57.1, 56.3, 55.6, 55.2, 48.7, 41.6, 39.4, 26.5, 24.9, 20.2, 17.8, 15.4, 9.2.

ESI-MS m/z: Calcd. for C$_{33}$H$_{36}$F$_3$N$_5$O$_8$: 687.63. Found (M+H)$^+$: 688.66.

Example 48

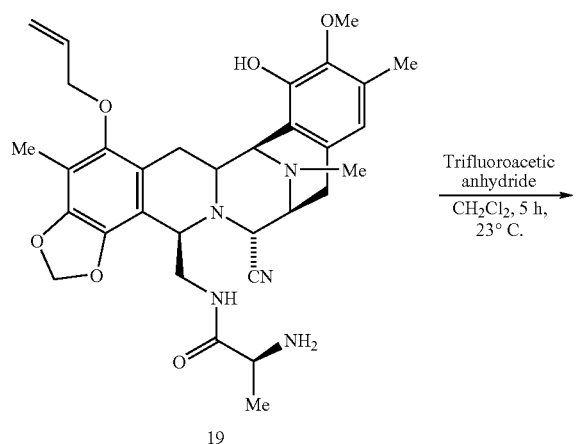

To a solution of 19 (11 mg, 0.0169 mmol) in CH$_2$Cl$_2$ (0.2 ml) trifluoroacetic anhydride (2.38 ml, 0.0169 mmol) was added at 23° C. The reaction mixture was stirred for 5 h and then, the solution was diluted with CH$_2$Cl$_2$ (5 ml) and washed with 0.1 N HCl (3 ml). The organic layer was dried over sodium sulphate, filtered, and the solvent was eliminated under reduced pressure. The residue was purified by flash column chromatography (SiO$_2$, Hex:ethyl acetate 3:2) to afford 54 (10.7 mg, 93%) as a white solid.

Rf: 0.6 (ethyl acetate:methanol 5:1).

$^1$H NMR (300 MHz, CDCl$_3$) δ 7.33 (d, J=6.3 Hz, 1H), 6.45 (s, 1H), 6.04 (m, 1H), 5.95 (d, J=1.5 Hz, 1H), 5.84 (d, J=1.5 Hz, 1H), 5.32 (m, 2 h), 5.21 (m, 1H), 4.11 (m, 4H), 3.73 (s, 3H), 3.64 (m, 2 h), 3.51 (m, 1H), 3.37 (d, J=7.8 Hz, 1H), 3.22 (m, 2 h), 3.03 (dd, 1H, J$_1$=8.1 Hz, J$_2$=18.3 Hz, 1H), 2.60 (d, J=18.3 Hz, 1H), 2.29 (s, 3H), 2.24 (s, 3H), 2.08 (s, 3H), 1.86 (dd, J$_1$=12 Hz, J$_2$=16.2 Hz, 1H), 0.82 (d, J=7.2 Hz, 3H).

$^{13}$C NMR (75 MHz, CDCl$_3$) δ 170.0, 156.0, 148.4, 147.1, 144.3, 143.0, 138.7, 133.8, 130.5, 129.4, 120.6, 120.4, 117.6, 117.5, 117.0, 113.5, 112.5, 112.4, 101.1, 74.1, 66.8, 60.4, 59.3, 56.9, 56.6, 56.3, 55.4, 48.7, 41.6, 40.1, 26.2, 25.0, 17.6, 15.4, 9.1.

ESI-MS m/z: Calcd. for C$_{35}$H$_{39}$F$_3$N$_5$O$_7$: 685.69. Found (M+H)$^+$: 686.3.

Example 49

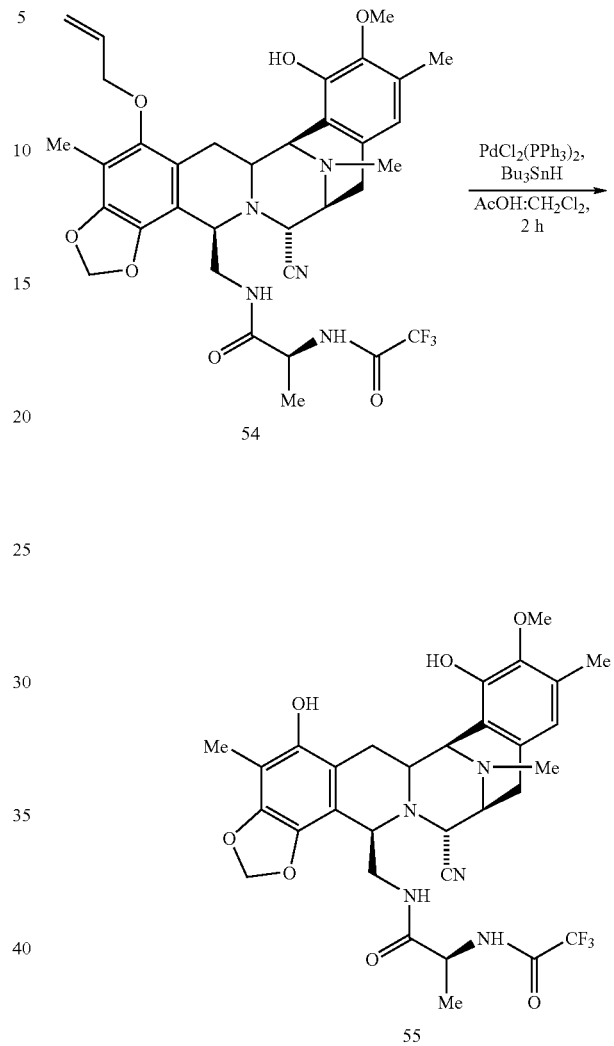

To a solution of 54 (100 mg, 0.415 mmol) in CH$_2$Cl$_2$ (4 ml), acetic acid (40 ml), (PPh$_3$)$_2$PdCl$_2$ (8.4 mg, 0.012 mmol) and Bu$_3$SnH (157 ml, 0.56 mmol) were added at 23° C. After stirring at that temperature for 2 h the reaction was poured into a pad of flash column (SiO$_2$, gradient Hex to hexane:ethyl acetate 2:1) to afford 55 (90 mg, 96%) as a white solid.

Rf: 0.6 (hexane:ethyl acetate 1:2).

$^1$H NMR (300 MHz, CDCl$_3$) δ 7.55 (d, J=7.2 Hz, 1H), 6.45 (s, 1H), 5.90 (d, J=1.2 Hz, 1H), 5.82 (d, J=1.2 Hz, 1H), 5.37 (t, J=6.0 Hz, 1H), 4.15 (d, J=2.1 Hz, 1H), 4.04 (d, J=1.8 Hz, 1H), 3.70 (s, 3H), 3.66-3.53 (m, 2 h), 3.37-3.31 (m, 2 h), 3.19-3.15 (d, J=11.7 Hz, 1H), 3.08-3.00 (m, 2 h), 2.56 (d, J=18.3 Hz, 1H), 2.30 (s, 3H), 2.24 (s, 3H), 2.04 (s, 3H), 1.91 (dd, J$_1$=12.0 Hz, J$_2$=15.6 Hz, 1H), 0.84 (d, J=6.9 Hz, 3H).

$^{13}$C NMR (75 MHz, CDCl$_3$) δ 170.1, 156.3, 147.3, 144.9, 144.4, 143.3, 136.7, 130.7, 129.3, 120.6, 117.6, 117.4, 114.4, 112.1, 107.7, 101.0, 85.8, 60.5, 59.3, 56.5, 56.4, 56.2, 55.2, 48.9, 41.6, 40.9, 25.7, 25.3, 18.0, 15.6, 8.7.

ESI-MS m/z: Calcd. for C$_{32}$H$_{35}$F$_3$N$_5$O$_7$: 645.63. Found (M+H)$^+$: 646.2.

Example 50

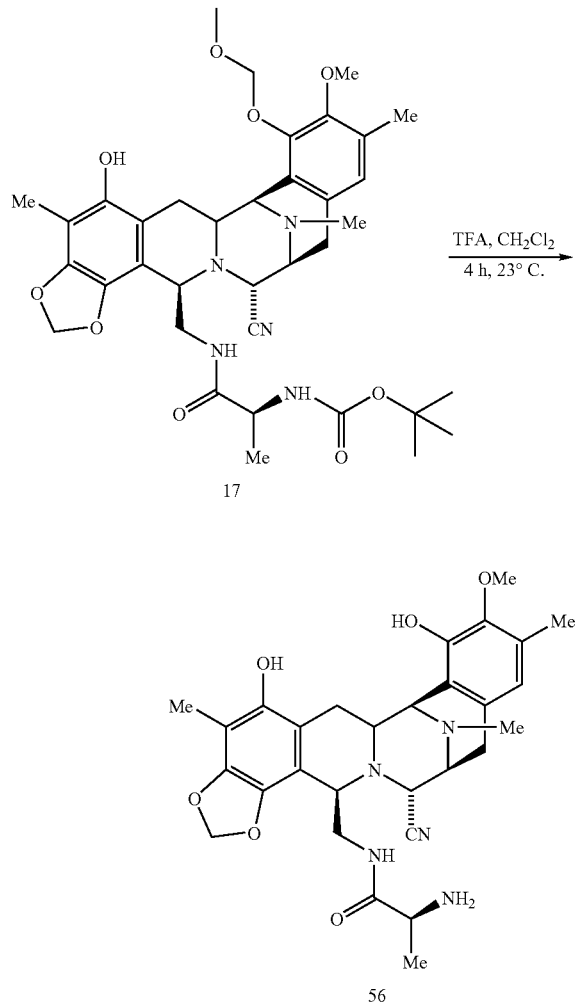

To a solution of 17 (200 mg, 0.288 mmol) in CH$_2$Cl$_2$ (1.44 ml), trifluoroacetic acid (888 ml, 11.53 mmol) was added and the reaction mixture was stirred for 4 h at 23° C. The reaction was quenched at 0° C. with saturated aqueous sodium bicarbonate (60 ml) and extracted with ethyl acetate (2×70 ml). The combined organic layers were dried (sodium sulphate) and concentrated in vacuo to afford 56 (147 mg, 93%) as a white solid that was used in subsequent reactions with no further purification.

Rf: 0.19 (ethyl acetate:methanol 5:1).

$^1$H NMR (300 MHz, CD$_3$OD). δ 6.48 (s, 1H), 5.88, d, J=0.9 Hz, 1H), 5.81 (d, J=0.9 Hz, 1H), 4.35 (d, J=2.4 Hz, 1H), 4.15 (d, J=1.8 Hz, 1H), 3.99-3.98 (m, 1H), 3.70 (s, 3H), 3.52-2.96 (m, 7H), 2.68 (d, J=18.3 Hz, 1H), 2.24 (s, 3H), 2.23 (s, 3H), 2.06 (s, 3H), 1.85 (dd, J$_1$=11.7 Hz, J$_2$=15.6 Hz, 1H), 0.91 (d, J=6.6 Hz, 3H).

$^{13}$C NMR (75 MHz, CD$_3$OD): δ 173.2, 149.1, 145.6, 144.9, 138.0, 132.2, 130.6, 121.4, 119.6, 117.4, 114.3, 109.2, 102.5, 82.3, 60.4, 58.4, 58.3, 57.8, 56.6, 50.1, 42.3, 41.6, 27.8, 26.2, 19.5, 15.5, 9.8.

ESI-MS m/z: Calcd. for C$_{29}$H$_{35}$N$_5$O$_6$: 549.62. Found (M+H)$^+$: 550.3.

Example 51

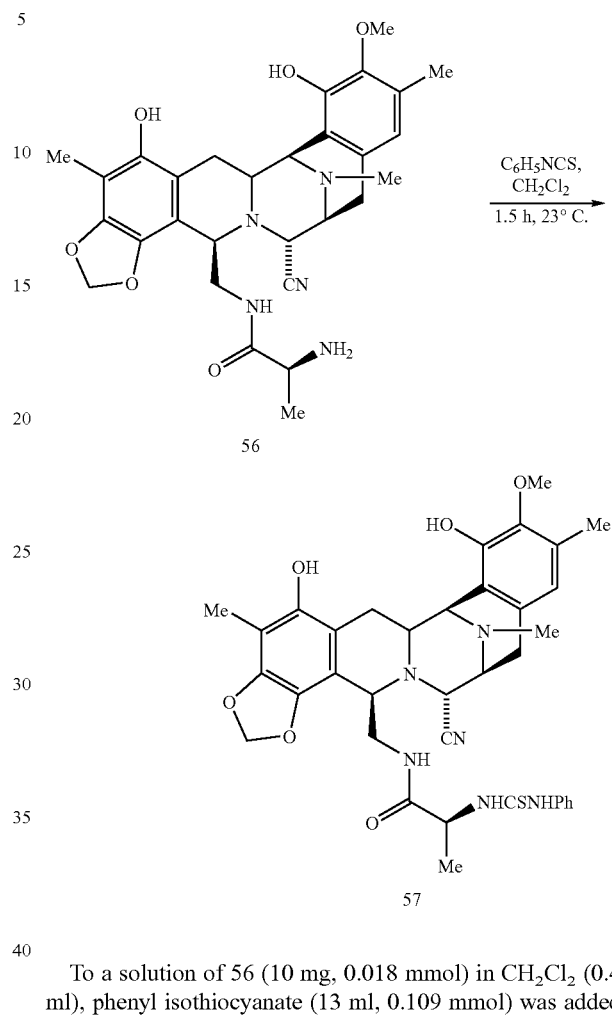

To a solution of 56 (10 mg, 0.018 mmol) in CH$_2$Cl$_2$ (0.4 ml), phenyl isothiocyanate (13 ml, 0.109 mmol) was added and the reaction was stirred at 23° C. for 1.5 h. The mixture was concentrated in vacuo and the residue was purified by flash column chromatography (SiO$_2$, gradient Hexane to 1:1 hexane:ethyl acetate) to afford 57 (8 mg, 65%) as a white solid.

Rf: 0.57 (ethyl acetate:methanol 10:1).

$^1$H NMR (300 MHz, CDCl$_3$): δ 7.88 (bs, 1H), 7.41-7.36 (m, 2 h), 7.27-7.22 (m, 1H), 7.02-7.00 (d, J=7.8 Hz, 2 h), 6.71 (d, J=7.2 Hz, 1H), 6.31 (s, 1H), 6.17 (bs, 1H), 5.93 (d, J=1.2 Hz, 1H), 5.83 (d, J=1.2 Hz, 1H), 5.55 (bs, 1H), 5.20-5.17 (m, 1H), 4.16 (d, J=1.8 Hz, 1H), 4.05 (bs, 1H), 4.02 (d, J=2.4 Hz, 1H), 3.79 (s, 3H), 3.75-3.71 (m, 1H), 3.35 (d, J=7.8 Hz, 1H), 3.28-3.19 (m, 2 h), 3.12-2.97 (m, 2 h), 2.50 (d, J=18.3 Hz, 1H), 2.32 (s, 3H), 2.21 (s, 3H), 2.15-2.09 (dd, J$_1$=11.4 Hz, J$_2$=15.9 Hz, 1H), 1.95 (s, 3H), 0.88 (d, J=6.9 Hz; 3H).

$^{13}$C NMR (75 MHz, CDCl$_3$): δ 178.5, 171.7, 147.2, 145.0, 144.3, 143.3, 137.0, 135.7, 130.6, 130.4, 129.6, 127.5, 124.3, 120.6, 117.7, 117.2, 115.3, 112.1, 108.3, 100.9, 60.9, 59.5, 56.7, 56.5, 56.2, 55.2, 54.1, 41.7, 41.1, 26.3, 25.4, 18.5, 15.8, 9.0.

ESI-MS m/z: Calcd. for C$_{36}$H$_{40}$N$_6$O$_6$S: 684.81. Found (M+H)$^+$: 685.3.

Example 52

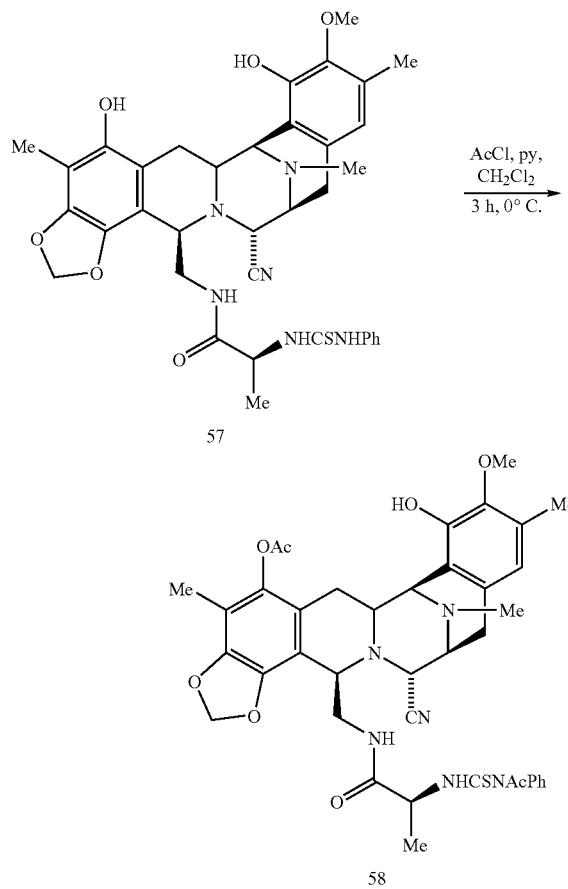

To a solution of 57 (45 mg, 0.065 mmol) in CH$_2$Cl$_2$ (0.5 ml), acetyl chloride (4.67 ml, 0.065 mmol) and pyridine (5.3 ml, 0.065 mmol) were added at 0° C. The reaction mixture was stirred for 3 h and then, the solution was diluted with CH$_2$Cl$_2$ (10 ml) and washed with 0.1 N HCl (5 ml). The organic layer was dried over sodium sulphate, filtered, and the solvent was eliminated under reduced pressure. The residue was purified by flash column chromatography (RP-18, CH$_3$CN: H$_2$O 40:60) to afford 58 (14 mg, 28%) as a white solid.

Rf: 0.34 (CH$_3$CN: H$_2$O 7:15).

$^1$H NMR (300 MHz, CDCl$_3$). δ 11.90 (d, J=6.6 Hz, 1H), 7.45-7.40 (m, 3H), 7.18-7.15 (m, 2 h), 6.58 (s, 1H), 6.00 (d, J=1.2 Hz, 1H), 5.89 (d, J=1.2 Hz, 1H), 5.70 (s, 1H), 5.37 (t, J=4.8 Hz, 1H), 4.48 (m, 1H), 4.23 (bs, 1H), 4.07 (bs, 2 h), 3.85-3.75 (m, 1H), 3.70 (s, 3H), 3.46-3.41 (m, 2 h), 3.24-3.20 (m, 1H), 3.00-2.95 (m, 1H), 2.87-2.75 (m, 1H), 2.31 (s, 3H), 2.28 (s, 3H), 2.24 (s, 3H), 2.00 (s, 3H), 1.85 (dd, J$_1$=11.4 Hz, J$_2$=15.6 Hz, 1H), 1.66 (s, 3H), 0.82 (d, J=6.0 Hz, 3H).

$^{13}$C NMR (75 MHz, CDCl$_3$)): δ 182.6, 174.3, 171.0, 146.6, 144.6, 142.7, 142.3, 140.7, 140.2, 131.3, 129.8, 129.3, 128.9, 128.8, 121.5, 120.4, 117.3, 116.6, 112.8, 112.0, 111.3, 101.5, 60.5, 59.0, 57.6, 56.2, 55.9, 55.3, 55.1, 41.6, 39.4, 27.8, 26.5, 24.8, 20.2, 17.1, 15.5, 9.3.

ESI-MS m/z: Calcd. for C$_{40}$H$_{44}$N$_6$O$_8$S: 768.88. Found (M+H)$^+$: 769.2.

Example 53

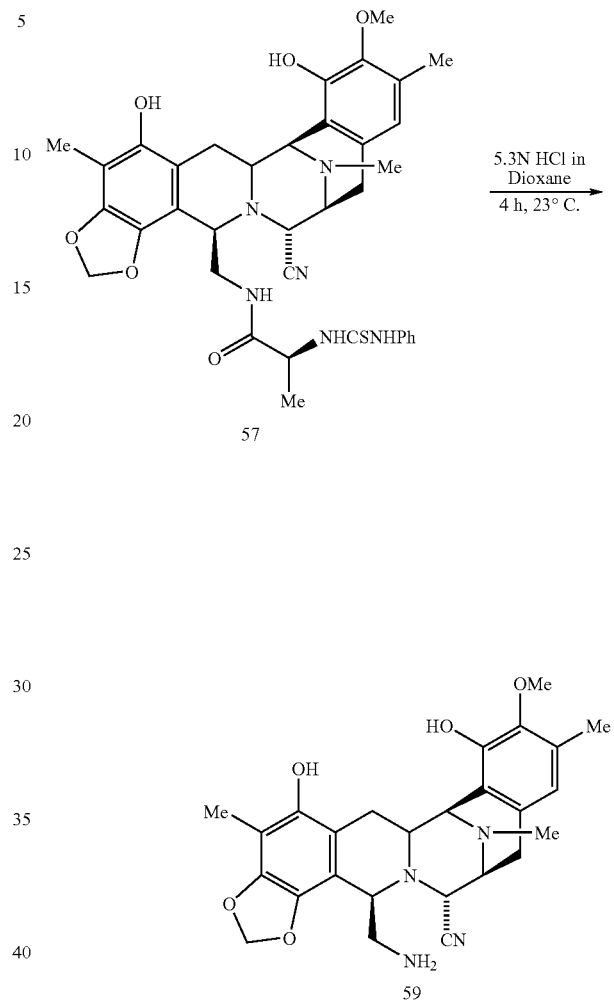

A solution of 57 (130 mg, 0.189 mmol) in dioxane (1 ml), 5.3N HCl/dioxane (1.87 ml) was added and the reaction was stirred at 23° C. for 4 h. Then, CH$_2$Cl$_2$ (15 ml) and H$_2$O (10 ml) were added to this reaction and the organic layer was decanted. The aqueous phase was basified with saturated aq sodium bicarbonate (60 ml) (pH=8) at 0° C. and then, extracted with ethyl acetate (2×50 ml). The combined organic extracts were dried (sodium sulphate), and concentrated in vacuo to afford 59 (63 mg, 70%) as a white solid.

Rf: 0.15 (ethyl acetate:methanol 5:1).

$^1$H NMR (300 MHz, CDCl$_3$). δ 6.67 (s, 1H), 5.99 (d, J=0.9 Hz, 1H), 5.91 (d, J=1.2 Hz, 1H), 5.10 (bs, 1H), 4.32 (d, J=7.2 Hz, 1H), 4.25 (dd, J$_1$=3.6 Hz, J$_2$=9.3 Hz, 1H), 3.7 (s, 3H), 3.71-3.64 (m, 2 h), 3.50 (dd, J$_1$=2.4 Hz, J$_2$=15.9 Hz, 1H), 3.42-3.37 (m, 2 h), 3.16 (dd, J$_1$=3.6 Hz, J$_2$=12.9 Hz, 1H), 2.57 (dd, J$_1$=9.3 Hz, J$_2$=12.9 Hz, 1H), 2.27 (s, 3H), 2.11 (s, 3H), 1.91 (dd, J$_1$=12.0 Hz, J$_2$=15.9 Hz, 1H).

ESI-MS m/z: Calcd. for C$_{26}$H$_{30}$N$_4$O$_5$: 478.5. Found (M+H)$^+$: 479.3.

Example 54

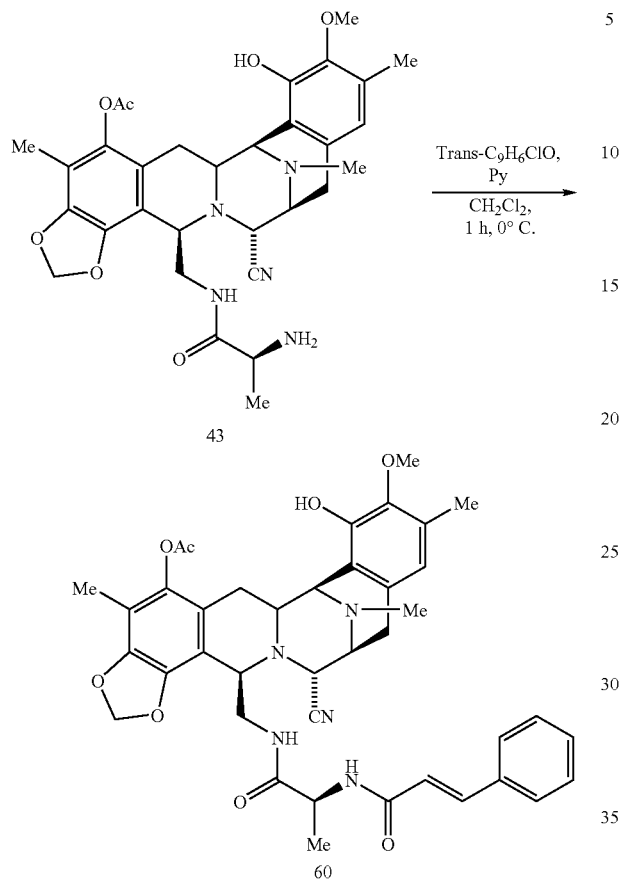

A solution of 43 (20 mg, 0.0338 mmol) in CH$_2$Cl$_2$ (0.3 ml), cinnamoyl chloride (5.63 mg, 0.0338 mmol) and pyridine (2.73 ml, 0.0338 mmol) were added at 0° C. The reaction mixture was stirred for 1 h and then, the solution was diluted with CH$_2$Cl$_2$ (10 ml) and washed with 0.1 N HCl (5 ml). The organic layer was dried over sodium sulphate, filtered, and the solvent was eliminated under reduced pressure. The residue was purified by flash column chromatography (SiO$_2$, EtOAc:MeOH 20:1) to afford 60 (22 mg, 90%) as a white solid.

Rf: 0.56 (EtOAc:MeOH 5:1).

$^1$H NMR (300 MHz, CDCl$_3$). δ 7.51 (s, 1H), 7.50-7.47 (m, 2H), 7.36-7.35 (m, 2H), 6.43 (s, 1H), 6.36 (brd, J=15.9 Hz, 2H), 6.01 (d, J=1.5 Hz, 1H), 5.90 (brd, J=1.5 Hz, 2H), 5.42 (t, J=6.0 Hz 1H), 4.12-4.07 (m, 3H), 3.96-3.95 (m, 1H), 3.73 (bs, 3H), 3.58 (bs, 2H), 3.39 (d, J=8.7 Hz, 1H), 3.25 (d, J=11.7 Hz, 1H), 3.0 (dd, J$_1$=7.5 Hz, J$_2$=17.7 Hz, 1H), 2.78 (d, J=15.9 Hz, 1H), 2.67 (d, J=16.5 Hz, 1H), 2.29 (s, 6H), 2.23 (s, 3H), 1.99 (s, 3H), 1.82 (dd, J$_1$=11.4 Hz, J$_2$=15.6 Hz, 1H), 0.83 (d, J=6.0 Hz, 3H).

$^{13}$C NMR (75 MHz, CDCl$_3$)): δ 172.0, 165.0, 146.9, 144.6, 143.1, 141.0, 140.5, 134.8, 131.0, 129.7, 129.1, 128.8, 127.8, 125.5, 123.8, 123.0, 121.1, 120.5, 117.7, 116.9, 112.8, 112.0, 101.9, 60.6, 59.2, 57.1, 56.4, 55.9, 55.3, 48.8, 41.7, 40.0, 26.5, 25.1, 20.3, 18.5, 15.7, 9.3.

ESI-MS m/z: Calcd. for C$_{40}$H$_{43}$N$_5$O$_8$: 721.8. Found (M+H)$^+$: 722.3.

Example 55

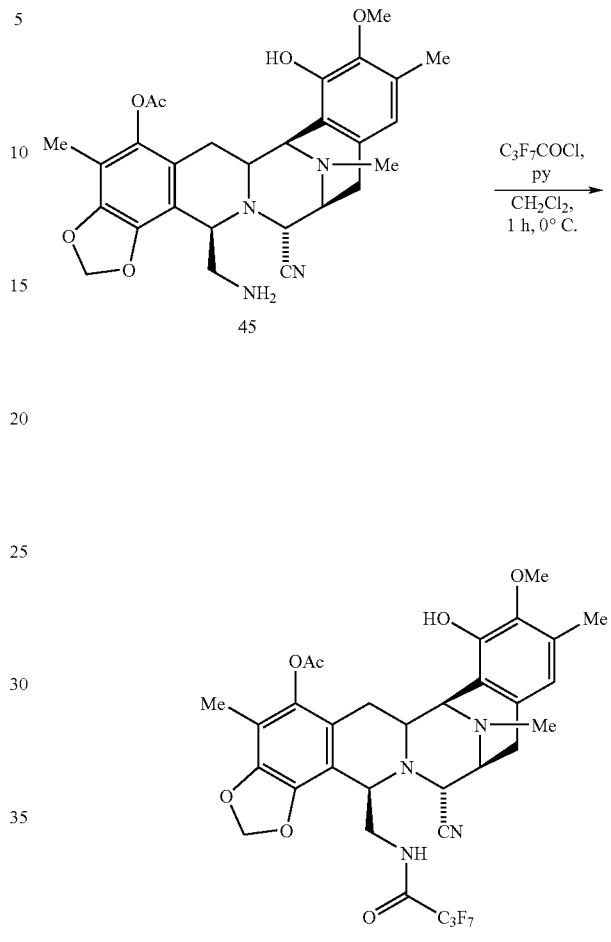

A solution of 45 (19 mg, 0.0364 mmol) in CH$_2$Cl$_2$ (0.3 ml), heptafluorobutyryl chloride (5.44 ml, 0.0364 mmol) and pyridine (2.95 ml, 0.0364 mmol) were added at 0° C. The reaction mixture was stirred for 1 h and then, the solution was diluted with CH$_2$Cl$_2$ (10 ml) and washed with 0.1 N HCl (5 ml). The organic layer was dried over sodium sulphate, filtered, and the solvent was eliminated under reduced pressure. The residue was purified by flash column chromatography (SiO$_2$, EtOAc:MeOH 20:1) to afford 61 (11.7 mg, 45%) as a white solid.

Rf: 0.76 (EtOAc:MeOH 5:1).

$^1$H NMR (300 MHz, CDCl$_3$) δ 6.46 (s, 1H), 6.12 (bs, 1H), 5.98 (d, J=1.2 Hz, 1H), 5.93 (d, J=1.2 Hz, 1H), 5.72 (bs, 1H), 4.13-4.11 (m, 2H), 4.0 (d, J=2.4 Hz, 1H), 3.98-3.96 (m, 1H), 3.73 (s, 3H), 3.39 (d, J=7.5 Hz, 1H), 3.39-3.28 (m, 2H), 3.09 (dd, J$_1$=8.1 Hz, J$_2$=18.0 Hz, 1H), 2.80 (d, J=16.2 Hz, 1H), 2.46 (d, J=18.3 Hz, 1H), 2.32 (s, 6H), 2.21 (s, 3H), 1.99 (s, 3H), 1.80 (dd, J$_1$=12.0 Hz, J$_2$=16.2 Hz, 1H).

ESI-MS m/z: Calcd. for C$_{32}$H$_{31}$F$_7$N$_4$O$_7$: 716.6. Found (M+H)$^+$: 717.2.

Example 56

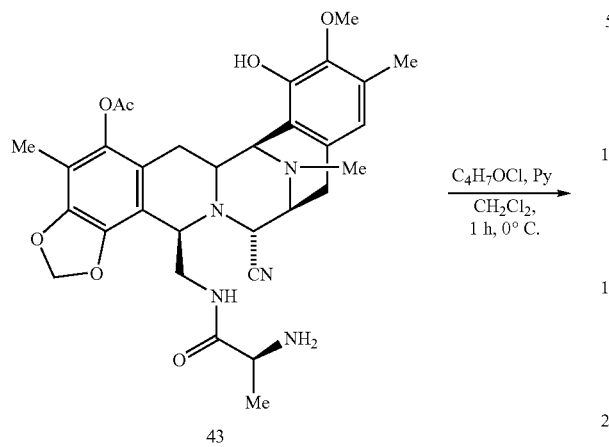

Example 57

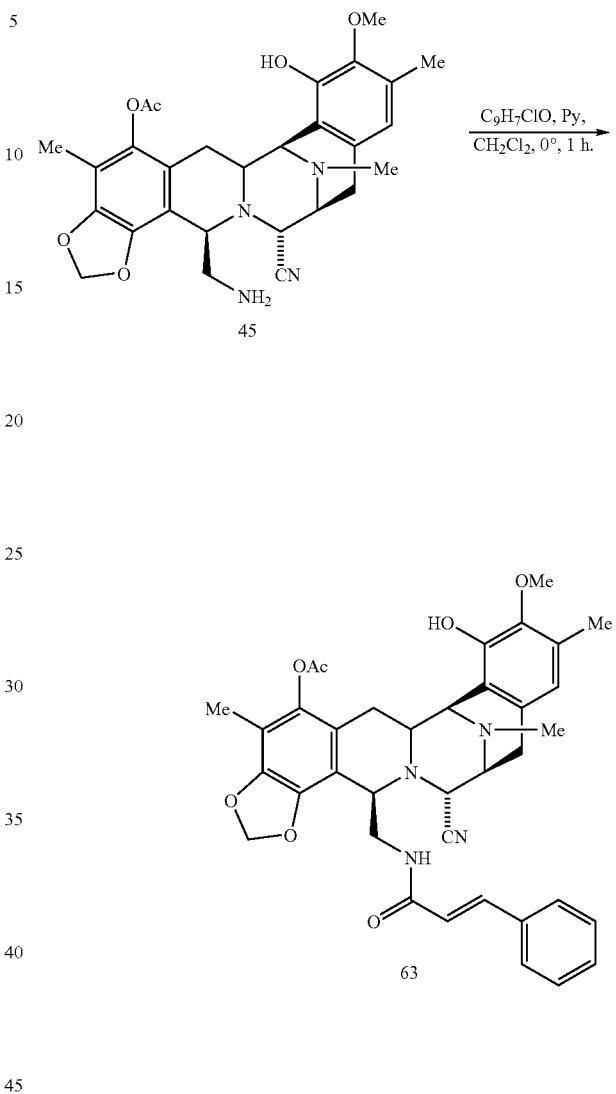

A solution of 43 (24 mg, 0.04 mmol) in CH$_2$Cl$_2$ (0.3 ml), butyryl chloride (4.15 ml, 0.04 mmol) and pyridine (3.28 ml, 0.04 mmol) were added at 0° C. The reaction mixture was stirred for 1 h and then, the solution was diluted with CH$_2$Cl$_2$ (10 ml) and washed with 0.1 N HCl (5 ml). The organic layer was dried over sodium sulphate, filtered, and the solvent was eliminated under reduced pressure. The residue was purified by flash column chromatography (SiO$_2$, EtOAc:MeOH 20:1) to afford 62 (24 mg, 90%) as a white solid.

Rf: 0.35 (EtOAc:MeOH 5:1).

$^1$H NMR (300 MHz, CDCl$_3$) δ 6.47 (s, 1H), 6.10 (d, J=6.5 Hz, 1H), 6.0 (d, J=1.5 Hz, 1H), 5.91 (d, J=1.5 Hz, 1H), 5.86 (bs, 1H), 5.31 (d, J=6.9 Hz, 1H), 4.11-4.06 (m, 3H), 3.85-3.81 (m, 1H), 3.75 (s, 3H), 3.59-3.53 (m, 2H), 3.38 (d, J=7.5 Hz, 1H), 3.27-3.22 (m, 1H), 3.0 (dd, J$_1$=7.8 Hz, J$_2$=17.4 Hz, 1H), 2.79 (d, J=15.3 Hz, 1H), 2.63 (d, J=17.7 Hz, 1H), 2.31 (s, 3H), 2.0 (s, 3H), 1.80 (dd, J$_1$=12.0 Hz, J$_2$=15.9 Hz, 1H), 1.58 (q, J=7.2 Hz, 2H), 0.89 (t, J=7.2 Hz, 3H), 0.76 (d, J=6.6 Hz, 3H).

ESI-MS m/z: Calcd. for C$_{35}$H$_{43}$N$_5$O$_8$: 661.64. Found (M+H)$^+$: 662.3

A solution of 43 (19 mg, 0.0364 mmol) in CH$_2$Cl$_2$ (0.3 ml), cinnamoyl chloride (6.06 mg, 0.0364 mmol) and pyridine (2.95 ml, 0.0364 mmol) were added at 0° C. The reaction mixture was stirred for 1h and then, the solution was diluted with CH$_2$Cl$_2$ (10 ml) and washed with 0.1 N HCl (5 ml). The organic layer was dried over sodium sulphate, filtered, and the solvent was eliminated under reduced pressure. The residue was purified by flash column chromatography (SiO$_2$, EtOAc: MeOH 20:1) to afford 63 (20.1 mg, 85%) as a white solid.

Rf: 0.65 (EtOAc:MeOH 5:1).

$^1$H NMR (300 MHz, CDCl$_3$) δ 7.39-7.29 (m, 5H), 6.42, (s, 1H), 6.01 (d, J=1.5 Hz, 1H), 5.92 (d, J=1.5 Hz, 1H), 5.73 (bs, 1H), 5.24 (t, J=6.8 Hz, 1H), 4.12-4.08 (m, 3H), 3.66-3.64 (m, 2H), 3.58 (bs, 3H), 3.36 (d, J=8.7 Hz, 1H), 3.29 (d, J=12.0 Hz, 1H), 2.98 (dd, J$_1$=8.1 Hz, J$_2$=18 Hz, 1H), 2.33 (s, 6H), 2.29 (s, 3H), 2.01 (s, 3H), 1.84 (dd, J$_1$=12.0 Hz, J$_2$=15.9 Hz, 1H).

ESI-MS m/z: Calcd. for C$_{37}$H$_{38}$N$_4$O$_7$: 650.72. Found (M+H)$^+$: 651.2.

Example 58

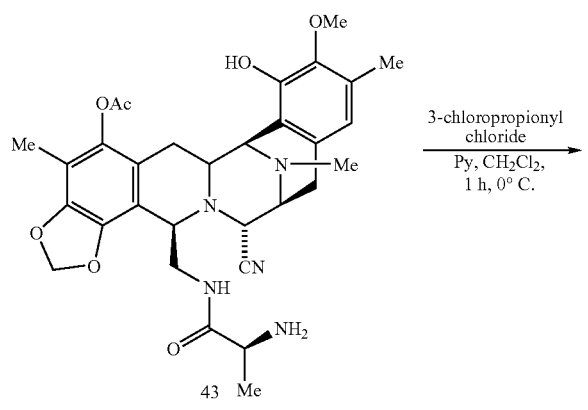

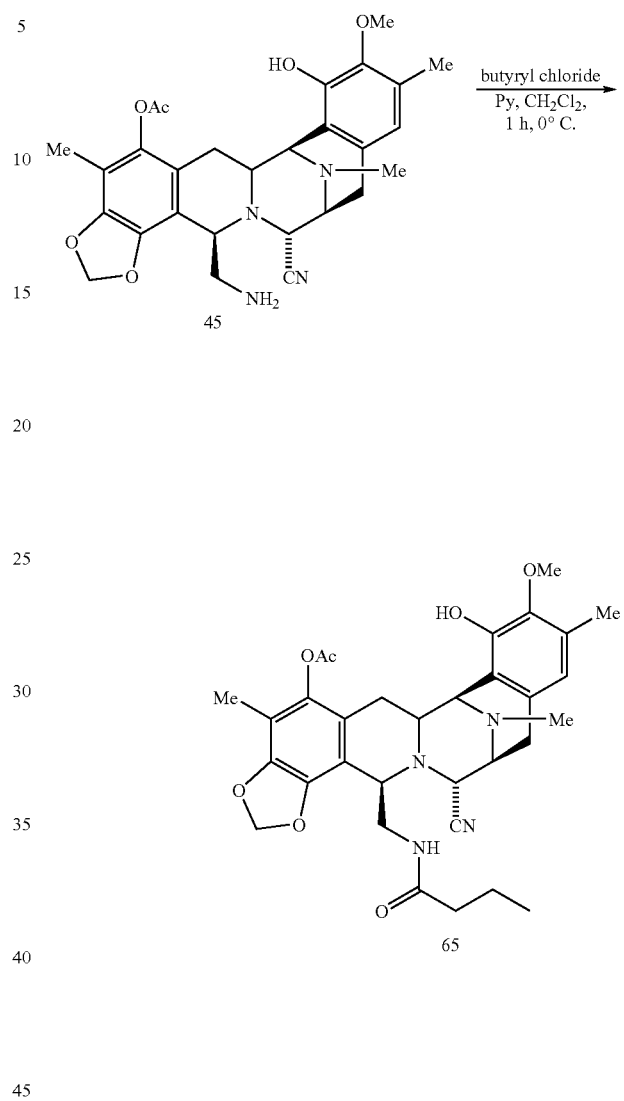

Example 59

A solution of 43 (20 mg, 0.0338 mmol) in CH$_2$Cl$_2$ (0.3 ml), 3-chloropropionyl chloride (3.22 ml, 0.0338 mmol) and pyridine (2.73 ml, 0.0338 mmol) were added at 0° C. The reaction mixture was stirred for 1 h and then, the solution was diluted with CH$_2$Cl$_2$ (10 ml) and washed with 0.1 N HCl (5 ml). The organic layer was dried over sodium sulphate, filtered, and the solvent was eliminated under reduced pressure. The residue was purified by flash column chromatography (SiO$_2$, EtOAc:MeOH 20:1) to afford 64 (20.5 mg, 89%) as a white solid.

Rf: 0.32 (EtOAc:Hexane 5:1).

$^1$H NMR (300 MHz, CDCl$_3$) δ 6.48 (s, 3H), 6.28 (m, 1H), 5.99 (d, J=1.2 Hz, 1H), 5.91 (d, J=1.2 Hz, 1H), 5.86 (bs, 1H), 5.31 (m, 1H), 4.08-4.07 (m, 3H), 3.75 (s, 3H), 3.72-3.53 (m, 5H), 3.39 (d, J=8.1 Hz, 1H), 3.24 (d, J=12.0 Hz, 1H), 3.00 (dd, J$_1$=8.1 Hz, J$_2$=18.0 Hz, 1H), 2.79 (d, J=13.5 Hz, 1H), 2.50 (t, J=6.3 Hz, 2H), 2.32 (s, 3H), 2.28 (s, 3H), 2.25 (s, 3H), 2.0 (s, 3H), 1.79 (dd, J$_1$=12.3 Hz, J$_2$=14.8 Hz, 1H), 0.81 (d, J=6.3 Hz, 3H).

A solution of 43 (19 mg, 0.0364 mmol) in CH$_2$Cl$_2$ (0.3 ml), butyl chloride (3.78 ml, 0.0364 mmol) and pyridine (2.95 ml, 0.0364 mmol) were added at 0° C. The reaction mixture was stirred for 1 h and then, the solution was diluted with CH$_2$Cl$_2$ (10 ml) and washed with 0.1 N HCl (5 ml). The organic layer was dried over sodium sulphate, filtered, and the solvent was eliminated under reduced pressure. The residue was purified by flash column chromatography (SiO$_2$, EtOAc:MeOH 20:1) to afford 64 (19 mg, 87%) as a white solid.

Rf: 0.60 (EtOAc:MeOH 5:1).

$^1$H NMR (300 MHz, CDCl$_3$) δ 6.50 (s, 1H), 5.98 (d, J=1.5 Hz, 1H), 5.91 (d, J=1.5 Hz, 1H), 5.75 (s, 1H), 5.01 (t, J=6.4 Hz, 1H), 4.10-4.09 (m, 1H), 4.06 (d, J=2.1 Hz, 1H), 4.03-4.02 (m, 1H), 3.76 (s, 3H), 3.67-3.60 (m, 1H), 3.42-3.35 (m, 2H), 3.29 (d, J=12.0 Hz, 1H), 3.02 (dd, J$_1$=7.8 Hz, J$_2$=17.7 Hz, 1H), 2.79 (d, J=14.1 Hz, 1H), 2.56 (d, J=18.3 Hz, 1H), 2.32 (s, 3H), 2.31 (s, 3H), 2.25 (s, 3H), 1.78 (dd, J$_1$=12.0 Hz, J$_2$=15.9 Hz, 1H), 1.63 (s, 3H), 1.53-1.46 (m, 2H), 1.28-1.16 (m, 2H), 0.68 (t, J=7.2 Hz, 3H).

ESI-MS m/z: Calcd. for C$_{32}$H$_{38}$N$_4$O$_7$: 590.67. Found (M+H)$^+$: 591.2.

Example 60

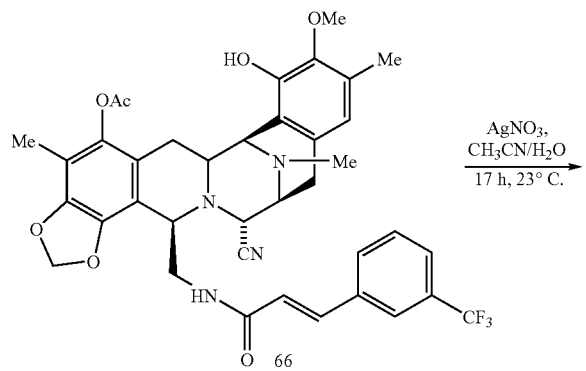

Example 61

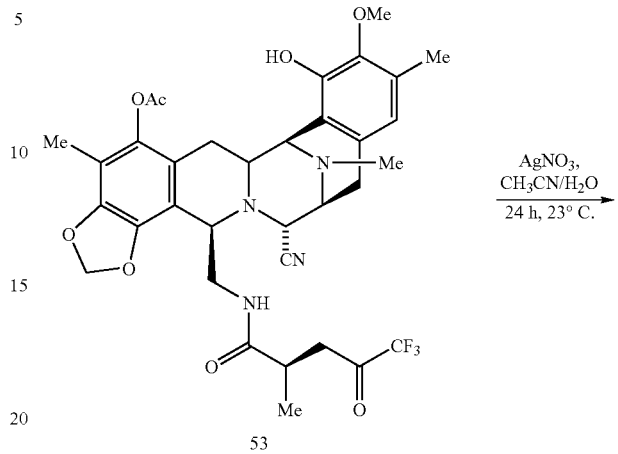

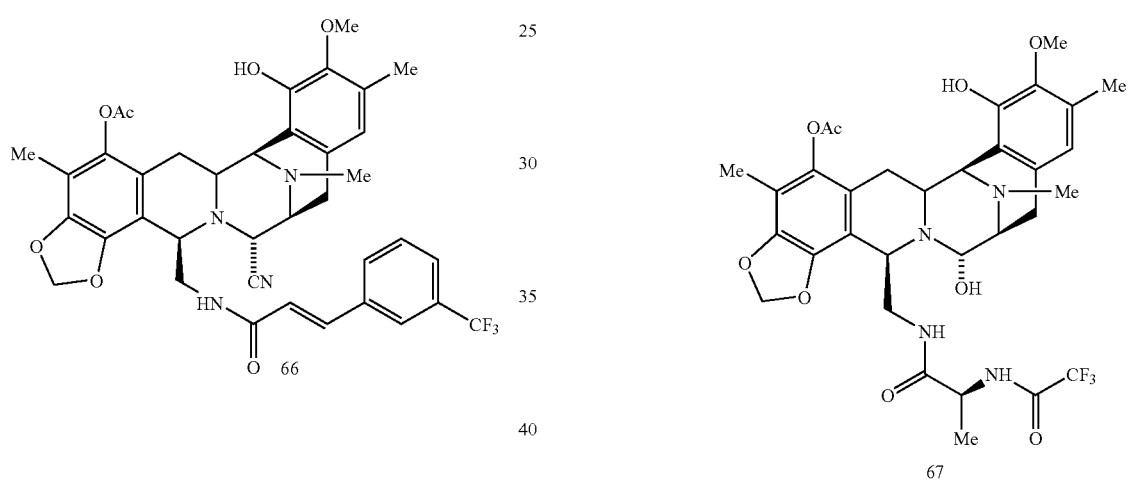

To a solution of 50 (31.7 mg, 0.044 mmol) in CH$_3$CN/H$_2$O (1.5 ml/0.5 ml), AgNO$_3$ (225 mg, 1.32 mmol) was added and the reaction was stirred at 23° C. for 17 h. Then brine (10 ml) and Aq sat NaHCO$_3$ (10 ml) were added at 0° C. and the mixture was stirred for 15 min, filtered through a pad of celite and washed with CH$_2$Cl$_2$ (20 ml). The solution was decanted and the organic layer was dried and concentrated in vacuo. The residue was purified by flash column chromatography (SiO$_2$, EtOAc:MeOH 5:1) to afford 66 (16 mg, 51%) as a white solid.

Rf: 0.26 (EtOAc:MeOH 5:1).

$^1$H NMR (300 MHz, CDCl$_3$) δ 7.66-7.42 (m, 4H), 7.20 (bs, 1H), 6.44 (s, 1H), 5.97 (b, J=1.2 Hz, 1H), 5.90 (d, J=1.2 Hz, 1H), 5.76 (bs, 1H), 5.28 (bs, 1H), 4.54 (bs, 1H), 4.43 (bs, 1H), 4.00 (bs, 1H), 3.68-3.57 (m, 4H), 3.47 (d, J=3.3 Hz, 1H), 3.40 (d, J=11.7 Hz, 1H), 3.17 (d, J=6.9 Hz, 1H), 2.92 (dd, J$_1$=8.1 Hz, J$_2$=17.7 Hz, 1H), 2.74 (d, J=17.1 Hz, 1H), 2.48 (d, J=18.6 Hz, 1H), 2.32 (s, 6H), 2.28 (s, 3H), 1.99 (s, 3H), 1.76 (dd, J$_1$=12.0 Hz, J$_2$=16.2 Hz, 1H).

ESI-MS m/z: Calcd. for C$_{37}$H$_{38}$F$_3$N$_3$O$_8$: 709. Found (M$^+$-17): 692.3.

To a solution of 53 (57 mg, 0.0828 mmol) in CH$_3$CN/H$_2$O (1.5 mL/0.5 ml), AgNO$_3$ (650 mg, 3.81 mmol) was added and the reaction was stirred at 23° C. for 24 h. Then, brine (10 ml) and Aq sat NaHCO$_3$ (10 ml) were added at 0° C. and the mixture was stirred for 15 min, filtered through a pad of celite and washed with CH$_2$Cl$_2$ (20 ml). The solution was decanted and the organic layer was dried and concentrated in vacuo. The residue was purified by flash column chromatography (SiO$_2$, EtOAc:MeOH 5:1) to afford 67 (28 mg, 50%) as a white solid.

Rf: 0.28 (EtOAc:MeOH 10:1).

$^1$H NMR (300 MHz, CDCl$_3$) δ 6.47 (s, 1H), 5.97 (s, 1H), 5.88 (s, 1H), 5.35 (bs, 1H), 4.51 (bs, 1H), 4.41 (bs, 1H), 4.12-4.05 (m, 1H), 4.00 (d, J=2.7 Hz, 1H), 3.77 (s, 3H), 3.64 (bs, 1H), 3.46 (d, J=3.3 Hz, 1H), 3.34 (d, J=11.4 Hz, 1H), 3.18 (d, J=7.5 Hz, 1H), 2.95 (dd, J$_1$=8.4 Hz, J$_2$=18.3 Hz, 1H), 2.70 (d, J=15.6 Hz, 1H), 2.48 (d, J=17.7 Hz, 1H), 2.28 (s, 3H), 2.27 (s, 3H), 2.26 (s, 3H), 1.98 (s, 3H), 1.68 (dd, J$_1$=12 Hz, J$_2$=15.6 Hz, 1H), 0.86 (d, J=6.3 Hz, 3H).

ESI-MS m/z: Calcd. for C$_{32}$H$_{37}$F$_3$N$_4$O$_9$: 678.66. Found (M$^+$-17): 661.2.

Example 62

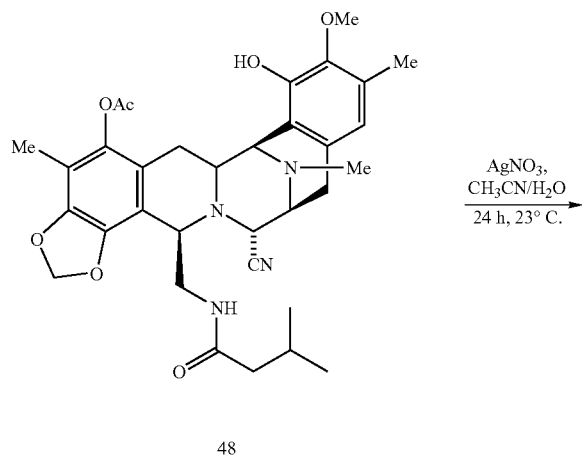

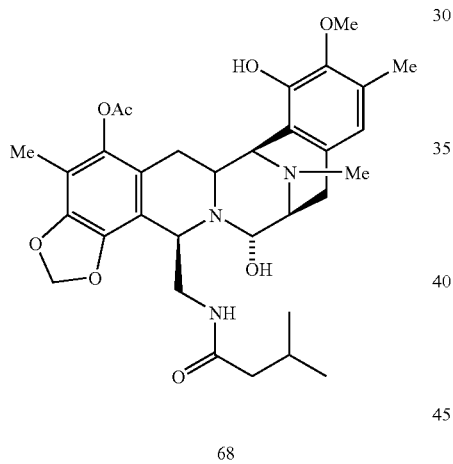

To a solution of 48 (32 mg, 0.0529 mmol) in CH$_3$CN/H$_2$O (1.5 ml/0.5 ml), AgNO$_3$ (270 mg, 1.58 mmol) was added and the reaction was stirred at 23° C. for 24 h. Then, brine (10 ml) and Aq sat NaHCO$_3$ (10 ml) were added at 0° C. and the mixture was stirred for 15 min, filtered through a pad of celite and washed with CH$_2$Cl$_2$ (20 ml). The solution was decanted and the organic layer was dried and concentrated in vacuo. The residue was purified by flash column chromatography (SiO$_2$, EtOAc:MeOH 5:1) to afford 68 (18 mg, 56%) as a white solid.

Rf: 0.40 (EtOAc:MeOH 5:1).

$^1$H NMR (300 MHz, CDCl$_3$) δ 6.50 (s, 1H), 5.95 (d, J=1.2 Hz, 1H), 5.88 (d, J=1.2 Hz, 1H), 5.23 (d, J=6.9 Hz, 1H), 4.45 (d, J=3.3 Hz, 1H), 4.38 (s, 1H), 4.01 (d, J=2.4 Hz, 1H), 3.78 (m, 1H), 3.77 (s, 3H), 3.41-3.37 (m, 1H), 3.17-3.15 (m, 1H), 2.96 (dd, J$_1$=7.8 Hz, J$_2$=18.0 Hz, 1H), 2.70 (d, J=15.3 Hz, 1H), 2.40 (d, J=18.0 Hz, 1H), 2.30 (s, 6H), 2.27 (s, 3H), 1.76-1.65 (m, 1H), 1.35-1.25 (m, 2H), 0.89-0.82 (m, 1H), 0.69 (d, J=6.6 Hz, 3H), 0.58 (d, J=6.6 Hz, 3H)

Example 63

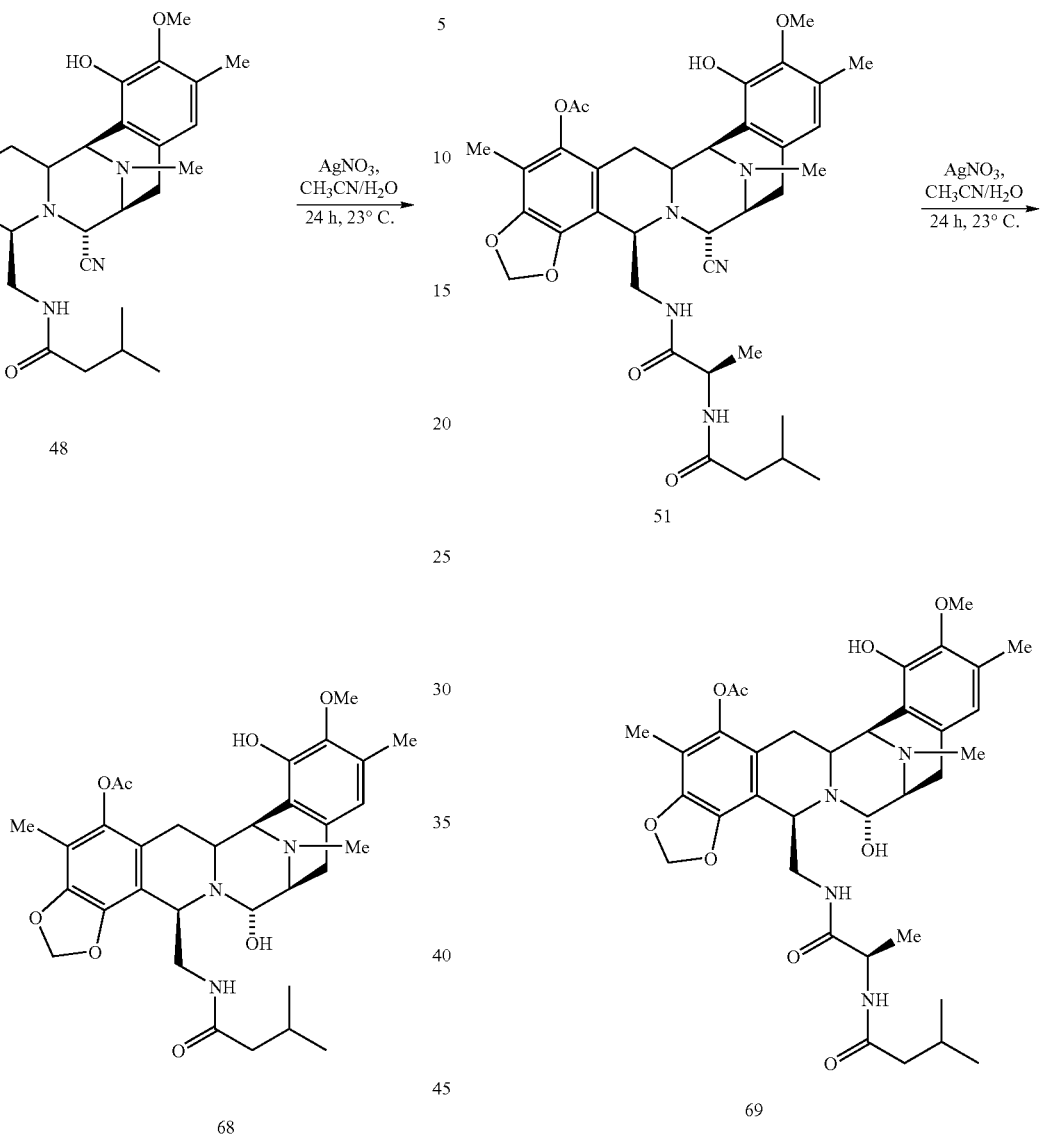

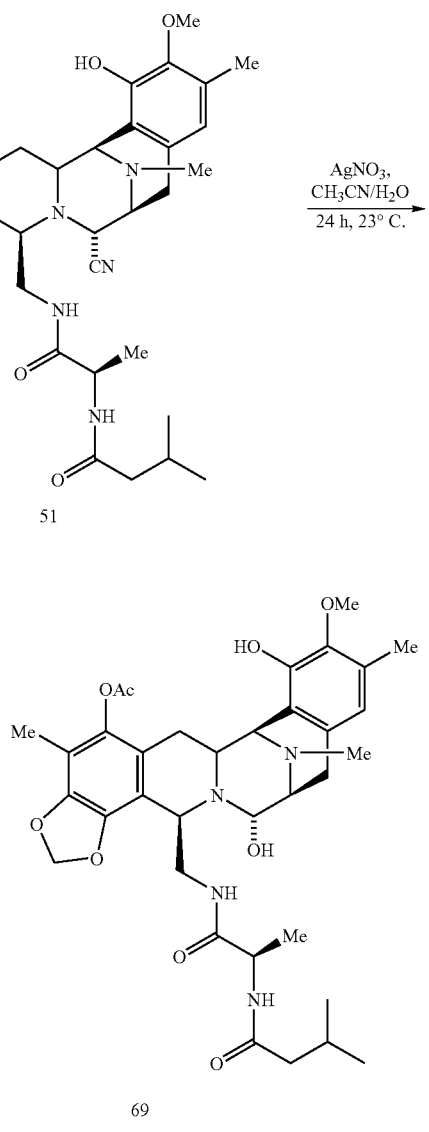

To a solution of 51 (27 mg, 0.04 mmol) in CH$_3$CN/H$_2$O (1.5 ml/0.5 ml), AgNO$_3$ (204 mg, 1.19 mmol) was added and the reaction was stirred at 23° C. for 24 h. Then, brine (10 ml) and Aq sat NaHCO$_3$ (10 ml) were added at 0° C. and the mixture was stirred for 15 min, filtered through a pad of celite and washed with CH$_2$Cl$_2$ (20 ml). The solution was decanted and the organic layer was dried and concentrated in vacuo. The residue was purified by flash column chromatography (SiO$_2$, EtOAc:MeOH 5:1) to afford 69 (10 mg, 38%) as a white solid.

Rf: 0.38 (EtOAc:MeOH 5:1).

$^1$H NMR (300 MHz, CDCl$_3$) δ 6.48 s, 1H), 6.16 (bs, 1H), 5.98 (d, J=1.5 Hz, 1H), 5.89 (d, J=1.5 Hz, 1H), 5.33 (t, J=6.0 Hz, 1H), 4.50 (m, 1H), 4.40 (m, 1H), 4.11-4.09 (m, 1H), 4.00 (d, J=2.6 Hz, 1H), 3.78 (s, 3H), 3.41-3.32 (m, 3H), 3.18 (d, J=8.4 Hz, 1H), 2.94 (dd, J$_1$=8.4 Hz, J$_2$=18.3 Hz, 1H), 2.70 (d, J=14.4 Hz, 1H), 4.45 (d, J=18.3 Hz, 1H), 2.31 (s, 3H), 2.28 (s, 3H), 2.27 (s, 3H), 2.04 (s, 3H), 2.00-1.86 (m, 3H), 1.73 (m, 1H), 0.87 (d, J=6.3 Hz, 6H).

Example 64

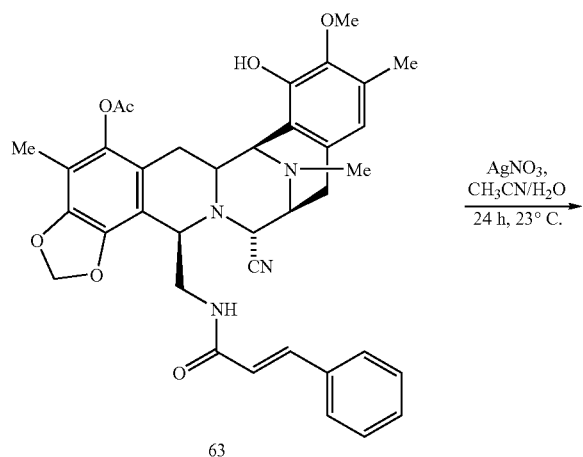

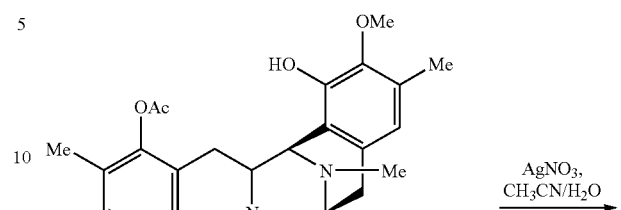

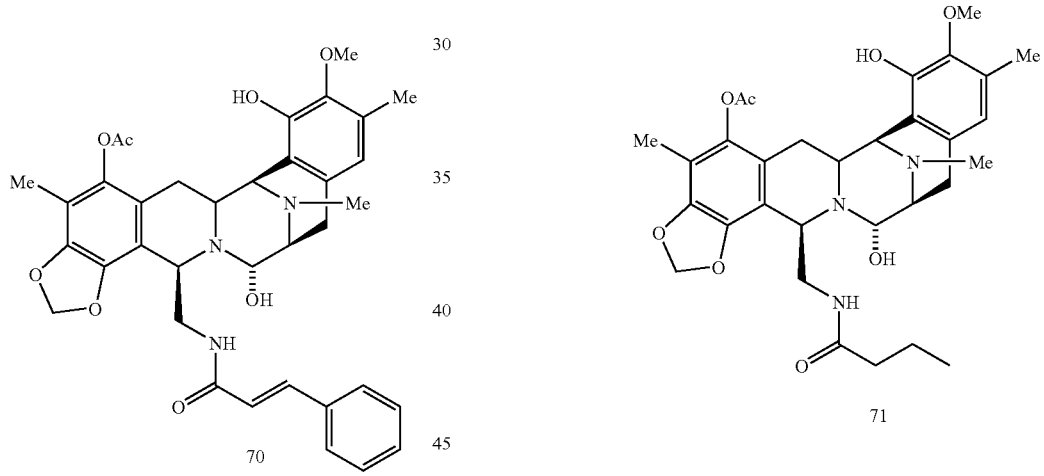

Example 65

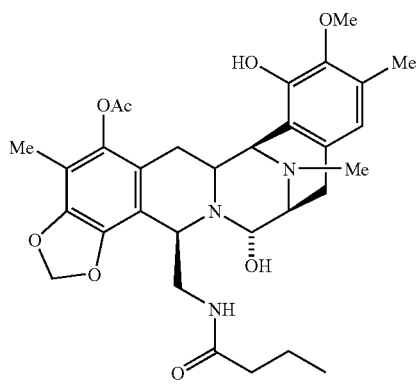

To a solution of 63 (15 mg, 0.023 mmol) in CH$_3$CN/H$_2$O (1.5 ml/0.5 ml), AgNO$_3$ (118 mg, 0.691 mmol) was added and the reaction was stirred at 23° C. for 24 h. Then, brine (10 ml) and Aq sat NaHCO$_3$ (10 ml) were added at 0° C. and the mixture was stirred for 15 min, filtered through a pad of celite and washed with CH$_2$Cl$_2$ (20 ml). The solution was decanted and the organic layer was dried and concentrated in vacuo. The residue was purified by flash column chromatography (SiO$_2$, EtOAc:MeOH 5:1) to afford 70 (20.1 mg, 85%) as a white solid.

Rf: 0.43 (EtOAc:MeOH 5:1).

$^1$H NMR (300 MHz, CDCl$_3$) δ 7.38-7.28 (m, 5H), 6.48 (s, 1H), 5.98 (d, J=1.5 Hz, 1H), 5.91 (d, J=1.5 Hz, 1H), 5.75 (bs, 1H), 5.38 (brd, 1H), 5.30 (bs, 1H), 4.53 (m, 1H), 4.42 (m, 1H), 4.02 (d, J=2.7 Hz, 1H), 3.78-3.65 (m, 5H), 3.46-3.40 (m, 2H), 3.17 (d, J=7.8 Hz, 1H), 2.94 (dd, J$_1$=7.8 Hz, J$_2$=17.7 Hz, 1H), 2.73 (d, J=16.8 Hz, 1H), 2.45 (d, J=18.0 Hz, 1H), 2.31 (s, 6H), 2.28 (s, 3H), 1.97 (s, 3H), 1.77 (dd, J$_1$=12.0 Hz, J$_2$=15.3 Hz, 1H).

To a solution of 65 (25 mg, 0.042 mmol) in CH$_3$CN/H$_2$O (1.5 ml/0.5 ml), AgNO$_3$ (215.56 mg, 1.269 mmol) was added and the reaction was stirred at 23° C. for 24 h. Then, brine (10 ml) and Aq sat NaHCO$_3$ (10 ml) were added at 0° C. and the mixture was stirred for 15 min, filtered through a pad of celite and washed with CH$_2$Cl$_2$ (20 ml). The solution was decanted and the organic layer was dried and concentrated in vacuo. The residue was purified by flash column chromatography (SiO$_2$, EtOAc:MeOH 5:2) to afford 71 (16 mg, 65%) as a white solid.

Rf: 0.0.5 (EtOAc:MeOH 5:2).

$^1$H NMR (300 MHz, CDCl$_3$) δ 6.50 (s, 1H), 5.95 (d, J=1.5 Hz, 1H), 5.78 (s, 1H), 5.19 (bs, 1H), 4.45 (d, J=3.3 Hz, 1H), 4.37 (bs, 1H), 4.11 (brd, J=4.8 Hz, 1H), 4.01 (d, J=2.1 Hz, 1H), 3.76 (s, 1H), 3.71-3.69 (m, 1H), 3.49-3.35 (m, 1H), 3.24 (d, J=13.5 Hz, 1H), 3.15 (d, J=9.3 Hz, 1H), 2.95 (dd, J$_1$=8.1 Hz, J$_2$=17.7 Hz, 1H), 2.70 (d, J=15.6 Hz, 1H), 2.40 (d, J=18.0 Hz, 1H), 2.31 (s, 3H), 2.29 (s, 3H), 2.26 (s, 3H), 1.96 (s, 3H), 1.75-1.66 (m, 1H), 1.52-1.17 (m, 2H), 0.66 (t, J=7.2 Hz, 3H).

Fermentation Procedures

Example A

Seed medium YMP3 containing 1% glucose; 0.25% beef extract; 0.5% bacto-peptone; 0.25% NaCl; 0.8% $CaCO_3$ was inoculated with 0.1% of a frozen vegetative stock of the microorganism, strain A2-2 of *Pseudomonas fluorescens*, and incubated on a rotary shaker (250 rpm) at 27° C. After 30 h of incubation, the seed culture was added to a agitated-vessel fermentor with a production medium composed of 2% dextrose; 4% mannitol, 2% dried brewer's yeast (Vitalevor® Biolux, Belgium); 1% $(NH_4)_2SO_4$; 0.04% $K_2HPO_4$; 0.8 KCl; 0.001% $FeCl_3$; 0.1% L-Tyr; 0.8% $CO_3Ca$; 0.05% PPG-2000; 0.2% anti-foam silicone (ASSAF-100, RHODIA UK). The sterilisation was carried out at 122° C. 30 minutes. The volume inoculated was a 2% (v/v). The temperature was 27° C. (0 to 16 h) and 24° C. from 16 h to final process (41 hours). The dissolve oxygen-pressure was upper to 25%. The pH was controlled at 6.0 with diluted sulphuric acid since 28 hours till final process. The overpressure was 0.5 bar. A 1% mannitol or sorbitol was added from 16 h to final process (for two days running) and 2% for three days fermentation-process.

After 41 or 64 hours, the fermentation broth must be extracted for recovery safracin B or KCN treatment in the clarified broth for recovery safracin B-cyano.

Example B

Obtention of Safracin B Cyano from the Crude Extract.

A clarification or filtration from the fermentation broth at pH 6 removes the solids. The clarified broth was adjusted a pH 9.5 with diluted sodium hydroxide and extracted twice with 2:1 (v/v) ethyl acetate, methylene chloride or butyl acetate. The extraction was carried out into an agitated-vessel during 20', the temperature of the mixture was maintained at 8 to 10° C. The two phases were separated by a liquid-liquid centrifuge. The organic phase was dried with sodium sulphate anhydrous or frozen and then filtered for removing ice. This organic phase (ethyl acetate layer) was evaporated until obtention of an oil-crude extract.

Example C

Obtention of Safracin B Cyano from the Clarified Broth.

A clarification or filtration from the fermentation broth at pH 6 removes the solids. The clarified broth was adjusted at pH 3.9 with concentrated acetic acid. 0.5 grams per litre of KCN are added to the clarified broth an incubated at 20° C. during 1 hour with agitation. Then, the temperature was decreased at 15° C. and the pH was adjusted at 9.5 with diluted sodium hydroxide and extracted with 2:1.5 (v/v) ethyl acetate. The extraction was carried out into an agitated-vessel during 20 minutes, the temperature of the mixture was maintained at 8 to 10° C. The two phases were separated by a liquid-liquid centrifuge. The organic phase was dried with sodium sulphate anhydrous. This organic phase (ethyl acetate layer) was evaporated until obtention of an oil-crude extract. This extract was purified by flash column chromatography ($SiO_2$, gradient 20:1 to 10: to 5:1 ethyl acetate:methanol) to afford quantitatively compound 2 as a light yellow solid.

Rf: 0.55 (ethyl acetate:methanol 5:1); .$t_R$=19.9 min [HPLC, Delta Pack C4, 5 μm, 300 A, 150×3 mm, λ=215 nm, flow=0.7 ml/min, temp=50° C., grad.: $CH_3CN$-aq. NaOAc (10 mM) 85%-70% (20')];

$^1$H NMR (300 Mhz, $CDCl_3$): δ 6.54 (dd, $J_1$=4.4 Hz, $J_2$=8.4 Hz, 1H), 6.44 (s, 1H), 4.12 (d, J=2.4 Hz, 1H), 4.04 (d, J=2.4 Hz, 1H), 4.00 (s, 3H), 3.87 (bs, 1H), 3.65 (ddd, $J_1$=1.5 Hz, $J_2$=8.7 Hz, $J_3$=9.9 Hz, 1H), 3.35 (br. D, J=8.4 Hz, 1H), 3.15-2.96 (m, 4H), 2.92 (q, J=7.2 Hz, 1H), 2.47 (d, J=18.3 Hz, 1H), 2.29 (s, 3H), 2.18 (s, 3H) 1.83 (s, 3H), 1.64 (ddd, $J_1$=2.7 Hz, $J_2$=11.1 Hz, $J_3$=14.1 Hz, 1H), 0.79 (d, J=7.2 Hz, 3H);

$^{13}$C NMR (75 Mhz, $CDCl_3$): δ 186.0 (q), 175.9 (q), 156.2 (q), 146.8 (q), 142.8 (q), 140.7 (q), 136.6 (q), 130.5 (q), 128.8 (q), 127.0 (q), 120.5 (s), 117.4 (q), 116.5 (q), 60.8 (t), 60.4 (s), 58.7 (t), 56.2 (s), 55.7 (s), 54.8 (s), 54.8 (s), 54.4 (s), 50.0 (s), 41.6 (t), 39.8 (d), 25.2 (d), 24.4 (d), 21.2 (t), 15.5 (t), 8.4 (t).

ESI-MS m/z: Calcd for $C_{29}H_{35}N_5O_6$: 549.6. Found $(M+Na)^+$: 572.3.

Example D

A medium (50 l) composed of dextrose (2%), mannitol (4%), dry brewer's yeast (2%), ammonium sulphate (1%), potassium secondary phosphate (0.04%), potassium chloride (0.8%), iron (III) chloride 6-hydrate (0.001%), L-tyrosine (0.1%), calcium carbonate (0.8%), poly(propylene glycol) 2000 (0.05%) and antifoam ASSAF 1000 (0.2%) was poured into a jar-fermentor with 75 l total capacity and, after sterilisation, inoculated with seed culture (2%) of A2-2 strain (FERM. BP-14) and aerated cultivation under agitation was carried out at 27° C. to 24° C. for 64 hours (aeration of 75 l per minute and agitation from 350 to 500 rpm). The pH was controlled by automatic feeding of diluted sulphuric acid from 27 hours to final process. A 2% mannitol was added from 16 hours to final process. The cultured medium (45 l) thus obtained was, after removal of cells by centrifugation, adjusted to pH 9.5 with diluted sodium hydroxide, extracted with 25 litres of ethyl acetate twice. The mixture was carried out into an agitated-vessel at 8° C. for 20 minutes. The two phases were separated by a liquid-liquid centrifuge. The organic phases were frozen at −20° C. and filtered for removing ice and evaporated ice and evaporated until obtention of a 40 g oil-dark-crude extract. After introduction of the cyanide group and purification, 3.0 grams of safracin B cyano were obtained.

Example E

A medium (50 l) composed of dextrose (2%), mannitol (4%), dry brewer's yeast (2%), ammonium sulphate (1%), potassium secondary phosphate (0.02%, potassium chloride (0.2%), Iron (III) chloride 6-hydrate (0.001%, L-tyrosine (0.1%), calcium carbonate (0.8%, poly(propylene glycol) 2000 (0.05%) and antifoam ASSAF 1000 (0.2%) was poured into a jar-fermentor with 75 l total capacity and, after sterilisation, inoculated with seed culture (2%) of A2-2 strain (FERM BP-14) and aerated cultivation under agitation was carried out at 27° C. to 24° C. for 41 hours (aeration of 75 l per minute and agitation from 350 to 500 rpm). The pH was controlled by automatic feeding of diluted sulphuric acid from 28 hours to final process. A 1% mannitol was added from 16 hours to final process. The cultured medium (45 l) thus obtained was, after removal of cells by centrifugation, adjusted to pH 3.9 with 200 ml of conc. acetic acid. 25 grams of potassium cyanide 97% were added and after 1 hour of agitation at 20° C., the pH was adjusted to 9.5 with 1500 ml of a solution 10% sodium hydroxide. Then, extracted with 35 litres of ethyl acetate. The mixture was carried out into an agitated-vessel at 8° C. for 20 minutes. The two phases were separated by a liquid-liquid centrifuge. The organic phase was dried by sodium sulphate anhydrous and evaporated until obtention of a 60 g oil-dark-crude extract.

After chromatography, 4.9 grams of safracin B cyano were obtained.

Example 66

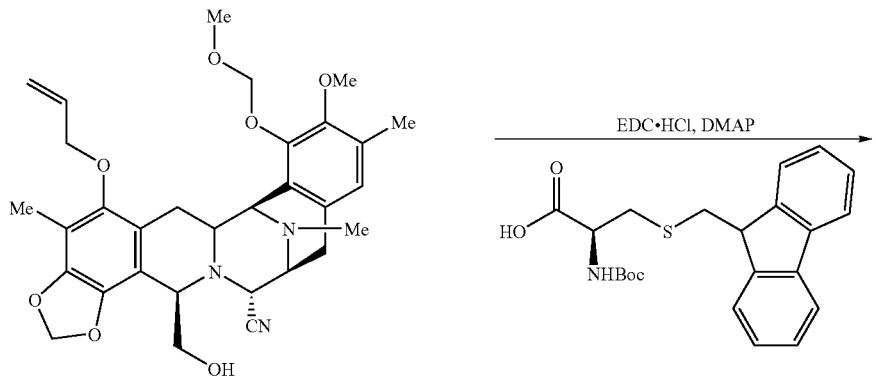

To a stirred solution of 25 (7.83 g, 0.0139 mol) and the commercial available Boc-Cys (Fm) derivative (Bachem) (8.33 g, 35.04 mmol) in dichloromethane (535 mL) under argon, dimethylaminopyridine (4.28 g, 35.04 mmol) and 1-[3-(Dimethylamino)propyl]-3-ethylcarbodiimide hydrochloride (6.66 g, 35.04 mmol) were added at 23° C. The mixture was then stirred at 23° C. for 2.5 hours. The reaction was quenched by addition of a saturated aqueous sodium bicarbonate solution (500 mL), the organic phase separated and the aqueous layer back-extracted with dichloromethane (250 mL). The combined organic extracts were dried over sodium sulphate, filtrated and evaporated to dryness under reduced pressure. The crude product was purified by flash column chromatography eluting with mixtures of ethyl acetate and hexane in a gradient manner, from 1:4 to 2:1 to yield 142 (12.21 g, 93%) as a light yellow solid. Rf=0.35 Hex:EtOAc 1:1.

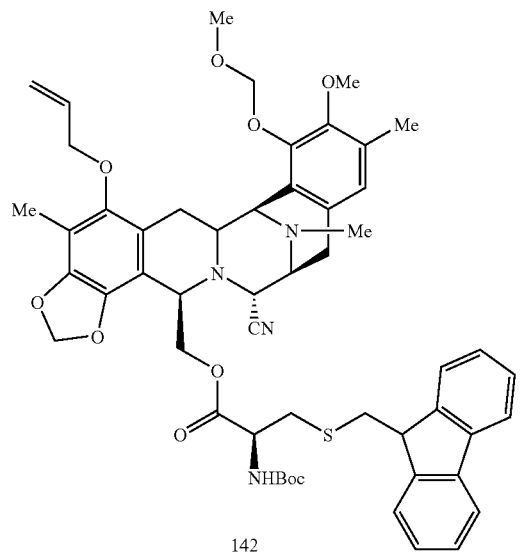

$^1$H-NMR (300 MHz, CDCl$_3$): δ 7.72 (d, J=7.3, 2.7 Hz 2H), 7.55 (dd, J$_1$=14.6, J$_2$=7.6 2H), 7.40-7.34 (m, 2H), 7.30-7.24 (m, 2H), 6.63 (s, 1H), 6.08-5.99 (m, 1H), 5.91 (d, J=1.5 Hz, 1H), 5.80 (d, J=1.5 Hz, 1H), 5.39 (dd, J$_1$=17.3, J$_2$=1.7 Hz 1H), 5.24 (dd, J$_1$=10.5, J$_2$=1.7 Hz, 1H), 5.09 (AB, J=4.48 Hz, 2H), 5.07 (t, J=7.8 Hz, 1H), 4.34-4.29 (m, 2H), 4.17 (d, J=1.9 Hz, 1H), 4.16-4.04 (m, 4H), 4.02-3.96 (m, 2H), 3.93 (t, J=5.3 Hz, 1H), 3.70 (s, 3H), 3.56 (s, 3H), 3.32 (d, J=8.0, 1H), 3.23-3.17 (m, 2H), 3.0-2.89 (m, 3H), 2.65-2.57 (m, 2H), 2.29 (s, 3H), 2.20 (s, 3H), 2.03 (s, 3H), 1.76 (dd, J$_1$=16.3, J$_2$=12.7 Hz, 1H), 1.45, 1.44 (s, 9H).

$^{13}$C-NMR (75 MHz, CDCl$_3$): δ 170.9, 155.3, 148.9, 148.6, 146.1, 146.0, 144.7, 141.2, 141.1, 139.4, 134.0, 131.0, 130.1, 127.8, 127.2, 125.2, 125.0, 124.3, 121.3, 121.2, 120.1, 118.1, 117.6, 112.9, 101.4, 99.5, 80.3, 74.2, 65.6, 60.4, 60.1, 57.9, 57.4, 57.2, 57.1, 56.9, 55.6, 53.2, 47.0, 41.8, 41.7, 36.7, 35.3, 28.5, 26.6, 25.3, 15.9, 9.4.

ESI-MS m/z: Calcd. For C$_{53}$H$_{60}$N$_4$O$_{10}$S: 945.13. Found (M+1)$^+$: 946.3.

Example 67

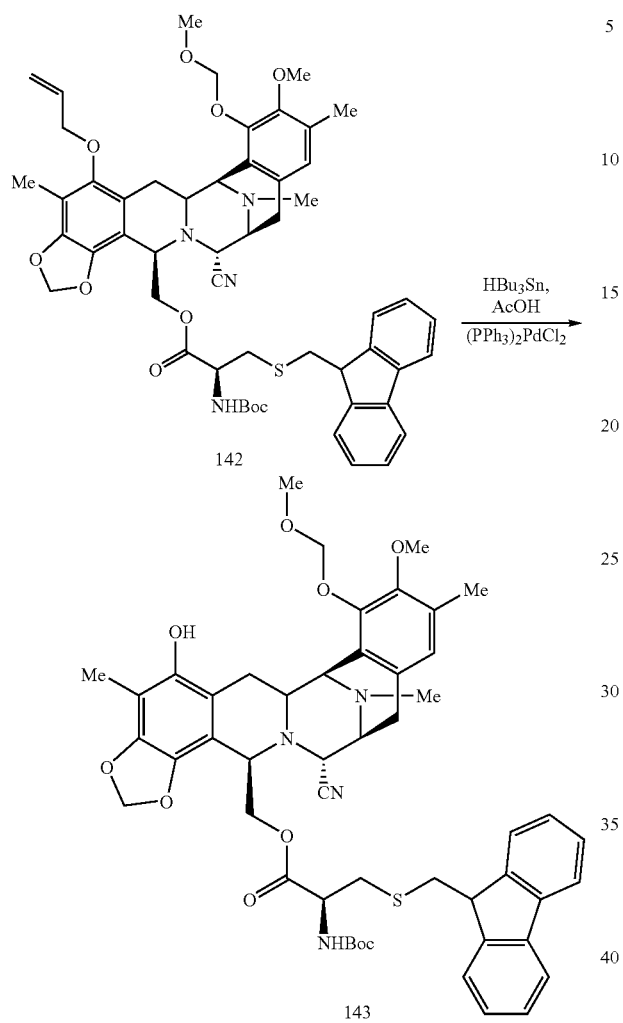

To a stirred solution of 142 (12.01 g, 0.0127 mol) in dichloromethane (318 mL), dichlorobis(triphenylphosphine) palladium (II) (0.71 g, 1.015 mmol) and acetic acid (3.6 mL, 0.176 mol) were added under argon at 23° C. Then, tributyl tin hydride (10.27 mL, 0.037 mol) was added in a dropwise manner. The mixture was stirred at 23° C. for 10 minutes. The reaction was then filtered through a silica gel column compacted with hexane. 143 (10.89 g, 95%) was obtained as a yellow solid by subsequent elution with mixtures of ethyl acetate and hexane in a gradient manner, from 1:4, 1:1 to 7:3. Rf=0.25 Hex:EtOAc 2:1.

$^1$H NMR (300 MHz, CDCl$_3$) δ 7.72 (d, J=7.6 Hz, 2H), 7.61 (d, J=6.6 Hz, 1H), 7.52 (d, J=7.3 Hz, 1H), 7.37 (t, J=7.8 Hz, 2H), 7.28 (m, 2H), 6.63 (s, 1H), 5.87 (d, J=1.5 Hz, 1H), 5.76 (d, J=1.5 Hz, 1H), 5.58 (bs, 1H), 5.31 (d, J=5.8 Hz, 1H), 5.17 (d, J=5.6 Hz, 1H), 4.91 (d, J=8.3 Hz, 1H), 4.17-4.06 (m, 4-6H), 3.85 (t, J=5.7 Hz, 1H), 3.70 (s, 3H), 3.68 (s, 3H), 3.34 (brd, J=6.6 Hz, 1H), 3.23 (brd, J=11.2 Hz, 1H), 3.06 (brd, J=12.9 Hz, 1H), 3.04-2.86 (m, 3H), 2.65-2.54 (m, 2H), 2.28 (s, 3H), 2.21 (s, 3H), 1.94 (s, 3H), 1.80 (dd, J$_1$=11.5 Hz, J$_2$=15.8 Hz, 1H), 1.45 (s, 9H).

$^{13}$C NMR (75 MHz, CDCl$_3$) δ 175.3, 170.5, 154.9, 149.1, 147.6, 145.9, 145.8, 145.7, 144.5, 140.9, 140.8, 136.1, 130.9, 127.4, 126.9, 124.3, 124.7, 122.9, 119.7, 117.6, 112.3, 111.4, 106.6, 100.7, 99.7, 80.0, 64.2, 60.3, 59.8, 57.6, 57.0, 56.5, 56.4, 55.2, 52.7, 46.7, 46.5, 41.4, 41.3, 36.9, 36.6, 34.9, 28.2, 26.0, 24.9, 20.9, 20.7, 15.7, 14.1, 8.5.

ESI-MS m/z: Calcd. For C$_{50}$H$_{56}$N$_4$O$_{10}$S: 905.5. Found (M+1)$^+$: 906.3.

Example 68

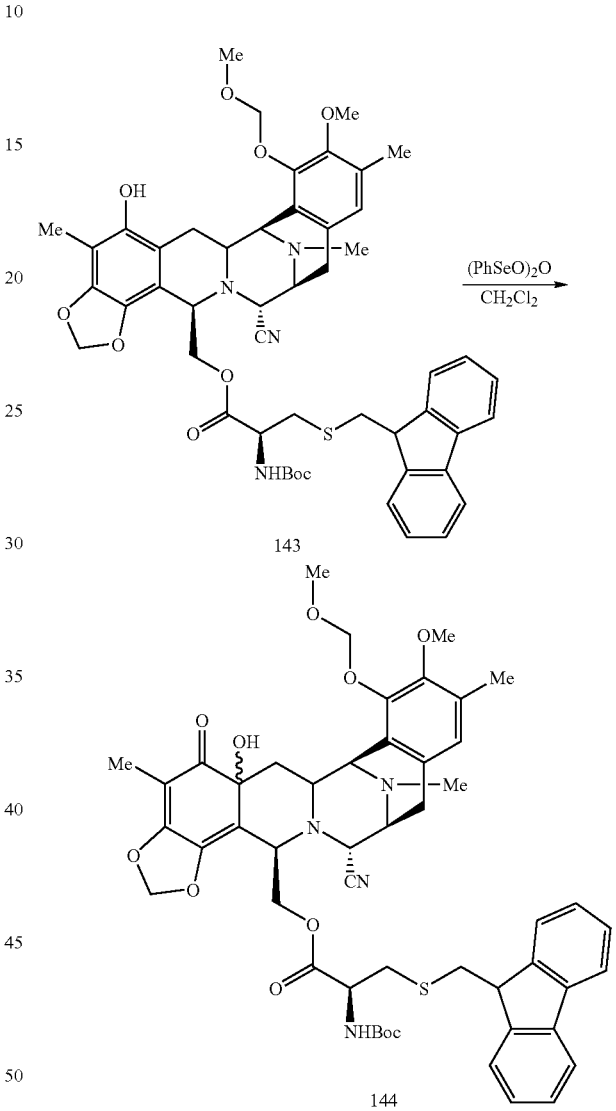

To a solution of 143 (10 g, 0.011 mol) in anhydrous dichloromethane (185 mL) at −10° C. (bath temperature −15° C.), a solution of benzeneseleninic anhydride (5.7 g, 0.011 mol) was added in anhydrous dichloromethane (185 mL), discarding any white solid present in the solution. The mixture was stirred for 10 minutes at the same temperature. The reaction was diluted with dichloromethane (200 mL) and a saturated aqueous sodium bicarbonate solution (500 mL) was added at −10° C. The organic phase was separated, dried over sodium sulphate, filtered and concentrated to dryness at reduced pressure. The residue was purified by flash column chromatography, eluting with mixtures of ethyl acetate and hexane in a gradient manner, from 1:1, 3:2, 7:3 to 4:1 to obtain 144 (9.34 g, 92%) as a yellow solid. The purified solid from chromatography was dissolved in dichloromethane (250 mL), charcoal (3.3 g) was added and the suspension was stirred at 23° C. for 1 hour. The mixture was filtered through celite and the celite was washed with dichloromethane (80 mL). The solvent was evaporated at reduced pressure maintaining the temperature at 25-30° C. to yield 144 (8.96 g, 88%) as a yellow solid. Rf=0.30 and 0.25 (mixture of isomers) Hex:EtOAc 1:1.

$^1$H NMR (300 MHz, CDCl$_3$) (mixture of isomers) δ 7.73-7.61 (m, 4H), 7.37-7.30 (m, 4H), 6.62 (s, 1H), 6.59 (s, 1H), 6.53 (s, 1H), 5.72 (s, 1H), 5.70 (s, 1H), 5.61 (s, 1H), 5.55 (bs, 1H), 5.34 (m, 2H), 5.08 (AB sist., J$_{AB}$=6.7 Hz, 1H), 5.00 (AB sist., J$_{AB}$=5.9 Hz, 1H), 4.67 (m, 1H), 4.50 (m, 1H), 4.38 (dd, J$_1$=4.9 Hz, J$_2$=12.9 Hz, 1H), 4.21 (dd, J$_1$=6.3 Hz, J$_2$=12.9 Hz, 1H), 4.11 (t, J=5.9 Hz, 1H), 4.02 (m, 3H), 3.87 (m, 1H), 3.83 (s, 3H), 3.72 (m, 1H), 3.61 (s, 3H), 3.49 (s, 3H), 3.27 (m, 1H), 3.15 (dd, J$_1$=1.8 Hz, J$_2$=6.2 Hz, 2H), 3.07 (d, J=6.3 Hz, 1H), 2.94 (m, 4H), 2.86 (m, 2H), 2.42 (m, 2H), 2.25 (s, 3H), 2.20 (s, 3H), 2.15 (s, 3H), 2.08 (dd, J$_1$=2.4 Hz, J$_2$=13.9 Hz, 1H), 1.77 (s, 3H), 1.76 (s, 3H), 1.43 (s, 9H).

$^{13}$C NMR (75 MHz, CDCl$_3$) (mixture of isomers) δ 200.6, 171.2, 160.4, 155.6, 148.9, 148.8, 148.3, 145.9, 145.8, 141.3, 141.2, 138.7, 130.9, 127.9, 127.4, 127.3, 127.3, 125.3, 125.1, 124.2, 120.1, 117.1, 111.9, 108.5, 105.0, 104.7, 101.7, 101.3, 99.5, 99.4, 80.5, 72.5, 70.8, 60.5, 60.1, 58.4, 58.0, 57.9, 56.9, 56.8, 56.3, 55.9, 55.5, 55.4, 53.8, 53.7, 47.1, 42.0, 41.8, 41.5, 37.4, 37.3, 35.6, 35.5, 28.5, 25.8, 25.7, 16.1, 16.0, 7.7, 7.3.

ESI-MS m/z: Calcd. for $C_{50}H_{56}N_4O_{11}S$: 921.3. Found (M+1)$^+$: 922.3.

Example 69

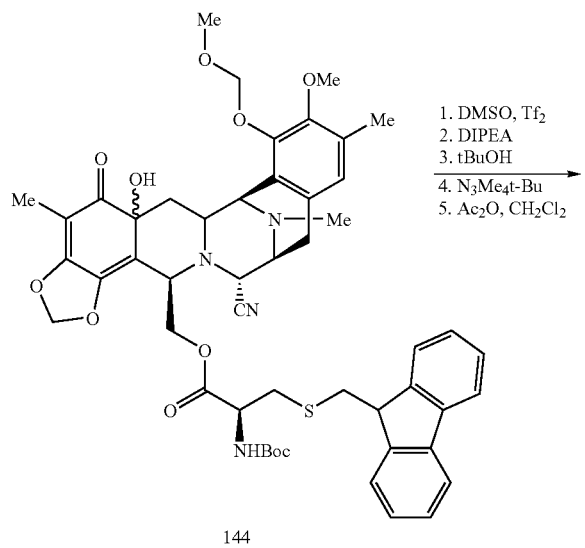

144

1. DMSO, Tf$_2$
2. DIPEA
3. tBuOH
4. N$_3$Me$_4$t-Bu
5. Ac$_2$O, CH$_2$Cl$_2$

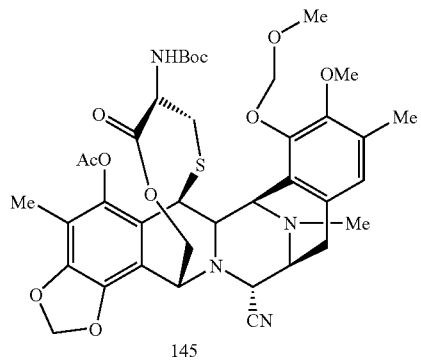

145

To a solution of DMSO (3.44 mL) in anhydrous dichloromethane (396 mL), triflic anhydride (3.27 mL, 19.45 mmol) was added under argon at −78° C. and the mixture was stirred at that temperature for 20 minutes. Then, a solution of 144 (8.92 g, 9.6 mmol) in anhydrous dichloromethane (124 mL) at −78° C. was added and the mixture was stirred under argon at 40° C. for 35 minutes. Diisopropylethylamine (13.5 mL, 73.43 mmol) was added and the mixture was stirred under argon for 45 minutes at 0° C. Tert-butanol (3.65 mL, 38.6 mmol) and tert-butyl tetramethyl guanidine (11.6 mL, 67.46 mmol) were added and the mixture was stirred under argon for 40 minutes at 23° C. Acetic anhydride (9.15 mL, 96.78 mmol) was then added and the reaction stirred for a further 1 hour at 23° C. The reaction was diluted with dichloromethane (250 mL) and a saturated aqueous ammonium chloride solution (500 mL) was added. The organic layer was separated and washed sequentially with a saturated aqueous sodium bicarbonate solution (500 mL) and a saturated aqueous sodium chloride solution (500 mL). The organic layer was separated, dried over sodium sulphate, filtered and concentrated to dryness at reduced pressure, maintaining the temperature at 25-30° C. The crude solid was then purified by flash column chromatography, eluting with mixtures of ethyl acetate and hexane in a gradient manner, from 1:4 to 2:3 to give 145 (4.99 g, 68%) as a yellow solid. Rf=0.44 Hex:EtOAc 3:2.

$^1$H NMR (300 MHz, CDCl$_3$) (mixture of isomers) δ 6.79 (s, 1H), 6.09 (s, 1H), 6.00 (s, 1H), 5.20 (d, J=5.4 Hz, 1H), 5.14 (d, J=5.6 Hz, 1H), 5.02 (d, J=11.7 Hz, 1H), 4.63 (d, J=9.0 Hz, 1H), 4.50 (m, 1H), 4.33 (d, J=5.4 Hz, 1H), 4.30 (m, 1H), 4.25 (bs, 1H), 4.18 (d, J=2.4 Hz, 1H), 4.17 (dd, J$_1$=1.3 Hz, J$_2$=11.7 Hz, 1H), 3.78 (s, 3H), 3.57 (s, 3H), 3.42 (m, 2H), 2.93 (m, 2H), 2.35 (m, 1H), 2.31 (s, 3H), 2.29 (s, 3H), 2.22 (s, 3H), 2.09 (m, 1H), 2.05 (s, 3H), 1.45 (s, 9H).).

$^{13}$C NMR (75 MHz, CDCl$_3$) δ 207.3, 170.9, 168.8, 155.4, 149.8, 148.6, 146.0, 141.1, 140.7, 131.7, 130.6, 125.1, 120.6, 118.3, 113.7, 102.2, 99.4, 80.0, 61.6, 60.4, 59.8, 59.4, 59.2, 57.7, 55.0, 54.7, 54.0, 41.9, 41.6, 33.1, 31.8, 28.7, 23.9, 20.6, 16.1, 14.3, 9.8.

ESI-MS m/z: Calcd. for $C_{38}H_{46}N_4O_{11}S$: 766.86. Found (M+1)$^+$: 767.3.

Example 70

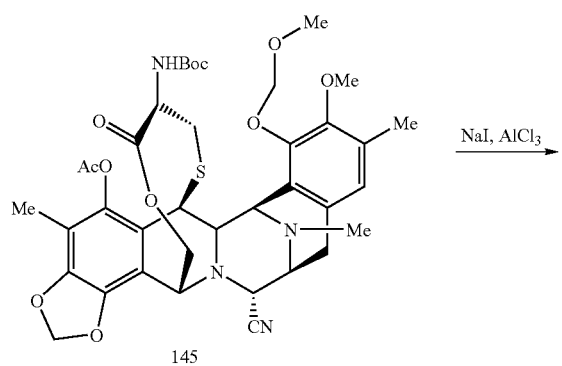

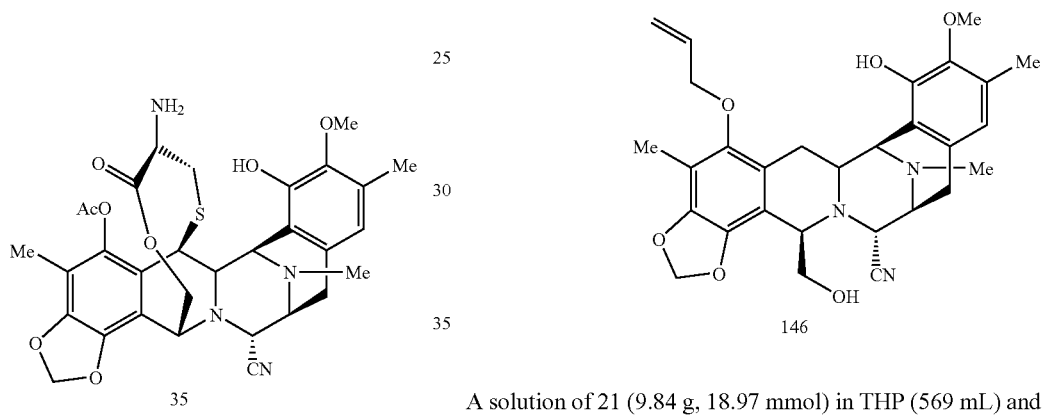

To a solution of 145 (1.0 g, 1.3 mmol) in acetonitrile (50 mL) and dichloromethane (25 mL), sodium iodide (1.52 g, 10.01 mmol) was added at 23° C. The mixture was then cooled to 0° C. and aluminium trichloride (1.33 g, 10.01 mmol) was added portionwise maintaining the temperature at 0° C. The mixture was then stirred for 2.5 hours at 0° C. The reaction was diluted with dichloromethane (25 mL) and a saturated aqueous solution of sodium potassium tartrate (100 mL) was added. The aqueous phase is separated and extracted with dichloromethane (2×75 mL). A saturated aqueous sodium bicarbonate solution (50 mL) was then added to the aqueous phase which was further extracted with dichloromethane (2×50 mL). The combined organic extracts were dried over sodium sulphate, filtered and evaporated to dryness under reduced pressure, maintaining the temperature below 25° C. The crude solid was then purified by column chromatography on amino-silicagel and eluting with mixtures of ethyl acetate and hexane in a gradient manner. 35 (487 mg, 60%) was obtained as a yellow solid. Experimental data of 35 were previously described in PCT/GB00/01852.

36, ET-770 and ET-743 were prepared following the same procedures than those previously described in PCT/GB00/01852.

Example 71

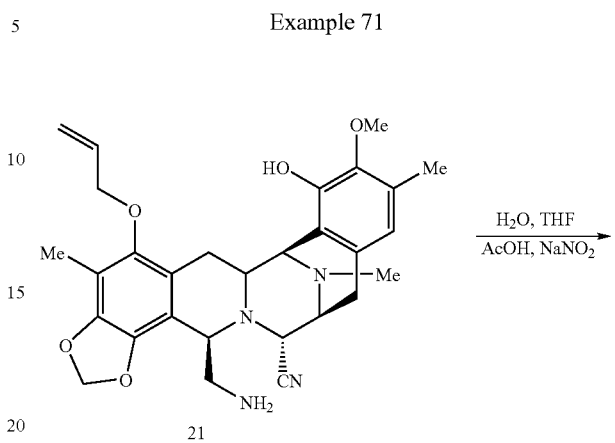

A solution of 21 (9.84 g, 18.97 mmol) in THF (569 mL) and $H_2O$ (285 mL) was cooled at 0° C. with an ice bath. Then, $NaNO_2$ (1.96 g, 28.45 mmol) and 90% aq. AcOH (18.97 mL, 0.33 mol) were added at 0° C. and the mixture was stirred at 23° C. for 18 h. After cooling down the reaction to 0° C., a saturated aqueous sodium bicarbonate solution (300 mL, basic pH) and dichloromethane (500 mL) were added. After extraction, the aqueous phase was further extracted with dichloromethane (2×300 mL). The combined organic extracts were dried over sodium sulphate and evaporated to dryness under reduced pressure. The crude solid was then disolved in MeOH (379 mL), and 1M NaOH (38 mL) was added at 0° C. The mixture was stirred at 23° C. for 4 h. After dilution with EtOAc (600 mL) at 0° C., the organic layer was washed with a mixture of water (400 mL) and, a saturated aqueous sodium bicarbonate solution (100 mL, basic pH). After extraction, the aqueous phase was further extracted with EtOAc (3×300 mL). The combined organic extracts were dried over $Na_2SO_4$, filtered and concentrated in vacuo. The residue was purified by flash column chromatography ($SiO_2$, Hex:EtOAc gradient from 3:1 to 2:1) to afford 146 (4.55 g, 46%) as a white solid. Rf: 0.33 (Hex:EtOAc 1:1).

$^1$H NMR (300 MHz, $CDCl_3$) δ 6.48 (s, 1H), 6.15-6.02 (m, 1H), 5.92 (d, J=1.5 Hz, 1H), 5.86 (d, J=1.5 Hz, 1H), 5.77 (s, 1H), 5.39 (dd, $J_1$=1.5 Hz, $J_2$=17.1 Hz, 1H), 5.26 (dd, $J_1$=1.5 Hz, $J_2$=10.5 Hz, 1H), 4.24-4.15 (m, 3H), 4.04 (d, J=2.4 Hz, 1H), 3.97 (t, J=3.3 Hz, 1H), 3.74 (s, 3H), 3.64 (dt, $J_1$=3.3 Hz, $J_2$=11.1 Hz, 1H), 3.43 (dd, $J_1$=3.3 Hz, $J_2$=10.5 Hz, 1H), 3.38-3.34 (m, 2H), 3.31 (t, J=2.7 Hz, 1H), 3.22 (dd, $J_1$=2.4 Hz, $J_2$=15.6 Hz, 1H), 3.10 (dd, $J_1$=8.1 Hz, $J_2$=18.3 Hz, 1H), 2.49 (d, J=18.3 Hz, 1H), 2.34 (s, 3H), 2.24 (s, 3H), 2.11 (s, 3H), 1.88 (dd, J₁=12 Hz, J₂=15.9 Hz, 1H).

$^{13}$C NMR (75 MHz, CDCl$_3$) δ 148.6, 146.7, 144.4, 143.0, 138.9, 133.9, 130.2, 129.1, 121.1, 120.9, 117.7, 117.4, 116.8, 113.3, 112.3, 101.1, 74.3, 63.7, 60.6, 60.1, 58.1, 56.9, 56.7, 55.4, 41.7, 26.2, 25.7, 15.7, 9.3.

ESI-MS m/z: Calcd. for $C_{29}H_{33}N_3O_6$: 519.59. Found (M+1)$^+$: 520.5.

Example 72

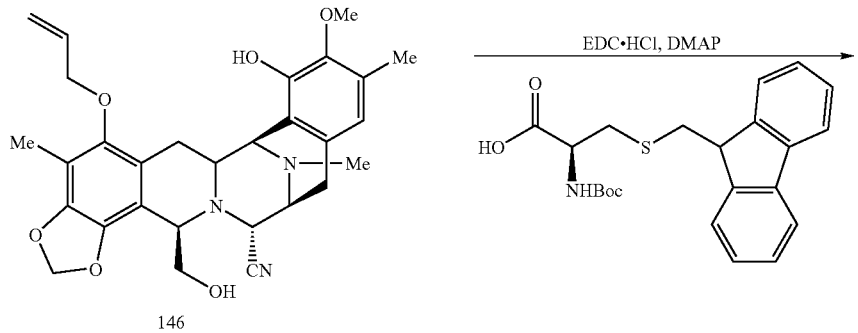

$^1$H NMR (300 MHz, CDCl$_3$) δ 7.73 (d, J=7.8 Hz, 2H), 7.63-7.55 (m, 2H), 7.39-7.35 (m, 2H), 7.29-7.25 (m, 2H), 6.41 (s, 1H), 6.07-5.97 (m, 1H), 5.92 (d, J=1.2 Hz, 1H), 5.80 (d, J=1.2 Hz, 1H), 5.67 (s, 1H), 5.34 (dd, J$_1$=1.8 Hz, J$_2$=17.4 Hz, 1H), 5.23 (dd, J$_1$=1.8 Hz, J$_2$=10.5 Hz, 1H), 5.04 (d, J=9.3 Hz, 1H), 4.32-4.29 (m, 1H), 4.13-3.91 (m, 9H), 3.72 (s, 3H), chromatography eluting with mixtures of ethyl acetate and hexane in a gradient manner, from 1:4 to 3:1 to yield 147 (74.3 g, 93%) as a white solid. Rf=0.5 Hex: EtOAc 1:1.

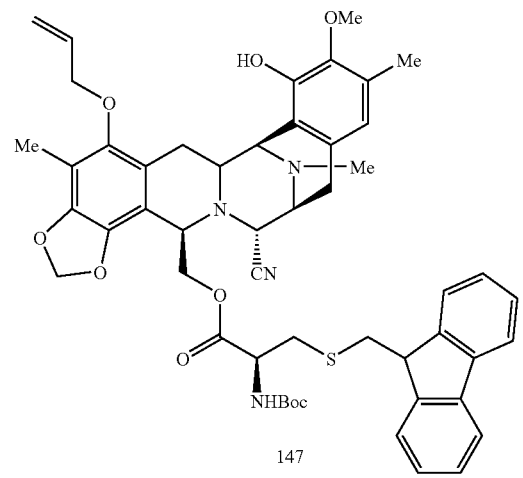

To a stirred solution of 146 (47.35 g, 0.091 mol) and the commercial available Boc-Cys (Fm) derivative (54.6 g, 0.137 mol) in dichloromethane (2.8 L) under argon, dimethylaminopyridine (5.6 g, 0.046 mol) and 1-[3-(Dimethylamino)propyl]-3-ethylcarbodiimide hydrochloride (43.6 g, 0.227 mol) were added dropwise during 1.5 h at 23° C. The mixture was then stirred at 23° C. for 1 more hour. The reaction was quenched by addition of a saturated aqueous sodium bicarbonate solution (1 L) and the organic phase was separated. The aqueous layer was back-extracted with dichloromethane (2×500 mL). The combined organic extracts were dried over sodium sulphate and evaporated to dryness under reduced pressure. The crude product was purified by flash column 3.31 (d, J=7.2 Hz, 1H), 3.26-3.17 (m, 2H), 2.96-2.87 (m, 3H), 2.68-2.54 (m, 2H), 2.27 (s, 3H), 2.24 (s, 3H), 2.05 (s, 3H), 1.83 (dd, J$_1$=12.6 Hz, J$_2$=15.9 Hz, 1H), 1.45 (s, 9H).

$^{13}$C NMR (75 MHz, CDCl$_3$) δ 170.9, 155.4, 149.0, 147.1, 146.2, 146.0, 144.7, 143.0, 141.1, 139.4, 134.1, 131.5, 129.1, 127.8, 127.2, 125.0, 121.3, 120.9, 120.1, 118.2, 117.6, 117.2, 112.9, 112.4, 101.4, 80.3, 76.6, 74.4, 65.3, 61.0, 60.4, 57.4, 56.9, 56.7, 55.6, 53.0, 46.9, 41.8, 36.7, 35.3, 31.8, 28.5, 26.6, 25.2, 22.9, 16.0, 14.4, 9.5.

ESI-MS m/z: Calcd. for $C_{51}H_{56}N_4O_9S$: 900.3. Found (M+1)$^+$: 901.3.

Example 73

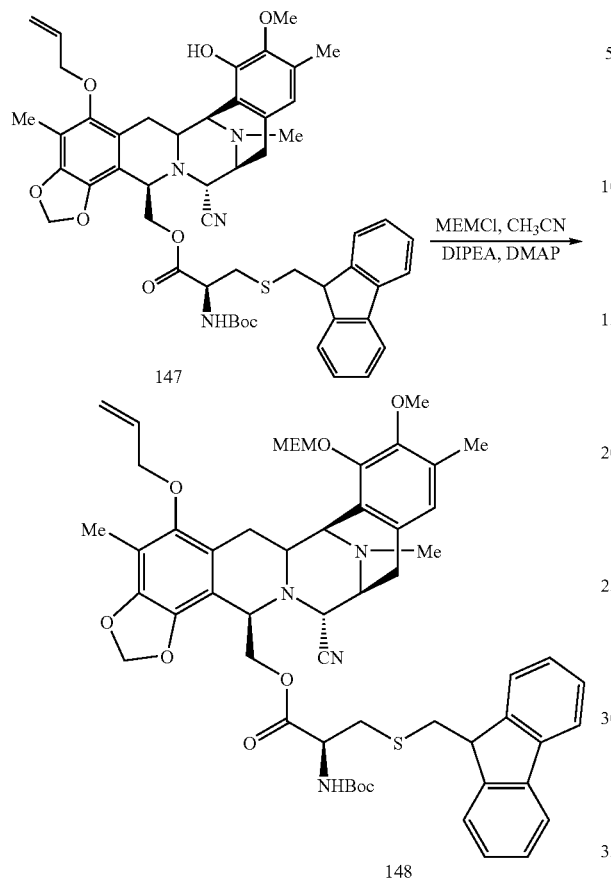

To a solution of 147 (0.562 g, 0.624 mol) in CH₃CN (3.12 mL), MEMCl (1.07 mL, 9.36 mmol), DIPEA (2.17 mL, 12.48 mmol) and DMAP (0.0076 g, 0.06 mmol) were added at 0° C. The mixture was stirred for 5.5 h at 23° C. The reaction was diluted with CH$_2$Cl$_2$ (50 mL) and extracted with 0.1N HCl (50 mL). The aqueous phase was extracted again with CH$_2$Cl$_2$ (50 mL). The combined organic phases were dried over Na$_2$SO$_4$, filtered and concentrated in vacuo to give a residue which was purified by flash column chromatography (CH$_2$Cl$_2$:EtOAc 10:1, 5:1) to give 148 (539 mg, 87%) as a white solid. Rf=0.50 CH$_2$Cl$_2$:AcOEt 6:1.

$^1$H NMR (300 MHz, CDCl$_3$) δ 7.73-7.71 (m, 2H), 7.57 (dd, J$_1$=7.2 Hz, J$_2$=15.3 Hz, 2H), 7.40-7.34 (m, 2H), 7.29-7.26 (m, 2H), 6.62 (s, 1H), 6.08-5.99 (m, 1H), 5.91 (d, J=1.2 Hz, 1H), 5.79 (d, J=1.2 Hz, 1H), 5.35 (dd, J$_1$=1.2 Hz, J$_2$=17.1 Hz, 1H), 5.23 (d, J=6.3 Hz, 1H), 5.21 (bs, 1H), 5.13 (d, J=6.3 Hz, 1H), 5.04 (brd, J=9 Hz, 1H), 4.33-4.29 (m, 2H), 4.16-3.90 (m, 8H), 3.85-3.78 (m, 1H), 3.69 (s, 3H), 3.60-3.55 (m, 2H), 3.38 (s, 3H), 3.31 (brd, J=8.1 Hz, 1H), 3.21-3.17 (m, 2H), 2.98-2.88 (m, 3H), 2.64-2.56 (m, 2H), 2.29 (s, 3H), 2.20 (s, 3H), 2.02 (s, 3H), 1.75 (dd, J$_1$=11.7 Hz, J$_2$=15.6 Hz, 1H), 1.47 (s, 9H).

$^{13}$C NMR (75 MHz, CDCl$_3$) δ 170.5, 155.0, 148.6, 148.5, 148.2, 145.77, 145.6, 144.4, 140.8, 140.7, 139.0, 133.6, 130.7, 130.5, 127.4, 126.9, 124.8, 124.6, 123.8, 120.8, 119.7, 117.8, 117.2, 122.5, 111.9, 101.0, 98.1, 80.0, 77.4, 77.0, 76.6, 73.8, 71.6, 69.2, 65.0, 60.2, 60.0, 59.8, 59.0, 56.8, 56.7, 56.6, 55.2, 52.7, 46.6, 41.3, 36.2, 34.9, 29.6, 28.2, 26.3, 24.9, 15.6, 14.1, 9.0.

ESI-MS m/z: Calcd. for C$_{55}$H$_{64}$N$_4$O$_{11}$S: 988.4. Found (M+1)$^+$: 989.3.

Example 74

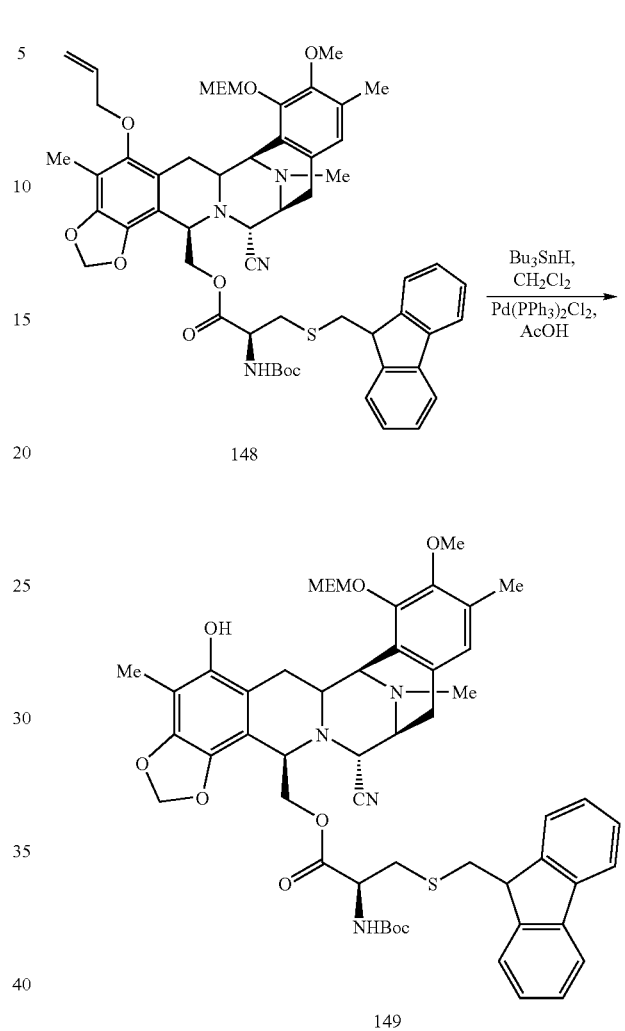

To a stirred solution of 148 (38.32 g. 0.039 mol) in dichloromethane (1 L), dichlorobis(triphenylphosphine) palladium (II) (2.17 g, 0.0031 mol) and acetic acid (11.1 mL, 0.195 mol) were added under argon at 23° C. Then, tributyl tin hydride (36.5 mL, 0.136 mol) was added in a dropwise manner. The mixture was stirred at 23° C. for 15 minutes. The reaction was then filtered through a silica gel column compacted with hexane. 149 (35.07 g, 95%) was obtained as a white solid by subsequent elution with mixtures of ethyl acetate and hexane in a gradient manner, from 0:100, 1:4, 1:3, 2:5, 2:3, 1:1, 2:1, 3:1 to 100:0. Rf=0.25 Hex:EtOAc 2:1.

$^1$H NMR (300 MHz, CDCl$_3$) δ 7.74 (d, J=7.2 Hz, 2H), 7.63-7.53 (m, 2H), 7.39-7.34 (m, 2H), 7.30-7.27 (m, 2H), 6.62 (s, 1H), 5.87 (m, 1H), 5.75 (s, 1H), 5.69 (bs, 1H), 5.37 (d, J=6 Hz, 1H), 5.23 (d, J=5.7 Hz, 1H), 4.96 (d, J=8.1 Hz, 1H), 4.44 (brd, J=8.7 Hz, 1H), 4.18-3.70 (m, 11H), 3.69 (s, 3H), 3.38 (s, 3H), 3.34-3.18 (m, 3H), 2.99-2.88 (m, 3H), 2.63-2.58 (m, 2H), 2.28 (s, 3H), 2.21 (s, 3H), 2.05 (s, 3H), 1.78 (dd, J$_1$=12.9 Hz, J$_2$=15.6 Hz, 1H), 1.41 (s, 9H).

$^{13}$C NMR (75 MHz, CDCl$_3$) δ 170.8, 155.2, 149.0, 148.0, 146.2, 146.0, 144.8, 141.1, 136.4, 131.3, 131.2, 127.8, 127.2, 125.1, 125.0, 123.2, 120.0, 118.1, 112.6, 111.6, 107.2, 101.0, 98.9, 98.8, 80.3, 71.8, 69.8, 64.9, 60.6, 60.2, 59.2, 57.1, 56.9, 55.5, 53.0, 47.0, 46.9, 41.8, 37.0, 35.3, 28.5, 26.2, 25.2, 21.9, 21.3, 16.1, 14.4, 9.0.

ESI-MS m/z: Calcd. for C$_{52}$H$_{60}$N$_4$O$_{11}$S: 948.4. Found (M+1)$^+$: 949.3.

Example 75

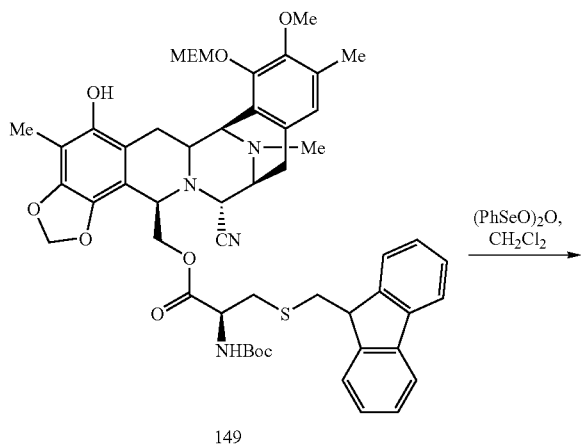

To a solution of 149 (15 g, 0.0158 mol) in anhydrous dichloromethane (265 mL) at −10° C. (bath temperature −15° C.), a solution of benzeneseleninic anhydride (7.4 g, 0.0143 mol) in anhydrous dichloromethane (265 mL) was added dropwise during 30 minutes, discarding any white solid present in the solution. The mixture was stirred for a further 10 minutes at the same temperature. The reaction was diluted with dichloromethane (200 mL) and a saturated aqueous sodium bicarbonate solution (500 mL) was added at −10° C. The organic phase was separated, dried over sodium sulphate, filtered and concentrated to dryness at reduced pressure. The residue was purified by flash column chromatography eluting with mixtures of ethyl acetate and hexane in a gradient manner, from 1:2 to 100:0 to obtain 150 (14.20 g, 89%) as a yellow solid. The purified solid from chromatography is dissolved in dichloromethane (250 mL) and charcoal (4.95 g) was added. The suspension was then stirred at 23° C. for 1 hour. The mixture was filtered through a pad of celite and the celite was washed with dichloromethane (80 mL). The solvent was evaporated at reduced pressure to yield 150 (13.72 g, 86%) as a white solid. Rf=0.37 Hex:EtOAc 1:2.

$^1$H NMR (300 MHz, CDCl$_3$) (mixture of isomers) δ 7.73 (t, J=6.7 Hz, 4H), 7.63 (m, 2H), 7.54 (d, J=7.6 Hz, 2H), 7.40-7.34 (m, 4H), 7.31-7.27 (m, 4H), 6.62 (s, 2H), 5.86 (s, 1H), 5.81 (s, 1H), 5.75 (s, 1H), 5.72 (s, 1H), 5.70 (s, 1H), 5.35 (d, J=5.9 Hz, 1H), 5.30 (d, J=8.4 Hz, 1H), 5.23 (d, J=5.9 Hz, 1H), 5.22 (d, J=5.9 Hz, 1H), 5.13 (d, J=5.9 Hz, 1H), 4.97 (d, J=8.8 Hz, 1H), 4.43 (m, 2H), 4.20-4.01 (m, 8H), 3.97-3.86 (m, 4H), 3.82 (s, 3H), 3.80-3.74 (m, 1H), 3.69 (s, 3H), 3.66-3.64 (m, 4H), 3.54 (m, 2H), 3.38 (s, 3H), 3.35 (s, 3H), 3.34-2.90 (m, 8H), 2.60-2.31 (m, 4H), 2.27 (s, 3H), 2.25 (s, 3H), 2.21 (s, 3H), 1.97 (s, 3H), 1.94-1.81 (m, 2H), 1.77 (s, 3H), 1.43 (s, 9H), 1.41 (s, 9H).

$^{13}$C NMR (75 MHz, CDCl$_3$) (mixture of isomers) δ 200.2, 198.3, 170.7, 170.5, 160.0, 155.2, 154.9, 148.5, 148.4, 145.5, 142.1, 140.9, 138.3, 130.9, 130.5, 130.0, 129.8, 127.5, 126.9, 125.0, 124.9, 124.7, 123.8, 122.5, 119.8, 117.2, 116.7, 111.5, 108.1, 104.6, 104.3, 101.3, 100.9, 98.0, 80.1, 72.1, 71.5, 70.5, 69.2, 69.0, 66.4, 63.5, 60.7, 60.1, 59.6, 58.9, 58.8, 58.0, 56.7, 56.4, 56.2, 55.9, 55.5, 55.0, 53.5, 46.7, 41.7, 41.3, 41.1, 36.9, 35.2, 35.1, 31.4, 28.1, 25.4, 25.3, 22.5, 15.7, 15.6, 14.0, 7.2.

ESI-MS m/z: Calcd. for C$_{52}$H$_{60}$N$_4$O$_{12}$S: 964.4. Found: 965.3 (M+1)$^+$, 987.3 (M+23)$^+$.

Example 76

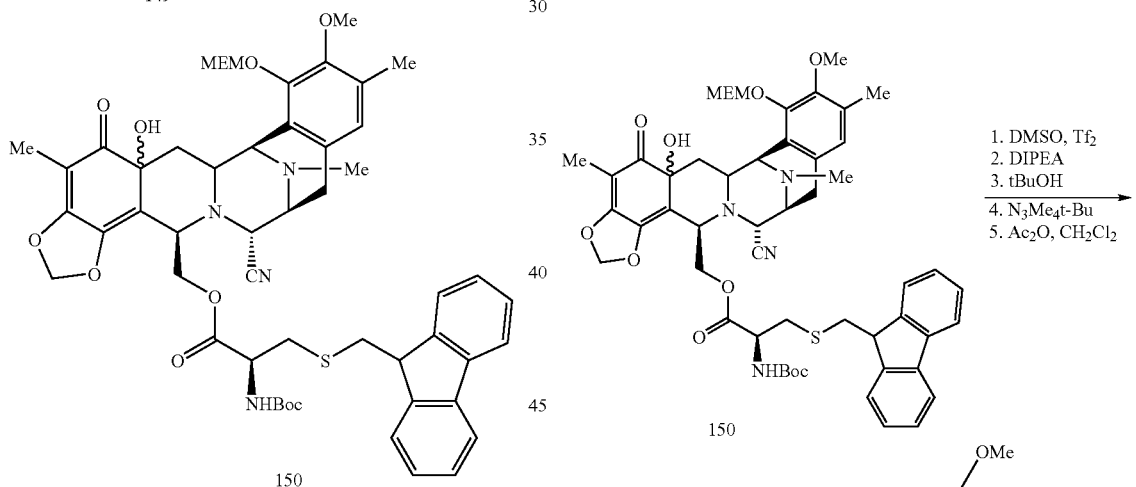

The reaction flask was flamed twice, purged vacuum/Argon several times and kept under Argon atmosphere for the reaction. To a solution of DMSO (385.0 μL) in anhydrous CH$_2$Cl$_2$ (42 mL) was dropwise added triflic anhydride (366.5 μL, 2.16 mmol) at −78° C. The reaction mixture was stirred at −78° C. for 20 minutes. Then, a solution of 150 (1 g, 1.03 mmol) in anhydrous CH$_2$Cl$_2$ (10 mL, for the main addition and 5 mL for washing) was added via canula (addition time: 5 min) at −78° C. During the addition the temperature was kept at −78° C. in both flasks and the color changed from yellow to brown. The reaction mixture was stirred at −40° C. for 35 minutes. During this period of time the solution was turned from yellow to dark green. After this time, $^i$Pr$_2$NEt (1.51 mL, 9.55 mmol) was dropwise added and the reaction mixture was kept at 0° C. for 45 minutes, the color of the solution turned brown during this time. Then, $^t$BuOH (409.5 □L, 4.33 mmol) and tert-butyl tetramethyl guanidine (1.31 mL, 7.61 mmol) were dropwise added and the reaction mixture was stirred at 23° C. for 40 minutes. After this time, acetic anhydride (1.03 mL, 10.89 mmol) was dropwise added and the reaction mixture was kept at 23° C. for 1 hour more. Then, the reaction mixture was diluted with CH$_2$Cl$_2$ (25 mL) and washed with aqueous saturated solution of NH$_4$Cl (50 mL), NaHCO$_3$ (50 mL), and NaCl (50 mL). The combined organic layers were dried over Na$_2$SO$_4$, filtered and concentrated. The residue was purified by flash column chromatography (inner diameter: 2.0 cm, height of silica: 9 cm; eluent: ethyl acetate/hexane in a gradient manner, from 20:80, 30:70 to 40:60) to afford 151 (832.6 mg, 99%) as a white solid. Rf=0.48 Hex:EtOAc 3:2.

$^1$H NMR (300 MHz, CDCl$_3$) δ 6.78 (s, 1H), 6.09 (d, J=1.2 Hz, 1H), 5.99 (d, J=1.2 Hz, 1H), 5.32 (d, J=5.8 Hz, 1H), 5.19 (d, J=5.6 Hz, 1H), 5.01 (d, J=11.7 Hz, 1H), 4.62 (d, J=9.8 Hz, 1H), 4.50 (bs, 1H), 4.34 (d, J=5.1 Hz, 1H), 4.28 (dd, J$_1$=2.4 Hz, J$_2$=6.8 Hz, 1H), 4.24 (s, 1H), 4.17 (m, 2H), 3.90 (m, 2H), 3.76 (s, 3H), 3.58 (t, J=4.8 Hz, 2H), 3.42-3.37 (m, 2H), 3.37 (s, 3H), 2.91 (m, 2H), 2.36-2.08 (m, 2H), 2.30 (s, 3H), 2.28 (s, 3H), 2.21 (s, 3H), 2.04 (s, 3H), 1.44 (s, 9H).

$^{13}$C NMR (75 MHz, CDCl$_3$) δ 170.9, 168.9, 168.0, 155.4, 149.8, 148.6, 146.0, 141.1, 140.6, 131.6, 131.1, 130.6, 129.0, 125.1, 120.6, 118.3, 102.2, 98.4, 79.9, 71.9, 69.4, 61.6, 60.4, 59.8, 59.4, 59.2, 54.9, 54.7, 54.0, 41.6, 30.6, 29.1, 28.7, 23.9, 23.2, 20.6, 16.1, 14.2, 11.2, 9.8.

ESI-MS m/z: Calcd. for C$_{40}$H$_{50}$N$_4$O$_{12}$S: 810.91. Found (M+1)$^+$: 811.3.

Example 77

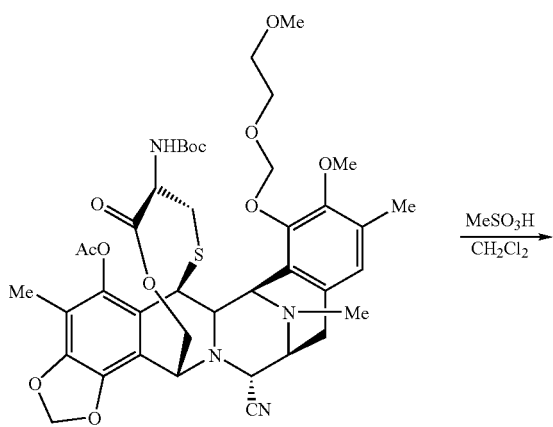

151

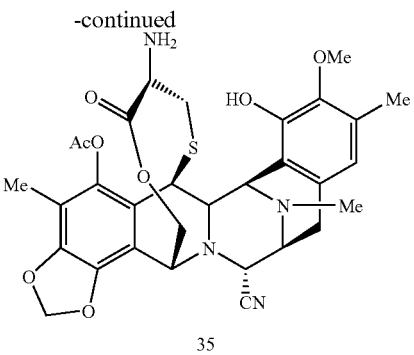

35

To a solution of 151 (2.9 g, 3.57 mmol) in CH$_2$Cl$_2$ (120 mL), MeSO$_3$H (1.4 mL, 21.46 mmol) was added at 23° C. After stirring the reaction for 30 minutes at 23° C., a saturated aqueous sodium bicarbonate solution (200 mL) was added at 0° C. The organic phase was separated, dried over sodium sulphate, filtered and concentrated to dryness at reduced pressure. The residue was purified by flash column chromatography, eluting with mixtures of ethyl acetate and hexane in a gradient manner, from 0:1 to 1:0 to obtain 35 (1.43 g, 64%) as a pale yellow solid. Experimental data of 35 was previously decribed in PCT/GB00/01852.

36, ET-770 and ET-743 were prepared following the same procedures than those previously described in PCT/GB00/01852.

Route 3

The first step of this Route (transformation of 21 into 146) was described above in Example 71.

Example 78

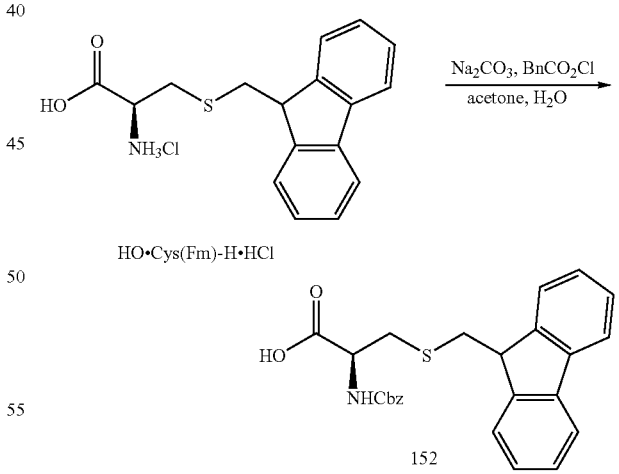

152

To a solution of the commercial available HO.Cys(Fm)-H.HCl (Bachem) (40 g, 0.119 mol) in acetone (500 mL) and water (500 mL), 1M Na$_2$CO$_3$ solution (238 mL) and BnCO$_2$Cl (18.7 mL, 0.131 mol) were added at 0° C. After stirring the reaction at 60° C. for 30 minutes, the mixture was quenched with 1N HCl (pH 01) and extracted with eter (3×400 mL). The organic phase was separated, dried over magnesium sulphate filtered and concentrated to dryness at reduced pressure. The crude solid was disolved in a mixture of EtOAc/CH₂Cl₂ 1:1, precipitated with hexane and kept at 4° C. overnight. Then, the suspension was filtered off, the solid washed with hexane (200 mL) and the filtrate was dried in vacuo to afford 152 (50.16 g, 97%) as a white solid.

$^1$H NMR (300 MHz, CDCl₃) δ 10.66 (bs, 1H), 7.74 (d, J=7.5 Hz, 2H), 7.69-7.64 (m, 2H), 7.62-7.29 (m, 9H), 5.67 (d, J=7.5 Hz, 1H), 5.14 (bs, 2H), 4.70-4.64 (m, 1H), 4.09-4.05 (m, 1H), 3.12-3.09 (m, 2H).

$^{13}$C NMR (75 MHz, CDCl₃) δ 175.2, 155.9, 145.5, 141.0, 135.8, 128.5, 128.2, 128.1, 127.5, 127.0, 124.7, 119.8, 84.8, 67.3, 46.8, 37.0.

ESI-MS m/z: Calcd. for $C_{25}H_{23}NO_4S$: 433.52. Found (M+1)$^+$: 434.4.

Example 79

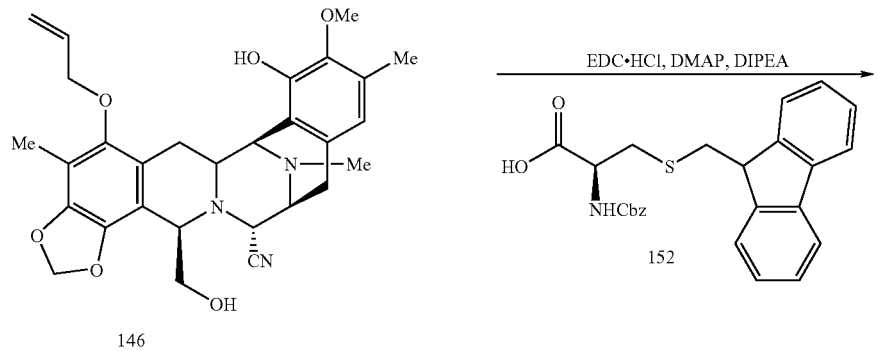

$^1$H NMR (300 MHz, CDCl₃) δ 7.74-7.72 (m, 2H), 7.61-7.53 (m, 2H), 7.37-7.24 (m, 9H), 6.39 (s, 1H), 6.09-5.96 (m, 1H), 5.90 (s, 1H), 5.84 (s, 1H), 5.78 (s, 1H), 5.34 (dd, J₁=1.5 Hz, J₂=17.4 Hz, 1H), 5.32 (bs, 1H), 5.24 (dd, J₁=1.5 Hz, J₂=10.2 Hz, 1H), 5.17-5.07 (m, 2H), 4.40 (dd, J₁=3.6 Hz, J₂=10.8 Hz, 1H), 4.30 (m, 1H), 4.18-4.01 (m, 6H), 3.92 (brt, J=6.3 Hz, 1H), 3.71 (s, 3H), 3.30-3.19 (m, 3H), 2.99-2.85 (m, 3H), 2.65 (dd, J₁=4.5 Hz, J₂=14.4 Hz, 1H), 2.55 (d, J=18.3 Hz, 1H), 2.26 (s, 3H), 2.21 (s, 3H), 2.06 (s, 3H), 1.86 (dd, J₁=11.7 Hz, J₂=15.9 Hz, 1H).

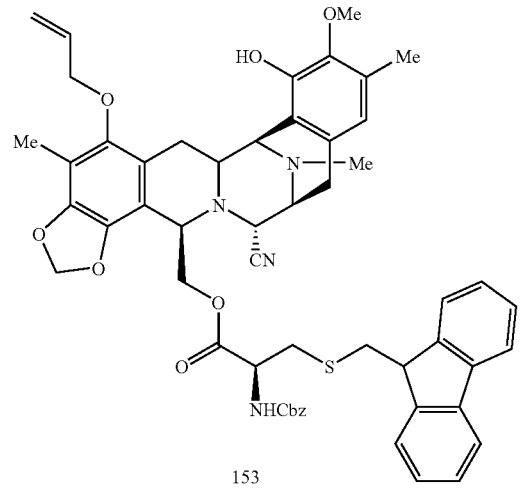

To a stirred solution of 146 (10 g, 19.2 mmol) and 152 (12.5 g, 28.8 mmol) in dichloromethane (800 mL) under argon, dimethylaminopyridine (705 mg, 5.77 mmol), 1-[3-(Dimethylamino)propyl]-3-ethylcarbodiimide hydrochloride (9.2 g, 48.1 mmol) and diisopropylethy amine (7.4 mL, 42.3 mmol) were added dropwise during 1 h at 0° C. The mixture was then stirred at 23° C. for 1.5 more hour. The reaction was quenched by addition of a saturated aqueous sodium bicarbonate solution (600 mL). The organic phase was separated and washed again with a saturated aqueous amonium chloride solution (500 mL) and a saturated sodium chloride solution (500 mL). The organic extract were dried over sodium sulphate, filtered and evaporated to dryness under reduced pressure. The crude product was purified by flash column chromatography (RP18, CH₃CN:H₂O 4:1) to yield 153 (13.89 g, 77%) as a pale yellow solid.

$^{13}$C NMR (75 MHz, CDCl₃) δ 170.2, 155.6, 148.6, 146.8, 145.7, 145.6, 144.3, 142.6, 140.7, 139.0, 133.7, 131.1, 128.8, 128.4, 128.1, 128.0, 127.4, 126.9, 124.7, 124.6, 121.0, 120.5, 119.7, 117.8, 117.3, 116.8, 112.5, 112.0, 101.0, 74.1, 67.0, 64.7, 60.7, 59.9, 57.0, 56.6, 56.3, 55.2, 53.1, 46.5, 41.4, 36.4, 34.8, 26.2, 24.8, 15.6, 9.2.

ESI-MS m/z: Calcd. for $C_{54}H_{54}N_4O_9S$: 934.36. Found (M+1)$^+$: 935.4.

Example 80

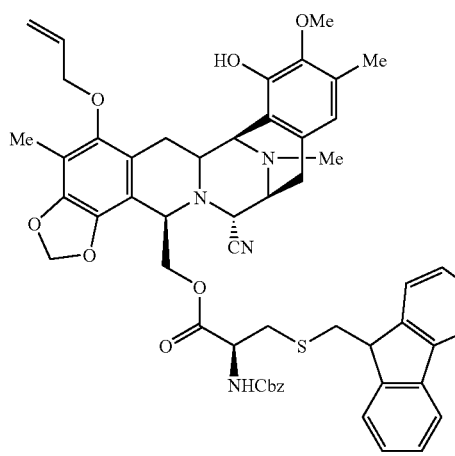

153

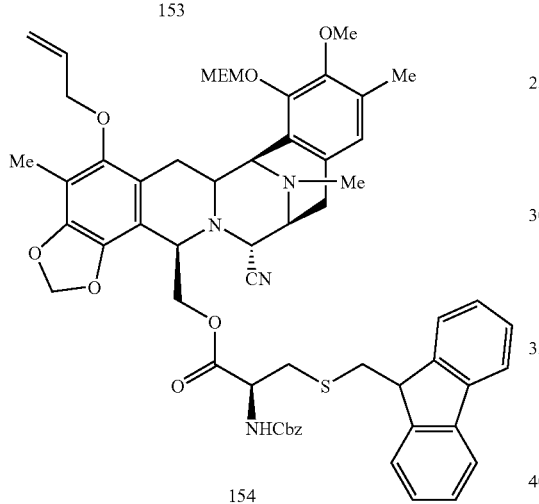

154

To a solution of 153 (13.89 g, 14.85 mmol) in CH$_3$CN (74.3 mL), MEMCl (25.4 mL, 223 mmol), DIPEA (52 mL, 297 mmol) and DMAP (0.181 g, 0.15 mmol) were added at 0° C. The mixture was stirred for 5 h at 23° C. The reaction was diluted with CH$_2$Cl$_2$ (400 mL) and extracted with 0.1N HCl (300 mL) and 3N HCl (pH=3). The aqueous phase was extracted again with CH$_2$Cl$_2$ (2×50 mL). The combined organic phases were dried over Na$_2$SO$_4$, filtered and concentrated in vacuo to give a residue which was purified by flash column chromatography (SiO$_2$, CH$_2$Cl$_2$:EtOAc 10:1, 5:1) to give 154 (13.47 g, 88%) as a white solid. Rf=0.27 CH$_2$Cl$_2$:AcOEt 6:1.

$^1$H NMR (300 MHz, CDCl$_3$) δ 7.73-7.70 (m, 2H), 7.58-7.50 (m, 2H), 7.38-7.22 (m, 9H), 6.59 (s, 1H), 6.08-5.98 (m, 1H), 5.89 (s, 1H), 5.77 (s, 1H), 5.35 (d, J=17.1 Hz, 1H), 5.31-5.28 (m, 1H), 5.23 (d, J=6.9 Hz, 1H), 5.13 (d, J=6.9 Hz, 1H), 5.12-5.05 (m, 2H), 4.37-4.29 (m, 2H), 4.15-3.77 (m, 9H), 3.68 (s, 3H), 3.58-3.55 (m, 2H), 3.37 (s, 3H), 3.30-3.27 (m, 1H), 3.21-3.16 (m, 2H), 2.96-2.84 (m, 4H), 2.64-2.58 (m, 1H), 2.55 (d, J=18 Hz, 1H), 2.27 (s, 3H), 2.16 (s, 3H), 2.02 (s, 3H), 1.75 (dd, J$_1$=12.3 Hz, J$_2$=16.2 Hz, 1H).

$^{13}$C NMR (75 MHz, CDCl$_3$) δ 171.9, 170.2, 155.5, 148.7, 148.6, 148.3, 145.8, 145.7, 144.5, 142.1, 140.9, 139.1, 136.1, 133.8, 130.8, 130.5, 128.5, 128.3, 128.1, 127.6, 127.0, 124.9, 124.7, 123.9, 122.2, 120.9, 119.8, 117.8, 117.3, 112.6, 112.0, 101.1, 98.2, 74.0, 71.7, 69.3, 67.1, 65.1, 60.1, 59.8, 59.0, 56.9, 56.8, 56.7, 55.3, 53.3, 46.7, 41.4, 36.5, 35.0, 31.6, 29.7, 26.4, 25.0, 22.6, 15.7, 14.1, 9.2.

ESI-MS m/z: Calcd. for C$_{58}$H$_{62}$N$_4$O$_{11}$S: 1023.2. Found (M+23)$^+$: 1046.3.

Example 81

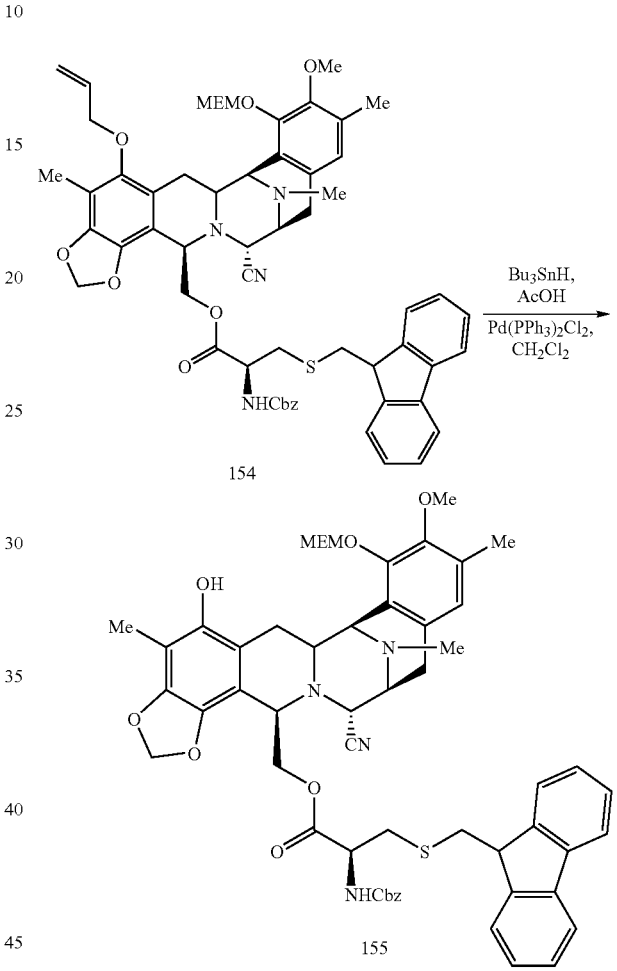

154

155

To a stirred solution of 154 (20.84 g. 0.02 mol) in dichloromethane (530 mL), dichlorobis(triphenylphosphine) palladium (II) (1.14 g, 1.63 mmol) and acetic acid (11.64 mL, 0.2 mol) were added under argon at 23° C. Then, tributyltin hydride (27.44 mL, 0.1 mol) was added in a dropwise manner. The mixture was stirred at 23° C. for 15 minutes. The reaction was then filtered through a silica gel column compacted with hexane. 155 (18.78 g, 94%) was obtained as a pale yellow solid by subsequent elution with mixtures of ethyl acetate and hexane in a gradient manner, from 1:4, 1:1, 3:2 to 7:3.

$^1$H NMR (300 MHz, CDCl$_3$) δ 7.71 (d, J=7.2 Hz, 2H), 7.59 (d, J=7.5 Hz, 1H), 7.53 (d, J=7.5 Hz, 1H), 7.41-7.23 (m, 9H), 6.60 (s, 1H), 5.87 (bs, 2H), 5.74 (s, 1H), 5.40 (d, J=6.3 Hz, 1H), 5.33 (d, J=5.8 Hz, 1H), 5.18 (d, J=9 Hz, 1H), 5.09 (d, J=12 Hz, 1H), 4.97 (d, J=12 Hz, 1H), 4.56 (dd, J$_1$=3 Hz, J$_2$=11.1 Hz, 1H), 4.19 (d, J=2.1 Hz, 1H), 4.16-3.87 (m, 9H), 3.66 (s, 3H), 3.38 (s, 3H), 3.32-3.20 (m, 3H), 2.96-2.87 (m, 3H), 2.62-2.54 (m, 2H), 2.28 (s, 3H), 2.19 (s, 3H), 1.97 (s, 3H), 1.82 (dd, J$_1$=13.2 Hz, J$_2$=15.6 Hz, 1H).

$^{13}$C NMR (75 MHz, CDCl$_3$) δ 170.0, 155.4, 149.0, 147.5, 145.7, 145.6, 144.4, 140.8, 135.9, 130.9, 128.4, 128.1, 128.0, 127.4, 126.9, 124.7, 124.6, 122.7, 119.7, 117.7, 112.4, 111.4, 100.6, 98.7, 71.5, 69.4, 67.0, 64.9, 63.9, 59.7, 59.6, 58.8, 57.0, 56.5, 56.4, 55.1, 54.9, 53.1, 52.5, 46.5, 41.4, 36.8, 34.9, 25.8, 24.7, 15.7, 8.7.

Example 82

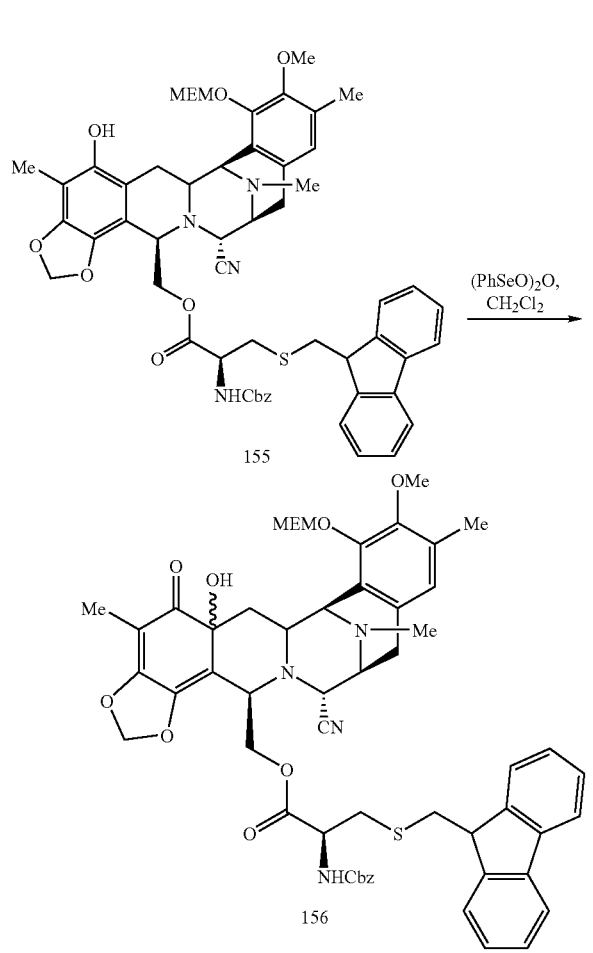

To a solution of 155 (18.5 g, 18.82 mmol) in anhydrous dichloromethane (530 mL) at −10° C. (bath temperature −15° C.), a solution of benzeneseleninic anhydride (9.68 g, 18.82 mmol) in anhydrous dichloromethane (290 mL) was added dropwise, discarding any white solid present in the solution. The mixture was stirred for 10 minutes at the same temperature. The reaction was then quenched with a saturated aqueous sodium bicarbonate solution (600 mL). The organic phase was separated, and the aqueous phase was extracted with CH$_2$Cl$_2$ (2×300 mL). The combined organic extracts were dried over sodium sulphate, fitltered, and concentrated to dryness under reduced pressure. The residue was purified by column chromatography, eluting with mixtures of ethyl acetate and hexane in a gradient manner, from 1:1, 3:2, 7:3 to 4:1 to obtain 156 (17.62 g, 88%) as a pale yellow solid.

$^1$H NMR (300 MHz, CDCl$_3$) (mixture of isomers) δ 7.73 (d, J=7.5 Hz, 2H), 7.63 (d, J=7.5 Hz, 2H), 7.40-7.29 (m, 9H), 6.59 (s, 1H), 6.52 (s, 1H), 5.68 (s, 1H), 5.66 (s, 1H), 5.58 (s, 1H), 5.56 (s, 1H), 5.23 (d, J=6 Hz, 1H), 5.15-5.05 (m, 4H), 4.76-4.68 (m, 1H), 4.64-4.55 (m, 1H), 4.40-4.37 (m, 1H), 4.15-3.68 (m, 8H), 3.60 (s, 3H), 3.57 (s, 3H), 3.39 (s, 3H), 3.36 (s, 3H), 3.25-2.78 (m, 7H), 2.38-2.24 (m, 2H), 2.20 (s, 3H), 2.18 (s, 3H), 2.15 (s, 3H), 2.09 (m, 1H), 2.04 (s, 3H), 1.77 (s, 3H), 1.58 (s, 3H).

ESI-MS m/z: Calcd. for C$_{55}$H$_{58}$N$_4$O$_{12}$S: 999.13. Found (M+1)$^+$: 1000.0.

Example 83

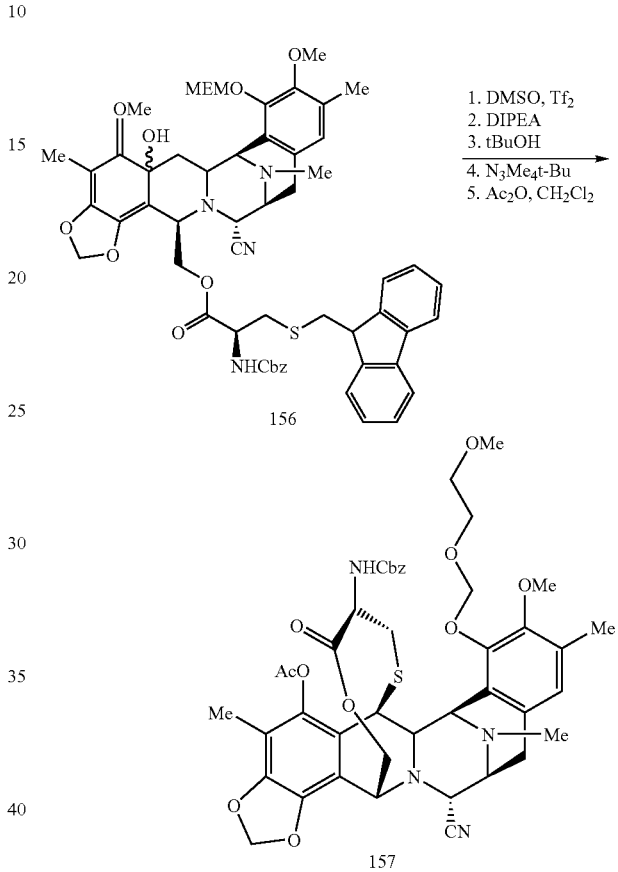

The reaction flask was flamed twice, purged vacuum/Argon several times and kept under Argon atmosphere for the reaction. To a solution of DMSO (178 µL) in anhydrous CH$_2$Cl$_2$ (20 mL) was dropwise added triflic anhydride (169 µL, 1 mmol) at −78° C. The reaction mixture was stirred at −78° C. for 20 minutes. Then, a solution of 156 (0.5 g, 0.5 mmol) in anhydrous CH$_2$Cl$_2$ (4 mL, for the main addition and 1.5 mL for washing) was added via canula (addition time: 5 min) at −78° C. During the addition the temperature was kept at −78° C. in both flasks and the color changed from yellow to brown. The reaction mixture was stirred at −40° C. for 35 minutes. During this period of time the solution was turned from yellow to dark green. After this time, $^i$Pr$_2$NEt (0.7 mL, 4.42 mmol) was dropwise added and the reaction mixture was kept at 0° C. for 45 minutes, the color of the solution turned brown during this time. Then $^t$BuOH (189 µL, 2 mmol) and tert-butyl tetramethyl guanidine (0.6 mL, 3.49 mmol) were dropwise added and the reaction mixture was stirred at 23° C. for 40 minutes. After this time, acetic anhydride (0.47 mL, 4.97 mmol) was dropwise added and the reaction mixture was kept at 23° C. for 1 hour more. Then, the reaction mixture was diluted with CH$_2$Cl$_2$ (15 mL) and washed with aqueous saturated solution of NH$_4$Cl (25 mL), NaHCO$_3$ (25 mL), and NaCl (25 mL). The combined organic layers were dried over Na$_2$SO$_4$, filtered and concentrated. The residue was purified by flash column chromatography (inner diameter: 2.0 cm, height of silica: 9 cm; eluent: ethyl acetate/hexane in a gradient manner, from 1:4, 1:3, 1:2 to 1:1) to afford 157 (128 mg, 30%) as a light yellow solid. Rf=0.37 Hex:EtOAc 3:2.

$^1$H NMR (300 MHz, CDCl$_3$) δ 7.37 (bs, 5H), 6.66 (s, 1H), 6.09 (s, 1H), 5.99 (s, 1H), 5.30 (d, J=5.4 Hz, 1H), 5.17 (d, J=6 Hz, 1H), 5.06 (d, J=7.8 Hz, 1H), 5.00 (s, 1H), 4.83 (d, J=9.3 Hz, 1H), 4.50 (s, 1H), 4.34-4.17 (m, 7H), 3.90-3.87 (m, 2H), 3.66 (s, 3H), 3.65-3.56 (m, 2H), 3.37 (s, 3H), 2.89-2.90 (m, 2H), 2.28 (s, 3H), 2.18 (s, 3H), 2.15-2.04 (m, 2H), 2.03 (s, 3H), 1.99 (s, 3H).

ESI-MS m/z: Calcd. for C$_{43}$H$_{48}$N$_4$O$_{12}$S: 844.93. Found (M+1)$^+$: 845.8.

Example 84

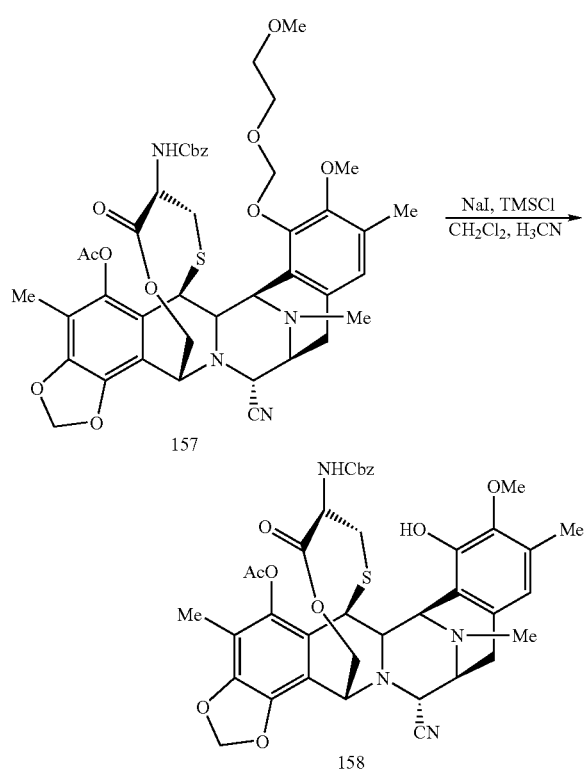

To a solution of 157 (100 mg, 0.118 mmol) in CH$_2$Cl$_2$ (2 mL) and CH$_3$CN (2 mL), NaI (71 mg, 0.472 mmol) and TMSCl (60 μL, 0.472 mmol) were added at 0° C. After stirring the reaction at 23° C. for 50 minutes, the mixture was quenched with water (30 mL) and extracted with CH$_2$Cl$_2$ (2×20 mL). The combined organic phases were washed successively with a saturated solution of NaCl (20 mL) and a saturated solution of sodium ditionite (20 mL), dried over Na$_2$SO$_4$, filtered and concentrated in vacuo. The residue was purified by flash column chromatography (eluent: ethyl acetate/hexane gradient from 1:4, 1:2 to 1:1) to afford 158 (62 mg, 70%) as white solid. Rf=0.21 Hex:EtOAc 1:1.

$^1$H NMR (300 MHz, CDCl$_3$) δ 7.36 (bs, 5H), 6.44 (s, 1H), 6.07 (d, J=1.2 Hz, 1H), 5.97 (d, J=1.2 Hz, 1H), 5.81 (bs, 1H), 5.10-5.00 (m, 3H), 4.82 (d, J=9.3 Hz, 1H), 4.49 (bs, 1H), 4.35-4.30 (m, 1H), 4.21-4.17 (m, 2H), 4.16-4.14 (m, 2H), 3.65 (s, 3H), 3.41-3.36 (m, 2H), 2.88-2.85 (m, 2H), 2.28 (s, 3H), 2.24-2.03 (m, 2H), 2.17 (s, 3H), 2.02 (s, 3H), 2.00 (s, 3H).

$^{13}$C NMR (75 MHz, CDCl$_3$) δ 170.5, 168.8, 155.9, 148.3, 146.0, 143.1, 141.2, 140.6, 136.6, 130.6, 130.0, 128.8, 128.7, 128.5, 121.0, 120.3, 118.3, 118.2, 113.7, 113.6, 102.2, 67.2, 61.5, 60.8, 60.3, 59.6, 59.5, 54.8, 54.7, 54.1, 41.9, 41.6, 32.9, 23.9, 20.8, 15.5, 9.8.

ESI-MS m/z: Calcd. for C$_{39}$H$_{40}$N$_4$O$_{10}$S: 756.82. Found (M+1)$^+$: 757.3.

Example 85

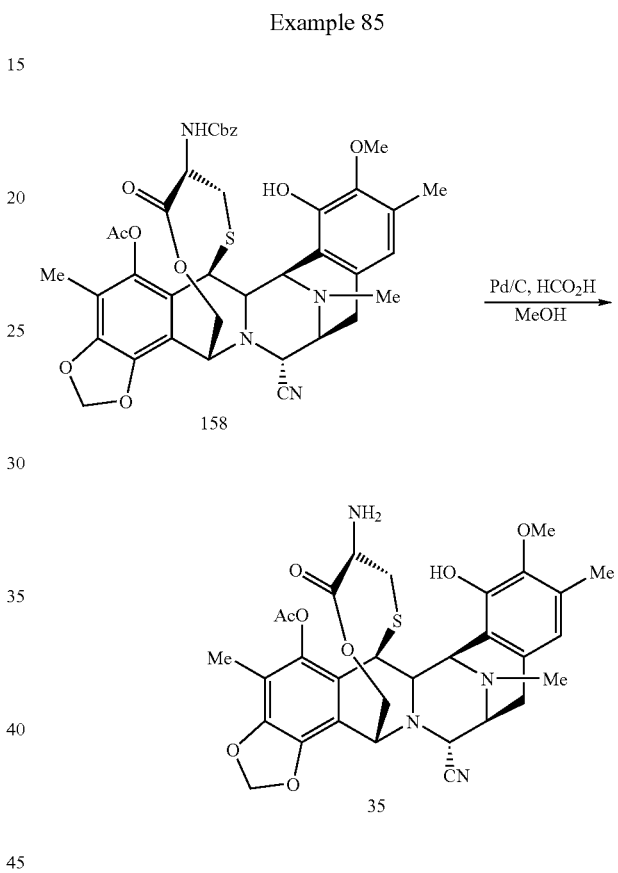

To a solution of 158 (100 mg, 0.132 mmol) in MeOH (6.8 mL), HCO$_2$H (360 μL) and 10% Pd/C (140 mg, 0.132 mmol) were added at 23° C. and the mixture was stirred for 15 minutes. Then, toluene (7 mL) was added to the reaction and the solvent was evaporated under reduced pressure. The azeotropic destination with toluene was repeated 3 times. The residue was then diluted with dichloromethane (15 mL) and a saturated aqueous solution of sodium bicarbonate (15 mL) was added. The aqueous phase was separated and extracted with dichloromethane (2×10 mL). The combined organic extracts were dried over sodium sulphate, filtered and evaporated to dryness under reduced pressure. The residue was then purified by flash column chromatography on amino-silicagel and eluting with mixtures of ethyl acetate and hexane in a gradient manner, from 1:2, 1:1 to 2:1 to give 35 (57 mg, 70%) as a yellow solid. Experimental data of 35 were previously described in PCT/GB00/01852.

36, ET-770 and ET-743 were prepared following the same procedures than those previously described in PCT/GB00/01852.

Route 4

The first step of this Route (transformation of 21 into 146) was described above in Example 71.

Example 86

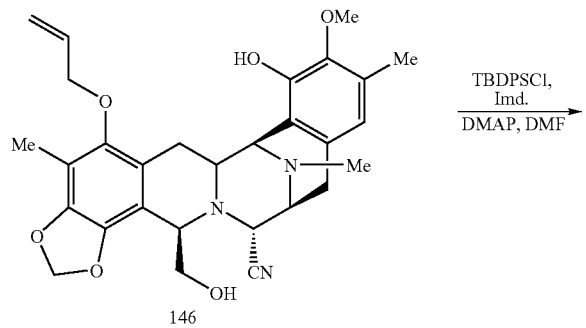

146

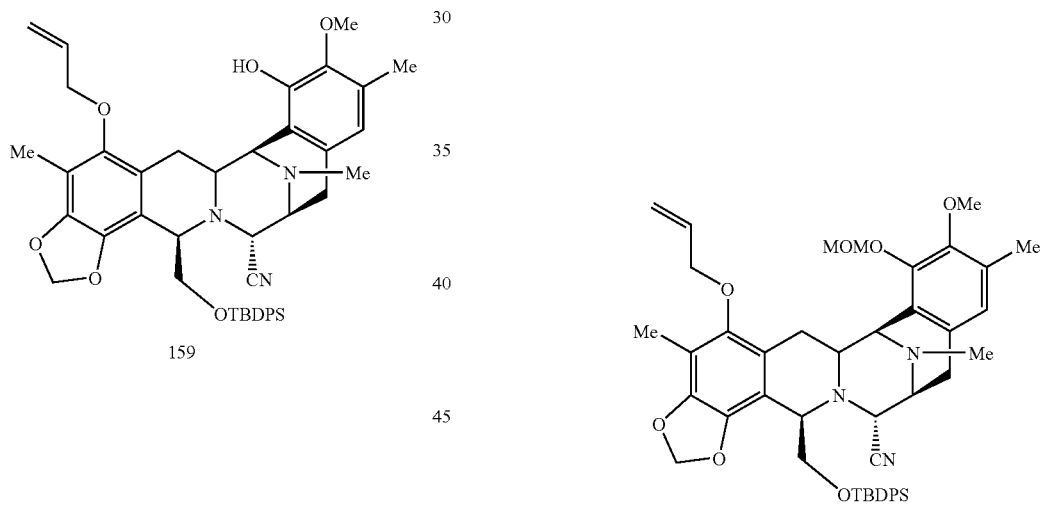

159

To a solution of 146 (18 mg, 0.032 mmol), cat. DMAP and imidazole (5 mg, 0.08 mmol) in DMF (0.05 mL) at 0° C., tert-buthyldiphenylsilyl chloride (12.5 μL, 0.048 mmol) was added and the reaction was stirred for 4 hours at 23° C. Then, water (30 mL) was added at 0° C. and the mixture was extracted with Hex:EtOAc 1:10 (2×40 mL). The combined organic phases were dried over sodium sulphate, filtered, and the solvent was removed under reduced pressure. The residue was puified by flash column chromatography (SiO$_2$, Hex: EtOAc 3:1) to afford 159 (27 mg, 88%) as a white solid. Rf=0.29 Hex:EtOAc 3:1.

$^1$H NMR (300 MHz, CDCl$_3$) δ 7.72-7.41 (m, 2H), 7.40-7.20 (m, 8H), 6.46 (s, 1H), 6.16-6.00 (m, 1H), 5.77 (d, J=1.5 Hz, 1H), 5.71 (s, 1H), 5.63 (d, J=1.5 Hz, 1H), 5.24 (dd, J$_1$=1.2 Hz, J$_2$=17.1 Hz, 1H), 5.23 (dd, J$_1$=1.2 Hz, J$_2$=10.2 Hz, 1H), 4.18 (d, J=2.4 Hz, 1H), 4.13-4.00 (m, 4H), 3.77 (s, 3H), 3.63 (dd, J$_1$=2.4 Hz, J$_2$=7.5 Hz, 1H), 3.39-3.19 (m, 4H), 2.99 (dd, J$_1$=8.1 Hz, J$_2$=18.0 Hz, 1H), 2.68 (d, J=17.7 Hz, 1H), 2.30 (s, 3H), 2.28 (s, 3H), 2.08 (s, 3H), 1.99 (dd, J$_1$=12.6 Hz, J$_2$=16.3 Hz, 1H), 0.89 (s, 9H).

$^{13}$C NMR (75 MHz, CDCl$_3$) δ 148.3, 146.6, 144.0, 142.5, 139.0, 135.7, 135.4, 133.9, 133.6, 132.2, 131.2, 129.5, 129.4, 128.3, 127.5, 127.4, 121.8, 120.9, 118.7, 117.3, 117.2, 112.9, 111.7, 100.8, 74.2, 68.0, 61.6, 60.6, 60.3, 59.0, 57.4, 56.7, 55.4, 41.7, 29.6, 26.6, 26.5, 25.5, 18.9, 15.8, 9.3.

ESI-MS m/z: Calcd. for C$_{45}$H$_{51}$N$_3$O$_6$Si: 757.9. Found (M+1)$^+$: 758.4.

Example 87

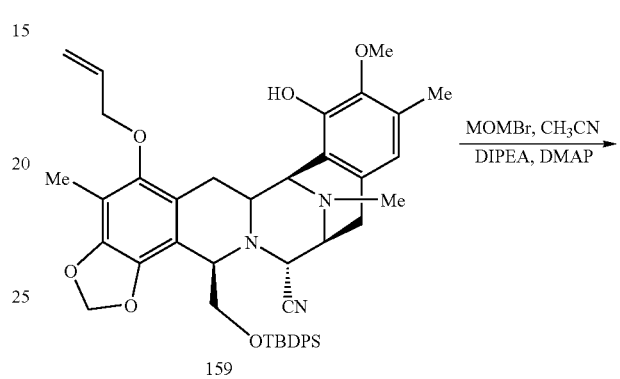

159

To a solution of 159 (2.4 g, 3.17 mmol) in CH$_3$CN (16 mL), MOMBr (2.6 mL, 31.75 mmol), DIPEA (8.3 mL, 47.6 mmol) and DMAP (16 mg, 0.127 mmol) were added at 0° C. The mixture was stirred for 6 h at 23° C. The reaction was diluted with CH$_2$Cl$_2$ (50 mL) and extracted with 0.1 N HCl (50 mL). The aqueous phase was extracted again with CH$_2$Cl$_2$ (50 mL). The combined organic phases were dried over Na$_2$SO$_4$, filtered and concentrated in vacuo to give a residue which was purified by flash column chromatography (SiO$_2$, CH$_2$Cl$_2$: EtOAc 15:1, 5:1) to give 26 (1.78 g, 70%) as a white solid. Experimental data of 26 were described previously in PCT/GB00/01852.

Experimental procedures for Int. 11, 160, 161, 162, and 163 were previously described in U.S. Pat. No. 5,721,362.

Example 88

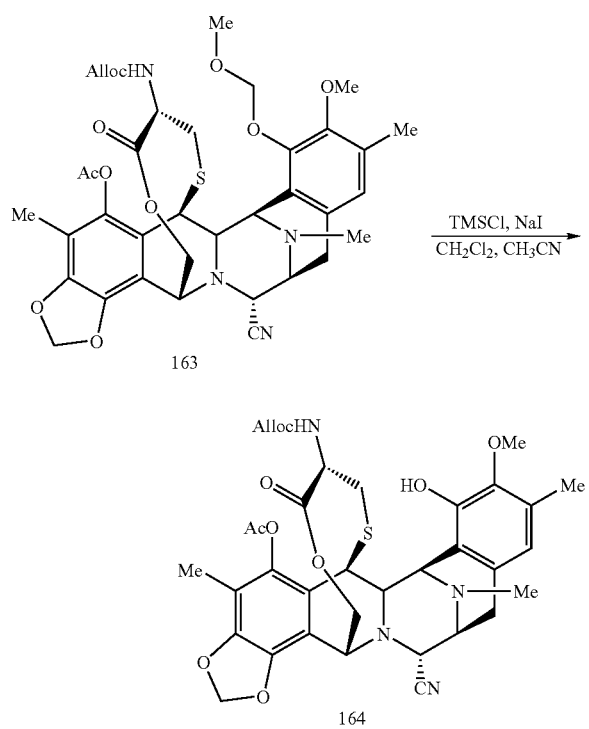

To a solution of 163 (15.8 g, 0.02 mol) in anhydrous CH$_2$Cl$_2$ (250 mL) and acetonitrile (300 mL), NaI (31.5 g, 0.21 mol) and ClTMS (freshly distilled over CaH$_2$, 26.7 mL, 0.21 mol) were added under argon atmosphere at 23° C. The reaction mixture was stirred for 40 minutes. Then the reaction was partitioned between CH$_2$Cl$_2$ (200 mL) and water (300 mL). The organic layer was washed with a saturated aqueous solution of NaCl (2×300 mL). The organic phase was dried over Na$_2$SO$_4$, filtered and the solvent was eliminated under reduced pressure. The crude was purified by flash column chromatography using ethyl acetate/hexane 2:3 as eluent to afford 164 (10.74 g, 76%) as a pale yellow solid. Rf=0.25 Hex:EtOAc 3:2.

$^1$H NMR (300 MHz, CDCl$_3$) δ 6.57 (s, 1H), 6.08 (d, J=1.5 Hz, 1H), 5.98 (d, J=1.5 Hz, 1H), 5.96-5.85 (m, 1H), 5.76 (bs, 1H), 5.30 (dd, J$_1$=1.5, J$_2$=17.3 Hz, 1H), 5.23 (dd, J$_1$=1.5, J$_2$=10.2 Hz, 1H), 5.00 (d, J=12.1 Hz, 1H), 4.81 (d, J=9.8 Hz, 1H), 4.58-4.45 (m, 3H), 4.34-4.28 (m, 1H), 4.23 (m, 2H), 4.17-4.00 (m, 2H), 3.76 (s, 3H), 3.40-3.38 (m, 2H), 2.91-2.85 (m, 2H), 2.30 (s, 3H), 2.29 (s, 3H), 2.24-2.23 (m, 2H), 2.19 (s, 3H), 2.02 (s, 3H).

$^{13}$C NMR (75 MHz, CDCl$_3$) 170.1, 168.4, 155.2, 148.0, 145.5, 142.8, 140.7, 140.1, 132.7, 130.2, 129.6, 120.7, 119.9, 117.8, 113.3, 101.9, 65.6, 61.0, 60.4, 59.9, 59.2, 59.0, 54.3, 53.6, 41.5, 41.2, 32.6, 29.5, 23.5, 20.4, 15.6, 9.4.

ESI-MS m/z: Calcd. for C$_{35}$H$_{38}$N$_4$O$_{10}$S: 706.76. Found (M+1)$^+$: 707.2.

Example 89

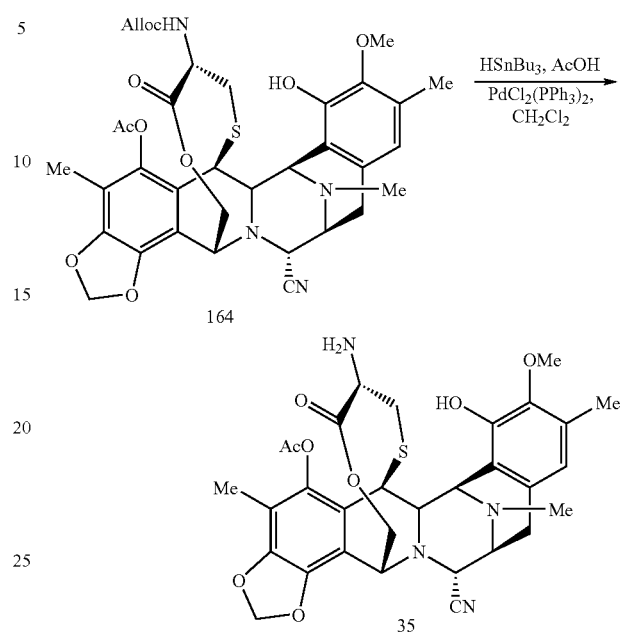

To a stirred solution of 164 (2 g. 2.85 mmol) in dichloromethane (142 mL), dichlorobis(triphenylphosphine) palladium (II) (0.2 g, 0.28 mmol) and acetic acid (0.65 mL, 11.4 mmol) were added under argon at 23° C. Then, tributyltin hydride (4.51 mL, 17.02 mmol) was added in a dropwise manner during 25 minutes. After addition of HsnBu$_3$, the mixture was stirred at 23° C. for 20 minutes more. The reaction was filtered through a silical gel column compacted with hexane. 35 (1.38 g, 78%) was obtained by subsequent elution with mixtures of ethyl acetate and hexane in a gradient manner, from 1:2 to 15:1. Experimental data of 35 were previously described in PCT/GB00/01852.

36, ET-770 and ET-743 were prepared following the same procedures than those previously described in PCT/GB00/01852.

Route 5

The first step of this Route (transformation of 21 into 146) was described above in Example 71.

Example 90

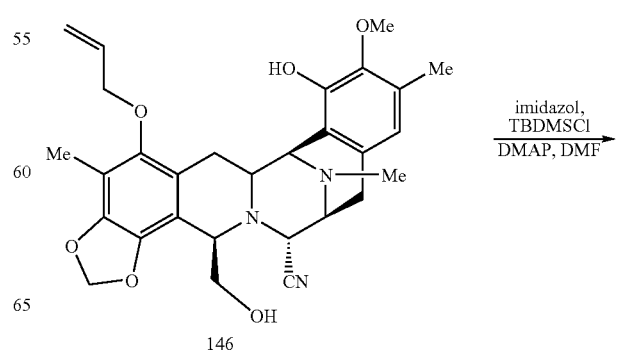

-continued

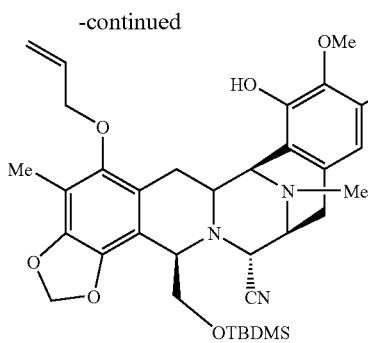

165

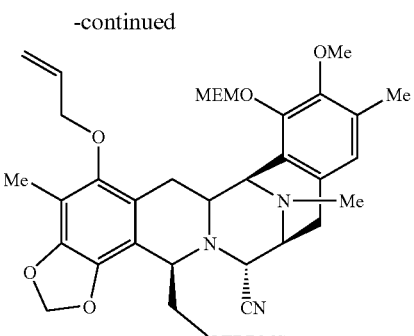

166

To a solution of 146 (8.72 g, 16.78 mmol) in DMF (20.1 mL), imidazol (3.43 g, 50.34 mmol), tert-butyl dimethyl chlorosilane (7.58 mL, 50.34 mmol) and DMAP (0.2 g, 1.7 mmol) were added at 0° C. After being stirred at 23° C. for 3.5 h, the reaction mixture was quenched with water (100 mL) and extracted with EtOAc/Hex 1:3 (2×75 mL). The combined organic phases were washed with 0.1 M HCl (50 mL) and the aqueous phase was extracted again with EtOAc/Hex 1:3 (40 mL). The combined organic phases were dried over sodium sulphate, filtered and concentrated in vacuo. The residue was purified by flash column chromatography (Hex:EtOAc 10:1, 3:1) to obtain 165 (9.85 g, 93%) as a white solid. Rf=0.39 in Hex:AcOEt 2:1.

$^1$H NMR (300 MHz, CDCl$_3$) δ 6.43 (s, 1H), 6:15-6.03 (m, 1H), 5.92 (d, J=1.2 Hz, 1H), 5.84 (d, J=1.2 Hz, 1H), 5.67 (s, 1H), 5.41 (dd, J$_1$=1.5, J$_2$=17.1 Hz, 1H), 5.26 (dd, J$_1$=1.5, J$_2$=10.5 Hz, 1H), 4.44 (d, J=2.7 Hz, 1H), 4.20-4.08 (m, 3H), 3.97 (dd, J$_1$=2.7, J$_2$=8.1 Hz, 1H), 3.75 (s, 3H), 3.61 (dd, J$_1$=2.71, J$_2$=9.9 Hz, 1H), 3.18 (brd, J=8.7 Hz, 1H), 3.22-3.16 (m, 2H), 2.99 (dd, J$_1$=8.1, J$_2$=17.4 Hz, 1H), 2.65 (d, J=17.4 Hz, 1H), 2.28 (s, 3H), 2.25 (s, 3H), 2.11 (s, 3H), 1.89 (dd, J$_1$=12, J$_2$=15.6 Hz, 1H), 0.8 (s, 9H), −0.05 (s, 3H), −0.09 (s, 3H).

$^{13}$C NMR (75 MHz, CDCl$_3$) □ 148.2, 146.5, 143.8, 142.4, 138.9, 133.8, 131.0, 128.0, 121.5, 120.4, 118.4, 117.1, 112.8, 111.6, 100.7, 74.0, 68.2, 61.5, 60.2, 58.6, 57.1, 56.5, 55.2, 41.3, 26.2, 25.4, 25.2, 20.6, 17.8, 15.3, 13.8, 9.0, −3.9, −6.0.

ESI-MS m/z: Calcd. for C$_{35}$H$_{47}$N$_3$O$_6$Si: 633.85. Found (M+1)$^+$: 634.2.

To a solution of 165 (7.62 g, 12.02 mmol) in THF (87.64 mL) and water (0.24 mL), MEMCl (2.33 mL, 20.43 mmol) was added at −6° C. After addition of 60% NaH (0.72 g, 18.03 mmol) in portions over 45 min, the mixture was stirred for 1.5 h at that temperature. The reaction was quenched with water (150 mL) and extracted with CH$_2$Cl$_2$ (2×100 mL). The combined organic phases were dried over Na$_2$SO$_4$, filtered and concentrated in vacuo to give 166 (8.69 g, 100%) as a white solid which was used in following steps with no further purification. Rf=0.24 Hex:AcOEt 2:1.

$^1$H NMR (300 MHz, CDCl$_3$) δ 6.64 (s, 1H), 6.16-6.05 (m, 1H), 5.92 (d, J=1.2 Hz, 1H), 5.85 (d, J=1.2 Hz, 1H), 5.41 (dd, J$_1$=1.51, J$_2$=17.1 Hz, 1H), 5.29-5.24 (m, 2H), 5.14 (d, J=6 Hz, 1H), 4.42 (d, J=2.7 Hz, 1H), 4.21-4.06 (m, 3H), 4.01-3.95 (m, 2H), 3.88-3.82 (m, 1H), 3.72 (s, 3H), 3.64-3.57 (m, 3H), 3.39 (s, 3H), 3.29 (brd J=7.5 Hz, 1H), 3.25-3.15 (m, 2H), 3.00 (dd, J$_1$=8.1, J$_2$=17.4 Hz, 1H), 2.65 (d, J=18 Hz, 1H), 2.30 (s, 3H), 2.21 (s, 3H), 2.11 (s, 3H), 1.82 (dd J$_1$=12, J$_2$=15.6 Hz, 1H), 0.79 (s, 9H), −0.06 (s, 3H), −0.11 (s, 3H).

$^{13}$C NMR (75 MHz, CDCl$_3$) δ 148.4, 148.1, 144.1, 139.2, 133.9, 130.9, 130.8, 130.2, 128.8, 125.1, 124.2, 121.5, 118.8, 117.45, 113.0, 111.9, 101.0, 98.2, 74.1, 71.7, 69.3, 68.3, 61.7, 59.6, 59.0, 58.9, 57.3, 57.1, 55.5, 41.6, 29.7, 26.4, 25.8, 25.5, 25.4, 15.7, 9.2, −5.6, −5.6.

ESI-MS m/z: Calcd. for C$_{39}$H$_{55}$N$_3$O$_8$Si: 721.3. Found (M+1)$^+$: 722.3.

Example 91

Example 92

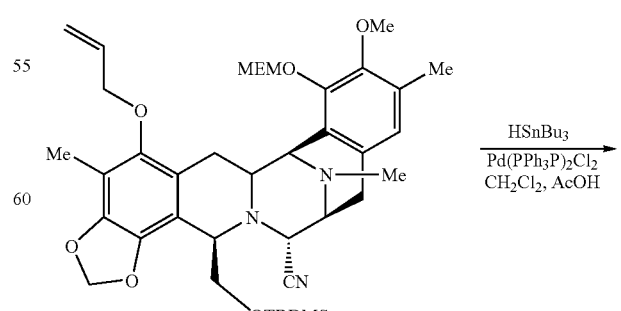

165 →(NaH, MEMCl)→ 166 →(HSnBu$_3$, Pd(PPh$_3$P)$_2$Cl$_2$, CH$_2$Cl$_2$, AcOH)→

-continued

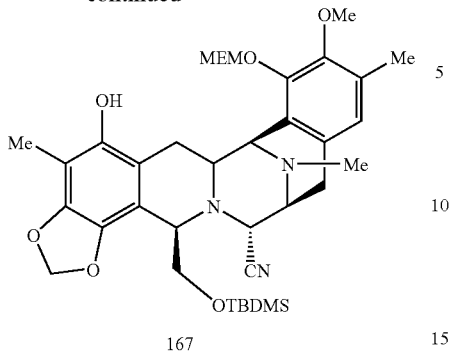

167

To a solution of 166 (10.76 g, 14.90 mmol) in anhydrous $CH_2Cl_2$ (275 mL), $Pd(PPh_3P)_2Cl_2$ (837 mg, 1.19 mmol), acetic acid (4.26 mL, 74.5 mmol) and tributyltin hydride (11.85 mL, 44.7 mmol) were added under Argon atmosphere at 23° C. The reaction mixture was stirred at 23° C. for 15 minutes. (TLC AcOEt/Hexane 1:1 showed no starting material). Hexane (100 mL) was added and the mixture was poured into a flash column chromatography, ($SiO_2$, EtOAc:Hexane in a gradient manner, from 0:100, 1:4, 2:3 to 1:1) to afford 167 (9.95 g, 98%) as a yellow solid. Rf=0.42 Hex:EtOAc 3:7.

$^1$H-RMN (300 MHz, $CDCl_3$): δ 6.63 (s, 1H), 5.89 (d, J=1.4 Hz, 1H), 5.79 (d, J=1.4 Hz, 1H), 5.76 (m, 1H), 5.38 (d, J=5.6 Hz, 1H), 5.23 (d, J=5.9 Hz, 1H), 4.53 (d, J=2.7 Hz, 1H), 4.17 (dd, $J_1$=1.95 Hz, $J_2$=6.05 Hz, 1H), 4.11 (dd, $J_1$=7.0 Hz, $J_2$=12.5 Hz, 1H), 4.01-3.92 (m, 2H), 3.70 (s, 3H), 3.67 (m, 3H), 3.40 (s, 3H), 3.29 (m, 1H), 3.24-3.13 (m, 3H), 2.99 (dd, $J_1$=8.0 Hz $J_2$=17.5 Hz, 1H), 2.67 (d, J=17.5 Hz, 1H), 2.28 (s, 3H), 2.09 (s, 3H), 2.05 (s, 3H), 1.80 (dd, $J_1$=11.2 Hz, $J_2$=14.9 Hz, 1H), 0.82 (s, 9H), −0.03 (s, 3H), −0.07 (s, 3H).

$^{13}$C-RMN (75 MHz, $CDCl_3$): δ 148.4, 147.3, 145.5, 144.1, 136.2, 134.9, 134.8, 130.9, 130.2, 124.8, 123.1, 118.6, 112.8, 112.1, 106.2, 100.4, 98.4, 71.5, 69.2, 68.9, 61.7, 59.6, 58.7, 58.6, 56.9, 56.6, 55.3, 41.5, 29.5, 25.7, 25.3, 17.9, 15.5, 8.7, −5.7, −5.8.

ESI-MS m/z: Calcd. for $C_{36}H_{51}N_3O_8Si$: 681.89. Found $(M+1)^+$: 682.3.

HPLC: Conditions: Column: Symmetry C18; mobile phase: AcN—buffer phosphate 25 mM, pH=5, isocratic of AcN (65%) in 5 minutes and gradient in AcN from 65-92% in 31 minutes, Ø: 0.6 mL/min, $t^a$: 40° C. Retention time: 27.89 minutes. HPLC purity in area: 89.62%.

Example 93

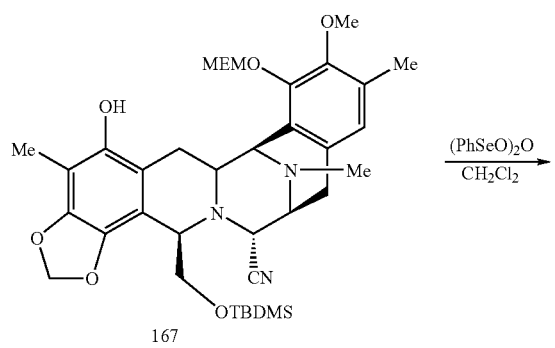

167

-continued

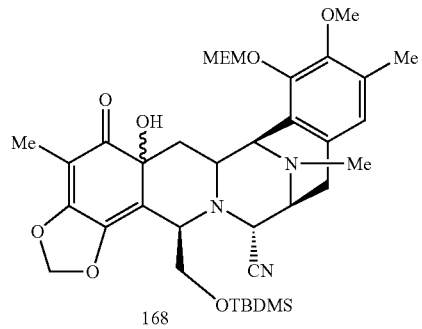

168

To a solution of 167 (9.95 g, 14.6 mmol) in anhydrous $CH_2Cl_2$ (300 mL), a solution of benceneseleninic anhydride (7.51 g, 14.6 mmol, reagent purity 70%) in anhydrous $CH_2Cl_2$ (120 mL) was dropwise added, under Argon atmosphere at −15° C. (the remaning white solid was discarded). The solution was then stirred at −15° C. for 15 minutes (TLC EtOAc/Hexane 2:3, showed no starting material). A saturated aqueous solution of sodium bicarbonate (500 mL) was added to the reaction mixture at this temperature. The organic phase was separated and the aqueous phase was extracted with $CH_2Cl_2$ (500 mL). The combined organic extracts were dried over sodium sulphate, filtered and the solvent was eliminated under reduced pressure. The crude of the reaction was purified by flash column chromatography, ($SiO_2$, EtOAc:Hexane in a gradient manner, from 2:3 to 3:1) to afford 168 (9.86 g, 97%) as a yellow solid. Rf=0.33 Hex:EtOAc 3:7).

$^1$H-RMN (300 MHz, $CDCl_3$) (Isomers ratio: ≈3:2): δ 6.59 (s, 1H), 6.57 (s, 1H), 5.77 (s, 1H), 5.76 (s, 1H), 5.68 (s, 1H), 5.63 (s, 1H), 5.19 (d, J=6.0 Hz, 1H), 5.09 (d, J=6.0 Hz, 1H), 5.07 (d, J=6.1 Hz, 1H), 5.00 (d, J=6.1 Hz, 1H), 4.40 (d, J=2.7 Hz, 1H), 4.27 (d, J=2.44 Hz, 1H), 4.22 (d, J=10.5 Hz, 1H), 3.95 (d, J=1.7 Hz, 1H), 3.86-3.75 (m, 2H), 3.81 (s, 3H), 3.72-3.68 (m, 2H), 3.65 (m, 2H), 3.54 (s, 3H), 3.50 (m, 3H), 3.31 (s, 3H), 3.29 (s, 3H); 3.24 (m, 1H), 3.09 (dt, J=3.2 Hz, J=7.6 Hz, 1H), 3.02 (d, J=11.2 Hz, 1H), 2.92 (m, 2H), 2.48 (d, J=9.5 Hz, 1H), 2.43 (d, J=9.3 Hz, 1H), 2.21 (s, 3H), 2.14 (s, 3H), 2.13 (s, 3H), 2.03 (m, 2H), 1.73 (s, 3H), 1.71 (s, 3H), 0.86 (s, 9H), 0.77 (s, 9H), 0.04 (s, 3H), 0.02 (s, 3H).

$^{13}$C-RMN (75 MHz, $CDCl_3$): 200.5, 197.2, 159.8, 157.7, 148.4, 148.2, 147.7, 140.0, 137.6, 130.5, 130.2, 129.9, 129.4, 124.9, 124.7, 124.0, 122.7, 117.1, 116.9, 113.4, 110.8, 103.9, 103.8, 101.0, 100.4, 97.8, 72.8, 71.3, 69.7, 68.9, 68.8, 65.4, 64.1, 60.2, 59.9, 59.3, 59.1, 59.0, 58.6, 58.5, 56.8, 56.5, 56.2, 55.5, 54.9, 54.8, 42.5, 41.1, 40.9, 35.8, 25.6, 25.5, 25.4, 25.3, 20.6, 17.9, 17.8, 15.5, 15.3, 13.8, 7.0, 6.7, −5.7, −6.0, −6.1.

ESI-MS m/z: Calcd. for $C_{36}H_{51}N_3O_9Si$: 697.89. Found $(M+1)^+$: 698.8 HPLC: Conditions: Column: Symmetry C18; mobile phase: AcN, buffer phosphate 25 mM, pH=5, gradient in AcN from 30-100% in 50 minutes. Ø: 1.2 mL/min, $t^a$: 40° C. Retention time: 30.70 minutes and 30.95 minutes (the two isomers). HPLC purity in area: 60.77% and 31.99%.

Example 94

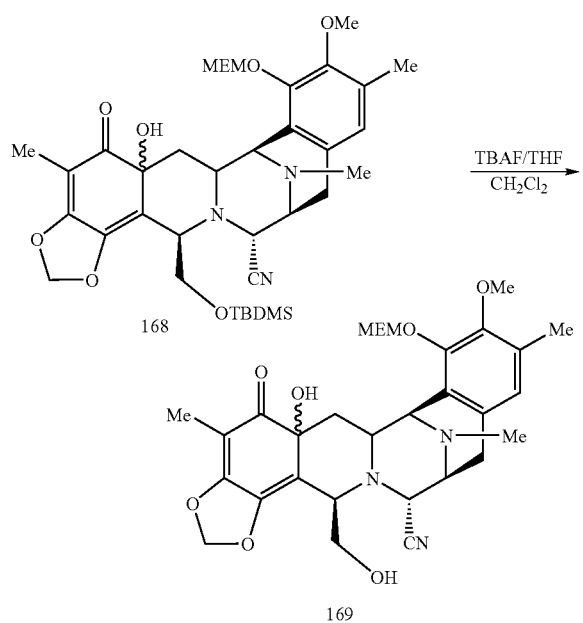

To a solution of 168 (16.38 g, 23.47 mmol) in anhydrous THF (727 mL, 0.03 M), a solution of TBAF in 1M THF (59 mL, 59 mmol) was dropwise added at 23° C. The reaction mixture was stirred at 23° C. for 45 minutes. Then, the mixture was partitioned between a saturated aqueous NaCl solution (850 mL) and $CH_2Cl_2$ (950 mL). Both layers were separated and the organic layer was dried over anhydrous $Na_2SO_4$, filtered and concentrated under reduced pressure. The residue was purified by flash column chromatography ($SiO_2$, EtOAc:Hexane in a gradient manner, from 40:60, 50:50, 70:30, 90:10 to 100:0) to afford 169 (12.17 g, 89%) as a light yellow solid. Rf=0.1 Hex:EtOAc 3:7.

$^1$H-RMN (300 MHz, $CDCl_3$) (Isomers ratio: 3:2): δ 6.63 (s, 1H), 6.57 (s, 1H), 5.79 (s, 1H), 5.77 (s, 1H), 5.75 (s, 1H), 5.62 (s, 1H), 5.23 (s, 1H), 5.18 (d, J=6.1 Hz, 1H), 5.08 (d, J=6.1 Hz, 1H), 5.01 (d, J=6.1 Hz, 1H), 4.22 (d, J=2.7 Hz, 1H), 4.09 (d, J=2.4 Hz, 1H), 4.00 (m, 4H), 3.82 (s, 3H), 3.87-3.64 (m, 6H), 3.55 (s, 3H), 3.51-3.44 (m, 2H), 3.30 (s, 3H), 3.29 (s, 3H), 3.26 (m, 1H), 3.18 (dt, $J_1$=2.9 Hz, $J_2$=7.3 Hz, 1H), 2.94 (m, 4H) 2.50 (m, 4H), 2.22 (s, 3H), 2.16 (s, 3H), 2.15 (s, 3H), 2.11 (s, 3H), 2.02 (d, J=7.3 Hz, 2H), 1.72 (s, 3H), 1.69 (s, 3H).

$^{13}$C-RMN (75 MHz, $CDCl_3$): 200.2, 200.1, 159.6, 158.5, 148.5, 148.4, 148.1, 147.9, 140.5, 137.4, 130.9, 130.4, 130.1, 130.0, 125.1, 124.9, 123.8, 122.7, 116.9, 116.6, 113.3, 110.7, 104.5, 103.9, 101.4, 100.7, 98.1, 97.9, 71.9, 71.5, 71.4, 70.1, 69.0, 69.0, 62.0, 60.1, 59.5, 58.7, 58.5, 58.1, 57.4, 56.9, 56.8, 56.4, 55.9, 55.1, 55.0, 41.3, 41.0, 36.1, 31.3, 25.3, 25.2, 22.4, 15.6, 15.5, 13.8, 7.0, 6.8.

ESI-MS m/z: Calcd. for $C_{30}H_{37}N_3O_9$: 583.63. Found $(M+1)^+$: 584.2.

Example 95

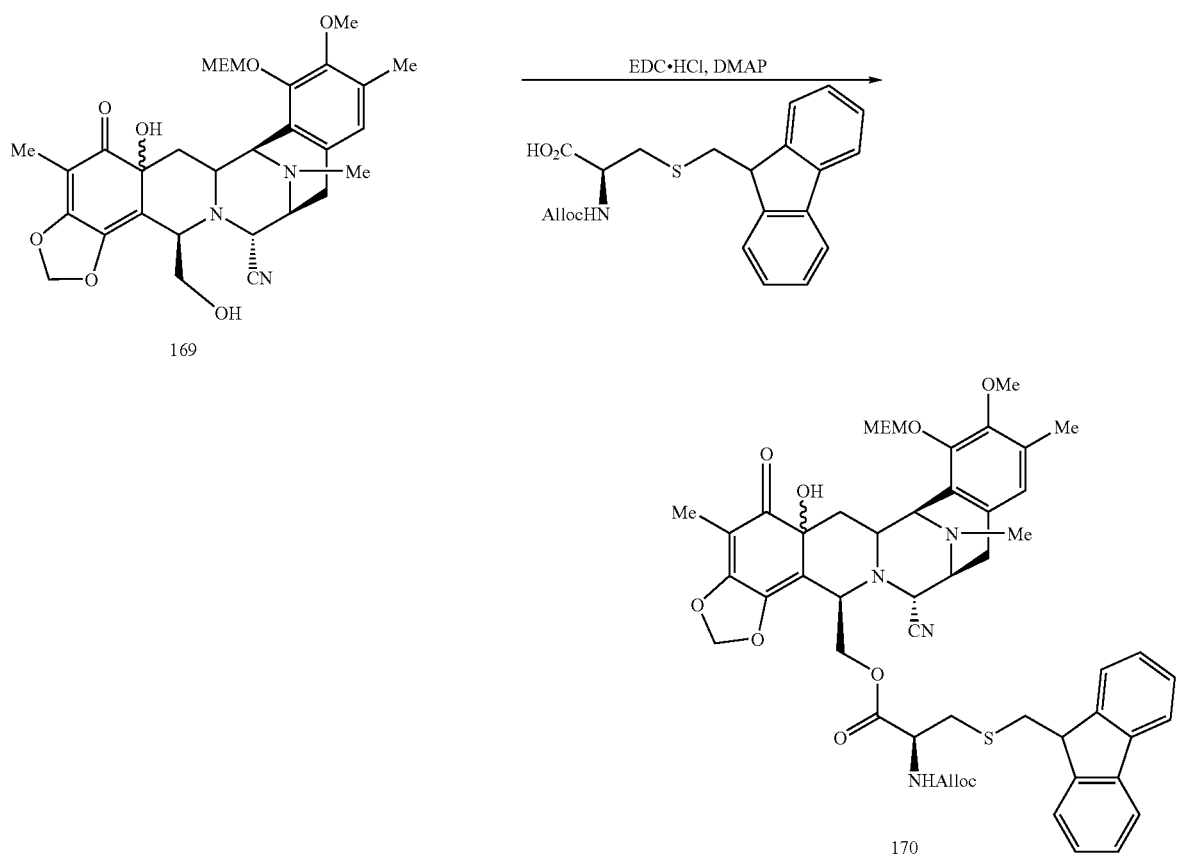

To a solution of 169 (11.49 g, 19.69 mmol) and Alloc-Cys-(Fm) (11.32 g, 29.53 mmol) (for its preparation see Kruse, C. H.; Holden, K. G., *J. Org. Chem.*, 1985, 50, pp. 2792-2794) in anhydrous CH$_2$Cl$_2$ (688 mL), DMAP (2.4 g, 19.69 mmol) and EDC-HCl (9.44 g, 49.22 mmol) were added at 23° C. Then, DIPEA (5.14 mL, 29.53 mmol) was added at 0° C. and the reaction was stirred at 23° C. for 3 hour. The mixture was washed successively with a saturated aqueous solution of NaHCO$_3$ (500 mL), NaCl (400 mL) and NH$_4$Cl (2×300 mL). The organic layer was dried over Na$_2$SO$_4$, filtered and concentrated under reduced pressure. The residue was purified by flash column chromatography (SiO$_2$, AcOEt:Hex in a gradient manner, from 1:1, 6:4 to 7:3) to afford 170 (14.76 g, 79%) as a pale yellow solid. Rf=0.31 and 0.40 Hex:EtOAc 3:7 (mixture of isomers).

$^1$H-RMN (300 MHz, CDCl$_3$): 7.74 (d, J=7.6 Hz, 4H), 7.63 (dd, J=7.0 Hz, J=15.3 Hz, 4H), 7.38 (t, J=7.3 Hz, 4H), 7.29 (m, 4H), 6.61 (s, 1H), 6.54 (s, 1H), 5.89 (m, 2H); 5.73 (s, 1H), 5.70 (s, 1H), 5.69 (s, 1H), 5.62 (s, 1H), 5.55 (m, 1H), 5.32 (d, J=15.1 Hz, 1H), 5.23 (d, J=6.1 Hz, 1H), 5.22 (d, J=10.6 Hz, 1H), 5.14 (d, J=5.9 Hz, 1H), 5.13 (d, J=6.0 Hz, 1H), 5.07 (d, J=6.3 Hz, 1H), 4.68 (m, 1H), 4.56 (m, 4H), 4.51 (m, 2H), 4.38 (dd, J$_1$=4.5 Hz, J$_2$=12.6 Hz, 1H), 4.22 (dd, J$_1$=6.2 Hz, J$_2$=11.1 Hz, 1H), 4.14-3.88 (m, 12H), 3.83 (s, 3H), 3.79-3.69 (m, 4H), 3.61 (s, 3H), 3.56 (m, 4H), 3.39 (s, 3H), 3.36 (s, 3H), 3.23 (m, 2H), 3.16 (d, J=6.0 Hz, 2H), 3.07 (d, J=6.1 Hz, 2H), 3.00-2.81 (m, 6H), 2.46-2.34 (m, 4H), 2.25 (s, 3H), 2.20 (s, 3H), 2.16 (s, 3H), 2.07 (m, 1H), 1.83 (dd, J$_1$=9.5 Hz, J$_2$=15.1 Hz, 1H), 1.78 (s, 3H), 1.77 (s, 3H).

$^{13}$C-RMN (75 MHz, CDCl$_3$): δ 200.3, 198.4, 170.3, 160.0, 158.1, 148.7, 148.7, 148.5, 148.2, 145.6, 145.6, 145.5, 142.2, 141.1, 141.0, 141.0, 138.5, 132.4, 132.3, 131.1, 130.6, 130.1, 129.8, 128.8, 127.6, 127.1, 127.1, 125.1, 125.0, 124.8, 124.7, 124.7, 124.0, 122.7, 119.9, 118.1, 118.0, 117.2, 116.8, 111.6, 108.3, 104.8, 104.5, 101.5, 101.0, 98.2, 98.2, 72.3, 71.7, 71.7, 70.6, 69.3, 69.2, 66.4, 66.0, 66.0, 65.5, 63.8, 60.8, 60.2, 59.8, 59.0, 58.9, 58.1, 56.8. 56.6, 56.5, 56.3, 56.1, 55.7, 55.3, 55.2, 53.9, 46.9, 41.9, 41.4, 41.2, 37.2, 36.9, 35.4, 31.5, 29.6, 25.6, 25.4, 22.6, 15.8, 15.7, 14.1, 7.3, 7.0.

ESI-MS m/z: Calcd. for C$_{51}$H$_{56}$N$_4$O$_{12}$S: 948.36. Found (M+1)$^+$: 949.3.

Example 96

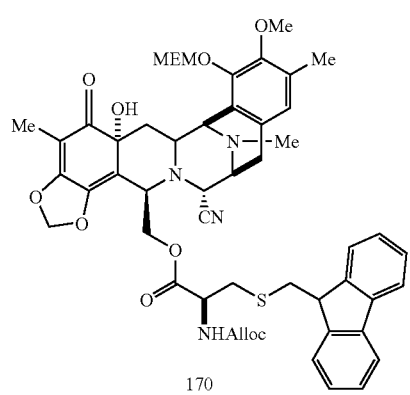

170

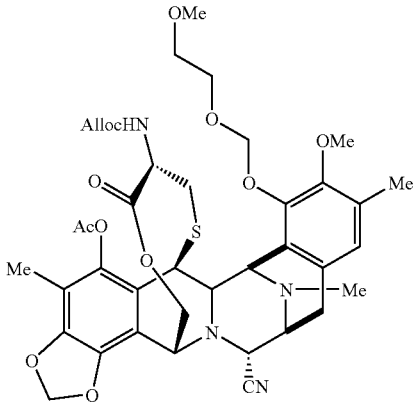

171

The reaction flask was flamed twice, purged vacuum/Argon several times and kept under Argon atmosphere for the reaction. To a solution of DMSO (5.4 mL) in anhydrous CH$_2$Cl$_2$ (554 mL) was dropwise added triflic anhydride (5.11 mL, 30.4 mmol) at −78° C. The reaction mixture was stirred at −78° C. for 20 minutes. Then, a solution of 170 (14.43 g, 15.2 mmol) in anhydrous CH$_2$Cl$_2$ (188 mL) at −78° C. was added via canula. During the addition the temperature was kept at −78° C. in both flasks and the color of the reaction was yellow. The reaction mixture was stirred at −40° C. for 35 minutes. During this period of time the solution was turned from yellow to dark green. After this time, $^i$Pr$_2$NEt (21.2 mL, 121.6 mmol) was dropwise added and the reaction mixture was kept at 0° C. for 45 minutes. The color of the solution turned to pale brown during this time. Then, $^t$BuOH (5.8 mL, 60.8 mmol) and tert-butyl tetramethyl guanidine (18.3 mL, 106.4 mmol) were dropwise added and the reaction mixture was stirred at 23° C. for 40 minutes. After this time, acetic anhydride (14.34 mL, 152 mmol) was dropwise added and the reaction mixture was kept at 23° C. for 1 hour more. Then, the reaction mixture was diluted with CH$_2$Cl$_2$ (38 mL) and washed with a saturated aqueous solution of NH$_4$Cl (500 mL), NaHCO$_3$ (500 mL), and NaCl (500 mL). The combined organic layers were dried over Na$_2$SO$_4$, filtered and concentrated. The residue was purified by flash column chromatography (SiO$_2$, EtOAc:Hex in a gradient manner, from 3:7 to 4:6) to afford 171 (6.24 g, 52%) as a pale yellow solid. Rf=0.38 Hex:EtOAc 1:1.

$^1$H-RMN (CDCl$_3$): 6.78 (s, 1H), 6.07 (d, J=1.2 Hz, 1H), 5.98 (d, J=1.2 Hz, 1H), 5.92 (m, 1H), 5.32 (d, J=5.9 Hz, 1H), 5.31 (dd, J$_1$=1.5 Hz, J$_2$=17.1 Hz, 1H), 5.23 (dd, J$_1$=1.5 Hz, J$_2$=10.4 Hz, 1H), 5.19 (d, J=5.6 Hz, 1H), 5.01 (d, J=11.5 Hz, 1H), 4.81 (d, J=9.8 Hz, 1H), 4.53-4.51 (m, 3H), 4.35-4.27 (m, 2H), 4.24 (s, 1H), 4.18-4.13 (m, 2H), 3.94-3.84 (m, 2H), 3.73 (s, 3H), 3.58 (t, J=4.7 Hz, 2H), 3.43-3.37 (m, 2H), 3.36 (s, 3H), 2.91 (m, 2H), 2.27 (s, 3H), 2.26 (s, 3H), 2.20 (s, 3H), 2.36-2.06 (m, 2H), 2.02 (s, 3H).

$^{13}$C-RMN (CDCl$_3$): 170.23, 168.49, 155.26, 149.62, 148.26, 145.63, 140.85, 140.24, 132.74, 131.60, 130.11, 124.89, 124.70, 120.14, 117.89, 117.84, 113.21, 101.89, 98.03, 92.67, 71.60, 69.04, 65.70, 61.20, 60.35, 59.36, 59.01, 58.89, 54.71, 54.42, 53.79, 41.53, 41.19, 32.68, 29.53, 23.57, 20.26, 15.62, 9.45.

ESI-MS m/z: Calcd. for $C_{39}H_{46}N_4O_{12}S$: 794.87. Found: 796 $(M+1)^+$, 817 $(M+23)^+$. HPLC: Conditions: Column: Simmetry C18, Mobile phase: AcN/buffer phosphate (pH: 5) in gradient from 45 to 65% in 15 minutes and 65-90% in 36 minutes. Ø=0.8 ml/min, $t^a$=40° C. Retention time: 19.734 minutes. HPLC purity in area: 83.17%

Example 97

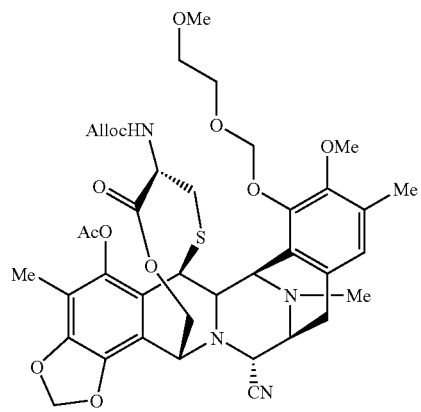

171

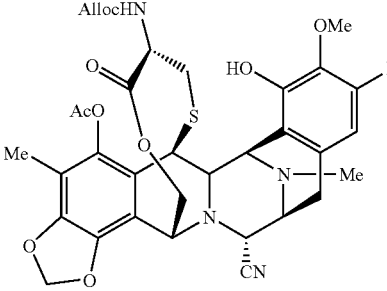

164

Transformation of 164 into 35 was previously described above in Example 89.

Intermediates 35, 36, ET-770 and ET-743 were prepared following the same procedures than those previously described in PCT/GB00/01852.

Route 6

Example 98

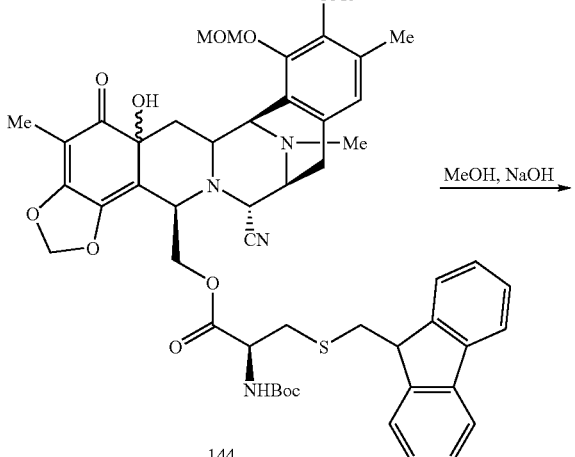

144

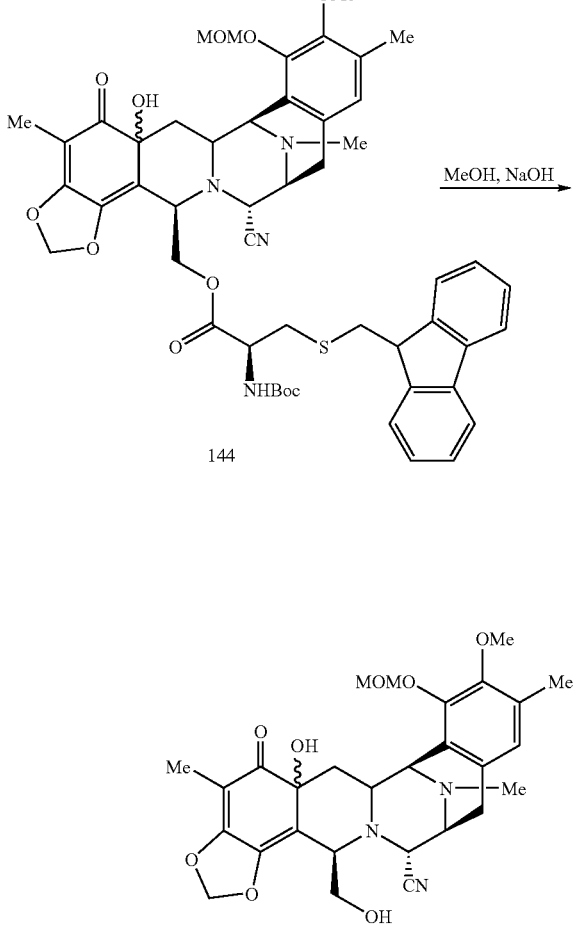

161

To a solution of 171 (2.26 g, 2.85 mmol) in anhydrous $CH_2Cl_2$ (74 mL) and acetonitrile (74 mL), NaI (3.42 g, 22.8 mmol) and TMSCl (freshly distilled over $CaH_2$) (2.6 mL, 22.8 mmol) were added at 0° C. and the reaction was stirred for 35 minutes. A saturated aqueous solution of sodium bicarbonate (150 mL) was added to the reaction mixture at this temperature. The organic phase was separated and the aqueous phase was extracted with $CH_2Cl_2$ (2×100 mL). The combined organic extracts were dried over sodium sulphate, filtered and the solvent was eliminated under reduced pressure to give 164 (2.4 g, 100%) as a pale yellow solid which was used in subsequent reactions with no further purification. Experimental data of 164 were described above in Example 88.

To a solution of 144 (7 g, 7.6 mmol) in MeOH (140 mL), 1M NaOH (15.1 mL) was added and the reaction was stirred for 10 minutes at 23° C. A saturated aqueous solution of $NH_4Cl$ (100 mL) was added to the reaction mixture. The organic phase was separated and washed with 5% HCl until the colour turned into yellow. The organic extract was dried over sodium sulphate, filtered and the solvent was eliminated under reduced pressure. The residue was purified by flash column chromatography ($SiO_2$, EtOAc:Hexane in a gradient manner, from 0:1, 1:3, 1:2, 1:1, 1:1 to 3:1) to afford 161 (3.76 g, 85%). Experimental data of 161 were previously described in U.S. Pat. No. 5,721,362.

Example 99

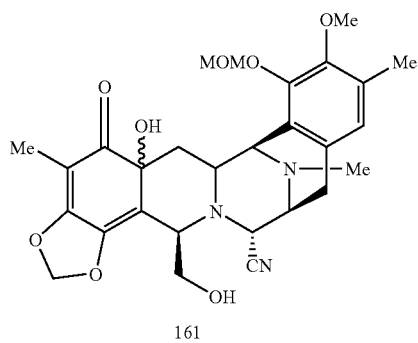 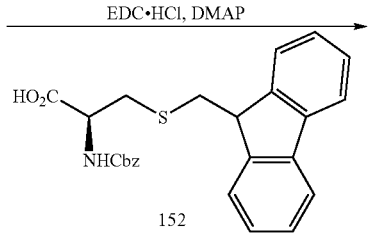

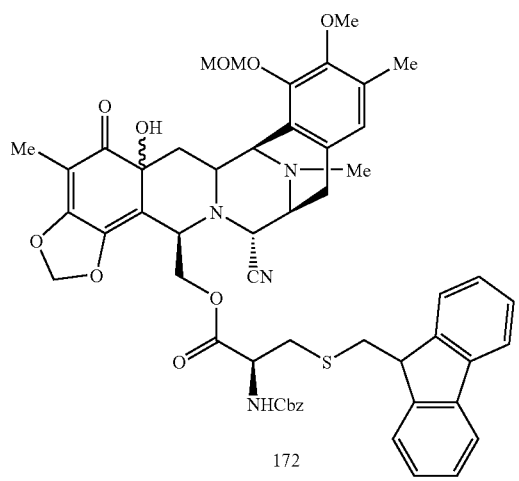

To a solution of 161 (200 mg, 0.37 mmol) and the cysteine 152 (240 mg, 0.55 mmol) in anhydrous $CH_2Cl_2$ (20 mL), DMAP (110 mg, 0.925 mmol) and EDC·HCl (170 mg, 0.925 mmol) were added at 23° C. and the reaction was stirred at that temperature for 1.5 hours. The mixture was then washed successively with a saturated aqueous solution of $NaHCO_3$ (15 mL), NaCl (15 mL) and $NH_4Cl$ (2×10 mL). The organic layer was dried over $Na_2SO_4$, filtered and concentrated under reduced pressure. The residue was purified by flash column chromatography with silica gel ($SiO_2$, AcOEt/Hexane in a gradient manner, from 1:4 to 1:2), to afford 172 (285 mg, 80%) as a white solid. Rf=0.3 Hex:EtOAc 2:1.

$^1$H RMN (CDCl$_3$) δ 7.73 (d, J=7.5 Hz, 2H), 7.59-7.57 (m, 2H), 7.40-7.28 (m, 9H), 6.60 (s, 1H), 5.69 (s, 1H), 5.65 (s, 1H), 5.54 (d, J=7.8 Hz, 1H), 5.11-5.08 (m, 4H), 4.52-4.49 (m, 1H), 4.21-3.90 (m, 6H), 3.83 (s, 3H), 3.49 (s, 3H), 3.21 (d, J=6.6 Hz, 1H), 3.09-2.90 (m, 6H), 2.41 (d, J=18 Hz, 1H), 2.34-2.31 (m, 1H), 2.25 (s, 3H), 2.19 (s, 3H), 1.88-1.83 (m, 1H), 1.77 (s, 3H).

$^{13}$C-RMN (CDCl$_3$) δ 198.7, 170.5, 158.4, 155.9, 148.9, 148.8, 145.8, 142.5, 141.3, 136.2, 131.4, 130.0, 128.8, 128.6, 128.4, 127.9, 127.3, 125.3, 125.0, 124.9, 123.0, 120.1, 117.5, 108.5, 104.8, 101.7, 99.5, 70.8, 67.4, 60.5, 57.8, 57.0, 56.5, 56.0, 55.5, 47.1, 41.6, 37.4, 37.1, 31.8, 25.8, 22.8, 15.9, 14.3, 7.6.

ESI-MS m/z: Calcd. for $C_{53}H_{54}N_4O_{11}S$: 954.35. Found (M+23)$^+$: 977.8.

Example 100

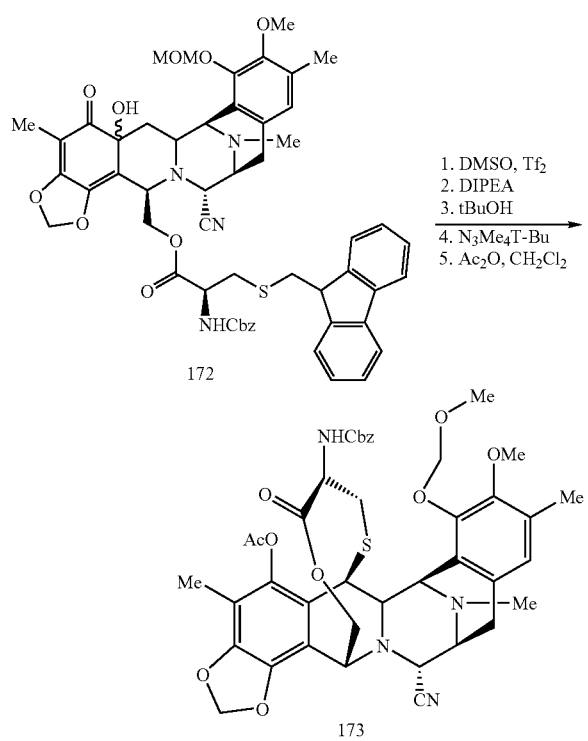

The reaction flask was flamed twice, purged vacuum/Argon several times and kept under Argon atmosphere for the reaction. To a solution of DMSO (977 μL) in anhydrous $CH_2Cl_2$ (118 mL) was dropwise added triflic anhydride (930 □L, 5.5 mmol) at −78° C. The reaction mixture was stirred at −78° C. for 20 minutes. Then, a solution of 172 (2.63 g, 2.75 mmol) in anhydrous $CH_2Cl_2$ (26 mL, for the main addition and 13 mL for washing) was added via canula (addition time: 5 min) at −78° C. During the addition the temperature was kept at −78° C. in both flasks and the color changed from yellow to brown. The reaction mixture was stirred at −40° C. for 35 minutes. During this period of time the solution was turned from yellow to dark green. After this time, $^i$Pr$_2$NEt (3.48 mL, 22 mmol) was dropwise added and the reaction mixture was kept at 0° C. for 45 minutes, the color of the solution turned brown during this time. Then, $^t$BuOH (1.04 mL, 11 mmol) and tert-butyl tetramethyl guanidine (3.31 mL, 19.25 mmol) were dropwise added and the reaction mixture was stirred at 23° C. for 40 minutes. After this time, acetic anhydride (2.6 mL, 27.5 mmol) was dropwise added and the reaction mixture was kept at 23° C. for 1 hour more. Then, the reaction mixture was diluted with $CH_2Cl_2$ (70 mL) and washed successively with a saturated aqueous solution of $NH_4Cl$ (180 mL), $NaHCO_3$ (180 mL), and NaCl (180 mL). The combined organic layers were dried over $Na_2SO_4$, filtered and concentrated at reduced pressure. The residue was purified by flash column chromatography ($SiO_2$, Hex:EtOAc in a gradient manner, from 4:1, 3:1, to 2:1) to afford 173 (1.145 g, 52%) as a white solid. Rf=0.31 Hex:EtOAc 3:2.

$^1$H RMN (CDCl$_3$) δ 7.37 (bs, 5H), 6.67 (s, 1H), 6.08 (d, J=1.2 Hz, 1H), 5.99 (d, J=1.2 Hz, 1H), 5.19-5.00 (m, 4H), 4.82 (d, J=9.3 Hz, 1H), 4.49 (bs, 1H), 4.32-4.15 (m, 5H), 3.67 (s, 3H), 3.55 (s, 3H), 3.44 (d, J=4.8 Hz, 1H), 3.39 (d, J=6 Hz, 1H), 2.90-2.87 (m, 2H), 2.28 (s, 3H), 2.19 (s, 3H), 2.15-2.07 (m, 2H), 2.03 (s, 3H), 2.00 (s, 3H).

$^{13}$C-RMN (CDCl$_3$) δ 170.6, 168.8, 155.8, 149.9, 148.5, 146.0, 141.2, 140.6, 136.6, 132.0, 130.4, 128.8, 128.7, 128.5, 125.2, 124.9, 120.5, 118.2, 113.7, 113.6, 102.2, 99.4, 67.2, 61.6, 60.7, 59.7, 59.3, 57.6, 55.1, 54.8, 54.2, 41.9, 41.6, 33.0, 29.9, 23.9, 20.6, 15.6, 9.8.

ESI-MS m/z: Calcd. for $C_{41}H_{44}N_4O_{11}S$: 800.87. Found (M+23)$^+$: 823.7.

Example 101

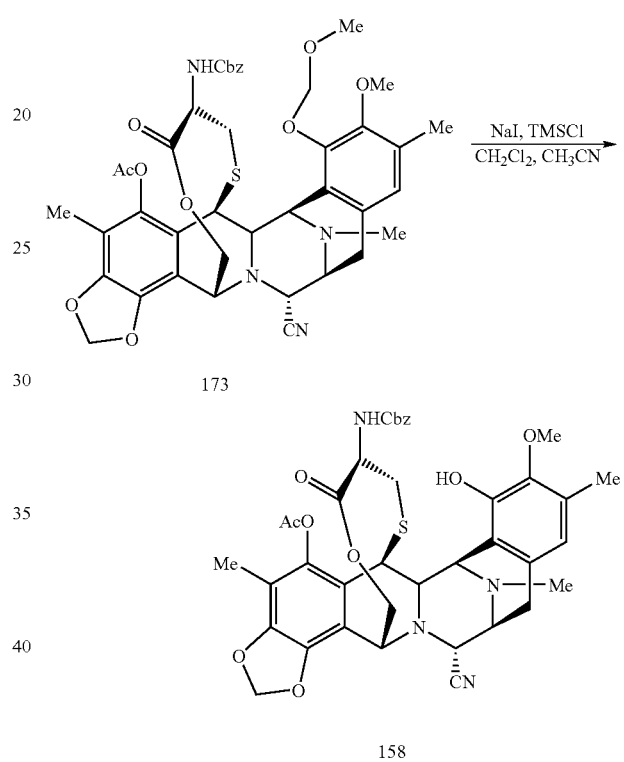

To a solution of 1713 (100 mg, 0.125 mmol) in $CH_2Cl_2$ (2 mL) and $CH_3CN$ (2 mL), NaI (75 mg, 0.5 mmol) and TMSCl (63 □L, 0.5 mmol) were added at 0° C. After stirring the reaction at 23° C. for 50 minutes, the mixture was quenched with water (30 mL) and extracted with $CH_2Cl_2$ (2×20 mL). The combined organic phases were washed successively with a saturated aqueous solution of NaCl (20 mL) and sodium ditionite (20 mL), dried over $Na_2SO_4$, filtered and concentrated in vacuo. The residue was purified by flash column chromatography ($SiO_2$, EtOAc:Hexane in a gradient manner, from 1:4, 1:2 to 1:1) to afford 158 (66 mg, 70%) as white solid. Rf=0.21 Hex:EtOAc 1:1. Experimental data of 158 was described above in Example 19.

Transformation of 158 into 35 was described above in Example 85.

Intermediates 36, ET-770 and ET-743 were prepared following the same procedures than those previously described in PCT/GB00/01852.

REFERENCES

European Patent 309,477.
U.S. Pat. No. 5,721,362.
Sakai, R., Jares-Erijman, E. A., Manzanares, I., Elipe, M. V. S., and Rinehart, K. L. J. Am. Chem. Soc. (1996) 118, 9017-9023
Martinez, E. J., Owa, T., Schreiber, S. L. and Corey, E. J. *Proc. Natl. Acad. Sci. USA*, 1999, 96, 3496-3501.
Japanese Kokai JP-A2 59/225189.
Japanese Kokai JP-A2 60/084,288.
Arai, T,; Kubo, A. In *The Alkaloids, Chemistry and Pharmacology*; Brossi, A. Ed.; Academic: New York, 1983, Vol 21; pp 56-110.
Remers, W. A.: In *The Chemistry of Antitumor Antibiotics*; Vol. 2; Wiley; New York, 1988, pp 93-118.
Gulavita N. K.; Scheuer, P. J.: Desilva, E. D. Abst. Indo-United States Symp. on Bioactive Compounds from Marine Organisms, Goa, India, Feb. 23-27, 1989, p 28.
Arai, T; Takahashi, K; Kubo, A. *J. Antibiot*, 1977, 30, 1015-1018.
Arai. T.; Takahashi, K.; Nakahara, S.; Kubo, A. *Experientia* 1980, 36, 1025-1028.
Mikami, Y.; Takahashi, K; Yazawa, K.; Hour-Young, C.; Arai, T.; Saito, N.; Kubo, A. *J. Antibiot*. 1988, 41, 734-740.
Arai, T.; Takahashi, K.; Ishiguro, K.; Yazawa, K. *J. Antibiot*. 1980, 33, 951-960.
Yazawa, K.; Takahashi, K.; Mikami, Y.; Arai, T.; Saito, N.; Kubo, A. *J. Antibiot*. 1986, 39, 1639-1650.
Arai, T.; Yazawa, K.; Takahashi, K.; Maeda, A.; Mikami, Y. *Antimicrob. Agent Chemother*. 1985, 28, 5-11.
Takahashi, K.; Yazawa, K.; Kishi, K.; Mikami, Y.; Arai, T.; Kubo, A. *J. Antibiot*. 1982, 35, 196-201.
Yazawa, K.; Asaoka, T.; Takahashi, K.; Mikami, Y.; Arai, T. *J. Antibiot*. 1982, 35, 915-917.
Frincke, J. M.; Faulkner, D. J. *J. Am. Chem. Soc*. 1982, 104, 265-269.
He, H.-Y.; Faulkner, D. J. *J. Org. Chem*. 1989, 54, 5822-5824.
Kubo, A.; Saito, N.; Kitahara, Y.; Takahashi, K.; Tazawa, K.; Arai, T. *Chem Pharm. Bull*. 1987, 35, 440-442.
Trowitzsch-Kienast, W.; Irschik, H.; Reichenback, H.; Wray, V.; Höfle, G. *Liebigs Ann. Chem*. 1988, 475-481.
Ikeda, Y.; Idemoto, H.; Hirayama, F.; Yamamoto, K.; Iwao, K.; Asano, T.; Munakata, T. *J. Antibiot*. 1983, 36, 1279-1283.
Asaoka, T.; Yazawa, K.; Mikami, Y. Arai, T.; Takahashi, K. *J. Antibiot*. 1982, 35, 1708-1710.
Lown, J. W.; Hanstock, C. C.; Joshua, A. V.; Arai, T; Takahashi, K. *J. Antibiot*. 1983, 36, 1184-1194.
Munakata et al. U.S. Pat. No. 4,400,752, 1984.
Y. Ikeda et al. The Journal of Antibiotics. VOL XXXVI, No.10, 1284, 1983.
R. Cooper, S. Unger. The Journal of Antibiotics. VOL XXXVIII, No.1, 1985.
Corey et al. U.S. Pat. No. 5,721,362. 1998.
Corey et al. J. Am. Chem. Soc. vol 118 pp 9202-92034, 1996.
Proc. Natl. Acad. Sci. USA. Vol. 96, pp 3496-3501, 1999.

The invention claimed is:

1. A process for the manufacture of an ecteinascidin compound, wherein the process comprises deprotecting a compound of formula (A) to give an α-aminelactone of formula (35), in accordance with the following scheme:

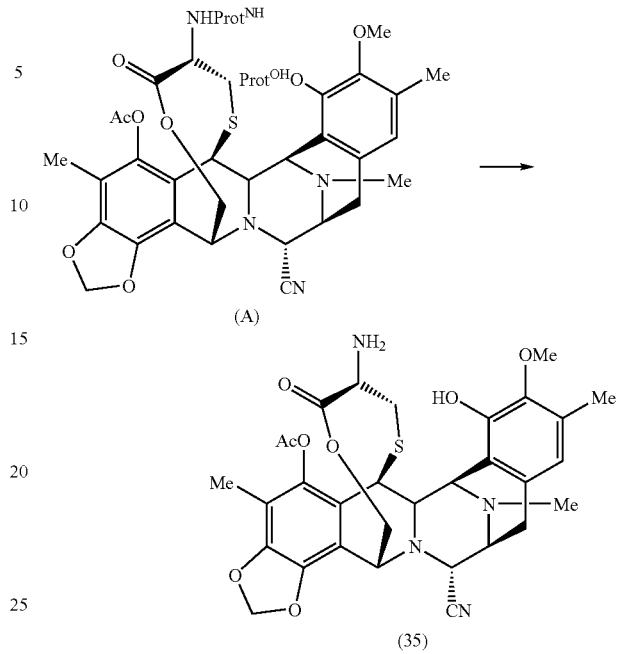

where $Prot^{NH}$ is amino protecting group, and $Prot^{OH}$ is a hydroxy protecting group, and wherein deprotecting the amino group protected with $Prot^{NH}$ and deprotecting the hydroxyl group protected with $Prot^{OH}$ is performed in a single step.

2. The process of claim 1, wherein $Prot^{NH}$ is t-butyloxycarbonyl and $Prot^{OH}$ is methoxymethyl.

3. The process of claim 1, wherein $Prot^{NH}$ is t-butyloxycarbonyl and $Prot^{OH}$ is methoxyethoxymethyl.

4. The process of claim 1, which further comprises the step of oxidising the α-aminelactone of formula (35) to form an α-ketolactone of formula (36) in accordance with the following scheme:

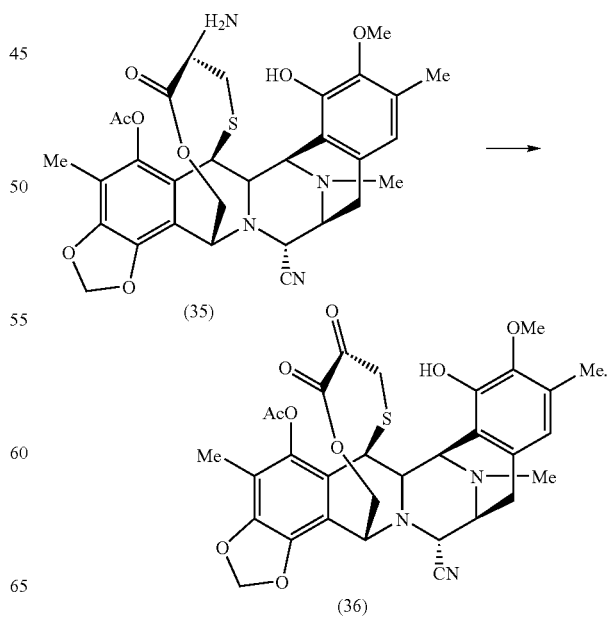

5. The process of claim 4, which further comprises converting stereospecifically the α-ketolactone of formula (36) to a spirotetrahydroisoquinoline compound Et770, in accordance with the following scheme:

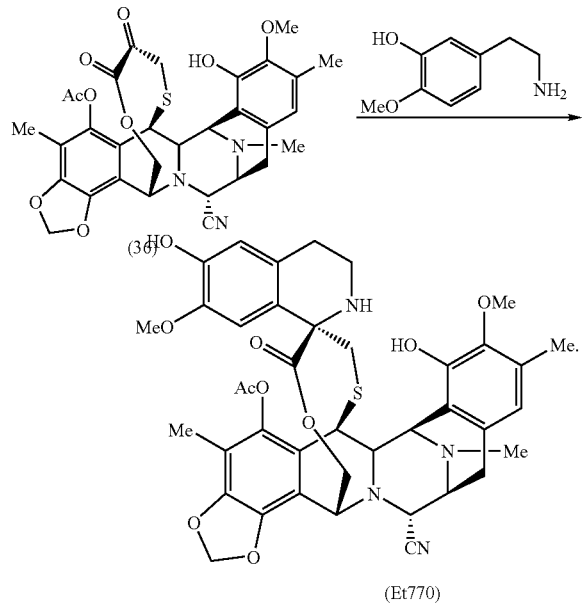

6. The process of claim 5, wherein converting stereospecifically the α-ketolactone of formula (36) comprises performing a Pictet-Spengler reaction.

7. The process of claim 5, which further comprises replacing the nitrile group at C-21 of Et770 with a hydroxy group to form Et743:

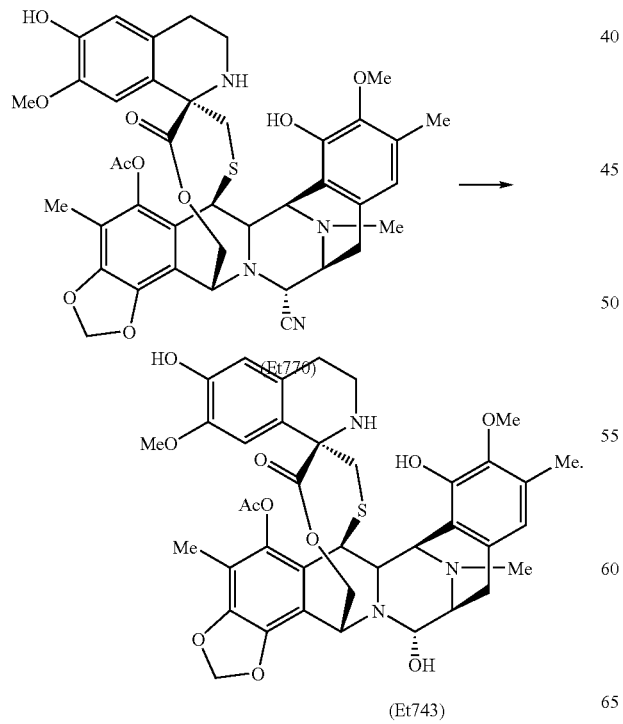

8. A process for the manufacture of an ecteinascidin compound, wherein the process comprises oxidizing an α-aminelactone of formula (35) to form an α-ketolactone of formula (36) in accordance with the following scheme:

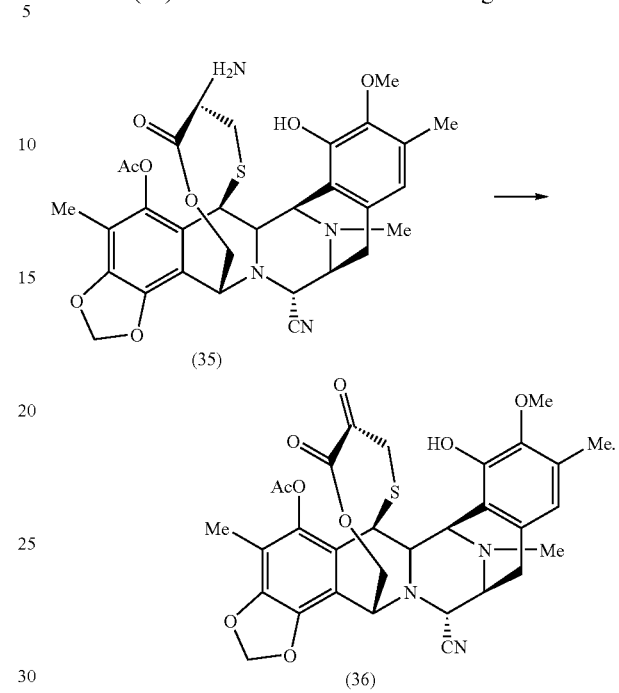

9. The process of claim 8, which further comprises converting stereospecifically the α-ketolactone of formula (36) to a spirotetrahydroisoquinoline compound Et770, in accordance with the following scheme:

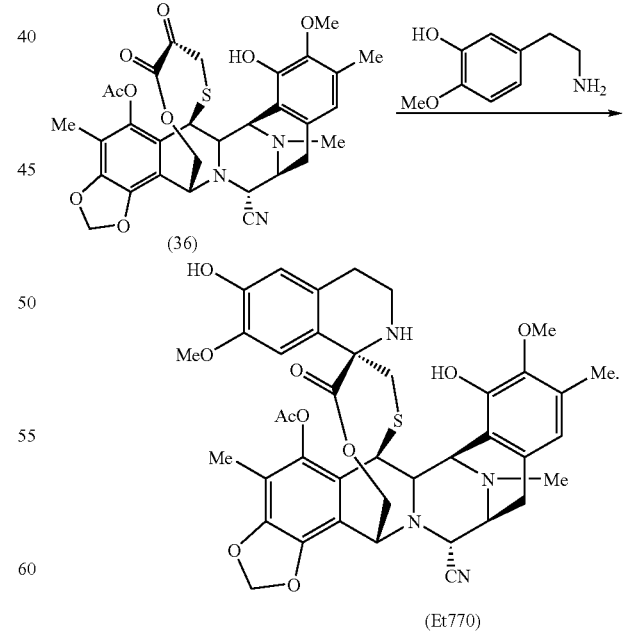

10. The process of claim 9, wherein converting stereospecifically the α-ketolactone of formula (36) comprises performing a Pictet-Spengler reaction.

11. The process of claim 9, which further comprises replacing the nitrile group at C-21 of Et770 with a hydroxy group to form Et743:

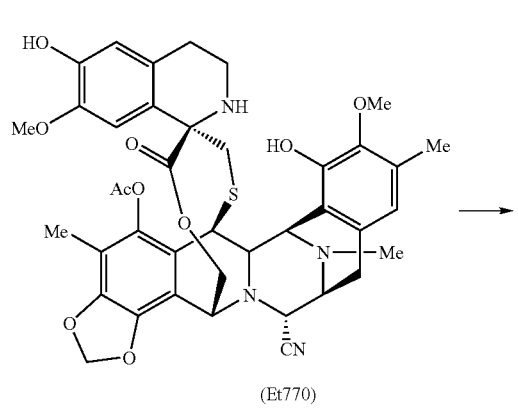

(Et770)

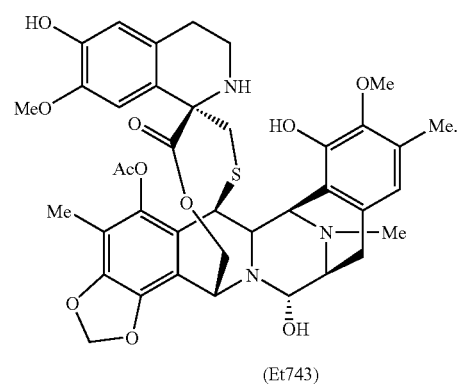

(Et743)

12. A process for the manufacture of an ecteinascidin compound, wherein the process comprises converting stereospecifically an α-ketolactone of formula (36) to a spirotetrahydroisoquinoline compound Et770, in accordance with the following scheme:

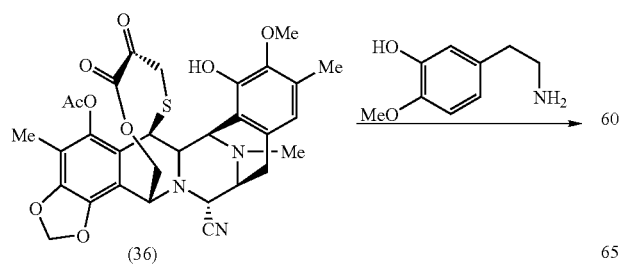

-continued

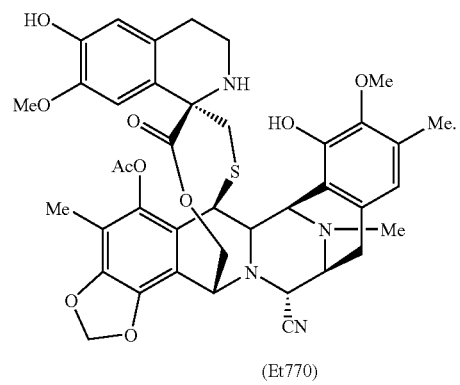

(Et770)

13. The process of claim 12, wherein converting stereospecifically the α-ketolactone of formula (36) comprises performing a Pictet-Spengler reaction.

14. The process of claim 12, which further comprises replacing the nitrile group at C-21 of Et770 with a hydroxy group to form Et743:

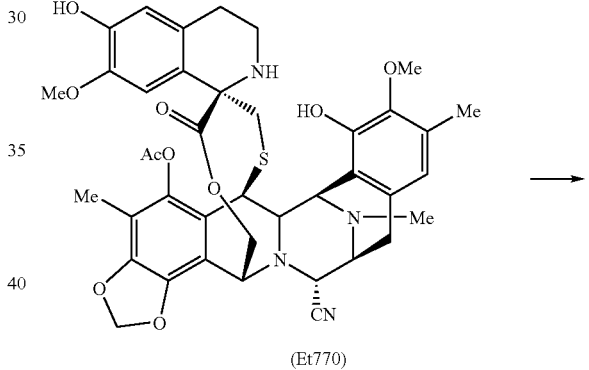

(Et770)

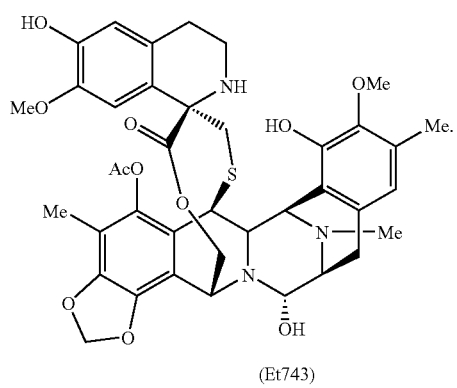

(Et743)

15. An intermediate for the synthesis of an ecteinascidin compound, the intermediate being of the formula (35):
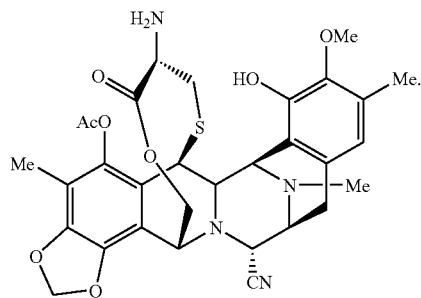
(35)
16. An intermediate for the synthesis of an ecteinascidin compound, the intermediate being of the formula (36):
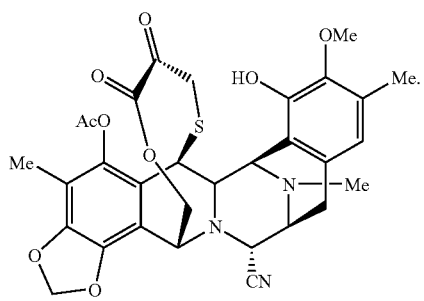
(36)
* * * * *

UNITED STATES PATENT AND TRADEMARK OFFICE
CERTIFICATE OF CORRECTION

PATENT NO. : 7,420,051 B2
APPLICATION NO. : 11/249172
DATED : October 11, 2005
INVENTOR(S) : Andres Francesch et al.

It is certified that error appears in the above-identified patent and that said Letters Patent is hereby corrected as shown below:

Column 11, line 30: The number "21" should be added below the formula as follows:

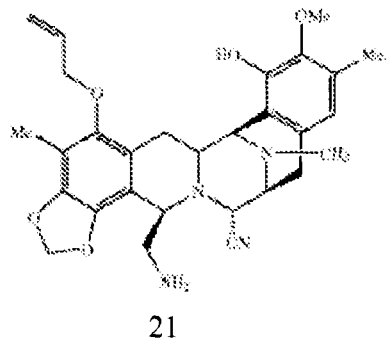

21

Column 17, lines 60-65: The reactive in scheme 2 should be amended from NaNO$_2$" to --NaNO$_3$--.

Column 21, lines 30-35: The formula 150 reading:

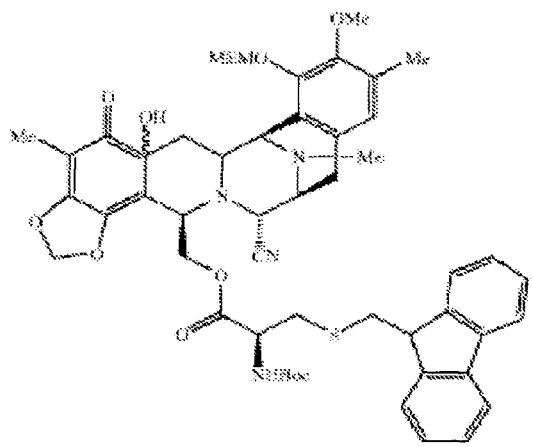

Signed and Sealed this
Eighteenth Day of January, 2011

David J. Kappos
*Director of the United States Patent and Trademark Office* should read:
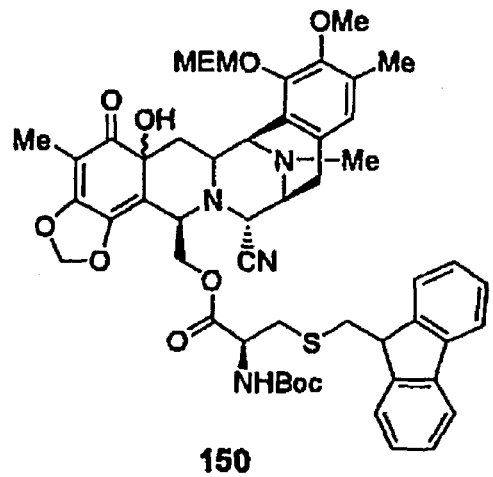
--     --.
Column 30, line 25-30: scheme 4, structure 146, the reactive "tmd" should read --Imd--.
Column 34, line 40-45: scheme 5, structure 146, the reactive "tmd" should read --Imd--.
Column 43, line 60: "-CH$^2$-NH-CO-CR$^{25a}$R$^{25b}$R$^{25c}$" should read -- -CH$_2$-NH-CO-CR$^{25a}$R$^{25b}$R$^{25c}$--.
Column 44, line 55-60: The formula (XVI) reading:
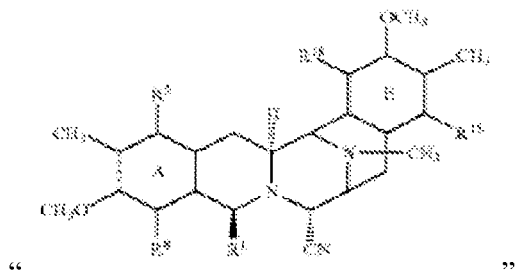
"                                    "

should read:
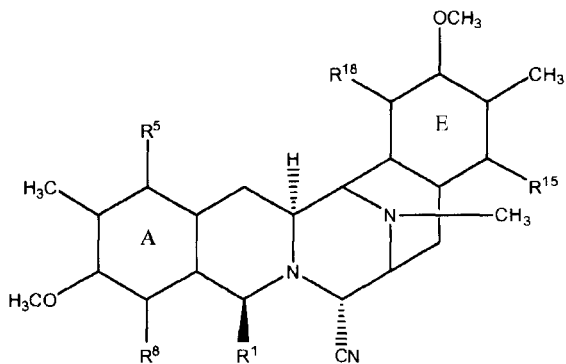
(XVI)
-- --.
Column 45, line 32: "allyl" should read --alkyl--.
Column 52, line 31: "(I" should read --(IV)--.
Column 66, line 50-65: The formula of the compound ET-743 reading:
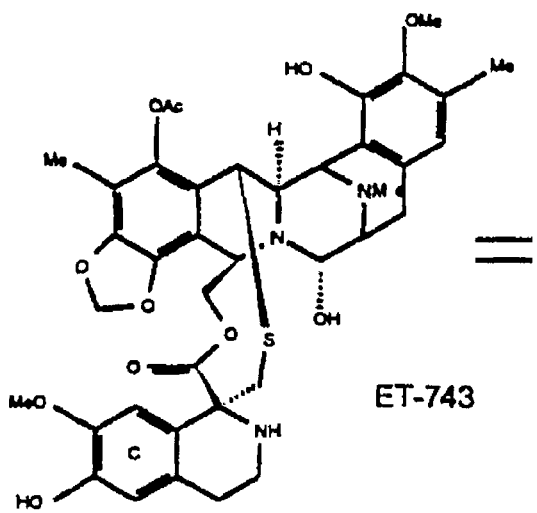
" "

should read:
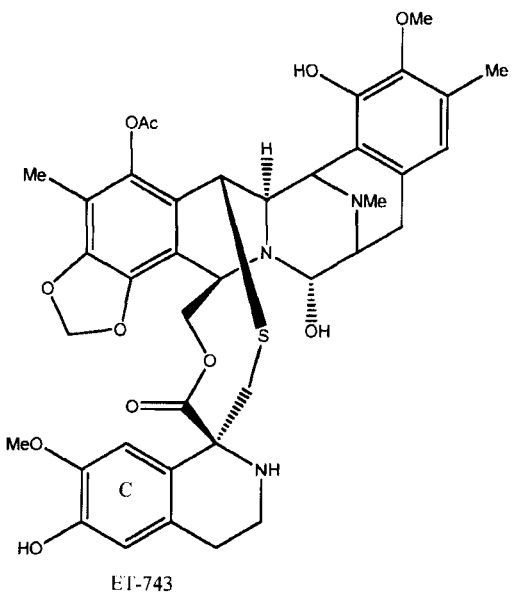
-- ET-743 --.
Column 67, line 5-15: The formula of the compound int-11 reading:
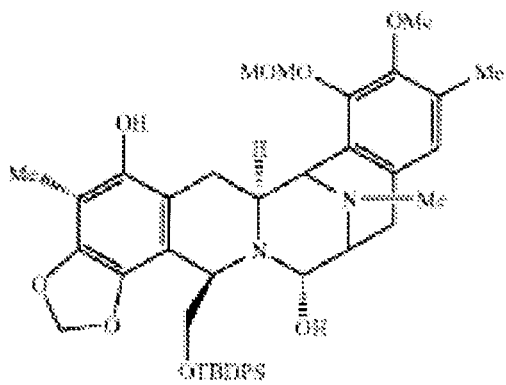
" int-11 "
should read:

CERTIFICATE OF CORRECTION (continued)
U.S. Pat. No. 7,420,051 B2

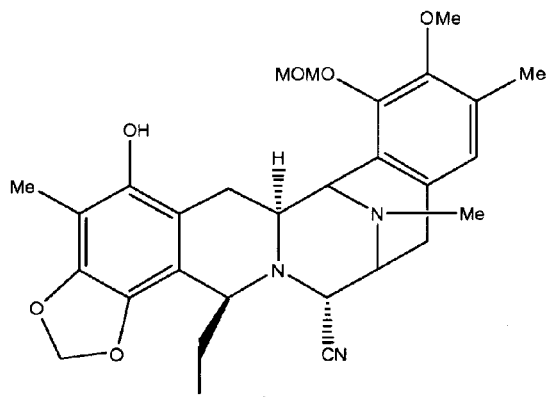

-- int-11 --.

Column 67, line 25-35: the formula reading:

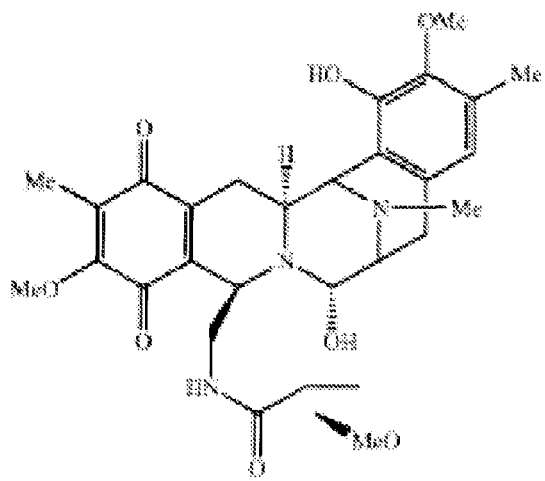

" "

should read:

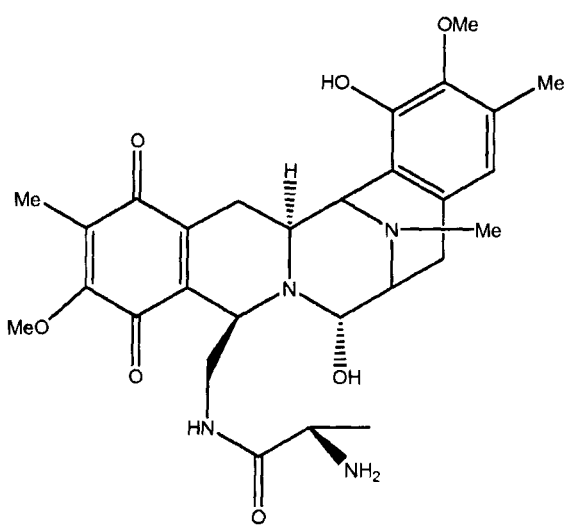

SAFRACIN B

-- --.

CERTIFICATE OF CORRECTION (continued)
U.S. Pat. No. 7,420,051 B2

Column 68, line 6: "(X)" should read --(XXI)--.

Column 68, line 34: "-CH$^2$-NH-CO-CR$^{25a}$R$^{25b}$R$^{25c}$" should read
-- -CH$_2$-NH-CO-CR$^{25a}$R$^{25b}$R$^{25c}$--.

Column 71, line 20: scheme VIII, first formula: the reactive "Phenyilsothiocyanate" should read --Phenylisothiocyanate--.

Column 75, line 25-35: The compound of formula (XXIIa) reading:

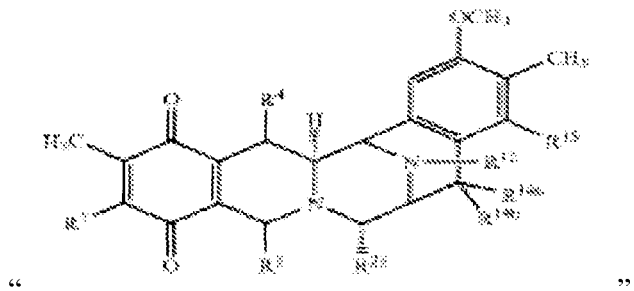

"

should read:

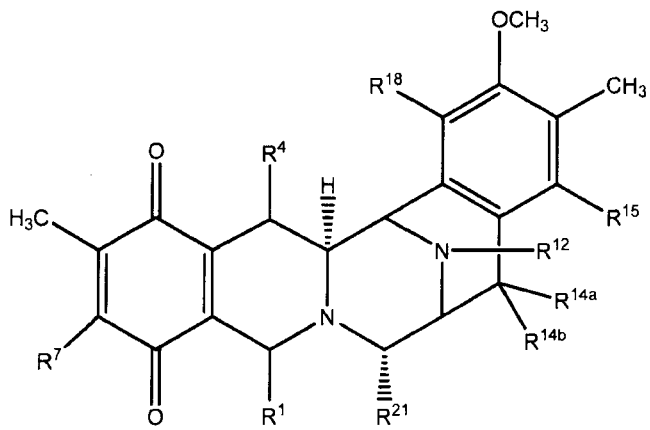

(XXIIa)

-- --.

Column 75, line 50-60: The compound of formula (XXIIb) reading:

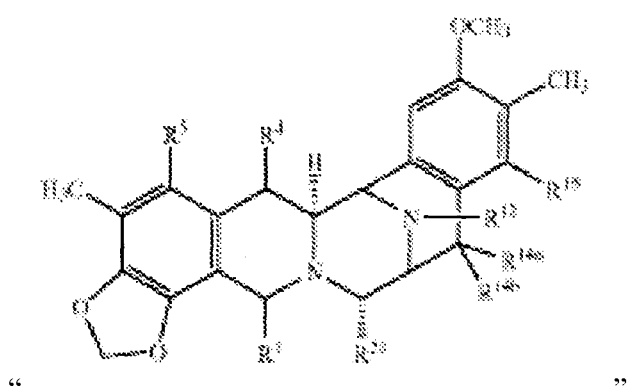

" "

CERTIFICATE OF CORRECTION (continued)
U.S. Pat. No. 7,420,051 B2 should read:

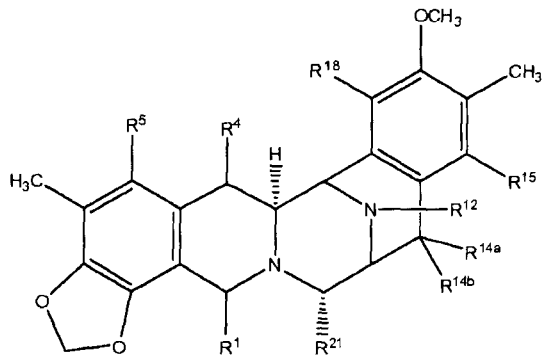

(XXIIb)

-- --.

Column 97, line 10-15: The compound 49 reading:

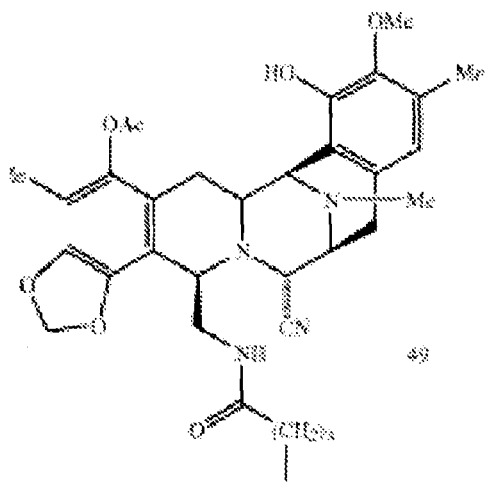

" "

should read:

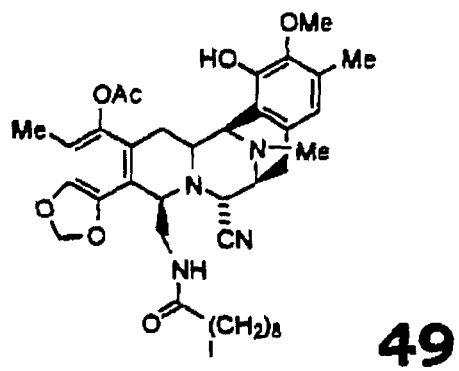

-- --.

Column 131, line 13: the term "1, 23° C" should read --1 h, 23 ° C--.

Column 133, line 9: the reative "TroCl" should read --TrocCl--.

Column 139, line 3: "(3 x 0.10 ml)" should read --(3 x 10 ml)--.

Column 145, line 67: "3.42 (d, 3=8.5 Hz, 1 H)" should read --3.42 (d, J=8.5 Hz, 1 H)--.

Column 184, line 48: "butyl chloride" should read --butyrylchloride--.

Column 184, line 66: "$C_{32}H_{38}N_{407}$" should read --$C_{32}H_{38}N_4O_7$--.

Column 185, line 18: first compound: "66" should read --50--.

Column 185, line 25-35: The compound reading:

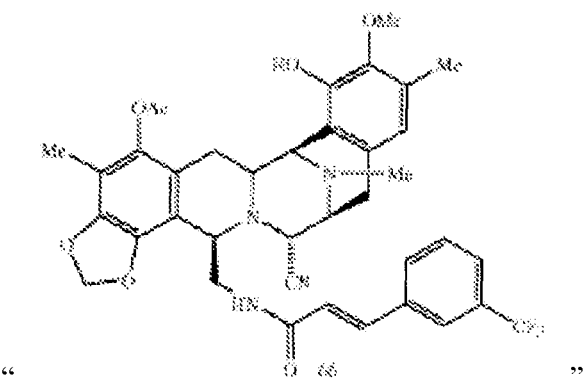

"         "

should read:

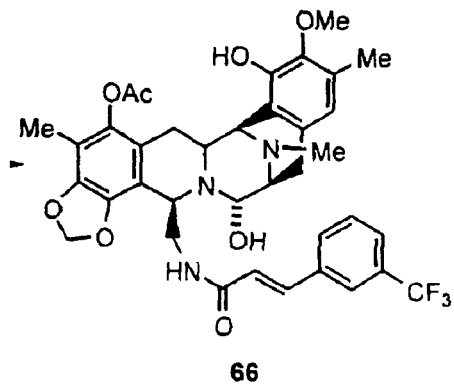

--          --.

Column 195, line 66: "8175.3" should read --δ 175.3--.

Column 198, line 30: "40° C" should read -- - 40° C--.

CERTIFICATE OF CORRECTION (continued)
U.S. Pat. No. 7,420,051 B2

Column 200, line 4: Please insert --Route 2-- before Example 71.

Column 200, line 38: "THP" should read --THF--.

Column 214, line 15-25: The compound 156 reading:

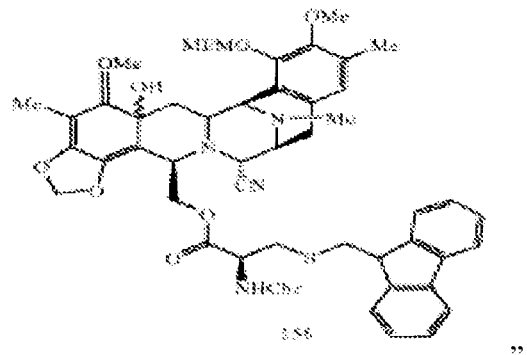

" "

should read

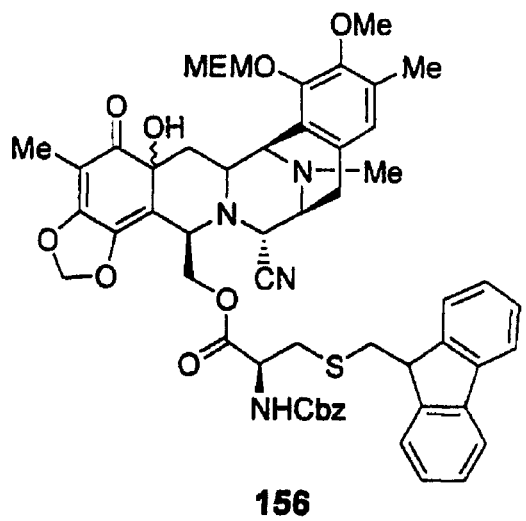

-- --.